(12) United States Patent
Christensen et al.

(10) Patent No.: US 11,034,973 B2
(45) Date of Patent: Jun. 15, 2021

(54) NUCLEOTIDE SEQUENCES AND POLYPEPTIDES ENCODED THEREBY USEFUL FOR MODIFYING PLANT CHARACTERISTICS IN RESPONSE TO COLD

(71) Applicant: Ceres, Inc., Thousands Oaks, CA (US)

(72) Inventors: Cory Christensen, Simi Valley, CA (US); Jack Okamuro, Oak Park, CA (US); Shing Kwok, Woodland Hills, CA (US); Roger Pennell, Malibu, CA (US)

(73) Assignee: Ceres, Inc., Thousand Oaks, CA (US)

(*) Notice: Subject to any disclaimer, the term of this patent is extended or adjusted under 35 U.S.C. 154(b) by 0 days.

(21) Appl. No.: 16/719,390

(22) Filed: Dec. 18, 2019

(65) Prior Publication Data

US 2020/0131525 A1     Apr. 30, 2020

Related U.S. Application Data

(60) Division of application No. 16/275,659, filed on Feb. 14, 2019, which is a division of application No. 15/362,633, filed on Nov. 28, 2016, now Pat. No. 10,240,166, which is a division of application No. 11/779,266, filed on Jul. 17, 2007, now abandoned, which is a continuation-in-part of application No. 11/778,060, filed on Jul. 15, 2007, now abandoned, which is a continuation-in-part of application No. 11/248,547, filed on Oct. 12, 2005, now Pat. No. 7,244,879.

(51) Int. Cl.
| | | |
|---|---|---|
| *C12N 15/82* | (2006.01) | |
| *C07K 14/415* | (2006.01) | |
| *A01H 1/02* | (2006.01) | |
| *C12Q 1/6895* | (2018.01) | |

(52) U.S. Cl.
CPC ........... *C12N 15/8273* (2013.01); *A01H 1/02* (2013.01); *C07K 14/415* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 5,990,387 | A * | 11/1999 | Tomes ............... | C12N 15/8207 435/412 |
| 10,508,284 | B2 | 12/2019 | Christensen et al. | |
| 2006/0107345 | A1 | 5/2006 | Alexandrov et al. | |
| 2006/0150283 | A1 | 7/2006 | Alexandrov et al. | |
| 2009/0094717 | A1 | 4/2009 | Troukhan et al. | |
| 2009/0265275 | A1 | 10/2009 | Alexandrov et al. | |
| 2010/0083407 | A1 | 4/2010 | Feldmann et al. | |
| 2013/0042367 | A1 | 2/2013 | Nadzan et al. | |
| 2016/0369294 | A9 * | 12/2016 | Nadzan .............. | C12N 15/8241 |
| 2018/0223303 | A1 | 8/2018 | Alexandrov et al. | |
| 2019/0241902 | A1 | 8/2019 | Christensen et al. | |
| 2019/0276836 | A1 | 9/2019 | Christensen et al. | |
| 2020/0109412 | A1 | 4/2020 | Christensen et al. | |
| 2020/0255853 | A1 | 8/2020 | Christensen et al. | |

FOREIGN PATENT DOCUMENTS

| | | | |
|---|---|---|---|
| EP | 1033405 | 9/2000 | |
| EP | 1033405 A2 * | 9/2000 | ........... C07K 14/415 |
| WO | WO 9902687 | 1/1999 | |
| WO | WO 2004035798 | 4/2004 | |

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495, 1994).*
Thornton et al. (Nature structural Biology, structural genomics supplement, Nov. 2000).*
Keskin et al. (Protein Science, 13:1043-1055, 2004).*
Seki et al. (NCBI, GenBank Sequence Accession No. AK118678.1, pp. 1-2, Published Dec. 6, 2002).*
Didierjean et al. (Planta, 199:1-8, 1996).*
U.S. Appl. No. 16/855,674, filed Apr. 22, 2020, Christensen et al.
U.S. Appl. No. 16/659,220, filed Oct. 21, 2019, Christensen, et al.
USPTO: Notice of Allowance and Fee(s) Due regarding U.S. Appl. No. 16/275,629, dated Aug. 2, 2019.
USPTO: Office Action regarding U.S. Appl. No. 16/275,659, dated Dec. 19, 2019.
Response to Office Action regarding U.S. Appl. No. 16/275,659, dated Feb. 4, 2020.
Supplemental Response to Office Action regarding U.S. Appl. No. 16/275,659, dated Feb. 11, 2020.
Kim et al., "Molecular cloning of low temperature-inducible ribosomal proteins from soybean," *Journal of Experimental Botany* 55:1153-1155, 2004.
Lu et al., "*Arabidopsis* Mutants Deficient in Diacylglycerol Acyltransferase Display Increased Sensitivity to Abscisic Acid, Sugards, and Osmotic Stress during Germination and Seedling Development," *Plant Physiology* 129:1352-1358, 2002.
Ngo et al., "Computational Complexity, Protein Structure Prediction, and the Levinthal Pradox," *The Protein Folding Problem and Tertiary Structure Prediction*, K. Merz and S. Le Grand (eds.), pp. 492-495, 1994.
Guo et al., "Protein tolerance to random amino acid change," *PNAS* 101:9205-9210, 2004.
GenBank Accession No. AY117196, dated Sep. 18, 2002.
Keskin et al., "A new, structurally nonredundant, diverse data set of protein-protein interfaces and its implications," *Protein Science* 13:1043-1055, 2004.

(Continued)

*Primary Examiner* — Vinod Kumar
(74) *Attorney, Agent, or Firm* — Dentons US LLP

(57) ABSTRACT

Methods and materials for modulating cold tolerance levels in plants are disclosed. For example, nucleic acids encoding cold tolerance-modulating polypeptides are disclosed as well as methods for using such nucleic acids to transform plant cells. Also disclosed are plants having increased levels of cold tolerance and plant products produced from plants having increased cold tolerance levels.

5 Claims, 8 Drawing Sheets

Specification includes a Sequence Listing.

(56) References Cited

OTHER PUBLICATIONS

Thornton et al., "From structure to function: Approaches and limitations," *Nature Structural Biology, Structural Gemonics Supplement*, Nov. 2000.
Wells, "Additivity of Mutational Effects in Proteins," *Biochemistry* 29:8509-8517, 1990.
USPTO: Notice of Allowance regarding U.S. Appl. No. 16/275,659 dated Feb. 28, 2020.

* cited by examiner

```
SEQ-ID-NO-17-CLONE-839727    MSAAE---GA VVFSEEKEAL VLKSWAIMKK DSANLGRFF LKIFEIAPSA    47
SEQ-ID-NO-16-CLONE-1554560   MALAEADDGA VVFGEEQEAL VLKSWAVMKK DAANLGRFF LKVFEIAPSA    50
SEQ-ID-NO-60-CLONE-1802327   MALAE---GN VIFGEEQEAL VLKSWALMKK DSADLGRFF LKIFEIAPSA    47
SEQ-ID-NO-9-CLONE-30469-FL   -MESE---GK VFTEEEQEAL VVKSWSVMKK NSAELGLKFF LKIFEIAPTA    46
SEQ-ID-NO-10-GI-30909306     -MESE---GK VFTEEEQEAL VVKSWNVMKK NSAELGLKFF LKIFEIAPTA    46
SEQ-ID-NO-13-CLONE-546001    -MTTLERG-- FSEEEQEAL VVKSWTVMKK NSGELGLKFF LKIFEIAPSA    46
SEQ-ID-NO-70-CLONE-1916866   MAIYE----CK VFTEEQEAL VVKSWTVMKK NAAELGLKFF LKIFEIAPSA    46

SEQ-ID-NO-17-CLONE-839727    RQMFPFLRDS DVPLETNPKL KTHAVSVFVM TCEAAAQLRK AGKITVRETT    97
SEQ-ID-NO-16-CLONE-1554560   KQMFSFLRDS DVPLEKNPKL KTHAMSVFVM ACEAAAQLRK AGKVTVRETT   100
SEQ-ID-NO-60-CLONE-1802327   KQMFSFLRDS DVPLEKNPKL KNHAMSVFVM TCEAAAQLRK AGKVTVRETT    97
SEQ-ID-NO-9-CLONE-30469-FL   KKMFSFLRDS PIPAEONPKL KPHAMSVFVM CCESAVQLRK TGKVTVRETT    96
SEQ-ID-NO-10-GI-30909306     KLFSFLRDS  PIPAEONPKL KPHAMSVFVM CCESAAQLRK TGKVTVKETT    96
SEQ-ID-NO-13-CLONE-546001    QKLFSFLRDS TVPLEQNPKL KPHAVSVFVM CDSAVQLRK  AGKVTVRESN    96
SEQ-ID-NO-70-CLONE-1916866   KKLFSFLRDS NVPLEQNTKL KPHAMSVFVM TCESAVQLRK AGKVTVRESN    96

SEQ-ID-NO-17-CLONE-839727    LKRLGCTHLK YGVADCHFEV TRFALLETIK EALPADMWGP EMRNAWGEAY   147
SEQ-ID-NO-16-CLONE-1554560   LKRLGATHLR YGVADGHFEV TGFALLETIK EALPADMWSL EMKKAWAEAY   150
SEQ-ID-NO-60-CLONE-1802327   LKRLGATHFK YGVADGHFEV TRFALLETIK EALPADMWSP EMKNAWSEAY   147
SEQ-ID-NO-9-CLONE-30469-FL   LKRLGASHSK YGVVDEHFEV AKYALLETIK EAVP-EMWSP EMKVAWGQAY   145
SEQ-ID-NO-10-GI-30909306     LKRLGANHSK YGVVDEHFEV TKYALLETIK EAVP-EMWSP EMKSAWGQAY   145
SEQ-ID-NO-13-CLONE-546001    LKKLGATHFR TGVANEHFEV TKFALLETIK EAVP-EMWSP AMKNAWGEAY   145
SEQ-ID-NO-70-CLONE-1916866   LKKLGATHFK YGVVDEHFEV TKFALLETIK EAVP-DMWSD EMKNAWGEAY   145

SEQ-ID-NO-17-CLONE-839727    DQLVAAIKQE MKPSE----    162
SEQ-ID-NO-16-CLONE-1554560   SQLVAAIKRE MKPDA----    165
SEQ-ID-NO-60-CLONE-1802327   NQLVAAIKQE MKPAA----    162
SEQ-ID-NO-9-CLONE-30469-FL   DHLVAAIKAE MNLSN----    160
SEQ-ID-NO-10-GI-30909306     DHLVAAIKAE MKPSH----    160
SEQ-ID-NO-13-CLONE-546001    DQLVDAIKSE MKPPSS---    161
SEQ-ID-NO-70-CLONE-1916866   DRLVAAIKIE MKACSQAA-    163
```

FIGURE 3

| SEQ-ID | | | | | | | | End |
|---|---|---|---|---|---|---|---|---|
| SEQ-ID-NO-221-CLONE-839727-T | MSAAE---GA | VVFSEEKEAL | VLKSWAIMKK | DSANLGLRFF | LKIFEIAPSA | | | 47 |
| SEQ-ID-NO-207-CLONE-1554560-T | MALAEADDGA | VVFGEEQEAL | VLKSWAVMKK | DAANLGLRFF | LKVFEIAPSA | | | 50 |
| SEQ-ID-NO-208-CLONE-1802327-T | MALAE---GN | VIFGEEQEAL | VLKSWALMKK | DSADLGLRFF | LKIFEIAPSA | | | 47 |
| SEQ-ID-NO-7-CLONE-30469 | MESE---GK | VFTEEQEAL | VVKSWSVMKK | NSAELGLKLF | LKIFEIAPTT | | | 46 |
| SEQ-ID-NO-227-GI-30909306-T | MESE---GK | VFTEEQEAL | VVKSWSVMKK | NSADLGLKLF | LKIFEIAPTA | | | 46 |
| SEQ-ID-NO-219-CLONE-546001-T | MITT---LE | RGFSEEQEAL | VVKSWNVMKK | NSCELCLKFF | LKIFEIAPSA | | | 46 |
| SEQ-ID-NO-212-CLONE-1916866-T | MATY---EG | KVFTEEQEAL | VVKSWTVMKK | NAAELGLKFF | LKIFEIAPSA | | | 46 |

| SEQ-ID | | | | | End |
|---|---|---|---|---|---|
| SEQ-ID-NO-221-CLONE-839727-T | RQMFPFLRDS | DVPLEINPKL | KTHAVSVFVM | -- | 77 |
| SEQ-ID-NO-207-CLONE-1554560-T | KQMFSFLRDS | DVPLEKNPKL | KTHAMSVFVM | -- | 80 |
| SEQ-ID-NO-208-CLONE-1802327-T | KQMFSFLRDS | DVPLEKNPKL | KNHAMSVFVM | -- | 77 |
| SEQ-ID-NO-7-CLONE-30469 | KKMFSFLRDS | PIPAEQNPKL | KPHAMSVFVM | YN | 78 |
| SEQ-ID-NO-227-GI-30909306-T | KKLFSFLRDS | PIPAEQNPKL | KPHAMSVFVM | -- | 76 |
| SEQ-ID-NO-219-CLONE-546001-T | QKLFSFLRDS | TVPLEQNPKL | KPHAVSVFVM | -- | 76 |
| SEQ-ID-NO-212-CLONE-1916866-T | KKLFSFLRDS | NVPLEQNTKL | KPHAMSVFVM | -- | 76 |

FIGURE 4

| | | | | | | |
|---|---|---|---|---|---|---|
| SEQ-ID-NO-20-CLONE-271922 | MAKRTKKVGI | VGKYGTRYGA | SIRKQIKKME | VSQHSKYFCE | FCGKYGVKRK | 50 |
| SEQ-ID-NO-54-CLONE-1627907 | MTKRTKKAGI | VGKYGTRYGA | SLRKQIKKME | VSQHAKYFCE | FCGKYAVKRQ | 50 |
| SEQ-ID-NO-25-CLONE-664936 | MTKRTKKAGI | VGKYGTRYGA | SLRKQIKKME | VSQHSKFFCE | FCGKYAVKRK | 50 |
| SEQ-ID-NO-28-CLONE-632613 | MTKRTKKAGI | VGKYGTRYGA | SLRKQIKKME | VSQHSKYFCE | FCGKFAVKRK | 50 |
| SEQ-ID-NO-29-CLONE-1390976 | MTKRTKKAGI | VGKYGTRYGA | SLRKQIKKME | VSQHSKYFCE | FCGKFAVKRK | 50 |
| SEQ-ID-NO-58-CLONE-1783890 | MTKRTKKAGI | VGKYGTRYGA | SLRKQIKKME | VSQHSKYFCE | FCGKFAVKRK | 50 |

| | | | | | | |
|---|---|---|---|---|---|---|
| SEQ-ID-NO-20-CLONE-271922 | AVGIWGCKDC | GKVKAGGAYT | MNTASAVTVR | STIRRLREQL | EG | 92 |
| SEQ-ID-NO-54-CLONE-1627907 | AVGIWGCKDC | GKVKAGGAYT | LNTASAVTVR | STIRRLREQT | ES | 92 |
| SEQ-ID-NO-25-CLONE-664936 | AVGIWGCKDC | GKVKAGGAYT | LNTASAVTVR | STIRRLREQT | EG | 92 |
| SEQ-ID-NO-28-CLONE-632613 | AVGIWGCKDC | GKVKAGGAYT | MNTASAVTVR | STIRRLREQT | EA | 92 |
| SEQ-ID-NO-29-CLONE-1390976 | AVGIWGCKDC | GKVKAGGAYT | MNTASAVTVR | STIRRLREQT | EA | 92 |
| SEQ-ID-NO-58-CLONE-1783890 | AVGIWGCKDC | GKVKAGGAYT | MNTASAVTVR | STIRRLREQT | EA | 92 |

FIGURE 5

| | | | | | | |
|---|---|---|---|---|---|---|
| SEQ-ID-NO-34-CLONE-2403-FL | MQIFVKTLTG | KTITLEVESS | DTIDNVKAKI | QDKEGIPPDQ | QRLIFAGKQL | 50 |
| SEQ-ID-NO-35-CLONE-1482731 | MQIFVKTLTG | KTITLEVESS | DTIDNVKAKI | QDKEGIPPDQ | QRLIFAGKQL | 50 |
| SEQ-ID-NO-36-CLONE-522921 | MQIFVKTLTG | KTITLEVESS | DTIDNVKAKI | QDKEGIPPDQ | QRLIFAGKQL | 50 |
| SEQ-ID-NO-37-CLONE-1036726 | MQIFVKTLTG | KTITLEVESS | DTIDNVKAKI | QDKEGIPPDQ | QRLIFAGKQL | 50 |
| SEQ-ID-NO-68-CLONE-1884696 | MQIFVKTLTG | KTITLEVESS | DTIDNVKAKI | QDKEGIPPDQ | QRLIFAGKQL | 50 |
| SEQ-ID-NO-80-CLONE-2034916 | MQIFVKTLTG | KTITLEVESS | DTIDNVKAKI | QDKEGIPPDQ | QRLIFAGKQL | 50 |
| SEQ-ID-NO-34-CLONE-2403-FL | EDGRTLADYN | QKESTLHLV | LRLRGGTMIK | VKTLTGKEIE | DIEPTDTID | 100 |
| SEQ-ID-NO-35-CLONE-1482731 | EDGRTLADYN | QKESTLHLV | LRLRGGTMIK | VKTLTGKEIE | DIEPTDTID | 100 |
| SEQ-ID-NO-36-CLONE-522921 | EDGRTLADYN | QKESTLHLV | LRLRGGTMIK | VKTLTGKEIE | DIEPTDTID | 100 |
| SEQ-ID-NO-37-CLONE-1036726 | EDGRTLADYN | QKESTLHLV | LRLRGGTMIK | VKTLTGKEIE | DIEPTDTID | 100 |
| SEQ-ID-NO-68-CLONE-1884696 | EDGRTLADYN | QKESTLHLV | LRLGGMQF | VKTLTGKTT | LEVESS | 100 |
| SEQ-ID-NO-80-CLONE-2034916 | EDGRTLADYN | QKESTLHLV | LRLGGMQF | VKTLTGKT | LEVESSDTID | 100 |
| SEQ-ID-NO-34-CLONE-2403-FL | RIKERVEEKE | GIPPVQQRLI | YAGKQLADDK | TAKDYAEGG | SVLHVLALR | 150 |
| SEQ-ID-NO-35-CLONE-1482731 | RIKERVEEKE | GIPPVQQRLI | YAGKQLADDK | TAKDYNIEGG | SVLHVLALR | 150 |
| SEQ-ID-NO-36-CLONE-522921 | RIKERVEEKE | GIPPVQQRLI | YAGKQLADDK | TAKEYNIEGG | SVLHVLALR | 150 |
| SEQ-ID-NO-37-CLONE-1036726 | RIKERVEEKE | GIPPVQQRLI | YAGKQLADDK | TXKDYNIEGG | SVSA-- | 144 |
| SEQ-ID-NO-68-CLONE-1884696 | NVKAKI QDKE | GIPPDQQRLI | FAGKQLEDGR | TLADYNIQKD | STLHVLRLR | 150 |
| SEQ-ID-NO-80-CLONE-2034916 | NVKVKI QDKE | GIPPDQQRLI | FAGKQLEDGR | TLADYNIQKE | STLHVLRLR | 150 |
| SEQ-ID-NO-34-CLONE-2403-FL | GGL------- | ---------- | ---------- | ---------- | ---------- | 153 |
| SEQ-ID-NO-35-CLONE-1482731 | GGS------- | ---------- | ---------- | ---------- | ---------- | 153 |
| SEQ-ID-NO-36-CLONE-522921 | GGT------- | ---------- | ---------- | ---------- | ---------- | 153 |
| SEQ-ID-NO-37-CLONE-1036726 | -SG------- | ---------- | ---------- | ---------- | ---------- | 146 |
| SEQ-ID-NO-68-CLONE-1884696 | GG-------- | ---------- | ---------- | ---------- | ---------- | 152 |
| SEQ-ID-NO-80-CLONE-2034916 | GGMQIFVKTL | TGKTITLEVE | SSDTIDNVKA | KIQDKEGIPP | DQQRLIFAGK | 200 |
| SEQ-ID-NO-34-CLONE-2403-FL | ---L | 154 |
| SEQ-ID-NO-35-CLONE-1482731 | ---D | 154 |
| SEQ-ID-NO-36-CLONE-522921 | ---Y | 154 |
| SEQ-ID-NO-37-CLONE-1036726 | ---S | 147 |
| SEQ-ID-NO-68-CLONE-1884696 | ---F | 153 |
| SEQ-ID-NO-80-CLONE-2034916 | QLEDGRTLAD YNI | 213 |

FIGURE 6

| | | | | | |
|---|---|---|---|---|---|
| SEQ-ID-NO-40-CLONE-2403 | MQIFVKTLTG | KTITLEVESS | DTIDNVKAKI | QDK | 33 |
| SEQ-ID-NO-205-CLONE-1036726-T | MQIFVKTLTG | KTITLEVESS | DTIDNVKAKI | QDK | 33 |
| SEQ-ID-NO-211-CLONE-1884696-T | MQIFVKTLTG | KTITLEVESS | DTIDNVKAKI | QDK | 33 |
| SEQ-ID-NO-213-CLONE-1950105-T | MQIFVKTLTG | KTITLEVESS | DTIDNVKAKI | QDK | 33 |
| SEQ-ID-NO-218-CLONE-522921-T | MQIFVKTLTG | KTITLEVESS | DTIDNVKAKI | QDK | 33 |
| SEQ-ID-NO-206-CLONE-1482731-T | MQIFVKTLTG | KTITLEVESS | DTIDNVKSKI | QDK | 33 |

FIGURE 7

| SEQ ID | Sequence | Pos |
|---|---|---|
| SEQ-ID-NO-46-CLONE-1055099 | MRKARPPQPQ P------QPSQQ SP-------- ------- E RYRGVRKR PSGRYAAEI R | 38 |
| SEQ-ID-NO-56-CLONE-1761125 | MMRDTAAMAV A--------- ---------- ---------- APRYRGVRKR PWGRFAAEI R | 31 |
| SEQ-ID-NO-83-GI-1255550159 | MCEAAA---- ---------- ---------- ---------- E RFRGVRKR PWGRYAAEI R | 25 |
| SEQ-ID-NO-45-CLONE-273307 | MRRRGVAAAP A--------- --------GD V--------- EPRYRGVRKR PWGRFAAEI R | 35 |
| SEQ-ID-NO-62-CLONE-1838364 | MRRGRGAAAA NAVARRPALQ ----------PS ---------- EPRYRGVRKR PWGRFAAEI R | 46 |
| SEQ-ID-NO-50-CLONE-1240330 | MRKGRGGGAS A--AAVDVN -------GS I LK EPRYRGVRKR PWGRFAAEI R | 42 |
| SEQ-ID-NO-42-CLONE-674166 | MGRGGTAAAA A-EVAEPGLR ----------PV YFK EQRYRGVRKR PWGRFAAEI R | 44 |
| SEQ-ID-NO-86-GI-56384582 | MGRGATTAA A---AVE ----------PV FFK EPRYRGVRKR PWGRFAAEI R | 39 |
| SEQ-ID-NO-48-ANNOT-1441430 | MGRIRTTTKQ A--VDPNGS ATQNMLVI AK EPRYRGVRKR PWGRFAAEI R | 47 |
| SEQ-ID-NO-87-GI-57012880 | MRRGRAAAP APVTGEPNGS CG SK EPRYRGVRKR PWGRFAAEI R | 44 |
| SEQ-ID-NO-44-CLONE-975672 | MRKGRGSSAV P--PALP------GS VK EPRYRGVRKR PWGRFAAEI R | 39 |
| SEQ-ID-NO-84-GI-15223609 | MRRGRGSSAV AGPTVVAAI N------GS VK ERFRGVRKR PWGRFAAEI R | 44 |

| SEQ ID | Sequence | Pos |
|---|---|---|
| SEQ-ID-NO-46-CLONE-1055099 | DPAKKI P WL GTFDCAEDAA RAYDSAARSL RGPT ARTNFP PSSAT QPPPR | 88 |
| SEQ-ID-NO-56-CLONE-1761125 | DPAKRARVWL GTFDSAEAAA RAYDV AARTL RGPL ARTNFP CASSRLPLPS | 81 |
| SEQ-ID-NO-83-GI-1255550159 | DPAKRARVWL GTYDSAEAAA RAYDM AARNL RGPL ARTNFP LVSSL PLPSP | 75 |
| SEQ-ID-NO-45-CLONE-273307 | DPAKKARVWL GTFDSAEDAA RAYDAAARTL RGPKARTNFP L PAAALHHP | 85 |
| SEQ-ID-NO-62-CLONE-1838364 | DPWKK T RVWL GTFDSAEDAA RAYDA AARM L RGPKAKTNFP I NSSNI PAFP | 96 |
| SEQ-ID-NO-50-CLONE-1240330 | DPLKKARVWL GTFDTAEEAA RAYDT AARTL RGPKAKTNFP P--------- | 88 |
| SEQ-ID-NO-42-CLONE-674166 | DPLKKARVWL GTFDTAEEAA RAYDT AARNL RGPKAKTNFP LSPFC | 90 |
| SEQ-ID-NO-86-GI-56384582 | DPWKK T RVWL GTFDSAEDAA RAYDAAARTL RGPKAKTNFP SPPFY | 85 |
| SEQ-ID-NO-48-ANNOT-1441430 | DPWKKT RVWL GTFDSAEEAA RAYDAAARAL RGA KAKTNFP AQPFY | 97 |
| SEQ-ID-NO-87-GI-57012880 | DPLKKSRVWL GTFDSAEDAA RAYDAAARNL RGPKAKTNFQ STT NQLFNH | 94 |
| SEQ-ID-NO-44-CLONE-975672 | DPLKKARVWL GTFDSAEDAA RAYDAAARNL RGPKAKTNFP PYAHHHQFN | 89 |
| SEQ-ID-NO-84-GI-15223609 | DPWKKARVWL GTFDSAEEAA RAYDSAARNL RGPKAKTNFP DCSPSSPL Q DESSPPPPN | 94 |

| SEQ ID | Sequence | Pos |
|---|---|---|
| SEQ-ID-NO-46-CLONE-1055099 | --------- --------- --------- --------- AAAA AAA T SSQ SST | 106 |
| SEQ-ID-NO-56-CLONE-1761125 | --------- --------- RHQGGC GGGL VAPPPA APTCSS--SST | 106 |
| SEQ-ID-NO-83-GI-1255550159 | --------- --------- HYHLPG KAAAAAPPVA GPACSA--SST | 100 |
| SEQ-ID-NO-45-CLONE-273307 | HMPAAA --------- TTYPTA TGVVSTPPVA RPIACSSLSST | 124 |
| SEQ-ID-NO-62-CLONE-1838364 | FET N AAAAPPY-- I DQRRLYPMG EFHDPEVNPQ RPTRSSMSST | 137 |
| SEQ-ID-NO-50-CLONE-1240330 | YP HHHNE GF GFH-DQHHHH NNNNL--NNPQ RPTSSCMSST | 128 |
| SEQ-ID-NO-42-CLONE-674166 | --------- HPTTDPFFYT SDH-RHFA-N TGEDF-HDHR RPTSS GMSST | 122 |
| SEQ-ID-NO-86-GI-56384582 | --------- HPDPF GEL-RFYAGG AGEGF-QDHR RPTSSLSST | 122 |
| SEQ-ID-NO-48-ANNOT-1441430 | QN PEAGNPF LDHHSI NP -QDNP-II SQ RPTSSLSST | 127 |
| SEQ-ID-NO-87-GI-57012880 | QNQN QSPT DPF VDS-RFYP-- -GEQEVVI S RPTSSSMSST | 129 |
| SEQ-ID-NO-44-CLONE-975672 | QGHN PNN-DPF MDH-RLYG-- --------- RP A SSSMSST | 126 |
| SEQ-ID-NO-84-GI-15223609 | PLHH RNQI DPF MDH-RLFT-D HQQQF-PI VN RPTSSSMSST | 138 |
| SEQ-ID-NO-84-GI-15223609 | LRFNQI RNQN QNQV DPF | |

FIGURE 7 (cont)

| SEQ ID | | | | | | |
|---|---|---|---|---|---|---|
| SEQ-ID-NO-46-CLONE-1055099 | VESWSCGGP | ---- | RAPARARSA | ARAGTAKEGE | EDCRSYCGSS | 144 |
| SEQ-ID-NO-56-CLONE-1761125 | VESSSGPRCA | PRAAAA | AAPRIRRRS | VKKPRPAAPD | DCHSDCASS | 151 |
| SEQ-ID-NO-83-GI-1255550159 | VESSSGPRGP | RPAA---- | TAAAVPRR- | VPRPAPPAPD | AGCHSDCASS | 143 |
| SEQ-ID-NO-45-CLONE-273307 | VESFSGARP- | ---- | RPVLPP-- | FPI----PPSI PD | GDCHSDCGSS | 158 |
| SEQ-ID-NO-62-CLONE-1838364 | VESFSGPRPA | QPPQKSAD- | FAVSTRKY | YPRPPPVEPE | DCHSDCDSS | 183 |
| SEQ-ID-NO-50-CLONE-1240330 | VESFSGPRPP | TTTTTTTT | ATPFLTATRR | YPRTPPLVPE | DCHSDCDSS | 177 |
| SEQ-ID-NO-42-CLONE-674166 | VESFSGPRAA | VPA---- | TAPVATCRR | YPRTPPVIPE | DCRSDCDSS | 163 |
| SEQ-ID-NO-86-GI-56384582 | VESFCGPRPV | RPPM---- | PPSAVTCRR | YPRTPPVAPG | DCRSDCDSS | 164 |
| SEQ-ID-NO-48-ANNOT-1441430 | VESFSGPRPP | QPTTTT-- | KSGNGPRRS | HPRIPPVVPE | DCHSDCDSS | 171 |
| SEQ-ID-NO-87-GI-57012880 | VESFSGPRPP | PAPR---- | QQTTASSRK | YTRSPPVVPD | DCRSDCDSS | 171 |
| SEQ-ID-NO-44-CLONE-975672 | VKSCSGVRPA | SS---- | SVAKAATKR | YPRIPPVAPE | DCHSDCDSS | 166 |
| SEQ-ID-NO-84-GI-15223609 | VESFSGPRPT | ---- | TMKPATTKR | YPRTPPVVPE | DCHSDCDSS | 176 |

| SEQ ID | | | | | | |
|---|---|---|---|---|---|---|
| SEQ-ID-NO-46-CLONE-1055099 | SSVLE | EGADDA | AAS | RSPLPFDLNM | PPPQEGAL | 177 |
| SEQ-ID-NO-56-CLONE-1761125 | ASV-VD | DGDDAS | TV- | RSRAPFDLNV | PAPVDGDH | 182 |
| SEQ-ID-NO-83-GI-1255550159 | ASV-VD | DDDDAS | TVR | SRVAAFDLNL | PPPLDRDH | 175 |
| SEQ-ID-NO-45-CLONE-273307 | ASV-VD | DDCTDA | AAS | PFFLPFDLNL | PPPLDLDL | 194 |
| SEQ-ID-NO-62-CLONE-1838364 | ASV-VD | DCDI-AL | SSC | RKITLPFDLNF | PPGGGAGV | 214 |
| SEQ-ID-NO-50-CLONE-1240330 | SSV-VD | DGDDNI | VSS | RKPLPFDLNA | PPLDEDG | 210 |
| SEQ-ID-NO-42-CLONE-674166 | SSV-VD | DGEDN- | SF- | REPLPFDLNA | LPLDDAA | 197 |
| SEQ-ID-NO-86-GI-56384582 | SSV-VD | DADNDN | VAS | RQPLPFDLNA | PPLDDAD | 202 |
| SEQ-ID-NO-48-ANNOT-1441430 | SSV-VD | DRDVAS | AASSTMLSFK | RKPLPFDLNF | PPLEECD | 205 |
| SEQ-ID-NO-87-GI-57012880 | SSV-VD | DNDNDN | AAS | RKPLPFDLNF | PPLDQVD | 214 |
| SEQ-ID-NO-44-CLONE-975672 | SSV-VE | EKENDN | JAS | KPPFEFDLNF | PPPMDDAG | 200 |
| SEQ-ID-NO-84-GI-15223609 | SSV-D | DGXDTA | SSS | NPPFQFDLNE | XPLDGVD | 210 |
| | | DDDDIA | SSS | ---RRR | PPLDCVD | |

| SEQ ID | | | | |
|---|---|---|---|---|
| SEQ-ID-NO-46-CLONE-1055099 | ----DAEADOM | TCRYDT | LLRL | 194 |
| SEQ-ID-NO-56-CLONE-1761125 | ----ALDL | C | TELRL | 192 |
| SEQ-ID-NO-83-GI-1255550159 | ----VDL | C | TDLRL | 184 |
| SEQ-ID-NO-45-CLONE-273307 | GFYADEEDEL | RL | TALRL | 211 |
| SEQ-ID-NO-62-CLONE-1838364 | ----RSPV | YC-FMSLIAM | PVMNDDDRLL | DLFFFFKKC | 246 |
| SEQ-ID-NO-50-CLONE-1240330 | ----ADDDL | RR | TALCL | 222 |
| SEQ-ID-NO-42-CLONE-674166 | ----VATDDL | FC | TVLCL | 210 |
| SEQ-ID-NO-86-GI-56384582 | -VANGLGEDL | HC | TLLCL | 218 |
| SEQ-ID-NO-48-ANNOT-1441430 | -LGSG-DDL | HC | TALCL | 219 |
| SEQ-ID-NO-87-GI-57012880 | ----ADDL | HC | TDLIXL | 225 |
| SEQ-ID-NO-44-CLONE-975672 | -LFVGA-DDX | XC | TDLXL | 215 |
| SEQ-ID-NO-84-GI-15223609 | -LFNGA-DDL | HC | TDLRL | 225 |

NUCLEOTIDE SEQUENCES AND POLYPEPTIDES ENCODED THEREBY USEFUL FOR MODIFYING PLANT CHARACTERISTICS IN RESPONSE TO COLD

This application is a divisional of copending application Ser. No. 16/275,659 filed on Feb. 14, 2019 which application is a divisional of application Ser. No. 15/362,633 filed on Nov. 28, 2016 (now U.S. Pat. No. 10,240,166), which application is a divisional of application Ser. No. 11/779,266 filed on Jul. 17, 2007, which application is a Continuation-In-Part of application Ser. No. 11/778,060 filed on Jul. 15, 2007, which is a Continuation-In-Part of copending application Ser. No. 11/248,547 filed on Oct. 12, 2005 (now U.S. Pat. No. 7,244,879), and this application is also a Continuation In Part of copending application Ser. No. 11/248,547 filed on Oct. 12, 2005, the entire contents of which are hereby incorporated by reference and for which priority is claimed under 35 U.S.C. § 120.

FIELD OF THE INVENTION

The present invention relates to isolated polynucleotides, polypeptides encoded thereby, and the use of those products for making transgenic plants with improved tolerances to environmental stresses such as low or chilling temperatures.

BACKGROUND OF THE INVENTION

Plants are constantly exposed to a variety of biotic (i.e. pathogen infection and insect herbivory) and abiotic (i.e. high or low temperature, drought, flood and salinity) stresses. To survive these challenges to their sessile life, plants have developed elaborate mechanisms to perceive external signals and to manifest adaptive responses with proper physiological and morphological changes (Bohnert et al. 1995). Plants exposed to cold or chilling conditions typically have low yields of biomass, seeds, fruit and other edible products. The term "chilling sensitivity" is used for the description of physiological and developmental damages in the plant caused by low, but above freezing, temperatures. Important agricultural crop plants such as corn, soybean, rice and cotton have tropical ancestors that make them chilling sensitive. In some countries or agricultural regions of the world chilling temperatures are a significant cause of crop losses and a primary factor limiting the geographical range and growing season of many crop species. Another example is that chilling conditions can cause significant concern in early spring planting of corn or canola. Poor germination and reduced growth of chilling sensitive crops in the spring results in less ground coverage, more erosion and increased occurrence of weeds leading to less nutrient supply for the crop.

Typically, chilling damage includes wilting, necrosis or ion leakage from cell membranes, especially calcium leakage, and decreased membrane fluidity, which consequently impacts membrane dependent processes such as: photosynthesis, protein synthesis, ATPase activity, uptake of nitrogen, etc. (see Levitt J (1980) Chilling injury and resistance. In Chilling, Freezing, and High Temperature Stresses: Responses of Plant to Environmental Stresses, Vol 1., T T Kozlowsky, ed, Academic Press, New York, pp 23-64; Graham and Patterson (1982) *Annu Rev Plant Physiol* 33: 347-372; Guy (1990) *Annu Rev Plant Physiol Plant Mol Biol* 41: 187-223; and Nishida and Murata (1996) *Annu Rev Plant Physiol Plant Mol Biol* 47: 541-568.). In addition, cold temperatures are often associated with wet conditions. The combination of cold and wet can result in hypoxic stress on the roots, causing an even more severe reduction of growth rate but, more critically, can be lethal to the plants, especially sensitive plant species such as corn and cotton.

Yet it has been observed that environmental factors, such as low temperature, can serve as triggers to induce cold acclimation processes allowing plants responding thereto to survive and thrive in low temperature environments. It would, therefore, be of great interest and importance to be able to identify genes that regulate or confer improved cold acclimation characteristics to enable one to create transformed plants (such as crop plants) with improved cold tolerance characteristics such as faster germination and/or growth and/or improved nitrogen uptake under cold conditions to improve survival or performance under low or chilling temperatures.

In the fields of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. There is a need for generally applicable processes that improve forest or agricultural plant growth potential. Therefore, the present invention relates to a process for increasing the growth potential in plants under low temperature, chilling or cold conditions, characterized by expression of recombinant DNA molecules stably integrated into the plant genome.

SUMMARY OF THE INVENTION

The present invention, therefore, relates to isolated polynucleotides, polypeptides encoded thereby and the use of those products for making transgenic plants with improved cold tolerance.

The present invention also relates to processes for increasing the growth potential in plants due to cold acclimation, recombinant nucleic acid molecules and polypeptides used for these processes and their uses, as well as to plants with an increased growth potential due to improved cold acclimation. Unless otherwise defined, all scientific and technical terms used herein have the same meaning as commonly understood by one of ordinary skilled in the art to which this invention belongs.

BRIEF DESCRIPTION OF THE FIGURES

FIG. 1 is an alignment of ME01451. In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE (Edgar (2004) Nuc. Acids Res. 32(5):1792-1797).

FIG. 2 is an alignment of ME02779.

FIG. 3 is an alignment of truncated mutant of ME02779.

FIG. 4 is an alignment of ME03944.

FIG. 5 is an alignment of ME05304.
FIG. 6 is an alignment of truncated mutant of ME05304.
FIG. 7 is an alignment of ME03186.

DETAILED DESCRIPTION OF THE INVENTION

1. Definitions

The following terms are utilized throughout this application:

Amino acid: As used herein, "amino acid" refers to one of the twenty biological occurring amino acids and to synthetic amino acids, including D/L optical isomers.

Cell type-preferential promoter or Tissue-preferential promoter: As used herein, these phrases refer to a promoter that drives expression preferentially in a target cell type or tissue, respectively, but may also lead to some transcription in other cell types or tissues as well.

Cold: Plant species vary in their capacity to tolerate low temperatures. Chilling-sensitive plant species, including many agronomically important species, can be injured by cold, above-freezing temperatures. At temperatures below the freezing-point of water most plant species will be damaged. Thus, "cold" can be defined as the temperature at which a given plant species will be adversely affected as evidenced by symptoms such as decreased photosynthesis and membrane damage (measured by electrolyte leakage). Since plant species vary in their capacity to tolerate cold, the precise environmental conditions that cause cold stress can not be generalized. However, cold tolerant plants are characterized by their ability to retain their normal appearance or recover quickly from low temperature conditions. Such cold tolerant plants produce higher biomass and yield than plants that are not cold tolerant. Differences in physical appearance, recovery and yield can be quantified and statistically analyzed using well known measurement and analysis methods.

Plant seeds vary considerably in their ability to germinate under cold conditions. Seeds of many plant species will not germinate at temperatures less than 10° C. Once seeds have imbibed water they become very susceptible to disease, water and chemical damage. Seeds that are tolerant to cold stress during germination can survive for relatively long periods under which the temperature is too low to germinate. Since plant species vary in their capacity to tolerate cold during germination, the precise environmental conditions that cause cold stress during germination can not be generalized. However, plants that tolerate cold during germination are characterized by their ability to remain viable or recover quickly from low temperature conditions. Such cold tolerant plants germinate, become established, grow more quickly and ultimately produce more biomass and yield than plants that are not cold tolerant. Differences in germination rate, appearance, recovery and yield can be quantified and statistically analyzed using well known measurement and analysis methods.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region, the 1' or 2' promoter derived from T-DNA of *Agrobacterium tumefaciens* and other transcription initiation regions from various plant genes, such as the maize ubiquitin-1 promoter, known to those of skill.

Control Plant: "Control plant" refers to a plant that does not contain the exogenous nucleic acid present in the transgenic plant of interest, but otherwise has the same of similar genetic background as such a transgenic plant. A suitable control plant can be a non-transgenic segregant from a transformation experiment, or a transgenic plant that contains an exogenous nucleic acid other than the exogenous nucleic acid of interest.

Domain: "Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

Down-regulation: "Down-regulation" refers to regulation that decreases production of expression products (mRNA, polypeptide, or both) relative to basal or native states.

Endogenous: The term "endogenous," within the context of the current invention refers to any polynucleotide, polypeptide or protein sequence which is a natural part of a cell or organism regenerated from said cell.

Exogenous: "Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Expression: As used herein, "expression" refers to the process of converting genetic information of a polynucleotide into RNA through transcription, which is catalyzed by an enzyme, RNA polymerase, and into protein, through translation of mRNA on ribosomes.

Functionally Comparable Proteins: This phrase describes those proteins that have at least one characteristic in common. Such characteristics include sequence similarity, biochemical activity, transcriptional pattern similarity and phenotypic activity. Typically, the functionally comparable proteins share some sequence similarity or at least one biochemical. Within this definition, homologs, orthologs and analogs are considered to be functionally comparable. In addition, functionally comparable proteins generally share at least one biochemical and/or phenotypic activity.

Functionally comparable proteins will give rise to the same characteristic to a similar, but not necessarily the same, degree. Typically, comparable proteins give the same characteristics where the quantitative measurement due to one of the comparables is at least 20% of the other; more typically, between 30 to 40%; even more typically, between 50-60%; even more typically between 70 to 80%; even more typically between 90 to 100% of the other.

Heterologous polypeptide: "Heterologous polypeptide" as used herein refers to a polypeptide that is not a naturally occurring polypeptide in a plant cell, e.g., a transgenic *Panicum* plant transformed with and expressing the coding sequence for a nitrogen transporter from a *Zea* plant.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter which can be utilized with the polynucleotides of the present invention is rd29a, the promoter from an *Arabidopsis* gene and which is induced by cold or dehydration (Baker et al. (1994) *Plant Mol. Biol.* 24:701). Examples of environmental conditions that may affect transcription by inducible promoters include anaerobic conditions, elevated temperature and/or the presence of light.

Isolated nucleic acid: "Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

Masterpool: The "master pools" discussed in these experiments are a pool of seeds from five independent transformation events of the same exogenous nucleotide sequence.

Modulation: As used herein, "Modulation" of the level of a compound or constituent refers to the change in the level of the indicated compound or constituent that is observed as a result of expression of, or transcription from, an exogenous nucleic acid in a plant cell. The change in level is measured relative to the corresponding level in control plants.

Misexpression: The term "misexpression" refers to an increase or a decrease in the transcription of a coding region into a complementary RNA sequence as compared to the wild-type. This term also encompasses expression of a gene or coding region for a different time period as compared to the wild-type and/or from a non-natural location within the plant genome.

Nucleic acid and polynucleotide: "Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

Operably linked: As used herein, "operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

Percentage of sequence identity: "Percentage of sequence identity," as used herein, is determined by comparing two optimally aligned sequences over a comparison window defined by the length of the longest sequence, where the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981) *Add. APL. Math.* 2:482, by the homology alignment algorithm of Needleman and Wunsch (1970) *J. Mol. Biol.* 48:443), by the search for similarity method of Pearson and Lipman (1988) *Proc. Natl. Acad. Sci.* (*USA*) 85: 2444, by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid and amino acid sequences were searched against subject nucleic acid or amino acid sequences residing in public or proprietary databases. Such searches were done using the Washington University Basic Local Alignment Search Tool Version 1.83 (WU-Blast2) program. The WU-Blast2 program is available on the internet from Washington University. A WU-Blast2 service for *Arabidopsis* can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A "plant promoter" is a promoter capable of initiating transcription in plant cells and can drive or facilitate transcription of a nucleotide sequence or fragment thereof of the instant invention. Such promoters need not be of plant origin. For example, promoters derived from plant viruses, such as the CaMV35S promoter or from *Agrobacterium tumefaciens*, such as the T-DNA promoters, can be plant promoters. A typical example of a plant promoter of plant origin is the maize ubiquitin-1 (ubi-1) promoter known to those of skill.

Polypeptide: "Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

Progeny: As used herein, "progeny" includes descendants of a particular plant or plant line. Progeny of an instant plant include seeds formed on $F_1, F_2, F_3, F_4, F_5, F_6$ and subsequent generation plants, or seeds formed on $BC_1, BC_2, BC_3$, and subsequent generation plants, or seeds formed on $F_1BC_1$, $F_1BC_2, F_1BC_3$, and subsequent generation plants. The designation $F_1$ refers to the progeny of a cross between two parents that are genetically distinct. The designations $F_2, F_3, F_4, F_5$ and $F_6$ refer to subsequent generations of self- or sib-pollinated progeny of an $F_1$ plant.

Regulatory region: As used herein, "regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

Specific Promoter: In the context of the current invention, "specific promoters" refers to promoters that have a high preference for being active in a specific tissue or cell and/or at a specific time during development of an organism. By "high preference" is meant at least a 3-fold, preferably 5-fold, more preferably at least 10-fold still more preferably at least a 20-fold, 50-fold or 100-fold increase in transcription in the desired tissue over the transcription in any other tissue. Typical examples of temporal and/or tissue specific promoters of plant origin that can be used with the polynucleotides of the present invention, are: SH-EP from *Vigna mungo* and EP-C1 from *Phaseolus vulgaris* (Yamauchi et al. (1996) *Plant Mol Biol.* 30:321-9.); RCc2 and RCc3, promoters that direct root-specific gene transcription in rice (Xu et al. (1995) *Plant Mol. Biol.* 27:237) and TobRB27, a root-specific promoter from tobacco (Yamamoto et al. (1991) *Plant Cell* 3:371).

Stringency: "Stringency" as used herein is a function of probe length, probe composition (G+C content), salt concentration, organic solvent concentration and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m=81.5-16.6(\log_{10}[Na^+])+0.41(\% G+C)-(600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m=81.5+16.6 \log\{[Na^+]/(1+0.7[Na^+])\}+ 0.41(\% G+C)-500/L 0.63(\% \text{ formamide}) \quad (2)$$

where L is the length of the probe in the hybrid (P. Tijessen, "Hybridization with Nucleic Acid Probes" In Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the Tm decreases about 1° C. for each 1% decrease in homology when a long probe is used (Bonner et al., (1973) *J. Mol. Biol.* 81:123), stringency conditions can be adjusted to favor detection of identical genes or related family members.

Equation (2) is derived assuming equilibrium. Therefore, hybridizations according to the present invention are most preferably performed under conditions of probe excess and for sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Superpool: As used in the context of the current invention, a "superpool" refers to a mixture of seed from 100 different "master pools." The master pools are of 5 different events with the same exogenous nucleotide sequence transformed into them. Thus, while the superpool contains an equal amount of seed from 500 different events, it only represents 100 transgenic plants with a distinct exogenous nucleotide sequence transformed into them.

$T_0$: As used in the current application, the term "$T_0$" refers to the whole plant, explant or callus tissue inoculated with the transformation medium.

$T_1$: As used in the current application, the term $T_1$ refers to either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. $T_3$ progeny are the result of self-fertilization or cross pollination of a $T_2$ plant.

Up-regulation: "Up-regulation" refers to regulation that increases the level of an expression product (mRNA, polypeptide, or both) relative to basal or native states.

Vector: "Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

2. Important Characteristics of the Polynuceotides of the Invention

The genes and polynucleotides of the present invention are of interest because when they are misexpressed (i.e. when expressed at a non-natural location or in an increased or decreased amount) they produce plants with improved low temperature, chilling or cold tolerance as discussed below and as evidenced by the results of various experiments. These traits can be used to exploit or maximize plant products. For example, the genes and polynucleotides of the present invention are used to increase the expression of genes that render the plant more tolerant to low temperature, chilling or cold conditions. As a consequence, such transgenic plants do better and grow faster under low temperature, chilling or cold conditions, leading to reduced costs for the farmer and, better yield under low temperatures.

3. The Polynucleotides and Polypeptides of the Invention

The polynucleotides of the invention and the proteins expressed thereby are set forth in the Sequence Listing. Such Sequence Listing consists of functionally comparable proteins.

Functionally comparable proteins are those proteins that have at least one characteristic in common. Such characteristics can include sequence similarity, biochemical activity and phenotypic activity. Typically, the functionally comparable proteins share some sequence similarity. Within this definition homologs, orthologs and analogs are considered to be functionally comparable.

Also, these comparables generally share at least one biochemical and/or phenotypic activity. For example, biochemical activity comparables are proteins that act on the same reactant to give the same product.

Another class of comparables is phenotypic comparables that both give the same physical characteristic, such as increased low temperature, chilling or cold tolerance. Proteins can be considered phenotypic comparables even if the proteins give rise to the same physical characteristic, but to a different degree.

4. Use of the Polynucleotides and Polypeptides to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector and which are suitable for transformation of plant cells. The construct can be made using standard recombinant DNA techniques (see Sambrook et al., Molecular Cloning: A Laboratory Manual, Second Edition, Cold Spring Harbor Laboratory Press, 1989, New York) and can be introduced to the species of interest by Agrobacterium-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al. (1992) *Proc. Natl. Acad. Sci. USA* 89: 8794-8797; Hamilton et al. (1996) *Proc. Natl. Acad. Sci. USA* 93: 9975-9979;
(b) YAC: Burke et al. (1987) *Science* 236:806-812;
(c) PAC: Sternberg N. et al. (1990) *Proc Natl Acad Sci USA.* January; 87:103-7;
(d) Bacteria-Yeast Shuttle Vectors: Bradshaw et al. (1995) *Nucl Acids Res* 23: 4850-4856;
(e) Lambda Phage Vectors: Replacement Vector, e.g., Frischauf et al. (1983) *J. Mol Biol* 170: 827-842; or Insertion vector, e.g., Huynh et al., In: Glover N M (ed) DNA Cloning: A practical Approach, Vol. 1 Oxford: IRL Press (1985); T-DNA gene fusion vectors: Walden et al. (1990) *Mol Cell Biol* 1: 175-194; and
(g) Plasmid vectors: Sambrook et al., infra.

Typically, the construct comprises a vector containing a sequence of the present invention with any desired transcriptional and/or translational regulatory sequences such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker typically encodes biocide resistance, particularly antibiotic resistance, such as resistance to kanamycin, bleomycin, or hygromycin, or herbicide resistance, such as resistance to glyphosate, chlorosulfuron or phosphinotricin.

A plant promoter is used that directs transcription of the gene in all tissues of a regenerated plant and may be a constitutive promoter, such as the Cauliflower Mosaic Virus 35S. Alternatively, the plant promoter directs transcription of a sequence of the invention in a specific tissue (tissue-specific promoters) or is otherwise under more precise environmental or developmental control (inducible promoters). Typically, preferred promoters to use in the present invention are cold inducible promoters. Many cold-inducible genes, including the cis-elements which confer cold induction, have been identified (Shinozaki et al. (2003) *Curr. Opin. Plant Biol.* 6:410). Examples of such cold-inducible genes include RD29A (Yamaguchi-Shinozaki and Shinozaki (1994) *Plant Cell* 6:251) and CBF/DREB1 (Stockinger et al. (1997) *PNAS* 94:1035. Another preferred embodiment of the present invention is to use seedling specific promoters, endosperm specific promoters and leaf specific promoters. Various plant promoters, including constitutive, tissue-specific and inducible, are known to those skilled in the art and can be utilized in the present invention.

Alternatively, misexpression can be accomplished using a two component system, whereby the first component consists of a transgenic plant comprising a transcriptional activator operatively linked to a promoter and the second component consists of a transgenic plant that comprises sequence of the invention operatively linked to the target-binding sequence/region of the transcriptional activator. The two transgenic plants are crossed and the sequence of the invention is expressed in their progeny. In another alternative, the misexpression can be accomplished by having the sequences of the two component system transformed in one transgenic plant line.

Transformation

Nucleotide sequences of the invention are introduced into the genome or the cell of the appropriate host plant by a variety of techniques. These techniques for transforming a wide variety of higher plant species are well known and described in the technical and scientific literature. See, e.g. Weising et al. (1988) *Ann. Rev. Genet.* 22:421; and Christou (1995) *Euphytica, v.* 85, n.1-3:13-27.

Processes for the transformation of monocotyledonous and dicotyledonous plants are known to the person skilled in the art. A variety of techniques is available for the introduction of DNA into a plant host cell. These techniques include transformation of plant cells by injection, microinjection, electroporation of DNA, PEG, use of biolistics, fusion of cells or protoplasts, and via T-DNA using *Agrobacterium tumefaciens* or *Agrobacterium rhizogenes* or other bacterial hosts, as well as further possibilities.

In addition, a number of non-stable transformation methods that are well known to those skilled in the art may be desirable for the present invention. Such methods include, but are not limited to, transient expression and viral transfection.

Seeds are obtained from the transformed plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleic acids of the invention can be used to confer the trait of increased tolerance to low temperature, chilling or cold conditions without reduction in fertility on essentially any plant, including chilling sensitive crop plants such as corn, soybean, rice and cotton.

The nucleotide sequences according to the invention encode appropriate proteins from any organism, in particular from plants, fungi, bacteria or animals.

The process according to the invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadales and Gnetales.

The process is preferably used with plants that are important or interesting for agriculture, horticulture, biomass for bioconversion and/or forestry. Examples are tobacco, oilseed rape, sugar beet, potatoes, tomatoes, cucumbers, peppers, beans, peas, citrus fruits, avocados, peaches, apples, pears, berries, plumbs, melons, eggplants, cotton, soybean, sunflowers, roses, poinsettia, petunia, guayule, cabbages, spinach, alfalfa, artichokes, corn, wheat, rice, rye, barley, grasses such as switch grass or turf grass, millet, hemp, bananas, poplars, eucalyptus trees and conifers.

Homologs Encompassed by the Invention

It is well known in the art that one or more amino acids in a native sequence can be substituted with other amino acid(s), the charge and polarity of which are similar to that of the native amino acid, i.e. a conservative amino acid substitution, resulting in a silent change. Conservative substitutes for an amino acid within the native polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

In a further aspect of the present invention, nucleic acid molecules of the present invention can comprise sequences that differ from those encoding a protein or fragment thereof selected from the group consisting of SEQ ID NOs: 2-5, 7, 9-18, 20-32, 34-38, 40 and 42-46 due to the fact that the different nucleic acid sequence encodes a protein having one or more conservative amino acid changes.

Polypeptides

Polypeptides described herein include cold tolerance-modulating polypeptides. Cold tolerance-modulating polypeptides can be effective to modulate cold tolerance levels when expressed in a plant or plant cell. Such polypeptides typically contain at least one domain indicative of cold tolerance-modulating polypeptides, as described in more detail herein. Cold tolerance-modulating polypeptides typically have an HMM bit score that is greater than 20, as described in more detail herein. In some embodiments, cold tolerance-modulating polypeptides have greater than 80% identity to SEQ ID NOs: 2, 7, 9, 20, 34, 40, and 42, as described in more detail herein.

In some embodiments, a cold tolerance-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the cold tolerance-modulating activity of a truncated polypeptide. In some embodiments, a truncated polypeptide is a dominant negative polypeptide. SEQ ID NOs 7 and 40 set forth the amino sequences of cold tolerance-modulating polypeptides that are truncated at the 3' end relative to the naturally occurring polypeptides SEQ ID NOs 9 and 34, respectively. Expression in a plant of such a truncated polypeptide confers a difference in the level of cold tolerance in a tissue of the plant as compared to the corresponding level in tissue of a control plant that does not comprise the truncation.

A. Functional Homologs Identified by Reciprocal BLAST

In some embodiments, one or more functional homologs of a reference cold tolerance-modulating polypeptide defined by one or more of the pfam descriptions indicated above are suitable for use as cold tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cold tolerance-modulating polypeptide, or by combining domains from the coding sequences for different naturally-occurring cold tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of cold tolerance-modulating polypeptides. Sequence analysis can involve BLAST, Reciprocal BLAST, or PSI-BLAST analysis of nonredundant databases using a cold tolerance-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a cold tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in cold tolerance-modulating polypeptides, e.g., conserved functional domains.

Conserved regions can be identified by locating a region within the primary amino acid sequence of a cold tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at the Wellcome Trust Sanger Institute and HMMI janelia farm research campus. A description of the information included at the Pfam database is described in Sonnhammer et al., *Nucl. Acids Res.,* 26:320-322 (1998); Sonnhammer et al., *Proteins,* 28:405-420 (1997); and Bateman et al., *Nucl. Acids Res.,* 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 1:
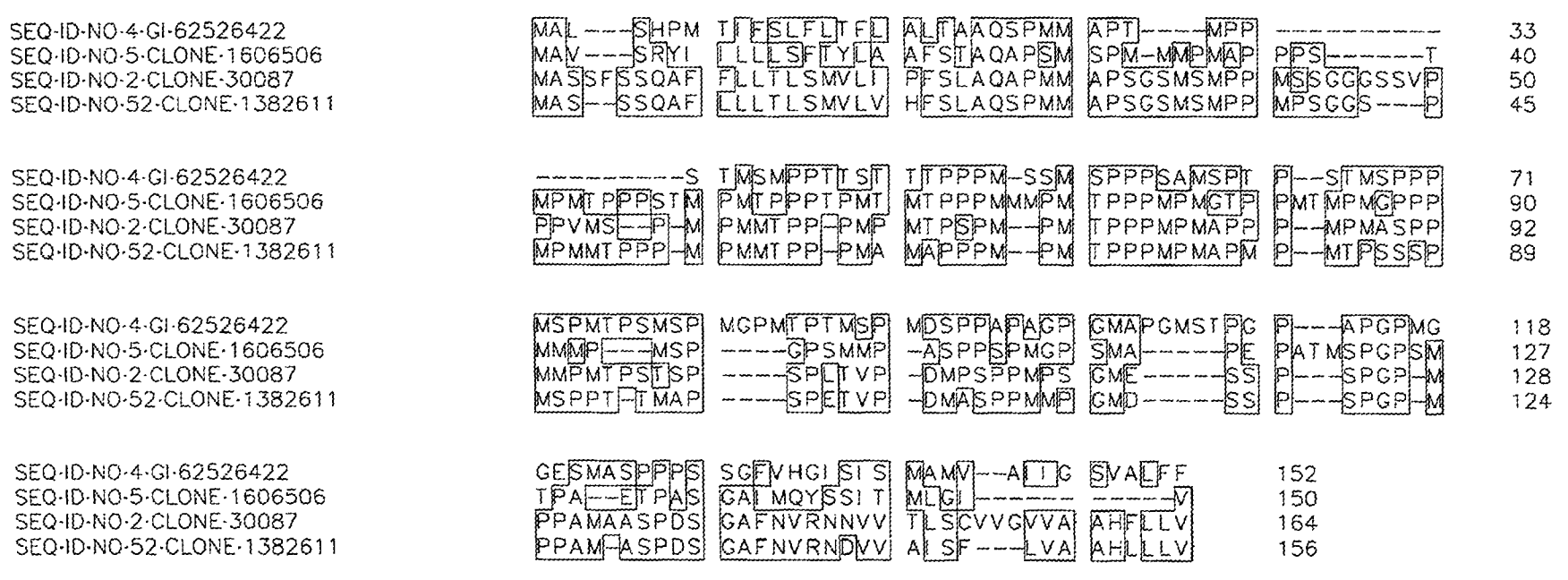

Amino acid sequences of functional homologs of the polypeptide set forth in SEQ ID NOs 2, 7, 9, 20, 34, 40 and 42 are provided in FIGS. 1-7, respectively. In some cases, a functional homolog of SEQ ID NOs 2, 7, 9, 20, 34, 40 and 42 has an amino acid sequence with at least 80% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in the Sequence Listing.

The identification of conserved regions in a cold tolerance-modulating polypeptide facilitates production of variants of cold tolerance-modulating polypeptides. Variants of cold tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in any one of FIGS. 1-7. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

B. Functional Homologs Identified by HMMER

In some embodiments, useful cold tolerance-modulating polypeptides include those that fit a Hidden Markov Model based on the polypeptides set forth in any one of FIGS. 1-7. A Hidden Markov Model (HMM) is a statistical model of a consensus sequence for a group of functional homologs. See, Durbin et al., *Biological Sequence Analysis: Probabilistic Models of Proteins and Nucleic Acids,* Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, --consistency REPS of 2; -ir, --iterative-refinement REPS of 100; -pre, --pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as the HMMER page on the HHMI janelia farm research campus website; the Eddy Lab Home page on the HHMI janelia farm research campus website; and HMMER 2.3.2 download available on the Fish & Richardson website. Hmmbuild outputs the model as a text file.

The HMM for a group of functional homologs can be used to determine the likelihood that a candidate cold tolerance-modulating polypeptide sequence is a better fit to that particular HMM than to a null HMM generated using a group of sequences that are not structurally or functionally related. The likelihood that a subject polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the subject sequence carries out one or more of the biochemical or physiological function(s) of the polypeptides used to generate the HMM. A high HMM bit score is at least 20, and often is higher.

The cold tolerance-modulating polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a cold tolerance-modulating polypeptide discussed below is about 50%, 60%, 70%, 80%, 90%, or 95% of the HMM bit score of a functional homolog provided in one of Table 7. In some embodiments, a cold tolerance-modulating polypeptide discussed below fits the indicated HMM with an HMM bit score greater than 20, and has a domain indicative of an cold tolerance-modulating polypeptide. In some embodiments, a cold tolerance-modulating polypeptide discussed below fits the indicated HMM with an HMM bit score greater than 20, and has 80% or greater sequence identity (e.g., 75%, 80%, 85%, 90%, 95%, or 100% sequence identity) to an amino acid sequence shown in any one of FIGS. 1-7.

Polypeptides are shown in Table 7 that have HMM bit scores greater than 20 when fitted to an HMM generated from the amino acid sequences set forth in FIGS. 1-7, respectively.

In another aspect, biologically functional equivalents of the proteins or fragments thereof of the present invention can have about 10 or fewer conservative amino acid changes, more preferably about 7 or fewer conservative amino acid changes and most preferably about 5 or fewer conservative amino acid changes. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Inhibition of Expression of a Cold Tolerance-Modulating Polypeptide

Polynucleotides and recombinant constructs described herein can be used to inhibit expression of a cold tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews* Genetics 5:355-365 (2004); Dorsett and Tuschl, *Nature Reviews Drug Discovery* 3: 318-329 (2004); and *Nature Reviews RNA interference collection*, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Antisense technology is one well-known method. In this method, a nucleic acid segment from a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid segment need not be the entire sequence of the gene to be repressed, but typically will be substantially complementary to at least a portion of the sense strand of the gene to be repressed. Generally, higher homology can be used to compensate for the use of a shorter sequence. Typically, a sequence of at least 30 nucleotides is used, e.g., at least 40, 50, 80, 100, 200, 500 nucleotides or more.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence of a cold tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand of the coding sequence of the cold tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region of an mRNA encoding a cold tolerance-modulating polypeptide, and the other strand of the stem portion of the double stranded RNA comprises a sequence that is similar or identical to the sequence that is complementary to the 3' or 5' untranslated region, respectively, of the mRNA encoding the cold tolerance-modulating polypeptide. In other embodiments, one strand of the stem portion of a double stranded RNA comprises a sequence that is similar or identical to the sequence of an intron in the pre-mRNA encoding a cold tolerance-modulating polypeptide, and the other strand of the stem portion comprises a sequence that is similar or identical to the sequence that is complementary to the sequence of the intron in the pre-mRNA. The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron. A double stranded RNA can have zero, one, two, three, four, five, six, seven, eight, nine, ten, or more stem-loop structures. A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence of a cold tolerance-modulating polypeptide. The transcription product can also be unpolyadenylated, lack a 5' cap structure, or contain an unsplicable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a cold tolerance-modulating polypeptide. In some embodiments, the sense or antisense sequence is identical or complementary to a sequence of the regulatory region that drives transcription of the gene encoding a cold tolerance-modulating polypeptide. In each case, the sense sequence is the sequence that is complementary to the antisense sequence.

The sense and antisense sequences can be any length greater than about 12 nucleotides (e.g., 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence encoding a cold tolerance-modulating polypeptide described herein. The sense sequence complementary to the antisense sequence can be a sequence present within the mRNA of the cold tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

In some embodiments, nucleic acid based inhibition of gene expression does not require transcription of the nucleic acid.

Identification of Useful Nucleotide Sequences

The nucleotide sequences of the invention were identified by use of a variety of screens under low temperature, chilling or cold conditions recognized by those skilled in the art to be predictive of nucleotide sequences that provide plants with improved tolerance to low temperature, chilling or cold conditions. One or more of the following screens were, therefore, utilized to identify the nucleotide (and amino acid) sequences of the invention.

1. Cold Germination Superpool Screen 0.5× MS Media is prepared and the pH adjusted to 5.7 using 10N KOH. Seven g/l of Phytagar is added prior to autoclaving.

Individual superpool and control seeds are sterilized in a 30% bleach solution for 5 minutes. Seeds are then rinsed repeatedly with sterile water to eliminate all bleach solution. Seeds are sown on media plates in a monolayer, including wild-type and positive controls. Plates are wrapped in aluminum foil and placed at 4° C. for three days to stratify. At the end of this time, the foil is removed and plates are transferred to an 8° C. Percival with fluorescent bulbs emitting a light intensity of ~100 μEinsteins.

Approximately 10 days after transfer to 8° C., seeds are examined microscopically to identify those that have germinated (defined as cotyledon emergence and expansion). Seedlings with more expanded and greener cotyledons compared to the wild-type population in the same plate are collected. DNA from these candidate seedlings is extracted and the transgene amplified using PCR. The PCR product is sequenced to determine the identity of the transgene and consequently the ME line from which the candidate is derived.

2. Cold Germination Assay

Independent transformation events of the ME lines identified in the Superpool screen are assayed in two generations to validate the cold tolerance phenotype. Media is prepared and seeds sterilized as described above for the Cold Germination Superpool Screen.

Two events with 27 seeds from each event are sown in a latin square layout on square Petri dishes together with 27 wild-type control seeds. Following 3 days of stratification at 4° C., plates are transferred to 8° C. in the light and grown as above. Approximately 10 days after transfer, plates are imaged on a flat-bed scanner. Plate images are analyzed using WinRhizo software to determine the area of each seedling. Subsequently, plates are transferred to 22° C. for several days of growth and then sprayed with Finale™ to identify transgenic seedlings. Seedling area and transgene status data are entered into a database. Events are considered positive for the low temperature, chilling or cold-tolerant phenotype if the seedling area of the transgenic plants within an event is significantly different by a one-tailed student's t-test than the seedling area of the pooled non-transgenic seedlings across all the events for that ME line.

REFERENCES

Levitt (1980) Chilling injury and resistance. In T T Kozlowsky, ed, Chilling, Freezing, and High Temperature Stresses: Responses of Plant to Environmental Stresses, Vol 1. Academic Press, New York, pp 23-64.

Graham and Patterson (1982) *Annu Rev Plant Physiol* 33: 347-372.

Guy (1990) *Annu Rev Plant Physiol Plant Mol Biol* 41: 187-223.

Nishida and Murata (1996) *Annu Rev Plant Physiol Plant Mol Biol* 47: 541-568.

EXAMPLES

Summary

| | |
|---|---|
| Trait | Cold |
| area(s) | |
| Sub-trait | Cold - germination and vigor |
| Area | |
| Coding sequence/ Species of Origin | 1. Vector Construct Sequence Identifier 14298746 corresponding to Clone 30087 - ME01451; encodes a 164 amino acid protein of unknown function from *Arabidopsis*. |
| | 2. Vector Construct Sequence Identifier 14298770 corresponding to Clone 30469 - ME02779 encodes a 78 amino acid protein with identity to the N-terminal half of an *Arabidopsis* class I nonsymbiotic hemoglobin. |
| | 3. Vector Construct Sequence Identifier 14301197 corresponding to Clone 271922 - ME03944 encodes a 92 amino acid 60s ribosomal protein L37a protein from *Arabidopsis*. |
| | 4. Vector Construct Sequence Identifier 14296769 corresponding to Clone 2403 - ME05304 encodes a truncated ubiquitin-like protein from *Arabidopsis*. |
| | 5. Vector Construct Sequence Identifier 14301334 corresponding to Clone 674166 -ME03186 from *Glycine max* encodes a 210 amino acid protein with similarity to the ethylene- responsive element binding protein (ERF) family. |
| Species in which Clone was Tested | *Arabidopsis thaliana* |
| Promoter | 35S, a strong constitutive promoter |
| Insert DNA type | cDNA |

Introduction

How plants respond to stress in the environment dictates their ability to survive and reproduce. There are probably many mechanisms by which plants regulate the temperatures under which they will germinate (Lu and Hills, 2003). Finding genes that result in stress tolerance when over-expressed has proved difficult because of the large amount of cross-talk and regulation among gene families.

Over-expression of these genes could be useful for increasing low temperature, chilling or cold tolerance in crops. If successfully deployed, low temperature, chilling or cold tolerant genes could enhance crop productivity following intermittent or sustained low temperature, chilling or cold periods that occur early in the growing season when seeds are germinating. Assuming conservation of processes controlling vegetative physiology across species, these genes and proteins are likely to function similarly in other species.

Assays described here focus on low temperature, chilling or cold tolerance in germinating seedlings. The ability to germinate and grow under low temperature, chilling or cold, and wet conditions would allow a longer growing season and mitigate damage caused by unexpected low temperature, chilling or cold periods. If this trait is recapitulated in crops overexpressing these genes, the result could be very valuable in agriculture in many crops and environments and make a significant contribution to sustainable farming. Furthermore, low temperature, chilling or cold tolerance may be modulated by expressing these clones under the control of a low temperature, chilling or cold inducible promoter.

Materials and Methods:
Generation and Phenotypic Evaluation of $T_1$ Events.

Wild-type *Arabidopsis Wassilewskija* (Ws) plants were transformed with a Ti plasmid containing different Clones in the sense orientation relative to the 35S promoter, by *Agrobacterium*-Mediated Transformation. The Ti plasmid vector used for this construct, CRS 338, contains the Ceres-constructed, plant selectable marker gene phosphinothricin acetyltransferase (PAT) which confers herbicide resistance to transformed plants. Ten independent transformation events were selected and evaluated for their qualitative phenotype in the $T_1$ generation by selecting Finale™-resistant plants and observing their physical characteristics.

Screening for Low Temperature, Chilling or Cold Germination Candidates.

All superpools (n=91) were screened for cold germination by plating seeds on MS media and germinating them at 8° C. Candidates were chosen based on a comparison to wild-type controls. The candidates were processed as follows.

Process Flow:

Procedure for 1) identifying the candidate from a cold germination superpool screen, 2) confirming the phenotype in the second and third generations and 3) determining the lack of significant negative phenotypes.

1. Superpools screened for Cold Germination
2. Cold tolerant candidates identified
3. Independent events tested for Cold Germination and Finale™ resistance in two generations
4. For all candidates, at least 2 Events were significantly tolerant to cold in 2 generations
5. Tested positive events for negative phenotypes Growth Conditions and Planting Schema Under Cold Germination.

Up to five independent $T_2$ transformation events were evaluated for each line under cold conditions. Subsequently, $T_3$ generation seeds for up to five events were evaluated under cold germination conditions. In these assays, the seedling area (a measure of timing of germination and cotyledon expansion) for transgenic plants within an event was compared to the seedling area for non-transgenic segregants pooled across all plates for that line.

Preparation of plates and seed sowing were performed by sowing seeds on 0.5× MS plates and grown at 8° C. Plates were scored on day 10, and analyzed for cotyledon area. After the Cold Germination Assay was complete, plates were transferred to 22° C. and insert-containing plants were identified by spraying the seedlings with Finale™. Transgenic plants are Finale™ resistant.

Screening for Negative Phenotypes.

The events described in this report were analyzed for negative phenotypes. None of the events had (a) reduction in germination of more than 25%, (b) delay in onset of flowering more than 4 days in 50% or more of plants relative to in-flat control, (c) reduction in fertility as evidenced by visual observation of reduction in silique fill or silique number, (d) a reduction in seed dry weight by 25% or more relative to control, or (e) more than 30% reduction in rosette diameter at maturity.

Results:

Example 1

ME01451

TABLE 1-1

| Construct | Event/Generation | Plant Stage | Assay | Result |
| --- | --- | --- | --- | --- |
| 35S:: 30087 | –01/$T_2$ Finale resistant plants | Seedling | Cold Germination | Significant at p ≤ .05 |
| 35S:: 30087 | –05/$T_2$ Finale resistant plants | Seedling | Cold Germination | Significant at p ≤ .05 |
| 35S:: 30087 | –01/$T_3$ Finale resistant plants | Seedling | Cold Germination | Significant at p ≤ .05 |
| 35S:: 30087 | –05/$T_3$ Finale resistant plants | Seedling | Cold Germination | Significant at p ≤ .05 |

Ectopic expression of Clone 30087 under the control of the 35S promoter induces the following phenotypes:
  Early germination at 8° C. resulting in larger seedlings after 10 days of growth in the cold.
Plants from Events -01 and -05 which are heterozygous or homozygous for Clone 30087 do not show any negative phenotypes under long-day conditions.
The gene corresponding to Clone 30087 is up-regulated in developing seedlings, seeds and siliques and down-regulated in drought, heat and ABA.

Two Events of ME01451 Showed Significant Early Germination Under Cold Conditions in Both Generations.

All five events of ME01451 were sown as described in the Cold Germination Assay in both the $T_2$ and the $T_3$ generations. Two events, -01 and -05, were significant in both generations at p=0.05 using a one-tailed t-test assuming unequal variance (Table 1-2). ME01451 transgenic seedlings were significantly larger than the pooled non-transgenic segregants.

TABLE 1-2

T-test comparison of seedling area between transgenic seedlings and pooled non-transgenic segregants after 10 days at 8° C.

| Line | Events | Transgenic | | | Pooled Non-Transgenics | | | t-test |
|---|---|---|---|---|---|---|---|---|
| | | Avg | SE | N | Avg | SE | N | p-value |
| ME01451 | ME01451-01 | 0.0086 | 0.0005 | 25 | 0.0067 | 0.0006 | 54 | 0.00702 |
| ME01451 | ME01451-01-99 | 0.0106 | 0.0006 | 22 | 0.0079 | 0.0010 | 14 | 0.01374 |
| ME01451 | ME01451-05 | 0.0104 | 0.0006 | 18 | 0.0067 | 0.0006 | 54 | 0.00002 |
| ME01451 | ME01451-05-99 | 0.0125 | 0.0007 | 25 | 0.0079 | 0.0010 | 14 | 0.00035 |

Two Events of ME01451 Show 3:1 and 15:1 Segregation for Finale™ Resistance.
Events -01 and -05 segregated 15:1 and 3:1 (R:S), respectively, for Finale™ resistance in the $T_2$ generation (data not shown).
Qualitative Analysis of the $T_1$ Plants:
The physical appearance of all ten $T_1$ plants was identical to the controls.
Qualitative and Quantitative Analysis of the $T_2$ Plants:
Events -01 and -05 of ME01451 exhibited no statistically relevant negative phenotypes.
Germination
No detectable reduction in germination rate.
General Morphology/Architecture
Plants appeared wild-type in all instances.
Days to Flowering
No observable or statistical differences between experimentals and controls.
Rosette Area 7 Days Post-Bolting
No observable or statistical differences between experimentals and controls.
Fertility (Silique Number and Seed Fill)
No observable or statistical differences between experimentals and controls Example 2

ME02779

TABLE 2-1

| Construct | Event/Generation | Plant Stage | Assay | Result |
|---|---|---|---|---|
| 35S:: 30469 | –01/$T_2$ Finale resistant plants | Seedling | Cold Germination | Significant at p ≤ .05 |
| 35S:: 30469 | –03/$T_2$ Finale resistant plants | Seedling | Cold Germination | Significant at p ≤ .05 |
| 35S:: 30469 | –01/$T_3$ Finale resistant plants | Seedling | Cold Germination | Significant at p ≤ .05 |
| 35S:: 30469 | –03/$T_3$ Finale resistant plants | Seedling | Cold Germination | Significant at p ≤ .05 |

Ectopic expression of Clone 30469 under the control of the 35S promoter induces the following phenotypes:
  Early germination at 8° C. resulting in larger seedlings after 10 days at 8° C.
  Plants from Events -01 and -03 which are heterozygous or homozygous for Clone 30469 do not show any negative phenotypes under long-day conditions.
  The gene corresponding to Clone 30469 is down-regulated in ABA, heat, and germinating seeds and up-regulated in high nitrogen and most cold and drought treatments.
  Clone 30469 encodes a class I nonsymbiotic hemoglobin. These proteins can play a role in acclimation to hypoxic conditions, possibly explaining the cold tolerance phenotype (Hunt et al., 2001). Clone 30469 is a splice variant of a gene that encodes a longer protein.
Two Events of ME02779 Showed Significant Early Germination Under Cold Conditions in Both Generations.
Five events of ME02779 were sown as described in the Cold Germination Assay in both the $T_2$ and the $T_3$ generations. Two events, -01 and -03 were significant in both generations at p=0.05 using a one-tailed t-test assuming unequal variance (Table 2-2). ME02779 transgenic seedlings were significantly larger than the pooled non-transgenic segregants.

TABLE 2-2

T-test comparison of seedling area between transgenic seedlings and pooled non-transgenic segregants after 10 days at 8° C.

| Line | Events | Transgenic | | | Pooled Non-Transgenics | | | t-test |
|---|---|---|---|---|---|---|---|---|
| | | Avg | SE | N | Avg | SE | N | p-value |
| ME02779 | ME02779-01 | 0.0077 | 0.0007 | 12 | 0.0040 | 0.0014 | 3 | 0.01738 |
| ME02779 | ME02779-01-99 | 0.0051 | 0.0005 | 21 | 0.0034 | 0.0002 | 29 | 0.00077 |
| ME02779 | ME02779-03 | 0.0111 | 0.0007 | 19 | 0.0085 | 0.0007 | 40 | 0.00433 |
| ME02779 | ME02779-03-99 | 0.0052 | 0.0006 | 20 | 0.0034 | 0.0002 | 29 | 0.00293 |

Two Events of ME02779 Show 3:1 Segregation for Finale™ Resistance.

Events -01 and -03 segregated 3:1 (R:S) for Finale™ resistance in the $T_2$ generation (data not shown).

Qualitative Analysis of the $T_1$ Plants:
The physical appearance of nine of the ten $T_1$ plants was identical to the controls except for Event -09, which exhibited small rosettes and reduced fertility.

Qualitative and Quantitative Analysis of the $T_2$ Plants:
Events -01 and -03 of ME02779 exhibited no statistically relevant negative phenotypes.
Germination
No detectable reduction in germination rate.
General Morphology/Architecture
Plants appeared wild-type in all instances.
Days to Flowering
No observable or statistical differences between experimentals and controls.
Rosette Area 7 Days Post-Bolting
No observable or statistical differences between experimentals and controls.
Fertility (Silique Number and Seed Fill)
No observable or statistical differences between experimentals and controls Example 3

ME03944

TABLE 3-1

| Construct | Event/Generation | Plant Stage | Assay | Result |
|---|---|---|---|---|
| 35S:: 271922 | -02/$T_2$ Finale resistant plants | Seedling | Cold Germination | Significant at p ≤ .05 |
| 35S:: 271922 | -06/$T_2$ Finale resistant plants | Seedling | Cold Germination | Significant at p ≤ .05 |
| 35S:: 271922 | -02/$T_3$ Finale resistant plants | Seedling | Cold Germination | Significant at p ≤ .05 |
| 35S:: 271922 | -06/$T_3$ Finale resistant plants | Seedling | Cold Germination | Significant at p ≤ .05 |

Ectopic expression of Clone 271922 under the control of the 35S promoter induces the following phenotypes:
Early germination at 8° C. resulting in larger seedlings after 10 days at 8° C.
Plants from Events -02 and -06 which are heterozygous or homozygous for Clone 271922 do not show any negative phenotypes under long-day conditions.
The gene corresponding to Clone 271922 shows little differential regulation in transcription profiling experiments on wildtype.
Clone 271922 encodes a 60s ribosomal protein L37a.

Two events of ME03944 Showed Significant Early Germination Under Cold Conditions in Both Generations.

Four events of ME03944 were sown as described in the Cold Germination Assay in both the $T_2$ and the $T_3$ generations. Two events, -02 and -06, were significant in both generations at p≤0.05 using a one-tailed t-test assuming unequal variance (Table 3-2). The $T_3$ lines are indicated as -99 which indicates that the seeds are the bulked progeny from several $T_2$ plants. ME03944 transgenic seedlings were significantly larger than the pooled non-transgenic segregants.

TABLE 3-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME03944 | ME03944-02 | 0.0115 | 0.0004 | 23 | 0.0069 | 0.0006 | 35 | 3.4023E−08 |
| ME03944 | ME03944-02-99 | 0.0070 | 0.0008 | 15 | 0.0051 | 0.0004 | 29 | 0.0173 |
| ME03944 | ME03944-06 | 0.0106 | 0.0006 | 18 | 0.0069 | 0.0006 | 35 | 2.7850E−05 |
| ME03944 | ME03944-06-99 | 0.0077 | 0.0007 | 21 | 0.0051 | 0.0004 | 29 | 0.0011 |

Two Events of ME03944 Show 3:1 Segregation for Finale™ Resistance.

Events -02 and -06 segregated 3:1 (R:S) for Finale™ resistance in the $T_2$ generation (data not shown).

Qualitative Analysis of the $T_1$ Plants:
The physical appearance of five of the six $T_1$ plants was identical to the controls. Event -03 exhibited a small rosette and curled leaves.

Other Characteristics:
Seedlings from ME03944-06 exhibited elongated hypocotyls. This phenotype co-segregated with Finale™ resistance.

Qualitative and Quantitative Analysis of the $T_2$ Plants:
Events -02 and -06 of ME03944 exhibited no statistically relevant negative phenotypes.
Germination
No detectable reduction in germination rate.
General Morphology/Achitecture
Plants appeared wild-type in all instances.
Days to Flowering
No observable or statistical differences between experimentals and controls.
Rosette Area 7 Days Post-Bolting
No observable or statistical differences between experimentals and controls.
Fertility (Silique Number and Seed Fill)
No observable or statistical differences between experimentals and controls Example 4

ME05304

TABLE 4-1

| Construct | Event/Generation | Plant Stage | Assay | Result |
|---|---|---|---|---|
| 35S:: 2403 | -01/$T_2$ Finale resistant plants | Seedling | Cold Germination | Significant at p ≤ .05 |

TABLE 4-1-continued

| Construct | Event/Generation | Plant Stage | Assay | Result |
|---|---|---|---|---|
| 35S:: 2403 | –04/T$_2$ Finale resistant plants | Seedling | Cold Germination | Significant at p ≤ .05 |
| 35S:: 2403 | –01/T$_3$ Finale resistant plants | Seedling | Cold Germination | Significant at p ≤ .05 |
| 35S:: 2403 | –04/T$_3$ Finale resistant plants | Seedling | Cold Germination | Significant at p ≤ .05 |

Ectopic expression of Clone 2403 under the control of the 35S promoter induces the following phenotypes:
  Early germination at 8° C. resulting in larger seedlings after 10 days at 8° C.
  Plants from Events -01 and -04 which are heterozygous or homozygous for Clone 2403 do not show any negative phenotypes under long-day conditions.
  The gene corresponding to Clone 2403 shows little differential regulation in transcript profiling experiments on wildtype.
  Clone 2403 encodes a truncated ubiquitin-like protein.

Two Events of ME05304 Showed Significant Early Germination Under Cold Conditions in Both Generations.

Four events of ME05304 were sown as described in the Cold Germination Assay in both the T$_2$ and the T$_3$ generations. Two events, -01 and -04 were significant in both generations at p<0.05 using a one-tailed t-test assuming unequal variance (Table 4-2). The T$_3$ lines are indicated as -99 which indicates that the seeds are the bulked progeny from several T$_2$ plants.

TABLE 4-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME05304 | ME05304-01 | 0.0142 | 0.0009 | 20 | 0.0079 | 0.0006 | 39 | 0.0000 |
| ME05304 | ME05304-01-99 | 0.0061 | 0.0005 | 17 | 0.0049 | 0.0003 | 27 | 0.0213 |
| ME05304 | ME05304-04 | 0.0101 | 0.0007 | 15 | 0.0079 | 0.0006 | 39 | 0.0099 |
| ME05304 | ME05304-04-99 | 0.0067 | 0.0005 | 22 | 0.0049 | 0.0003 | 27 | 0.0014 |

Two Events of ME05304 Show 3:1 Segregation for Finale™ Resistance.
Events -01 and -04 segregated 3:1 (R:S) for Finale™ resistance in the T$_2$ generation (data not shown).

Qualitative Analysis of the T$_1$ Plants:
  The physical appearance of seven of the ten T$_1$ plants was identical to the controls. The other three events exhibited the following phenotypes: late flowering (Events -01, -02 and -08), dark green rosette leaves (Events -01 and -08) and shorter petioles (Events -02 and -08). Event -01 did not reproduce the late-flowering phenotype in the T$_2$ generation.
Qualitative and Quantitative Analysis of the T$_2$ Plants:
Events -01 and -04 of ME05304 exhibited no statistically relevant negative phenotypes.

Germination
  No detectable reduction in germination rate.
General Morphology/Architecture
  Plants appeared wild-type in all instances.
Days to Flowering
  No observable or statistical differences between experimentals and controls.
Rosette Area 7 Days Post-Bolting
  No observable or statistical differences between experimentals and controls.
Fertility (Silique Number and Seed Fill)
  No observable or statistical differences between experimentals and controls.

Example 5

ME03186

TABLE 5-1

| Construct | Event/Generation | Plant Stage | Assay | Result |
|---|---|---|---|---|
| 35S::674166 | –04/T$_3$Finale resistant plants | Seedling | Cold Germination | Significant at p ≤ .05 |
| 35S::674166 | –04/T$_4$ Finale resistant plants | Seedling | Cold Germination | Significant at p ≤ .05 |
| 35S::674166 | –05/T$_2$ Finale resistant plants | Seedling | Cold Germination | Significant at p ≤ .05 |
| 35S::674166 | –05/T$_3$ Finale resistant plants | Seedling | Cold Germination | Significant at p ≤ .05 |

Ectopic expression of Clone 674166 under the control of the 35S promoter results in early germination at 8° C. resulting in larger seedlings after 10 days at 8° C.

Plants from Events -04 and -05 which are hemizygous or homozygous for Clone 674166 do not show any negative phenotypes under long-day conditions.

Two events of ME03186 Showed Significant Early Germination Under Cold Conditions in Both Generations.

Two events, -04 and -05 were significant in two generations at p≤0.05 using a one-tailed t-test assuming unequal variance (Table 5-2). '-99' signifies that seeds were pooled from several plants.

TABLE 5-2

T-test comparison of seedling area between transgenic seedlings and control non-transgenic segregants after 10 days at 8° C.

| Events | Event-Gen | Transgenic Avg | SE | N | Control Non-Transgenics[a] Avg | SE | N | t-test p-value |
|---|---|---|---|---|---|---|---|---|
| ME03186-04-99[b] | 04-T3 | 0.0045 | 0.0003 | 35 | 0.0030 | 0.0002 | 31 | 1.37E−05 |
| ME03186-04-99 | 04-T3 | 0.0092 | 0.0003 | 48 | 0.0051 | 0.0005 | 12 | 3.72E−10 |
| ME03186-04-99-03 | 04-T4 | 0.0107 | 0.0002 | 70 | 0.0083 | 0.0005 | 34 | 2.72E−05 |
| ME03186-04-99-04 | 04-T4 | 0.0120 | 0.0004 | 62 | 0.0083 | 0.0005 | 34 | 3.61E−08 |
| ME03186-04-99-07 | 04-T4 | 0.0107 | 0.0003 | 69 | 0.0083 | 0.0005 | 34 | 4.91E−05 |
| ME03186-04-99-08 | 04-T4 | 0.0110 | 0.0003 | 69 | 0.0083 | 0.0005 | 34 | 5.53E−06 |
| ME03186-05[b] | 05-T2 | 0.0051 | 0.0005 | 22 | 0.0038 | 0.0005 | 6 | 0.0332 |
| ME03186-05 | 05-T2 | 0.0067 | 0.0003 | 53 | 0.0054 | 0.0005 | 9 | 0.0106 |
| ME03186-05-04 | 05-T3 | 0.0050 | 0.0003 | 50 | 0.0037 | 0.0003 | 9 | 0.0008 |

[a]Transgenic seedlings were compared to non-transgenic segregants within a seed line except for the $T_4$ generation of Event-04. Since these seed lines were homozygous, they were compared to pooled non-transgenic segregants from another $T_4$ generation event that was grown in the same flat as the $T_4$ generation of Event -04.
[b]These events were sown twice. The first time was to identify ME03186 as a hit. They were repeated the second time with two generations to identify ME03186 as a candidate.

Two Events of ME03186 Show 3:1 Segregation for Finale™ Resistance.

Event -05 segregated 3:1 (R:S) for Finale™ resistance in the $T_2$ generation. $T_2$ generation seed was not available for Event -04. However, the $T_3$ generation seeds that were pooled from several $T_2$ plants segregated approximately 2:1 in a manner consistent with a single insert (see Table 5-2).
Qualitative and Quantitative Analysis of the $T_2$ Plants (Screening for Negative Phenotypes):
Events -04 and -05 of ME03186 exhibited no statistically significant negative phenotypes.
Germination
No detectable reduction in germination rate.
General Morphology/Architecture
Plants appeared wild-type in all instances.
Days to Flowering
No observable or statistical differences between experimentals and controls.
Rosette Area 7 Days Post-Bolting

REFERENCES

Hunt et ak, (2001) Plant Mol Biol 47: 677-692.
Lu and Hills (2002) Plant Physiol. 129:1352-8

Example 6

Clone 1055099 (SEQ ID NO: 46)—ME 24967

In the same manner as Example 5, transgenics made with a construct of 35S—Clone 1055099 were screened for cold tolerance. Clone 1055099 (SEQ ID NO: 46) is a wheat functional homolog of clone 674166 (SEQ ID NO: 42), and showed the following results in the seedling cold tolerance assay.

TABLE 6-1

Cold Germination Assay results for ME24967.

| Event | p-values Internal[a] | p-values Pooled[b] | Avg. Seedling Area Transgenic | Avg. Seedling Area Internal | Avg. Seedling Area Pooled | Sample No. Transgenic | Sample No. Internal | Sample No. Pooled |
|---|---|---|---|---|---|---|---|---|
| ME03186-04-99[c] | 0.00224438 | 0.00224438 | 0.0032 | 0.0017 | 0.0017 | 30 | 40 | 40 |
| ME24967-02 | 0.12660455 | 0.45511103 | 0.0053 | 0.0071 | 0.0054 | 29 | 5 | 83 |
| ME24967-03 [d] | 0.01488322 | 0.04610112 | 0.0069 | 0.0031 | 0.0054 | 31 | 3 | 83 |
| ME24967-05 [d] | 0.08783497 | 3.0406E−08 | 0.0115 | 0.0092 | 0.0054 | 23 | 12 | 83 |
| ME24967-10 | 0.40686041 | 0.25206736 | 0.0049 | 0.0053 | 0.0054 | 28 | 6 | 83 |
| ME24967-11 | 0.19290195 | 0.40123421 | 0.0051 | 0.0038 | 0.0054 | 5 | 25 | 83 |
| ME24967-12 | 0.3021565 | 0.00329335 | 0.0032 | 0.0050 | 0.0054 | 27 | 2 | 83 |
| ME24967-13 | 0.24672812 | 0.31347649 | 0.0060 | 0.0077 | 0.0054 | 23 | 7 | 83 |
| ME24967-14 | 0.17548824 | 0.29369895 | 0.0050 | 0.0032 | 0.0054 | 26 | 5 | 83 |
| ME24967-15 | 0.29278326 | 0.38586196 | 0.0057 | 0.0048 | 0.0054 | 22 | 11 | 83 |
| ME24967-16 | | 0.05451794 | 0.0041 | 0.0018 | 0.0054 | 34 | 1 | 83 |
| ME24967-17 | 0.27484717 | 0.13660585 | 0.0044 | 0.0058 | 0.0054 | 26 | 6 | 83 |

[a]Internal controls are segregating non-transgenic seedlings within an Event.
[b]Pooled controls are all of the segregating non-transgenic seedlings from all of the Events within a line.
[c]ME03186 is a positive control to verify that the experimental conditions were appropriate.
[d] These events show significantly improved seedling area for at least internal or pooled controls.

Example 7

Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA*, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NOs: 2, 7, 9, 20, 34, 40 and 42 are shown in FIGS. 1-7, respectively. The BLAST percent identities and E-values of functional homologs to SEQ ID NOs: 2, 7, 9, 20, 34, 40 and 42 are shown in the Sequence Listing. The BLAST sequence identities and E-values given in the Sequence Listing were taken from the forward search round of the Reciprocal BLAST process.

Example 8

Determination of Functional Homologs by Hidden Markov Models

Hidden Markov Models (HMMs) were generated by the program HMMER 2.3.2. To generate each HMM, the default HMMER 2.3.2 program parameters, configured for glocal alignments, were used.

An HMM was generated using the sequences shown in each of FIGS. 1-7 as input. Additional sequences were input into the model, and the HMM bit scores for the additional sequences are shown in the Sequence Listing. The results indicate that these additional sequences are functional homologs of SEQ ID NOs: 2, 7, 9, 20, 34, 40 and 42, respectively. The bit score results are provided in Table 7.

TABLE 7

| Query Identifier | Functional Homolog | Sequence Type | Species | Seq Id No | Length | Pfam |
| --- | --- | --- | --- | --- | --- | --- |
|  | Ceres CLONE ID no. 30087 | DNA | *Arabidopsis thaliana* | 1 | 828 |  |
| Ceres CLONE ID no. 30087 | Ceres CLONE ID no. 30087 | PRT | *Arabidopsis thaliana* | 2 | 164 |  |
| Ceres Clone ID no. 30087 | Ceres CLONE ID no. 947579 | PRT | *Brassica napus* | 3 | 155 |  |
| Ceres Clone ID no. 30087 | Public GI no. 62526422 | PRT | *Brassica napus* | 4 | 152 |  |
| Ceres Clone ID no. 30087 | Ceres CLONE ID no. 1606506 | PRT | *Parthenium argentatum* | 5 | 150 |  |
|  | Ceres CLONE ID no. 30469 | DNA | Artificial Sequence | 6 | 586 |  |
| Ceres CLONE ID no. 30469 | Ceres CLONE ID no. 30469 | PRT | Artificial Sequence | 7 | 78 | Globin |
|  | Ceres CLONE ID no. 30469_FL | DNA | *Arabidopsis thaliana* | 8 | 483 |  |
| Ceres Clone ID no. 30469 | Ceres CLONE ID no. 30469_FL | PRT | *Arabidopsis thaliana* | 9 | 160 | Globin |
| Ceres Clone ID no. 30469 | Public GI no. 30909306 | PRT | *Raphanus sativus* | 10 | 160 | Globin |
| Ceres Clone ID no. 30469 | Public GI no. 37903656 | PRT | *Arabidopsis thaliana* | 11 | 158 | Globin |
| Ceres Clone ID no. 30469 | Public GI no. 15824736 | PRT | *Arabidopsis thaliana* | 12 | 163 | Globin |
| Ceres Clone ID no. 30469 | Ceres CLONE ID no. 546001 | PRT | *Glycine max* | 13 | 161 | Globin |
| Ceres Clone ID no. 30469 | Public GI no. 11095158 | PRT | *Glycine max* | 14 | 160 | Globin |
| Ceres Clone ID no. 30469 | Public GI no. 12963875 | PRT | *Glycine max* | 15 | 152 | Globin |
| Ceres Clone ID no. 30469 | Ceres CLONE ID no. 1554560 | PRT | *Zea mays* | 16 | 165 | Globin |
| Ceres Clone ID no. 30469 | Ceres CLONE ID no. 839727 | PRT | *Triticum aestivum* | 17 | 162 | Globin |
| Ceres Clone ID no. 30469 | Public GI no. 14701800 | PRT | *Triticum aestivum* | 18 | 169 | Globin |
|  | Ceres CLONE ID no. 271922 | DNA | *Arabidopsis thaliana* | 19 | 416 |  |
| Ceres CLONE ID no. 271922 | Ceres CLONE ID no. 271922 | PRT | *Arabidopsis thaliana* | 20 | 92 | Ribosomal_L37ae; |
| Ceres Clone ID no. 271922 | Public GI no. 4090257 | PRT | *Arabidopsis thaliana* | 21 | 92 | Ribosomal_L37ae |
| Ceres Clone ID no. 271922 | Public GI no. 4741896 | PRT | *Arabidopsis thaliana* | 22 | 92 | Ribosomal_L37ae |
| Ceres Clone ID no. 271922 | Ceres CLONE ID no. 36046 | PRT | *Arabidopsis thaliana* | 23 | 92 | Ribosomal_L37ae |

TABLE 7-continued

| | | | | | | |
|---|---|---|---|---|---|---|
| Ceres Clone ID no. 271922 | Public GI no. 6016699 | PRT | Arabidopsis thaliana | 24 | 92 | Ribosomal_L37ae |
| Ceres Clone ID no. 271922 | Ceres CLONE ID no. 664936 | PRT | Glycine max | 25 | 92 | Ribosomal_L37ae |
| Ceres Clone ID no. 271922 | Ceres CLONE ID no. 658438 | PRT | Glycine max | 26 | 92 | Ribosomal_L37ae |
| Ceres Clone ID no. 271922 | Ceres CLONE ID no. 1049262 | PRT | Glycine max | 27 | 92 | Ribosomal_L37ae |
| Ceres Clone ID no. 271922 | Ceres CLONE ID no. 632613 | PRT | Triticum aestivum | 28 | 92 | Ribosomal_L37ae |
| Ceres Clone ID no. 271922 | Ceres CLONE ID no. 1390976 | PRT | Zea mays | 29 | 92 | Ribosomal_L37ae |
| Ceres Clone ID no. 271922 | Ceres CLONE ID no. 1457185 | PRT | Zea mays | 30 | 92 | Ribosomal_L37ae |
| Ceres Clone ID no. 271922 | Public GI no. 56202147 | PRT | Zea mays | 31 | 92 | Ribosomal_L37ae |
| Ceres Clone ID no. 271922 | Public GI no. 58578274 | PRT | Zea mays | 32 | 92 | Ribosomal_L37ae |
| | Ceres CLONE ID no. 2403_FL | DNA | Arabidopsis thaliana | 33 | 632 | |
| Ceres CLONE ID no. 2403 | Ceres CLONE ID no. 2403_FL | PRT | Arabidopsis thaliana | 34 | 154 | ubiquitin; |
| Ceres CLONE ID no. 2403 | Ceres CLONE ID no. 2403_FL | PRT | Arabidopsis thaliana | 34 | 154 | ubiquitin; |
| Ceres Clone ID no. 2403 | Ceres CLONE ID no. 1482731 | PRT | Zea mays | 35 | 169 | ubiquitin |
| Ceres Clone ID no. 2403 | Ceres CLONE ID no. 1482731 | PRT | Zea mays | 35 | 169 | ubiquitin |
| Ceres Clone ID no. 2403 | Ceres CLONE ID no. 522921 | PRT | Glycine max | 36 | 154 | ubiquitin |
| Ceres Clone ID no. 2403 | Ceres CLONE ID no. 522921 | PRT | Glycine max | 36 | 154 | ubiquitin |
| Ceres Clone ID no. 2403 | Ceres CLONE ID no. 1036726 | PRT | Brassica napus | 37 | 160 | ubiquitin |
| Ceres Clone ID no. 2403 | Ceres CLONE ID no. 1036726 | PRT | Brassica napus | 37 | 160 | ubiquitin |
| Ceres Clone ID no. 2403 | Ceres CLONE ID no. 513071 | PRT | Glycine max | 38 | 188 | ubiquitin |
| Ceres Clone ID no. 2403 | Ceres CLONE ID no. 513071 | PRT | Glycine max | 38 | 188 | ubiquitin |
| | Ceres CLONE ID no. 2403 | DNA | Artificial Sequence | 39 | 620 | |
| Ceres CLONE ID no. 2403 | Ceres CLONE ID no. 2403 | PRT | Artificial Sequence | 40 | 33 | ubiquitin; |
| | Ceres CLONE ID no. 674166 | DNA | Glycine max | 41 | 1106 | |
| Ceres CLONE ID no. 674166 | Ceres CLONE ID no. 674166 | PRT | Glycine max | 42 | 210 | AP2; |
| Ceres Clone ID no. 674166 | Public GI no. 12322345 | PRT | Glycine max | 43 | 225 | AP2 |
| Ceres Clone ID no. 674166 | Ceres CLONE ID no. 975672 | PRT | Brassica napus | 44 | 215 | AP2 |
| Ceres Clone ID no. 674166 | Ceres CLONE ID no. 273307 | PRT | Zea mays | 45 | 211 | AP2 |
| Ceres Clone ID no. 674166 | Ceres CLONE ID no. 1055099 | PRT | Triticum aestivum | 46 | 194 | AP2 |
| | Ceres ANNOT ID no. 1441430 | DNA | Populus balsamifera subsp. trichocarpa | 47 | 660 | |
| Ceres CLONE ID no. 674166 | Ceres ANNOT ID no. 1441430 | PRT | Populus balsamifera subsp. trichocarpa | 48 | 219 | AP2 |
| | Ceres CLONE ID no. 1240330 | DNA | Glycine max | 49 | 985 | |
| Ceres CLONE ID no. 674166 | Ceres CLONE ID no. 1240330 | PRT | Glycine max | 50 | 222 | AP2 |
| | Ceres CLONE ID no. 1382611 | DNA | Zea mays | 51 | 726 | |
| Ceres CLONE ID no. 30087 | Ceres CLONE ID no. 1382611 | PRT | Zea mays | 52 | 156 | |
| | Ceres CLONE ID no. 1627907 | DNA | Papaver somniferum | 53 | 580 | |
| Ceres CLONE ID no. 271922 | Ceres CLONE ID no. 1627907 | PRT | Papaver somniferum | 54 | 92 | Ribosomal_L37ae |
| | Ceres CLONE ID no. 1761125 | DNA | Panicum virgatum | 55 | 983 | |
| Ceres CLONE ID no. 674166 | Ceres CLONE ID no. 1761125 | PRT | Panicum virgatum | 56 | 192 | AP2 |
| | Ceres CLONE ID no. 1783890 | DNA | Panicum virgatum | 57 | 594 | |
| Ceres CLONE ID no. 271922 | Ceres CLONE ID no. 1783890 | PRT | Panicum virgatum | 58 | 92 | Ribosomal_L37ae |
| | Ceres CLONE ID no. 1802327 | DNA | Panicum virgatum | 59 | 880 | |
| Ceres Clone ID no. 30469 | Ceres CLONE ID no. 1802327 | PRT | Panicum virgatum | 60 | 162 | Globin |
| | Ceres CLONE ID no. 1838364 | DNA | Gossypium hirsutum | 61 | 1017 | |
| Ceres CLONE ID no. 674166 | Ceres CLONE ID no. 1838364 | PRT | Gossypium hirsutum | 62 | 246 | AP2 |
| | Ceres CLONE ID no. 1876458 | DNA | Panicum virgatum | 63 | 708 | |
| Ceres Clone ID no. 30469 | Ceres CLONE ID no. 1876458 | PRT | Panicum virgatum | 64 | 162 | Globin |
| | Ceres CLONE ID no. 1879148 | DNA | Panicum virgatum | 65 | 712 | |
| Ceres Clone ID no. 30469 | Ceres CLONE ID no. 1879148 | PRT | Panicum virgatum | 66 | 164 | Globin |
| | Ceres CLONE ID no. 1884696 | DNA | Gossypium hirsutum | 67 | 1129 | |
| Ceres CLONE ID no. 2403 | Ceres CLONE ID no. 1884696 | PRT | Gossypium hirsutum | 68 | 153 | ubiquitin |
| Ceres CLONE ID no. 2403 | Ceres CLONE ID no. 1884696 | PRT | Gossypium hirsutum | 68 | 153 | ubiquitin |
| | Ceres CLONE ID no. 1916866 | DNA | Gossypium hirsutum | 69 | 679 | |
| Ceres Clone ID no. 30469 | Ceres CLONE ID no. 1916866 | PRT | Gossypium hirsutum | 70 | 163 | Globin |
| | Ceres CLONE ID no. 1950105 | DNA | Panicum virgatum | 71 | 1003 | |
| Ceres CLONE ID no. 2403 | Ceres CLONE ID no. 1950105 | PRT | Panicum virqatum | 72 | 229 | ubiquitin |
| Ceres CLONE ID no. 2403 | Ceres CLONE ID no. 1950105 | PRT | Panicum virgatum | 72 | 229 | ubiquitin |
| Ceres CLONE ID no. 2403 | Ceres CLONE ID no. 1950105 | PRT | Panicum virgatum | 72 | 229 | ubiquitin |
| | Ceres CLONE ID no. 1990746 | DNA | Panicum virgatum | 73 | 724 | |
| Ceres Clone ID no. 30469 | Ceres CLONE ID no. 1990746 | PRT | Panicum virgatum | 74 | 164 | Globin |
| | Ceres CLONE ID no. 2007485 | DNA | Panicum virgatum | 75 | 696 | |
| Ceres CLONE ID no. 674166 | Ceres CLONE ID no. 2007485 | PRT | Panicum virgatum | 76 | 201 | AP2 |
| | Ceres CLONE ID no. 2033803 | DNA | Panicum virgatum | 77 | 698 | |
| Ceres Clone ID no. 30469 | Ceres CLONE ID no. 2033803 | PRT | Panicum virgatum | 78 | 156 | Globin |
| | Ceres CLONE ID no. 2034916 | DNA | Panicum virgatum | 79 | 724 | |
| Ceres CLONE ID no. 2403 | Ceres CLONE ID no. 2034916 | PRT | Panicum virqatum | 80 | 213 | ubiquitin |
| Ceres CLONE ID no. 2403 | Ceres CLONE ID no. 2034916 | PRT | Panicum virgatum | 80 | 213 | ubiquitin |
| Ceres CLONE ID no. 2403 | Ceres CLONE ID no. 2034916 | PRT | Panicum virgatum | 80 | 213 | ubiquitin |
| | Ceres CLONE ID no.651581 | DNA | Glycine max | 81 | 1194 | |
| Ceres CLONE ID no. 674166 | Ceres CLONE ID no. 651581 | PRT | Glycine max | 82 | 224 | AP2 |
| Ceres CLONE ID no. 674166 | Public GI ID no. 125550159 | PRT | Oryza sativa subsp. indica | 83 | 184 | AP2 |
| Ceres CLONE ID no. 674166 | Public GI ID no. 15223609 | PRT | Arabidopsis thaliana | 84 | 225 | AP2 |
| Ceres Clone ID no. 30087 | Public GI ID no. 30683885 | PRT | Arabidopsis thaliana | 85 | 164 | |
| Ceres CLONE ID no. 674166 | Public GI ID no. 56384582 | PRT | Pisum sativum | 86 | 218 | AP2 |
| Ceres CLONE ID no. 674166 | Public GI ID no. 57012880 | PRT | Nicotiana tabacum | 87 | 225 | AP2 |
| Ceres Clone ID no. 30469 | Public GI ID no. 62548111 | PRT | Gossypium hirsutum | 88 | 163 | Globin |
| Ceres CLONE ID no. 2403 | Ceres CLONE ID no. 100021733 | PRT | Gossypium hirsutum | 89 | 153 | ubiquitin |
| Ceres CLONE ID no. 2403 | Ceres CLONE ID no. 100021733 | PRT | Gossypium hirsutum | 89 | 153 | ubiquitin |

TABLE 7-continued

| | | | | | | |
|---|---|---|---|---|---|---|
| | Ceres CLONE ID no. 947579 | DNA | Brassica napus | 90 | 775 | |
| | Ceres CLONE ID no. 36046 | DNA | Arabidopsis thaliana | 91 | 1032 | |
| | Ceres CLONE ID no. 1606506 | DNA | Parthenium argentatum | 92 | 492 | |
| | Ceres CLONE ID no. 546001 | DNA | Glycine max | 93 | 970 | |
| | Ceres CLONE ID no. 1554560 | DNA | Zea mays | 94 | 604 | |
| | Ceres CLONE ID no. 839727 | DNA | Triticum aestivum | 95 | 846 | |
| | Ceres CLONE ID no. 664936 | DNA | Glycine max | 96 | 440 | |
| | Ceres CLONE ID no. 658438 | DNA | Glycine max | 97 | 463 | |
| | Ceres CLONE ID no. 1049262 | DNA | Glycine max | 98 | 458 | |
| | Ceres CLONE ID no. 632613 | DNA | Triticum aestivum | 99 | 600 | |
| | Ceres CLONE ID no. 1390976 | DNA | Zea mays | 100 | 546 | |
| | Ceres CLONE ID no. 1457185 | DNA | Zea mays | 101 | 550 | |
| | Ceres CLONE ID no. 1482731 | DNA | Zea mays | 102 | 668 | |
| | Ceres CLONE ID no. 522921 | DNA | Glycine max | 103 | 752 | |
| | Ceres CLONE ID no. 1036726 | DNA | Brassica napus | 104 | 484 | |
| | Ceres CLONE ID no. 513071 | DNA | Glycine max | 105 | 580 | |
| | Ceres CLONE ID no. 975672 | DNA | Brassica napus | 106 | 987 | |
| | Ceres CLONE ID no. 273307 | DNA | Zea mays | 107 | 1034 | |
| | Ceres CLONE ID no. 1055099 | DNA | Triticum aestivum | 108 | 911 | |
| Ceres Clone ID no. 30469 | Ceres GI ID no. GI_15226675 | PRT | Arabidopsis thaliana | 109 | 160 | Globin |
| | Ceres Promoter 21876 | DNA | Arabidopsis thaliana | 110 | 1823 | |
| | Ceres Promoter PT0668 | DNA | Arabidopsis thaliana | 111 | 1000 | |
| | Ceres Promoter PT0535 | DNA | Arabidopsis thaliana | 112 | 1000 | |
| | Ceres Promoter PT0585 | DNA | Arabidopsis thaliana | 113 | 999 | |
| | Ceres Promoter PT0613 | DNA | Arabidopsis thaliana | 114 | 1000 | |
| | Ceres Promoter PT0625 | DNA | Arabidopsis thaliana | 115 | 351 | |
| | Ceres Promoter PT0633 | DNA | Arabidopsis thaliana | 116 | 1022 | |
| | Ceres Promoter PT0650 | DNA | Arabidopsis thaliana | 117 | 1000 | |
| | Ceres Promoter PT0660 | DNA | Arabidopsis thaliana | 118 | 998 | |
| | Ceres Promoter PT0665 | DNA | Arabidopsis thaliana | 119 | 1000 | |
| | Ceres Promoter PT0672 | DNA | Arabidopsis thaliana | 120 | 999 | |
| | Ceres Promoter PT0676 | DNA | Arabidopsis thaliana | 121 | 1000 | |
| | Ceres Promoter PT0678 | DNA | Arabidopsis thaliana | 122 | 998 | |
| | Ceres Promoter PT0683 | DNA | Arabidopsis thaliana | 123 | 1000 | |
| | Ceres Promoter PT0688 | DNA | Arabidopsis thaliana | 124 | 1000 | |
| | Ceres Promoter PT0695 | DNA | Arabidopsis thaliana | 125 | 1000 | |
| | Ceres Promoter PT0708 | DNA | Arabidopsis thaliana | 126 | 1000 | |
| | Ceres Promoter PT0710 | DNA | Arabidopsis thaliana | 127 | 1000 | |
| | Ceres Promoter PT0723 | DNA | Arabidopsis thaliana | 128 | 1002 | |
| | Ceres Promoter PT0740 | DNA | Arabidopsis thaliana | 129 | 1001 | |
| | Ceres Promoter PT0743 | DNA | Arabidopsis thaliana | 130 | 1024 | |
| | Ceres Promoter PT0758 | DNA | Arabidopsis thaliana | 131 | 1000 | |
| | Ceres Promoter PT0829 | DNA | Arabidopsis thaliana | 132 | 921 | |
| | Ceres Promoter PT0837 | DNA | Arabidopsis thaliana | 133 | 763 | |
| | Ceres Promoter PT0838 | DNA | Arabidopsis thaliana | 134 | 751 | |
| | Ceres Promoter PT0848 | DNA | Arabidopsis thaliana | 135 | 669 | |
| | Ceres Promoter PT0863 | DNA | Arabidopsis thaliana | 136 | 702 | |
| | Ceres Promoter PT0879 | DNA | Arabidopsis thaliana | 137 | 435 | |
| | Ceres Promoter PT0886 | DNA | Arabidopsis thaliana | 138 | 397 | |
| | Ceres Promoter YP0007 | DNA | Arabidopsis thaliana | 139 | 1024 | |
| | Ceres Promoter YP0008 | DNA | Arabidopsis thaliana | 140 | 1000 | |
| | Ceres Promoter YP0019 | DNA | Arabidopsis thaliana | 141 | 999 | |
| | Ceres Promoter YP0028 | DNA | Arabidopsis thaliana | 142 | 1024 | |
| | Ceres Promoter YP0039 | DNA | Arabidopsis thaliana | 143 | 1024 | |
| | Ceres Promoter YP0050 | DNA | Arabidopsis thaliana | 144 | 1024 | |
| | Ceres Promoter YP0086 | DNA | Arabidopsis thaliana | 145 | 999 | |
| | Ceres Promoter YP0088 | DNA | Arabidopsis thaliana | 146 | 1024 | |
| | Ceres Promoter YP0092 | DNA | Arabidopsis thaliana | 147 | 1024 | |
| | Ceres Promoter YP0096 | DNA | Arabidopsis thaliana | 148 | 1020 | |
| | Ceres Promoter YP0097 | DNA | Arabidopsis thaliana | 149 | 1000 | |
| | Ceres Promoter YP0101 | DNA | Arabidopsis thaliana | 150 | 1004 | |
| | Ceres Promoter YP0102 | DNA | Arabidopsis thaliana | 151 | 1000 | |
| | Ceres Promoter YP0103 | DNA | Arabidopsis thaliana | 152 | 1004 | |
| | Ceres Promoter YP0107 | DNA | Arabidopsis thaliana | 153 | 1003 | |
| | Ceres Promoter YP0110 | DNA | Arabidopsis thaliana | 154 | 1024 | |
| | Ceres Promoter YP0111 | DNA | Arabidopsis thaliana | 155 | 1024 | |
| | Ceres Promoter YP0115 | DNA | Arabidopsis thaliana | 156 | 996 | |
| | Ceres Promoter YP0117 | DNA | Arabidopsis thaliana | 157 | 1024 | |
| | Ceres Promoter YP0119 | DNA | Arabidopsis thaliana | 158 | 1000 | |
| | Ceres Promoter YP0120 | DNA | Arabidopsis thaliana | 159 | 999 | |
| | Ceres Promoter YP0121 | DNA | Arabidopsis thaliana | 160 | 999 | |
| | Ceres Promoter YP0128 | DNA | Arabidopsis thaliana | 161 | 1004 | |
| | Ceres Promoter YP0137 | DNA | Arabidopsis thaliana | 162 | 1001 | |
| | Ceres Promoter YP0143 | DNA | Arabidopsis thaliana | 163 | 1001 | |
| | Ceres Promoter YP0144 | DNA | Arabidopsis thaliana | 164 | 1003 | |
| | Ceres Promoter YP0156 | DNA | Arabidopsis thaliana | 165 | 1004 | |
| | Ceres Promoter YP0158 | DNA | Arabidopsis thaliana | 166 | 1000 | |
| | Ceres Promoter YP0188 | DNA | Arabidopsis thaliana | 167 | 1005 | |
| | Ceres Promoter YP0190 | DNA | Arabidopsis thaliana | 168 | 1002 | |

TABLE 7-continued

| | | | | | | |
|---|---|---|---|---|---|---|
| | Ceres Promoter YP0212 | DNA | *Arabidopsis thaliana* | 169 | 995 | |
| | Ceres Promoter YP0214 | DNA | *Arabidopsis thaliana* | 170 | 1024 | |
| | Ceres Promoter YP0263 | DNA | *Arabidopsis thaliana* | 171 | 911 | |
| | Ceres Promoter YP0275 | DNA | *Arabidopsis thaliana* | 172 | 999 | |
| | Ceres Promoter YP0285 | DNA | *Arabidopsis thaliana* | 173 | 981 | |
| | Ceres Promoter YP0286 | DNA | *Arabidopsis thaliana* | 174 | 996 | |
| | Ceres Promoter YP0337 | DNA | *Arabidopsis thaliana* | 175 | 1000 | |
| | Ceres Promoter YP0356 | DNA | *Arabidopsis thaliana* | 176 | 1000 | |
| | Ceres Promoter YP0374 | DNA | *Arabidopsis thaliana* | 177 | 1000 | |
| | Ceres Promoter YP0377 | DNA | *Arabidopsis thaliana* | 178 | 998 | |
| | Ceres Promoter YP0380 | DNA | *Arabidopsis thaliana* | 179 | 999 | |
| | Ceres Promoter YP0381 | DNA | *Arabidopsis thaliana* | 180 | 1000 | |
| | Ceres Promoter YP0384 | DNA | *Arabidopsis thaliana* | 181 | 999 | |
| | Ceres Promoter YP0385 | DNA | *Arabidopsis thaliana* | 182 | 998 | |
| | Ceres Promoter YP0396 | DNA | *Arabidopsis thaliana* | 183 | 1000 | |
| | Ceres Promoter p13879 | DNA | *Arabidopsis thaliana* | 184 | 1514 | |
| | Ceres Promoter p326 | DNA | *Arabidopsis thaliana* | 185 | 1954 | |
| | Ceres Promoter p32449 | DNA | *Arabidopsis thaliana* | 186 | 2016 | |
| | Ceres Promoter PD1367 | DNA | *Arabidopsis thaliana* | 187 | 667 | |
| | Ceres Promoter p530c10 | DNA | *Oryza sativa* | 188 | 1836 | |
| | Ceres Promoter pOsFIE2-2 | DNA | *Oryza sativa* | 189 | 3000 | |
| | Ceres Promoter pOsMEA | DNA | *Oryza sativa* | 190 | 2023 | |
| | Ceres Promoter pOsYp102 | DNA | *Oryza sativa* | 191 | 2034 | |
| | Ceres Promoter pOsYp285 | DNA | *Oryza sativa* | 192 | 1877 | |
| | Ceres Promoter PT0565 | DNA | *Arabidopsis thaliana* | 193 | 1000 | |
| | Ceres Promoter YP0015 | DNA | *Arabidopsis thaliana* | 194 | 999 | |
| | Ceres Promoter YP0087 | DNA | *Arabidopsis thaliana* | 195 | 999 | |
| | Ceres Promoter YP0093 | DNA | *Arabidopsis thaliana* | 196 | 1000 | |
| | Ceres Promoter YP0108 | DNA | *Arabidopsis thaliana* | 197 | 999 | |
| | Ceres Promoter YP0022 | DNA | *Arabidopsis thaliana* | 198 | 999 | |
| | Ceres Promoter YP0080 | DNA | *Arabidopsis thaliana* | 199 | 999 | |
| | Ceres Promoter PR0924 | DNA | *Arabidopsis thaliana* | 200 | 3000 | |
| | Ceres Promoter YP0388 | DNA | *Arabidopsis thaliana* | 201 | 1000 | |
| | Ceres Promoter PD0901 | DNA | *Arabidopsis thaliana* | 202 | 283 | |
| | Ceres Promoter PT0623 | DNA | *Arabidopsis thaliana* | 203 | 1000 | |
| Ceres Clone ID no. 2403 | Truncated version of Ceres CLONE ID no. 100021733 | PRT | Artificial Sequence | 204 | 33 | ubiquitin |
| Ceres Clone ID no. 2403 | Truncated version of Ceres CLONE ID no. 1036726 | PRT | Artificial Sequence | 205 | 33 | ubiquitin |
| Ceres Clone ID no. 2403 | Truncated version of Ceres CLONE ID no. 1482731 | PRT | Artificial Sequence | 206 | 33 | ubiquitin |
| Ceres Clone ID no. 30469 | Truncated Version of Ceres CLONE ID no. 1554560 | PRT | Artificial Sequence | 207 | 80 | Globin |
| Ceres Clone ID no. 30469 | Truncated Version of Ceres CLONE ID no. 1802327 | PRT | Artificial Sequence | 208 | 77 | Globin |
| Ceres Clone ID no. 30469 | Truncated Version of Ceres CLONE ID no. 1876458 | PRT | Artificial Sequence | 209 | 77 | Globin |
| Ceres Clone ID no. 30469 | Truncated Version of Ceres CLONE ID no. 1879148 | PRT | Artificial Sequence | 210 | 79 | Globin |
| Ceres Clone ID no. 2403 | Truncated version of Ceres CLONE ID no. 1884696 | PRT | Artificial Sequence | 211 | 33 | ubiquitin |
| Ceres Clone ID no. 30469 | Truncated Version of Ceres CLONE ID no. 1916866 | PRT | Artificial Sequence | 212 | 76 | Globin |
| Ceres Clone ID no. 2403 | Truncated version of Ceres CLONE ID no. 1950105 | PRT | Artificial Sequence | 213 | 33 | ubiquitin |
| Ceres Clone ID no. 30469 | Truncated Version of Ceres CLONE ID no. 1990746 | PRT | Artificial Sequence | 214 | 79 | Globin |
| Ceres Clone ID no. 30469 | Truncated Version of Ceres CLONE ID no. 2033803 | PRT | Artificial Sequence | 215 | 79 | Globin |
| Ceres Clone ID no. 2403 | Truncated version of Ceres CLONE ID no. 2034916 | PRT | Artificial Sequence | 216 | 33 | ubiquitin |
| Ceres Clone ID no. 2403 | Truncated version of Ceres CLONE ID no. 513071 | PRT | Artificial Sequence | 217 | 33 | ubiquitin |
| Ceres Clone ID no. 2403 | Truncated version of Ceres CLONE ID no. 522921 | PRT | Artificial Sequence | 218 | 33 | ubiquitin |
| Ceres Clone ID no. 30469 | Truncated Version of Ceres CLONE ID no. 546001 | PRT | Artificial Sequence | 219 | 76 | Globin |
| Ceres Clone ID no. 30469 | Truncated Version of Ceres CLONE ID no. 651581 | PRT | Artificial Sequence | 220 | 76 | Globin |
| Ceres Clone ID no. 30469 | Truncated Version of Ceres CLONE ID no. 839727 | PRT | Artificial Sequence | 221 | 77 | Globin |
| Ceres Clone ID no. 30469 | Truncated Version of Public GI ID no. 11095158 | PRT | Artificial Sequence | 222 | 76 | Globin |
| Ceres Clone ID no. 30469 | Truncated Version of Public GI ID no. 12963875 | PRT | Artificial Sequence | 223 | 71 | Globin |
| Ceres Clone ID no. 30469 | Truncated Version of Public GI ID no. 14701800 | PRT | Artificial Sequence | 224 | 84 | Globin |
| Ceres Clone ID no. 30469 | Truncated Version of Public GI ID no. 15226675 | PRT | Artificial Sequence | 225 | 76 | Globin |

TABLE 7-continued

| Ceres Clone ID no. 30469 | Truncated Version of Public GI ID no. 15824736 | PRT | Artificial Sequence | 226 | 76 | Globin |
| Ceres Clone ID no. 30469 | Truncated Version of Public GI ID no. 30909306 | PRT | Artificial Sequence | 227 | 76 | Globin |
| Ceres Clone ID no. 30469 | Truncated Version of Public GI ID no. 37903656 | PRT | Artificial Sequence | 228 | 73 | Globin |
| Ceres Clone ID no. 30469 | Truncated Version of Public GI ID no. 62548111 | PRT | Artificial Sequence | 229 | 76 | Globin |

| Query Identifier | Functional Homolog | Pfam Description | Start | End | Profile | HMM Bit Score | FL_Profile | FL_Score |
|---|---|---|---|---|---|---|---|---|
| Ceres CLONE ID no. 30087 | Ceres CLONE ID no. 30087 | | | | | | | |
| Ceres CLONE ID no. 30087 | Ceres CLONE ID no. 30087 | | | | Y | | | |
| Ceres Clone ID no. 30087 | Ceres Clone ID no. 947579 | | | | Y | | | |
| Ceres Clone ID no. 30087 | Public GI no. 62526422 | | | | | | | |
| Ceres Clone ID no. 30087 | Ceres CLONE ID no. 1606506 | | | | Y | | | |
| Ceres CLONE ID no. 30469 | Ceres CLONE ID no. 30469 | Globin | 13 | 74 | Y | 184.6 | | 66 |
| Ceres Clone ID no. 30469 | Ceres CLONE ID no. 30469_FL | Globin | 13 | 152 | | 184.6 | Y | 404.9 |
| Ceres Clone ID no. 30469 | Public GI no. 30909306 | Globin | 13 | 152 | | 185.7 | Y | 410.4 |
| Ceres Clone ID no. 30469 | Public GI no. 37903656 | Globin | 10 | 149 | | 172.6 | | 387.2 |
| Ceres Clone ID no. 30469 | Public GI no. 15824736 | Globin | 13 | 152 | | 184.2 | | 405.4 |
| Ceres Clone ID no. 30469 | Ceres CLONE ID no. 546001 | Globin | 13 | 152 | | 182.8 | Y | 402.3 |
| Ceres Clone ID no. 30469 | Public GI no. 11095158 | Globin | 13 | 152 | | 167.8 | | 387.2 |
| Ceres Clone ID no. 30469 | Public GI no. 12963875 | Globin | 8 | 147 | | 145.8 | | 337.1 |
| Ceres Clone ID no. 30469 | Ceres CLONE ID no. 1554560 | Globin | 17 | 157 | | 185.7 | Y | 404.5 |
| Ceres Clone ID no. 30469 | Ceres CLONE ID no. 839727 | Globin | 14 | 154 | | 187.8 | Y | 415.2 |
| Ceres Clone ID no. 30469 | Public GI no. 14701800 | Globin | 21 | 161 | | 170.1 | | 386.9 |
| Ceres CLONE ID no. 271922 | Ceres CLONE ID no. 271922 | Ribosomal L37ae protein family | 2 | 91 | Y | 266.3 | | |
| Ceres Clone ID no. 271922 | Public GI no. 4090257 | Ribosomal L37ae protein family | 2 | 91 | | 265.8 | | |
| Ceres Clone ID no. 271922 | Public GI no. 4741896 | Ribosomal L37ae protein family | 2 | 91 | | 264 | | |
| Ceres Clone ID no. 271922 | Ceres CLONE ID no. 36046 | Ribosomal L37ae protein family | 2 | 91 | | 257.8 | | |
| Ceres Clone ID no. 271922 | Public GI no. 6016699 | Ribosomal L37ae protein family | 2 | 91 | | 257.4 | | |
| Ceres Clone ID no. 271922 | Ceres CLONE ID no. 664936 | Ribosomal L37ae protein family | 2 | 91 | Y | 268.8 | | |
| Ceres Clone ID no. 271922 | Ceres CLONE ID no. 658438 | Ribosomal L37ae protein family | 2 | 91 | | 269 | | |
| Ceres Clone ID no. 271922 | Ceres CLONE ID no. 1049262 | Ribosomal L37ae protein family | 2 | 91 | | 268.9 | | |
| Ceres Clone ID no. 271922 | Ceres CLONE ID no. 632613 | Ribosomal L37ae protein family | 2 | 91 | Y | 269 | | |
| Ceres Clone ID no. 271922 | Ceres CLONE ID no. 1390976 | Ribosomal L37ae protein family | 2 | 91 | Y | 269 | | |
| Ceres Clone ID no. 271922 | Ceres CLONE ID no. 1457185 | Ribosomal L37ae protein family | 2 | 91 | | 269 | | |
| Ceres Clone ID no. 271922 | Public GI no. 56202147 | Ribosomal L37ae protein family | 2 | 91 | | 269 | | |

TABLE 7-continued

| | | | | | | | |
|---|---|---|---|---|---|---|---|
| Ceres Clone ID no. 271922 | Public GI no. 58578274 | Ribosomal L37ae protein family | 2 | 91 | | 267.2 | |
| Ceres CLONE ID no. 2403 | Ceres CLONE ID no. 2403_FL | Ubiquitin family | 1 | 74 | | 118.7 | 416.2 |
| Ceres CLONE ID no. 2403 | Ceres CLONE ID no. 2403_FL | Ubiquitin family | 77 | 150 | | 118.7 | Y | 416.2 |
| Ceres Clone ID no. 2403 | Ceres CLONE ID no. 1482731 | Ubiquitin family | 1 | 74 | | 118.3 | Y | 417 |
| Ceres Clone ID no. 2403 | Ceres CLONE ID no. 1482731 | Ubiquitin family | 77 | 150 | | 118.3 | Y | 417 |
| Ceres Clone ID no. 2403 | Ceres CLONE ID no. 522921 | Ubiquitin family | 1 | 74 | | 118.7 | Y | 418.4 |
| Ceres Clone ID no. 2403 | Ceres CLONE ID no. 522921 | Ubiquitin family | 77 | 150 | | 118.7 | Y | 418.4 |
| Ceres Clone ID no. 2403 | Ceres CLONE ID no. 1036726 | Ubiquitin family | 1 | 74 | | 118.7 | Y | 384.4 |
| Ceres Clone ID no. 2403 | Ceres CLONE ID no. 1036726 | Ubiquitin family | 77 | 142 | | 118.7 | Y | 384.4 |
| Ceres Clone ID no. 2403 | Ceres CLONE ID no. 513071 | Ubiquitin family | 1 | 74 | | 114.3 | | 408.6 |
| Ceres Clone ID no. 2403 | Ceres CLONE ID no. 513071 | Ubiquitin family | 77 | 150 | | 114.3 | | 408.6 |
| Ceres CLONE ID no. 2403 | Ceres CLONE ID no. 2403 | Ubiquitin family | 1 | 33 | Y | 87.6 | | −83.1 |
| Ceres CLONE ID no. 674166 | Ceres CLONE ID no. 674166 | AP2 domain | 26 | 89 | Y | 491.8 | |
| Ceres Clone ID no. 674166 | Public GI no. 12322345 | AP2 domain | 26 | 89 | | 522.4 | |
| Ceres Clone ID no. 674166 | Ceres CLONE ID no. 975672 | AP2 domain | 21 | 84 | Y | 481.7 | |
| Ceres Clone ID no. 674166 | Ceres CLONE ID no. 273307 | AP2 domain | 17 | 80 | Y | 419.7 | |
| Ceres Clone ID no. 674166 | Ceres CLONE ID no. 1055099 | AP2 domain | 20 | 83 | Y | 358.4 | |
| Ceres CLONE ID no. 674166 | Ceres ANNOT ID no. 1441430 | AP2 domain | 29 | 92 | Y | 504.4 | |
| Ceres CLONE ID no. 674166 | Ceres CLONE ID no. 1240330 | AP2 domain | 24 | 87 | | 483.3 | |
| Ceres CLONE ID no. 30087 | Ceres CLONE ID no. 1382611 | | | | Y | | |
| Ceres CLONE ID no. 271922 | Ceres CLONE ID no. 1627907 | Ribosomal L37ae protein family | 2 | 91 | Y | 268.1 | |
| Ceres CLONE ID no. 674166 | Ceres CLONE ID no. 1761125 | AP2 domain | 13 | 76 | Y | 363 | |
| Ceres CLONE ID no. 271922 | Ceres CLONE ID no. 1783890 | Ribosomal L37ae protein family | 2 | 91 | Y | 269 | |
| Ceres Clone ID no. 30469 | Ceres CLONE ID no. 1802327 | Globin | 14 | 154 | | 191.4 | Y | 417.9 |
| Ceres CLONE ID no. 674166 | Ceres CLONE ID no. 1838364 | AP2 domain | 28 | 91 | Y | 484.1 | |
| Ceres Clone ID no. 30469 | Ceres CLONE ID no. 1876458 | Globin | 14 | 154 | | 191.9 | | 415.3 |
| Ceres Clone ID no. 30469 | Ceres CLONE ID no. 1879148 | Globin | 16 | 156 | | 185.7 | | 411.2 |
| Ceres CLONE ID no. 2403 | Ceres CLONE ID no. 1884696 | Ubiquitin family | 1 | 74 | | 175.2 | Y | 408 |
| Ceres CLONE ID no. 2403 | Ceres CLONE ID no. 1884696 | Ubiquitin family | 77 | 150 | | 175.2 | Y | 408 |
| Ceres Clone ID no. 30469 | Ceres CLONE ID no. 1916866 | Globin | 13 | 152 | | 188.3 | Y | 409.8 |
| Ceres CLONE ID no. 2403 | Ceres CLONE ID no. 1950105 | Ubiquitin family | 1 | 74 | | 262.8 | | 504.1 |

TABLE 7-continued

| | | | | | | | |
|---|---|---|---|---|---|---|---|
| Ceres CLONE ID no. 2403 | Ceres CLONE ID no. 1950105 | Ubiquitin family | 77 | 150 | 262.8 | | 504.1 |
| Ceres CLONE ID no. 2403 | Ceres CLONE ID no. 1950105 | Ubiquitin family | 153 | 226 | 262.8 | | 504.1 |
| Ceres Clone ID no. 30469 | Ceres CLONE ID no. 1990746 Ceres CLONE ID no. 1990746 | Globin | 16 | 156 | 184.9 | | 405.6 |
| Ceres CLONE ID no. 674166 | Ceres CLONE ID no. 2007485 Ceres CLONE ID no. 2007485 | AP2 domain | 17 | 80 | 369.2 271.2 | | |
| Ceres Clone ID no. 30469 | Ceres CLONE ID no. 2033803 Ceres CLONE ID no. 2033803 | Globin | 16 | 148 | 184.9 | | 369.2 |
| Ceres CLONE ID no. 2403 | Ceres CLONE ID no. 2034916 Ceres CLONE ID no. 2034916 | Ubiquitin family | 1 | 74 | 259.2 | Y | 460.4 |
| Ceres CLONE ID no. 2403 | Ceres CLONE ID no. 2034916 | Ubiquitin family | 77 | 150 | 259.2 | Y | 460.4 |
| Ceres CLONE ID no. 2403 | Ceres CLONE ID no. 2034916 | Ubiquitin family | 153 | 213 | 259.2 | Y | 460.4 |
| Ceres CLONE ID no. 674166 | Ceres CLONE ID no.651581 Ceres CLONE ID no. 651581 | AP2 domain | 24 | 87 | 469.5 | | |
| Ceres CLONE ID no. 674166 | Public GI ID no. 125550159 | AP2 domain | 7 | 70 | Y | 344 | |
| Ceres CLONE ID no. 674166 | Public GI ID no. 15223609 | AP2 domain | 26 | 89 | Y | 522.4 | |
| Ceres CLONE ID no. 30087 | Public GI ID no. 30683885 | | | | | | |
| Ceres CLONE ID no. 674166 | Public GI ID no. 56384582 | AP2 domain | 21 | 84 | Y | 484.2 | |
| Ceres CLONE ID no. 674166 | Public GI ID no. 57012880 | AP2 domain | 26 | 89 | Y | 521.4 | |
| Ceres Clone ID no. 30469 | Public GI ID no. 62548111 | Globin | 13 | 152 | 188.3 | | 409.8 |
| Ceres CLONE ID no. 2403 | Ceres CLONE ID no. 100021733 | Ubiquitin family | 1 | 74 | 175.2 | | 410.3 |
| Ceres CLONE ID no. 2403 | Ceres CLONE ID no. 100021733 | Ubiquitin family | 77 | 150 | 175.2 | | 410.3 |
| | Ceres CLONE ID no. 947579 Ceres CLONE ID no. 36046 Ceres CLONE ID no. 1606506 Ceres CLONE ID no. 546001 Ceres CLONE ID no. 1554560 Ceres CLONE ID no. 839727 Ceres CLONE ID no. 664936 Ceres CLONE ID no. 658438 Ceres CLONE ID no. 1049262 Ceres CLONE ID no. 632613 Ceres CLONE ID no. 1390976 Ceres CLONE ID no. 1457185 Ceres CLONE ID no. 1482731 Ceres CLONE ID no. 522921 Ceres CLONE ID no. 1036726 Ceres CLONE ID no. 513071 Ceres CLONE ID no. 975672 Ceres CLONE ID no. 273307 Ceres CLONE ID no. 1055099 | | | | | | |
| Ceres Clone ID no. 30469 | Ceres GI ID no. GI_15226675 Ceres Promoter 21876 Ceres Promoter PT0668 Ceres Promoter PT0535 Ceres Promoter PT0585 Ceres Promoter PT0613 Ceres Promoter PT0625 Ceres Promoter PT0633 Ceres Promoter PT0650 Ceres Promoter PT0660 Ceres Promoter PT0665 Ceres Promoter PT0672 Ceres Promoter PT0676 Ceres Promoter PT0678 Ceres Promoter PT0683 Ceres Promoter PT0688 Ceres Promoter PT0695 Ceres Promoter PT0708 Ceres Promoter PT0710 Ceres Promoter PT0723 Ceres Promoter PT0740 Ceres Promoter PT0743 Ceres Promoter PT0758 Ceres Promoter PT0829 Ceres Promoter PT0837 Ceres Promoter PT0838 | Globin | 13 | 152 | 184.6 | | 404.9 |

TABLE 7-continued

| | | | | | | | |
|---|---|---|---|---|---|---|---|
| | Ceres Promoter PT0848 | | | | | | |
| | Ceres Promoter PT0863 | | | | | | |
| | Ceres Promoter PT0879 | | | | | | |
| | Ceres Promoter PT0886 | | | | | | |
| | Ceres Promoter YP0007 | | | | | | |
| | Ceres Promoter YP0008 | | | | | | |
| | Ceres Promoter YP0019 | | | | | | |
| | Ceres Promoter YP0028 | | | | | | |
| | Ceres Promoter YP0039 | | | | | | |
| | Ceres Promoter YP0050 | | | | | | |
| | Ceres Promoter YP0086 | | | | | | |
| | Ceres Promoter YP0088 | | | | | | |
| | Ceres Promoter YP0092 | | | | | | |
| | Ceres Promoter YP0096 | | | | | | |
| | Ceres Promoter YP0097 | | | | | | |
| | Ceres Promoter YP0101 | | | | | | |
| | Ceres Promoter YP0102 | | | | | | |
| | Ceres Promoter YP0103 | | | | | | |
| | Ceres Promoter YP0107 | | | | | | |
| | Ceres Promoter YP0110 | | | | | | |
| | Ceres Promoter YP0111 | | | | | | |
| | Ceres Promoter YP0115 | | | | | | |
| | Ceres Promoter YP0117 | | | | | | |
| | Ceres Promoter YP0119 | | | | | | |
| | Ceres Promoter YP0120 | | | | | | |
| | Ceres Promoter YP0121 | | | | | | |
| | Ceres Promoter YP0128 | | | | | | |
| | Ceres Promoter YP0137 | | | | | | |
| | Ceres Promoter YP0143 | | | | | | |
| | Ceres Promoter YP0144 | | | | | | |
| | Ceres Promoter YP0156 | | | | | | |
| | Ceres Promoter YP0158 | | | | | | |
| | Ceres Promoter YP0188 | | | | | | |
| | Ceres Promoter YP0190 | | | | | | |
| | Ceres Promoter YP0212 | | | | | | |
| | Ceres Promoter YP0214 | | | | | | |
| | Ceres Promoter YP0263 | | | | | | |
| | Ceres Promoter YP0275 | | | | | | |
| | Ceres Promoter YP0285 | | | | | | |
| | Ceres Promoter YP0286 | | | | | | |
| | Ceres Promoter YP0337 | | | | | | |
| | Ceres Promoter YP0356 | | | | | | |
| | Ceres Promoter YP0374 | | | | | | |
| | Ceres Promoter YP0377 | | | | | | |
| | Ceres Promoter YP0380 | | | | | | |
| | Ceres Promoter YP0381 | | | | | | |
| | Ceres Promoter YP0384 | | | | | | |
| | Ceres Promoter YP0385 | | | | | | |
| | Ceres Promoter YP0396 | | | | | | |
| | Ceres Promoter p13879 | | | | | | |
| | Ceres Promoter p326 | | | | | | |
| | Ceres Promoter p32449 | | | | | | |
| | Ceres Promoter PD1367 | | | | | | |
| | Ceres Promoter p530c10 | | | | | | |
| | Ceres Promoter pOsFIE2-2 | | | | | | |
| | Ceres Promoter pOsMEA | | | | | | |
| | Ceres Promoter pOsYp102 | | | | | | |
| | Ceres Promoter pOsYp285 | | | | | | |
| | Ceres Promoter PT0565 | | | | | | |
| | Ceres Promoter YP0015 | | | | | | |
| | Ceres Promoter YP0087 | | | | | | |
| | Ceres Promoter YP0093 | | | | | | |
| | Ceres Promoter YP0108 | | | | | | |
| | Ceres Promoter YP0022 | | | | | | |
| | Ceres Promoter YP0080 | | | | | | |
| | Ceres Promoter PR0924 | | | | | | |
| | Ceres Promoter YP0388 | | | | | | |
| | Ceres Promoter PD0901 | | | | | | |
| | Ceres Promoter PT0623 | | | | | | |
| Ceres Clone ID no. 2403 | Truncated version of Ceres CLONE ID no. 100021733 | Ubiquitin family | 1 | 33 | | 87.6 | −83.1 |
| Ceres Clone ID no. 2403 | Truncated version of Ceres CLONE ID no. 1036726 | Ubiquitin family | 1 | 33 | Y | 87.6 | −83.1 |
| Ceres Clone ID no. 2403 | Truncated version of Ceres CLONE ID no. 1482731 | Ubiquitin family | 1 | 33 | Y | 87.1 | −85 |
| Ceres Clone ID no. 30469 | Truncated Version of Ceres CLONE ID no. 1554560 | Globin | 17 | 78 | Y | 185.7 | 61.3 |
| Ceres Clone ID no. 30469 | Truncated Version of Ceres CLONE ID no. 1802327 | Globin | 14 | 75 | Y | 191.4 | 67.2 |

TABLE 7-continued

| | | | | | | | |
|---|---|---|---|---|---|---|---|
| Ceres Clone ID no. 30469 | Truncated Version of Ceres CLONE ID no. 1876458 | Globin | 14 | 75 | | 191.9 | 67.7 |
| Ceres Clone ID no. 30469 | Truncated Version of Ceres CLONE ID no. 1879148 | Globin | 16 | 77 | | 185.7 | 61.3 |
| Ceres Clone ID no. 2403 | Truncated version of Ceres CLONE ID no. 1884696 | Ubiquitin family | 1 | 33 | Y | 87.6 | 65 |
| Ceres Clone ID no. 30469 | Truncated Version of Ceres CLONE ID no. 1916866 | Globin | 13 | 74 | Y | 188.3 | 65 |
| Ceres Clone ID no. 2403 | Truncated version of Ceres CLONE ID no. 1950105 | Ubiquitin family | 1 | 33 | Y | 87.6 | 60.7 |
| Ceres Clone ID no. 30469 | Truncated Version of Ceres CLONE ID no. 1990746 | Globin | 16 | 77 | | 184.9 | 60.7 |
| Ceres Clone ID no. 30469 | Truncated Version of Ceres CLONE ID no. 2033803 | Globin | 16 | 77 | | 184.9 | 60.7 |
| Ceres Clone ID no. 2403 | Truncated version of Ceres CLONE ID no. 2034916 | Ubiquitin family | 1 | 33 | | 87.6 | 63.3 |
| Ceres Clone ID no. 2403 | Truncated version of Ceres CLONE ID no. 513071 | Ubiquitin family | 1 | 33 | | 85.9 | 44.7 |
| Ceres Clone ID no. 2403 | Truncated version of Ceres CLONE ID no. 522921 | Ubiquitin family | 1 | 33 | Y | 87.6 | 22.4 |
| Ceres Clone ID no. 30469 | Truncated Version of Ceres CLONE ID no. 546001 | Globin | 13 | 74 | Y | 182.8 | 59.6 |
| Ceres Clone ID no. 30469 | Truncated Version of Ceres CLONE ID no. 651581 | Globin | 13 | 74 | | 185.7 | 63.9 |
| Ceres Clone ID no. 30469 | Truncated Version of Ceres CLONE ID no. 839727 | Globin | 14 | 75 | Y | 187.8 | 63.3 |
| Ceres Clone ID no. 30469 | Truncated Version of Public GI ID no. 11095158 | Globin | 13 | 76 | | 167.8 | 44.7 |
| Ceres Clone ID no. 30469 | Truncated Version of Public GI ID no. 12963875 | Globin | 8 | 69 | | 145.8 | 22.4 |
| Ceres Clone ID no. 30469 | Truncated Version of Public GI ID no. 14701800 | Globin | 21 | 82 | | 170.1 | 45.8 |
| Ceres Clone ID no. 30469 | Truncated Version of Public GI ID no. 15226675 | Globin | 13 | 74 | | 184.6 | 63 |
| Ceres Clone ID no. 30469 | Truncated Version of Public GI ID no. 15824736 | Globin | 13 | 74 | | 184.2 | 60.9 |
| Ceres Clone ID no. 30469 | Truncated Version of Public GI ID no. 30909306 | Globin | 13 | 74 | Y | 185.7 | 63.9 |
| Ceres Clone ID no. 30469 | Truncated Version of Public GI ID no. 37903656 | Globin | 10 | 71 | | 172.6 | 49.6 |
| Ceres Clone ID no. 30469 | Truncated Version of Public GI ID no. 62548111 | Globin | 13 | 74 | | 188.3 | 65 |

The invention claimed is:

1. A method of producing a plant, said method comprising growing plant cells transformed with an exogenous nucleic acid, said exogenous nucleic acid comprising a polynucleotide operably linked to a heterologous promoter, said polynucleotide comprising a nucleotide sequence encoding a polypeptide that is 33 amino acids long and comprising an amino acid sequence having 95 percent or greater amino acid sequence identity to the amino acid sequence of SEQ ID NO:40;
   producing transformed plants from said transformed plant cells; and
   selecting for a transformed plant from said transformed plants that overexpresses said polypeptide and has an increased level of cold tolerance as compared to the corresponding level in tolerance to cold of a control plant of the same species grown under identical conditions and that does not comprise said exogenous nucleic acid.

2. The method of claim 1, wherein said polypeptide comprises the amino acid sequence of SEQ ID NO:40.

3. The method of claim 1, wherein said polypeptide comprises an amino acid sequence that has 97 percent or greater amino acid sequence identity to the amino acid sequence of SEQ ID NO:40.

4. The method of claim 1, wherein said polypeptide comprises an amino acid sequence that has 99 percent or greater amino acid sequence identity to the amino acid sequence of SEQ ID NO:40.

5. The method of claim 1, wherein said plant is a member of a species selected from the group consisting of *Panicum virgatum, Sorghum bicolor, Miscanthus giganteus, Saccharum* sp., *Populus balsamifera, Zea mays, Glycine max, Brassica napus, Triticum aestivum, Gossypium hirsutum, Oryza sativa, Helianthus annuus, Medicago sativa, Beta vulgaris*, and *Pennisetum glaucum*.

* * * * *

SEQUENCE LISTING

```
<160> NUMBER OF SEQ ID NOS: 229

<210> SEQ ID NO 1
<211> LENGTH: 828
<212> TYPE: DNA
<213> ORGANISM: Arabidopsis thaliana
<220> FEATURE:
<221> NAME/KEY: misc_feature
<223> OTHER INFORMATION: Ceres CLONE ID no. 30087
<220> FEATURE:
<221> NAME/KEY: misc_feature
<223> OTHER INFORMATION: Ceres SEED LINE ID no. ME01451
<220> FEATURE:
<221> NAME/KEY: misc_feature
<223> OTHER INFORMATION: Encodes the protein at SEQ ID NO: 2

<400> SEQUENCE: 1 aactttctc tcccactctt tcttttacta ctctcacaca tatctctgtc tatatatcac      60
tttacataaa ccactattcc acacacaaac acacatagcc atggcctctt ctttctcttc     120
acaagccttc ttcttgctca cattgtctat ggttttaatt cctttctctt tagctcaagc     180
tcccatgatg gctccttctg gctcaatgtc catgccgcct atgtctagcg gcggtggaag     240
ctcggttcct cctccagtga tgtctccgat gccaatgatg actccaccac ctatgcctat     300
gactccatca cccatgccca tgactccacc acctatgcct atggctccac caccaatgcc     360
```

-continued

```
catggcttca ccaccaatga tgccaatgac tccatctaca agcccaagcc cattaacagt    420
tccggatatg ccttcgccgc cgatgccatc cggaatggaa tcttcacctt ctccaggacc    480
catgccaccg gcaatggcgg cttcgccgga ttcgggagct ttcaatgtta gaaacaacgt    540
cgtaacactt tcatgcgttg ttggagttgt tgcagctcat tttctcctcg tttgaaatga    600
ttattgaatt ggtcagcctc gatcgttttc ttgtaattta ctttcatatt tttttttccct   660 caaattatta gtggtcatca ttttataata tttgagtttg tgtttgatgt acgattcaga    720
catttgtttg cattatgtgc ttaataagtt tatcgttgac tctacttgaa gagagacttt    780
gtgtgtgatg taaatttctt ctatctatgg aacattgcat tcgtagcc                 828
```

<210> SEQ ID NO 2
<211> LENGTH: 164
<212> TYPE: PRT
<213> ORGANISM: Arabidopsis thaliana
<220> FEATURE:
<221> NAME/KEY: misc_feature
<223> OTHER INFORMATION: Ceres CLONE ID no. 30087
<220> FEATURE:
<221> NAME/KEY: misc_feature
<223> OTHER INFORMATION: Ceres SEED LINE ID no. ME01451

<400> SEQUENCE: 2

```
Met Ala Ser Ser Phe Ser Ser Gln Ala Phe Phe Leu Leu Thr Leu Ser
1               5                   10                  15

Met Val Leu Ile Pro Phe Ser Leu Ala Gln Ala Pro Met Met Ala Pro
            20                  25                  30

Ser Gly Ser Met Ser Met Pro Pro Met Ser Ser Gly Gly Gly Ser Ser
        35                  40                  45

Val Pro Pro Val Met Ser Pro Met Pro Met Met Thr Pro Pro Pro
    50                  55                  60

Met Pro Met Thr Pro Ser Pro Met Pro Met Thr Pro Pro Pro Met Pro
65                  70                  75                  80

Met Ala Pro Pro Met Pro Met Ala Ser Pro Pro Met Met Pro Met
            85                  90                  95

Thr Pro Ser Thr Ser Pro Ser Pro Leu Thr Val Pro Asp Met Pro Ser
            100                 105                 110

Pro Pro Met Pro Ser Gly Met Glu Ser Ser Pro Ser Pro Gly Pro Met
        115                 120                 125

Pro Pro Ala Met Ala Ala Ser Pro Asp Ser Gly Ala Phe Asn Val Arg
    130                 135                 140

Asn Asn Val Val Thr Leu Ser Cys Val Val Gly Val Val Ala Ala His
145                 150                 155                 160

Phe Leu Leu Val
```

<210> SEQ ID NO 3
<211> LENGTH: 155
<212> TYPE: PRT
<213> ORGANISM: Brassica napus
<220> FEATURE:
<221> NAME/KEY: misc_feature
<223> OTHER INFORMATION: Ceres CLONE ID no. 947579
<220> FEATURE:
<221> NAME/KEY: misc_feature
<223> OTHER INFORMATION: Functional homolog of Ceres Clone ID no. 30087
         given in SEQ ID NO: 2

```
<400> SEQUENCE: 3

Met Ala Ala Ser Gln Ala Phe Leu Leu Leu Thr Leu Ser Met Ala Leu
1               5                   10                  15

Val His Phe Ser Leu Ala Gln Ser Pro Met Met Ala Pro Ser Gly Ser
                20                  25                  30

Met Ser Met Pro Pro Met Pro Ser Gly Gly Ser Pro Met Pro Met Met
            35                  40                  45

Thr Pro Pro Pro Met Pro Met Met Thr Pro Pro Met Pro Met Ala Met Ala
    50                  55                  60

Pro Pro Pro Met Pro Met Thr Pro Pro Met Pro Met Ala Pro Met
65              70                  75                  80

Pro Met Thr Pro Ser Ser Pro Met Ser Pro Pro Thr Thr Met Ala
                85                  90                  95

Pro Ser Pro Glu Thr Val Pro Asp Met Ala Ser Pro Pro Met Met Pro
                100                 105                 110

Gly Met Glu Ser Ser Pro Ser Pro Gly Pro Met Pro Pro Ala Met Ala
            115                 120                 125

Ser Pro Asp Ser Gly Ala Phe Asn Val Arg Asn Asp Val Val Ala Ile
    130                 135                 140

Ser Phe Leu Val Ala Ala His Leu Leu Leu Val
145                 150                 155

<210> SEQ ID NO 4
<211> LENGTH: 152
<212> TYPE: PRT
<213> ORGANISM: Brassica napus
<220> FEATURE:
<221> NAME/KEY: misc_feature
<223> OTHER INFORMATION: Public GI no. 62526422
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 4

Met Ala Leu Ser His Pro Met Thr Ile Phe Ser Leu Phe Leu Thr Phe
1               5                   10                  15

Leu Ala Leu Thr Ala Ala Gln Ser Pro Met Met Ala Pro Thr Met Pro
                20                  25                  30

Pro Ser Thr Met Ser Met Pro Pro Thr Thr Ser Thr Thr Thr Pro Pro
            35                  40                  45

Pro Met Ser Ser Met Ser Pro Pro Pro Ser Ala Met Ser Pro Thr Pro
    50                  55                  60

Ser Thr Met Ser Pro Pro Pro Met Ser Pro Met Thr Pro Ser Met Ser
65              70                  75                  80

Pro Met Gly Pro Met Thr Pro Thr Met Ser Pro Met Asp Ser Pro Pro
                85                  90                  95

Ala Pro Ala Gly Pro Gly Met Ala Pro Gly Met Ser Thr Pro Gly Pro
                100                 105                 110

Ala Pro Gly Pro Met Gly Gly Glu Ser Met Ala Ser Pro Pro Pro Ser
            115                 120                 125

Ser Gly Phe Val His Gly Ile Ser Ile Ser Met Ala Met Val Ala Ile
    130                 135                 140

Ile Gly Ser Val Ala Leu Phe Phe
145                 150
```

<210> SEQ ID NO 5
<211> LENGTH: 150
<212> TYPE: PRT
<213> ORGANISM: Parthenium argentatum
<220> FEATURE:
<221> NAME/KEY: misc_feature
<223> OTHER INFORMATION: Ceres CLONE ID no. 1606506
<220> FEATURE:
<221> NAME/KEY: misc_feature
<223> OTHER INFORMATION: Functional homolog of Ceres Clone ID no. 30087
     given in SEQ ID NO: 2

<400> SEQUENCE: 5

```
Met Ala Val Ser Arg Tyr Ile Ile Leu Leu Ser Phe Thr Tyr Leu
1               5                   10                  15

Ala Ala Phe Ser Thr Ala Gln Ala Pro Ser Met Ser Pro Met Met Met
                20                  25                  30

Pro Met Ala Pro Pro Pro Ser Thr Met Pro Met Thr Pro Pro Pro Ser
            35                  40                  45

Thr Met Pro Met Thr Pro Pro Thr Pro Met Thr Met Thr Pro Pro
        50                  55                  60

Pro Met Met Met Pro Met Thr Pro Pro Met Pro Met Gly Thr Pro
65                  70                  75                  80

Pro Met Thr Met Pro Met Gly Pro Pro Met Met Met Pro Met Ser
                85                  90                  95

Pro Gly Pro Ser Met Met Pro Ala Ser Pro Pro Ser Pro Met Gly Pro
            100                 105                 110

Ser Met Ala Pro Glu Pro Ala Thr Met Ser Pro Gly Pro Ser Met Thr
        115                 120                 125

Pro Ala Glu Thr Pro Ala Ser Gly Ala Ile Met Gln Tyr Ser Ser Ile
    130                 135                 140

Thr Met Leu Gly Ile Val
145                 150
```

<210> SEQ ID NO 6
<211> LENGTH: 586
<212> TYPE: DNA
<213> ORGANISM: Artificial Sequence
<220> FEATURE:
<223> OTHER INFORMATION: Ceres CLONE ID no. 30469
<220> FEATURE:
<221> NAME/KEY: misc_feature
<223> OTHER INFORMATION: Ceres SEED LINE ID no. ME02779
<220> FEATURE:
<221> NAME/KEY: misc_feature
<223> OTHER INFORMATION: Encodes the protein at SEQ ID NO: 7

<400> SEQUENCE: 6

```
aaaagatcta caaaacagag agttgtatac tttaaatcat ttagaggttg tgaaatatta    60
tggagagtga aggaaagatt tgttcacag aagagcaaga ggctcttgta gtgaagtctt    120
ggagtgtcat gaagaaaaac tcagctgaat taggtctcaa actcttcatc aagatctttg    180
agattgcacc aacaacgaag aagatgttct ctttcttgag agactcacca attcctgctg    240
agcaaaatcc aaagctcaag cctcacgcaa tgtctgtttt tgtcatgtac aactgaggaa    300
aacagggaaa gttacggtga gggagactac tttgaagaga cttggagcca gccattctaa    360
atacggtgtc gttgacgaac actttgaggt ggccaagtat gcattgttgg agacgataaa    420
ggaggcagtg ccggagatgt ggtcaccgga gatgaaggtg gcttgggtc aggcttatga     480 tcaccttgtt gctgccatta agctgaaat gaatctttcc aactaaaaaa tcatatacta    540
ttatatagtt gtaaacttgt aataaatatt tcattttgaa ttgttc              586
```

<210> SEQ ID NO 7
<211> LENGTH: 78
<212> TYPE: PRT
<213> ORGANISM: Artificial Sequence
<220> FEATURE:
<223> OTHER INFORMATION: Ceres CLONE ID no. 30469
<220> FEATURE:
<221> NAME/KEY: misc_feature
<223> OTHER INFORMATION: Ceres SEED LINE ID no. ME02779
<220> FEATURE:
<221> NAME/KEY: misc_feature
<222> LOCATION: (13)..(74)
<223> OTHER INFORMATION: Pfam Name: Globin
      Pfam Description: Globin

<400> SEQUENCE: 7

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Tyr Asn
65                  70                  75

<210> SEQ ID NO 8
<211> LENGTH: 483
<212> TYPE: DNA
<213> ORGANISM: Arabidopsis thaliana
<220> FEATURE:
<221> NAME/KEY: misc_feature
<223> OTHER INFORMATION: Ceres CLONE ID no. 30469_FL
<220> FEATURE:
<221> NAME/KEY: misc_feature
<223> OTHER INFORMATION: Encodes the protein at SEQ ID NO: 9

<400> SEQUENCE: 8
atggagagtg aaggaaagat tgtgttcaca gaagagcaag aggctcttgt agtgaagtct      60
tggagtgtca tgaagaaaaa ctcagctgaa ttaggtctca aactcttcat caagatcttt     120
gagattgcac caacaacgaa gaagatgttc tctttcttga gagactcacc aattcctgct     180
gagcaaaatc caaagctcaa gcctcacgca atgtctgttt ttgtcatgtg ttgtgaatca     240
gcagtacaac tgaggaaaac agggaaagtt acggtgaggg agactacttt gaagagactt     300
ggagccagcc attctaaata cggtgtcgtt gacgaacact ttgaggtggc caagtatgca     360
ttgttggaga cgataaagga ggcagtgccg gagatgtggt caccggagat gaaggtggct     420
tggggtcagg cttatgatca ccttgttgct gccattaaag ctgaaatgaa tctttccaac     480
taa                                                                    483

<210> SEQ ID NO 9
<211> LENGTH: 160
<212> TYPE: PRT
<213> ORGANISM: Arabidopsis thaliana
<220> FEATURE:
<221> NAME/KEY: misc_feature
<223> OTHER INFORMATION: Ceres CLONE ID no. 30469_FL
<220> FEATURE:
<221> NAME/KEY: misc_feature
<222> LOCATION: (13)..(152)
<223> OTHER INFORMATION: Pfam Name: Globin
      Pfam Description: Globin

```
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 9
```

| | | | | | | | | | | | | | | | |
|---|---|---|---|---|---|---|---|---|---|---|---|---|---|---|---|
|Met|Glu|Ser|Glu|Gly|Lys|Ile|Val|Phe|Thr|Glu|Glu|Gln|Glu|Ala|Leu|
|1| | | |5| | | | |10| | | | |15| |
|Val|Val|Lys|Ser|Trp|Ser|Val|Met|Lys|Lys|Asn|Ser|Ala|Glu|Leu|Gly|
| | | |20| | | | |25| | | | |30| | |
|Leu|Lys|Leu|Phe|Ile|Lys|Ile|Phe|Glu|Ile|Ala|Pro|Thr|Thr|Lys|Lys|
| | |35| | | | |40| | | | |45| | | |
|Met|Phe|Ser|Phe|Leu|Arg|Asp|Ser|Pro|Ile|Pro|Ala|Glu|Gln|Asn|Pro|
|50| | | | |55| | | | |60| | | | | |
|Lys|Leu|Lys|Pro|His|Ala|Met|Ser|Val|Phe|Val|Met|Cys|Cys|Glu|Ser|
|65| | | |70| | | | |75| | | | |80| |
|Ala|Val|Gln|Leu|Arg|Lys|Thr|Gly|Lys|Val|Thr|Val|Arg|Glu|Thr|Thr|
| | | | |85| | | | |90| | | | |95| |
|Leu|Lys|Arg|Leu|Gly|Ala|Ser|His|Ser|Lys|Tyr|Gly|Val|Val|Asp|Glu|
| | | |100| | | | |105| | | | |110| | |
|His|Phe|Glu|Val|Ala|Lys|Tyr|Ala|Leu|Leu|Glu|Thr|Ile|Lys|Glu|Ala|
| | |115| | | | |120| | | | |125| | | |
|Val|Pro|Glu|Met|Trp|Ser|Pro|Glu|Met|Lys|Val|Ala|Trp|Gly|Gln|Ala|
| | |130| | | | |135| | | | |140| | | |
|Tyr|Asp|His|Leu|Val|Ala|Ala|Ile|Lys|Ala|Glu|Met|Asn|Leu|Ser|Asn|
|145| | | | |150| | | | |155| | | | |160|

```
<210> SEQ ID NO 10
<211> LENGTH: 160
<212> TYPE: PRT
<213> ORGANISM: Raphanus sativus
<220> FEATURE:
<221> NAME/KEY: misc_feature
<223> OTHER INFORMATION: Public GI no. 30909306
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 10
```

| | | | | | | | | | | | | | | | |
|---|---|---|---|---|---|---|---|---|---|---|---|---|---|---|---|
|Met|Glu|Ser|Glu|Gly|Lys|Ile|Val|Phe|Thr|Glu|Glu|Gln|Glu|Ala|Leu|
|1| | | |5| | | | |10| | | | |15| |
|Val|Val|Lys|Ser|Trp|Ser|Val|Met|Lys|Lys|Asn|Ser|Ala|Asp|Leu|Gly|
| | | |20| | | | |25| | | | |30| | |
|Leu|Lys|Leu|Phe|Ile|Lys|Ile|Phe|Glu|Ile|Ala|Pro|Thr|Ala|Lys|Lys|
| | |35| | | | |40| | | | |45| | | |
|Leu|Phe|Ser|Phe|Leu|Arg|Asp|Ser|Pro|Ile|Pro|Ala|Glu|Gln|Asn|Pro|
|50| | | | |55| | | | |60| | | | | |
|Lys|Leu|Lys|Pro|His|Ala|Met|Ser|Val|Phe|Val|Met|Cys|Cys|Glu|Ser|
|65| | | |70| | | | |75| | | | |80| |
|Ala|Ala|Gln|Leu|Arg|Lys|Thr|Gly|Lys|Val|Thr|Val|Lys|Glu|Thr|Thr|
| | | | |85| | | | |90| | | | |95| |
|Leu|Lys|Arg|Leu|Gly|Ala|Asn|His|Ser|Lys|Tyr|Gly|Val|Val|Asp|Glu|
| | | |100| | | | |105| | | | |110| | |

```
His Phe Glu Val Thr Lys Tyr Ala Leu Leu Glu Thr Ile Lys Glu Ala
            115                 120                 125

Val Pro Glu Met Trp Ser Pro Glu Met Lys Ser Ala Trp Gly Gln Ala
        130                 135                 140

Tyr Asp His Leu Val Ala Ala Ile Lys Ala Glu Met Lys Pro Ser His
145                 150                 155                 160

<210> SEQ ID NO 11
<211> LENGTH: 158
<212> TYPE: PRT
<213> ORGANISM: Arabidopsis thaliana
<220> FEATURE:
<221> NAME/KEY: misc_feature
<223> OTHER INFORMATION: Public GI no. 37903656
<220> FEATURE:
<221> NAME/KEY: misc_feature
<222> LOCATION: (10)..(149)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 11

Met Glu Gly Lys Val Phe Thr Glu Glu Gln Glu Thr Leu Val Val Lys
1               5                   10                  15

Ser Trp Gly Val Met Lys Lys Asn Ala Ala Glu Leu Gly Leu Lys Phe
            20                  25                  30

Phe Leu Lys Ile Phe Glu Ile Ala Pro Ser Ala Gln Lys Leu Phe Ser
        35                  40                  45

Phe Leu Arg Asp Ser Asp Ile Pro Leu Glu Lys Asn Pro Lys Leu Lys
    50                  55                  60

Pro His Ala Met Ser Val Phe Val Met Thr Cys Glu Ser Ala Val Gln
65                  70                  75                  80

Leu Arg Lys Ala Gly Lys Val Thr Val Arg Glu Ser Thr Leu Lys Arg
                85                  90                  95

Leu Gly Gly Val His Phe Lys Ser Gly Val Val Asp Glu His Tyr Glu
            100                 105                 110

Val Thr Lys Phe Ala Leu Leu Glu Thr Ile Lys Glu Ala Leu Pro Glu
        115                 120                 125

Met Trp Ser Pro Glu Met Lys Asn Ala Trp Gly Glu Ala Tyr Asp Gln
    130                 135                 140

Leu Val Ala Ala Ile Lys Ser Glu Met Lys Pro Pro Leu Asn
145                 150                 155

<210> SEQ ID NO 12
<211> LENGTH: 163
<212> TYPE: PRT
<213> ORGANISM: Arabidopsis thaliana
<220> FEATURE:
<221> NAME/KEY: misc_feature
<223> OTHER INFORMATION: Public GI no. 15824736
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
```

<400> SEQUENCE: 12

Met Ala Thr Tyr Glu Gly Lys Val Phe Thr Glu Glu Gln Ala Leu
1               5                   10                  15

Val Val Lys Ser Trp Thr Val Met Lys Lys Thr Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Asp Met Trp Ser Asp Glu Met Lys Asn Ala Trp Gly Glu Ala
    130                 135                 140

Tyr Asp Arg Leu Val Ala Ala Ile Lys Ile Glu Met Lys Ala Cys Ser
145                 150                 155                 160

Gln Ala Ala

<210> SEQ ID NO 13
<211> LENGTH: 161
<212> TYPE: PRT
<213> ORGANISM: Glycine max
<220> FEATURE:
<221> NAME/KEY: misc_feature
<223> OTHER INFORMATION: Ceres CLONE ID no. 546001
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 13

Met Thr Thr Thr Leu Glu Arg Gly Phe Ser Glu Gln Glu Ala Leu
1               5                   10                  15

Val Val Lys Ser Trp Asn Val Met Lys Lys Asn Ser Gly Glu Leu Gly
            20                  25                  30

Leu Lys Phe Phe Leu Lys Ile Phe Glu Ile Ala Pro Ser Ala Gln Lys
        35                  40                  45

Leu Phe Ser Phe Leu Arg Asp Ser Thr Val Pro Leu Glu Gln Asn Pro
    50                  55                  60

Lys Leu Lys Pro His Ala Val Ser Val Phe Val Met Thr Cys Asp Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Arg Thr Gly Val Ala Asn Glu
            100                 105                 110

His Phe Glu Val Thr Lys Phe Ala Leu Leu Glu Thr Ile Lys Glu Ala
        115                 120                 125

Val Pro Glu Met Trp Ser Pro Ala Met Lys Asn Ala Trp Gly Glu Ala

Tyr Asp Gln Leu Val Asp Ala Ile Lys Ser Glu Met Lys Pro Pro Ser
145                 150                 155                 160

Ser

<210> SEQ ID NO 14
<211> LENGTH: 160
<212> TYPE: PRT
<213> ORGANISM: Glycine max
<220> FEATURE:
<221> NAME/KEY: misc_feature
<223> OTHER INFORMATION: Public GI no. 11095158
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 14

Met Gly Thr Leu Asp Thr Lys Gly Phe Thr Glu Glu Gln Glu Ala Leu
1               5                   10                  15

Val Val Lys Ser Trp Asn Ala Met Lys Lys Asn Ser Ala Glu Leu Gly
                20                  25                  30

Leu Lys Leu Phe Leu Lys Ile Phe Glu Ile Ala Pro Ser Ala Gln Lys
            35                  40                  45

Leu Phe Ser Phe Leu Lys Asp Ser Lys Val Pro Leu Glu Gln Asn Thr
    50                  55                  60

Lys Leu Lys Pro His Ala Met Ser Val Phe Leu Met Thr Cys Glu Ser
65                  70                  75                  80

Ala Val Gln Leu Arg Lys Ser Gly Lys Val Thr Val Arg Glu Ser Ser
                85                  90                  95

Leu Lys Lys Leu Gly Ala Asn His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Glu Met Trp Ser Pro Ala Met Lys Asn Ala Trp Gly Glu Ala
    130                 135                 140

Tyr Asp Gln Leu Val Asn Ala Ile Lys Ser Glu Met Lys Pro Ser Ser
145                 150                 155                 160

<210> SEQ ID NO 15
<211> LENGTH: 152
<212> TYPE: PRT
<213> ORGANISM: Glycine max
<220> FEATURE:
<221> NAME/KEY: misc_feature
<223> OTHER INFORMATION: Public GI no. 12963875
<220> FEATURE:
<221> NAME/KEY: misc_feature
<222> LOCATION: (8)..(147)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 15

Met Ser Ser Phe Ser Glu Glu Gln Glu Ala Leu Val Val Lys Ser Trp
1               5                   10                  15

-continued

```
Gly Ser Met Lys Lys Asp Ala Gly Glu Trp Gly Leu Lys Phe Phe Leu
            20                  25                  30

Lys Ile Phe Glu Ile Ala Pro Ser Ala Lys Lys Met Phe Ser Phe Leu
        35                  40                  45

Lys Asp Ser Asn Val Pro Leu Asp Gln Asn Pro Lys Leu Lys Ile His
    50                  55                  60

Ala Lys Ser Val Leu Val Met Thr Cys Glu Ala Val Gln Leu Arg
65                  70                  75                  80

Lys Ala Gly Lys Val Val Arg Asp Ser Thr Leu Lys Lys Ile Gly
                85                  90                  95

Ala Thr His Phe Lys Tyr Gly Val Val Asp Glu His Phe Glu Val Thr
            100                 105                 110

Lys Tyr Ala Leu Leu Glu Thr Ile Lys Glu Ala Ser Gln Glu Met Trp
        115                 120                 125

Ser Val Glu Met Lys Asn Ala Trp Gly Glu Ala Tyr Asp Gln Leu Val
    130                 135                 140

Ser Ala Ile Lys Thr Glu Met Lys
145                 150

<210> SEQ ID NO 16
<211> LENGTH: 165
<212> TYPE: PRT
<213> ORGANISM: Zea mays
<220> FEATURE:
<221> NAME/KEY: misc_feature
<223> OTHER INFORMATION: Ceres CLONE ID no. 1554560
<220> FEATURE:
<221> NAME/KEY: misc_feature
<222> LOCATION: (17)..(157)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 16

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45

Ser Ala Lys Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

Thr Cys Glu Ala Ala Ala Gln Leu Arg Lys Ala Gly Lys Val Thr Val
                85                  90                  95

Arg Glu Thr Thr Leu Lys Arg Leu Gly Ala Thr His Leu Arg Tyr Gly
            100                 105                 110

Val Ala Asp Gly His Phe Glu Val Thr Gly Phe Ala Leu Leu Glu Thr
        115                 120                 125

Ile Lys Glu Ala Leu Pro Ala Asp Met Trp Ser Glu Met Lys Lys
    130                 135                 140

Ala Trp Ala Glu Ala Tyr Ser Gln Leu Val Ala Ala Ile Lys Arg Glu
145                 150                 155                 160

Met Lys Pro Asp Ala
```

<210> SEQ ID NO 17
<211> LENGTH: 162
<212> TYPE: PRT
<213> ORGANISM: Triticum aestivum
<220> FEATURE:
<221> NAME/KEY: misc_feature
<223> OTHER INFORMATION: Ceres CLONE ID no. 839727
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in
 SEQ ID NO: 7

<400> SEQUENCE: 17

Met Ser Ala Ala Glu Gly Ala Val Val Phe Ser Glu Glu Lys Glu Ala
1               5                   10                  15

Leu Val Leu Lys Ser Trp Ala Ile Met Lys Lys Asp Ser Ala Asn Leu
            20                  25                  30

Gly Leu Arg Phe Phe Leu Lys Ile Phe Glu Ile Ala Pro Ser Ala Arg
        35                  40                  45

Gln Met Phe Pro Phe Leu Arg Asp Ser Asp Val Pro Leu Glu Thr Asn
    50                  55                  60

Pro Lys Leu Lys Thr His Ala Val Ser Val Phe Val Met Thr Cys Glu
65                  70                  75                  80

Ala Ala Ala Gln Leu Arg Lys Ala Gly Lys Ile Thr Val Arg Glu Thr
                85                  90                  95

Thr Leu Lys Arg Leu Gly Gly Thr His Leu Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Gly Pro Glu Met Arg Asn Ala Trp Gly
    130                 135                 140

Glu Ala Tyr Asp Gln Leu Val Ala Ala Ile Lys Gln Glu Met Lys Pro
145                 150                 155                 160

Ser Glu

<210> SEQ ID NO 18
<211> LENGTH: 169
<212> TYPE: PRT
<213> ORGANISM: Triticum aestivum
<220> FEATURE:
<221> NAME/KEY: misc_feature
<223> OTHER INFORMATION: Public GI no. 14701800
<220> FEATURE:
<221> NAME/KEY: misc_feature
<222> LOCATION: (21)..(161)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 18

Met Ala Leu Val Glu Gly Asn Asn Gly Val Ser Gly Gly Ala Val Ser
1               5                   10                  15

Phe Ser Glu Glu Gln Glu Ala Leu Val Leu Lys Ser Trp Ala Ile Met

```
                    20                  25                  30
Lys Lys Asp Ser Ala Asn Ile Gly Leu Arg Phe Phe Leu Lys Ile Phe
            35                  40                  45

Glu Val Ala Pro Ser Ala Ser Gln Met Phe Ser Phe Leu Arg Asn Ser
        50                  55                  60

Asp Val Pro Leu Glu Lys Asn Pro Lys Leu Lys Thr His Ala Met Ser
 65                  70                  75                  80

Val Phe Val Met Thr Cys Glu Ala Ala Gln Leu Arg Lys Ala Gly
                    85                  90                  95

Lys Val Thr Val Arg Asp Thr Thr Leu Lys Arg Leu Gly Ala Thr His
                100                 105                 110

Phe Lys Tyr Gly Val Gly Asp Ala His Phe Glu Val Thr Arg Phe Ala
            115                 120                 125

Leu Leu Glu Thr Ile Lys Glu Ala Val Pro Val Asp Met Trp Ser Pro
        130                 135                 140

Ala Met Lys Ser Ala Trp Ser Glu Ala Tyr Asn Gln Leu Val Ala Ala
145                 150                 155                 160

Ile Lys Gln Glu Met Lys Pro Ala Glu
                165
```

<210> SEQ ID NO 19
<211> LENGTH: 416
<212> TYPE: DNA
<213> ORGANISM: Arabidopsis thaliana
<220> FEATURE:
<221> NAME/KEY: misc_feature
<223> OTHER INFORMATION: Ceres CLONE ID no. 271922
<220> FEATURE:
<221> NAME/KEY: misc_feature
<223> OTHER INFORMATION: Ceres SEED LINE ID no. ME03944
<220> FEATURE:
<221> NAME/KEY: misc_feature
<223> OTHER INFORMATION: Encodes the protein at SEQ ID NO: 20

<400> SEQUENCE: 19

```
gctcattagg gtttctcatc tacgacggcg tggtgttcct ccttcctgct ctgaaaaatg    60
gcgaagagaa cgaagaaggt tggaatcgtc ggcaaatacg gaacacgtta tggtgcgagt   120
atcaggaagc agattaagaa gatggaggtc agccagcaca gcaagtactt ctgtgagttc   180
tgtggcaagt acggagtgaa gcgaaaggct gttggtatct ggggttgcaa ggattgtggc   240
aaggtcaagg caggtggtgc ttacacaatg aacaccgcca gtgcggtcac tgttagaagc   300
acgatcagaa ggttgaggga gcagatcgag ggttaaaagt ctgctggctt tttatatttg   360
gtttccttgt tttgacaatt taagttttgc atcaacagtg agaacatgtt ttgatt       416
```

<210> SEQ ID NO 20
<211> LENGTH: 92
<212> TYPE: PRT
<213> ORGANISM: Arabidopsis thaliana
<220> FEATURE:
<221> NAME/KEY: misc_feature
<223> OTHER INFORMATION: Ceres CLONE ID no. 271922
<220> FEATURE:
<221> NAME/KEY: misc_feature
<223> OTHER INFORMATION: Ceres SEED LINE ID no. ME03944
<220> FEATURE:
<221> NAME/KEY: misc_feature
<222> LOCATION: (2)..(91)
<223> OTHER INFORMATION: Pfam Name: Ribosomal_L37ae;
      Pfam Description: Ribosomal L37ae protein family

<400> SEQUENCE: 20

Met Ala Lys Arg Thr Lys Lys Val Gly Ile Val Lys Tyr Gly Thr
1               5                   10                  15

Arg Tyr Gly Ala Ser Ile Arg Lys Gln Ile Lys Lys Met Glu Val Ser
                20                  25                  30

Gln His Ser Lys Tyr Phe Cys Glu Phe Cys Gly Lys Tyr Gly Val Lys
            35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Ile Glu Gly
                85                  90

<210> SEQ ID NO 21
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 4090257
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 21

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Phe Phe Cys Glu Phe Cys Gly Lys Phe Ala Val Lys
            35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Pro Ser Ala Val Thr Val Arg
65                  70                  75                  80

Ser Thr Ile Arg Arg Leu Arg Glu Gln Thr Glu Gly
                85                  90

<210> SEQ ID NO 22
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 4741896
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 22

Met Thr Lys Arg Thr Lys Lys Ala Gly Ile Val Gly Lys Tyr Gly Thr
1               5                   10                  15

```
Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Tyr Ala Val Lys
            35                  40                  45

Arg Lys Ala Val Gly Ile Trp Gly Cys Lys Ala Cys Gly Lys Val Lys
50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 23
<211> LENGTH: 92
<212> TYPE: PRT
<213> ORGANISM: Arabidopsis thaliana
<220> FEATURE:
<221> NAME/KEY: misc_feature
<223> OTHER INFORMATION: Ceres CLONE ID no. 36046
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<222> LOCATION: (45)..(45)
<223> OTHER INFORMATION: Xaa is any aa, unknown, or other
<220> FEATURE:
<221> NAME/KEY: misc_feature
<222> LOCATION: (49)..(49)
<223> OTHER INFORMATION: Xaa is any aa, unknown, or other
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 23

Met Ala Lys Arg Thr Lys Lys Val Gly Ile Val Gly Lys Tyr Gly Thr
1               5                   10                  15

Arg Tyr Gly Ala Ser Ile Arg Lys Gln Ile Lys Lys Met Glu Val Ser
                20                  25                  30

Gln His Ser Lys Tyr Phe Cys Glu Phe Cys Gly Lys Xaa Gly Val Lys
            35                  40                  45

Xaa Lys Ala Val Gly Ile Trp Gly Cys Lys Asp Cys Gly Lys Val Lys
50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Ile Glu Gly
                85                  90

<210> SEQ ID NO 24
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 6016699
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20
```

<400> SEQUENCE: 24

Met Thr Lys Arg Thr Lys Lys Ala Arg Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Asn Lys Tyr Phe Cys Glu Phe Cys Gly Lys Tyr Ser Val Lys
        35                  40                  45

Arg Lys Val Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 25
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 664936
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 25

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Phe Phe Cys Glu Phe Cys Gly Lys Tyr Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Gly
                85                  90

<210> SEQ ID NO 26
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 658438
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 26

Met Thr Lys Arg Thr Lys Lys Ala Gly Ile Val Gly Lys Tyr Gly Thr

```
                1               5                   10                  15
Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 27
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 1049262
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 27

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Phe Phe Cys Glu Phe Cys Gly Lys Tyr Ala Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 28
<211> LENGTH: 92
<212> TYPE: PRT
<213> ORGANISM: Triticum aestivum
<220> FEATURE:
<221> NAME/KEY: misc_feature
<223> OTHER INFORMATION: Ceres CLONE ID no. 632613
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 28

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
```

```
                    20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
 65                 70                  75                  80

Ser Thr Ile Arg Arg Leu Arg Glu Gln Thr Glu Ala
                85                  90

<210> SEQ ID NO 29
<211> LENGTH: 92
<212> TYPE: PRT
<213> ORGANISM: Zea mays
<220> FEATURE:
<221> NAME/KEY: misc_feature
<223> OTHER INFORMATION: Ceres CLONE ID no. 1390976
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 29

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
 65                 70                  75                  80

Ser Thr Ile Arg Arg Leu Arg Glu Gln Thr Glu Ala
                85                  90

<210> SEQ ID NO 30
<211> LENGTH: 92
<212> TYPE: PRT
<213> ORGANISM: Zea mays
<220> FEATURE:
<221> NAME/KEY: misc_feature
<223> OTHER INFORMATION: Ceres CLONE ID no. 1457185
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 30

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
```

```
                          35                  40                  45

Arg Lys Ala Val Gly Ile Trp Gly Cys Lys Asp Cys Gly Lys Val Lys
 50                  55                  60

Ala Gly Gly Ala Tyr Thr Met Asn Thr Ala Ser Ala Val Thr Val Arg
 65                  70                  75                  80

Ser Thr Ile Arg Arg Leu Arg Glu Gln Thr Glu Ala
                 85                  90

<210> SEQ ID NO 31
<211> LENGTH: 92
<212> TYPE: PRT
<213> ORGANISM: Zea mays
<220> FEATURE:
<221> NAME/KEY: misc_feature
<223> OTHER INFORMATION: Public GI no. 56202147
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 31

Met Thr Lys Arg Thr Lys Lys Ala Gly Ile Val Gly Lys Tyr Gly Thr
  1               5                  10                  15

Arg Tyr Gly Ala Ser Leu Arg Lys Gln Ile Lys Lys Met Glu Val Ser
                 20                  25                  30

Gln His Ser Lys Tyr Phe Cys Glu Phe Cys Gly Lys Phe Ala Val Lys
                 35                  40                  45

Arg Lys Ala Val Gly Ile Trp Gly Cys Lys Asp Cys Gly Lys Val Lys
 50                  55                  60

Ala Gly Gly Ala Tyr Thr Met Asn Thr Ala Ser Ala Val Thr Val Arg
 65                  70                  75                  80

Ser Thr Ile Arg Arg Leu Arg Glu Gln Thr Glu Ala
                 85                  90

<210> SEQ ID NO 32
<211> LENGTH: 92
<212> TYPE: PRT
<213> ORGANISM: Zea mays
<220> FEATURE:
<221> NAME/KEY: misc_feature
<223> OTHER INFORMATION: Public GI no. 58578274
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 32

Met Thr Lys Arg Thr Lys Lys Ala Gly Ile Val Gly Lys Tyr Gly Thr
  1               5                  10                  15

Arg Tyr Gly Ala Ser Leu Arg Lys Gln Ile Lys Lys Met Glu Val Ser
                 20                  25                  30

Gln His Ser Glu Tyr Phe Cys Glu Phe Cys Gly Lys Tyr Ala Val Lys
                 35                  40                  45

Arg Lys Ala Val Gly Ile Trp Gly Cys Lys Asp Cys Gly Lys Val Lys
```

```
                   50                  55                  60

Ala Gly Gly Ala Tyr Thr Leu Asn Thr Ala Ser Ala Val Thr Val Arg
 65                  70                  75                  80

Ser Thr Ile Arg Arg Leu Arg Glu Gln Thr Glu Ser
                 85                  90

<210> SEQ ID NO 33
<211> LENGTH: 632
<212> TYPE: DNA
<213> ORGANISM: Arabidopsis thaliana
<220> FEATURE:
<221> NAME/KEY: misc_feature
<223> OTHER INFORMATION: Ceres CLONE ID no. 2403_FL

<400> SEQUENCE: 33 attcccatc gcacagaccc gcctaagaat ccgagagaga agaagagata atgcagatct      60
tcgtcaaaac cctcaccggc aaaactataa ccctagaggt tgagagcagc gacaccatcg    120
acaatgttaa agccaaaatc caggacaaat agggcatacc acctgatcaa cagaggctga    180
tttttgctgg taagcaattg gaagatggcc ggaccttagc tgactacaac atccagaaag    240
agtctactct tcatcttgtc ctcaggctca gaggtggaac catgatcaag gtgaagacac    300
tcactggaaa agaaatcgag attgatatcg aaccaaccga cactattgat cggatcaaag    360
aacgtgttga agagaaagaa ggcatccctc ctgttcaaca aaggctcatc tatgccggaa    420
aacagcttgc tgatgacaaa acggccaaag attatgcgat agagggaggc tctgttcttc    480
atttggttct tgctcttagg ggtggtcttc tctgatctga ataaataagc ttttcaacaa    540
acatctttcc cctcactatt gtcctccttt tgtggaattc atgacacaca aaaattgcta    600
tgggaaattg gaatattatg atgttttttc tc                                  632

<210> SEQ ID NO 34
<211> LENGTH: 154
<212> TYPE: PRT
<213> ORGANISM: Arabidopsis thaliana
     220>
<221> NAME/KEY: misc_feature
<223> OTHER INFORMATION: Ceres CLONE ID no. 2403_FL
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 34

Met Gln Ile Phe Val Lys Thr Leu Thr Gly Lys Thr Ile Thr Leu Glu
  1               5                  10                  15

Val Glu Ser Ser Asp Thr Ile Asp Asn Val Lys Ala Lys Ile Gln Asp
                 20                  25                  30

Lys Glu Gly Ile Pro Pro Asp Gln Gln Arg Leu Ile Phe Ala Gly Lys
             35                  40                  45

Gln Leu Glu Asp Gly Arg Thr Leu Ala Asp Tyr Asn Ile Gln Lys Glu
         50                  55                  60

Ser Thr Leu His Leu Val Leu Arg Leu Arg Gly Gly Thr Met Ile Lys
```

```
                    65                  70                  75                  80
Val Lys Thr Leu Thr Gly Lys Glu Ile Glu Ile Asp Ile Glu Pro Thr
                    85                  90                  95

Asp Thr Ile Asp Arg Ile Lys Glu Arg Val Glu Glu Lys Glu Gly Ile
                100                 105                 110

Pro Pro Val Gln Gln Arg Leu Ile Tyr Ala Gly Lys Gln Leu Ala Asp
            115                 120                 125

Asp Lys Thr Ala Lys Asp Tyr Ala Ile Glu Gly Ser Val Leu His
    130                 135                 140

Leu Val Leu Ala Leu Arg Gly Gly Leu Leu
145                 150
```

```
<210> SEQ ID NO 35
<211> LENGTH: 154
<212> TYPE: PRT
<213> ORGANISM: Zea mays
<220> FEATURE:
<221> NAME/KEY: misc_feature
<223> OTHER INFORMATION: Ceres CLONE ID no. 1482731
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 35

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ala Asp Tyr Asn Ile Gln Lys Glu
        50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                    85                  90                  95

Asp Thr Ile Asp Arg Ile Lys Glu Arg Val Glu Glu Lys Glu Gly Ile
                100                 105                 110

Pro Pro Val Gln Gln Arg Leu Ile Tyr Ala Gly Lys Gln Leu Ala Asp
            115                 120                 125

Asp Lys Thr Ala Lys Asp Tyr Asn Ile Glu Gly Gly Ser Val Leu His
    130                 135                 140

Leu Val Leu Ala Leu Arg Gly Gly Ser Asp
145                 150
```

```
<210> SEQ ID NO 36
<211> LENGTH: 154
<212> TYPE: PRT
<213> ORGANISM: Glycine max
<220> FEATURE:
<221> NAME/KEY: misc_feature
```

-continued

```
<223> OTHER INFORMATION: Ceres CLONE ID no. 522921
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 36

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
                100                 105                 110

Pro Pro Val Gln Gln Arg Leu Ile Tyr Ala Gly Lys Gln Leu Ala Asp
            115                 120                 125

Asp Lys Thr Ala Lys Glu Tyr Asn Ile Glu Gly Gly Ser Val Leu His
        130                 135                 140

Leu Val Leu Ala Leu Arg Gly Gly Thr Tyr
145                 150

<210> SEQ ID NO 37
<211> LENGTH: 147
<212> TYPE: PRT
<213> ORGANISM: Brassica napus
<220> FEATURE:
<221> NAME/KEY: misc_feature
<223> OTHER INFORMATION: Ceres CLONE ID no. 1036726
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(142)
<223> OTHER INFORMATION: Pfam Name: ubiquitin
      Pfam Description: Ubiquitin family
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 37

Met Gln Ile Phe Val Lys Thr Leu Thr Gly Lys Thr Ile Thr Leu Glu
1               5                   10                  15
```

```
Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Xaa Lys Asp Tyr Asn Ile Glu Gly Gly Ser Val Ser Ala
    130                 135                 140

Ser Gly Ser
145

<210> SEQ ID NO 38
<211> LENGTH: 153
<212> TYPE: PRT
<213> ORGANISM: Glycine max
<220> FEATURE:
<221> NAME/KEY: misc_feature
<223> OTHER INFORMATION: Ceres CLONE ID no. 513071
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 38

Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Ser Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
```

```
                115                 120                 125
Asp Lys Thr Ala Lys Asp Tyr Asn Ile Glu Gly Gly Ser Val Leu His
        130                 135                 140

Leu Xaa Leu Ala Leu Arg Gly Gly Tyr
145                 150

<210> SEQ ID NO 39
<211> LENGTH: 620
<212> TYPE: DNA
<213> ORGANISM: Arabidopsis thaliana
<220> FEATURE:
<223> OTHER INFORMATION: Ceres CLONE ID no. 2403
<220> FEATURE:
<221> NAME/KEY: misc_feature
<223> OTHER INFORMATION: Ceres SEED LINE ID no. ME05304
<220> FEATURE:
<221> NAME/KEY: misc_feature
<223> OTHER INFORMATION: Encodes the protein at SEQ ID NO: 40

<400> SEQUENCE: 39
attccccatc gcacagaccc ccctaagaat ccgagagaga agaagagata atgcagatct      60
tcgtcaaaac cctcaccggc aaaactataa ccctagaagt tgagagcagc gacaccatcg     120
acaatgttaa agccaaaatc caggacaaag agggcatacc acctgatcaa cagaggctga     180 ttttgctgg taagcaattg gaagatggcc ggaccttagc tgattacaac atccagaaag      240
agtctactct tcatcttgtc ctcaggctca gaggtggaac catgatcaag gtgaagacac     300
tcactggaaa agaaatcgag attgatatcg aaccaaccga cactattgat cggatcaaag     360
aacgtgttga agagaaagaa ggcatccctc ctgttcaaca aaggctcata tatgccggaa     420
aacagcttgc tgatgacaaa acggccaaag attatgcgat agagggaggc tctgttcttc     480
atttggttct tgctcttagg ggtggtcttc tctgatctta ataaataagc ttttcaacaa     540
acatcttttc cctcactatt gtcctcctta tgtggaattc atgacacacc aaaattgcta     600
tgggaaattg gaatattatg                                                 620

<210> SEQ ID NO 40
<211> LENGTH: 33
<212> TYPE: PRT
<213> ORGANISM: Arabidopsis thaliana
<220> FEATURE:
<223> OTHER INFORMATION: Ceres CLONE ID no. 2403
<220> FEATURE:
<221> NAME/KEY: misc_feature
<223> OTHER INFORMATION: Ceres SEED LINE ID no. ME05304
<220> FEATURE:
<221> NAME/KEY: misc_feature
<222> LOCATION: (1)..(33)
<223> OTHER INFORMATION: Pfam Name: ubiquitin
      Pfam Description: Ubiquitin family

<400> SEQUENCE: 40

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 41
<211> LENGTH: 1106
<212> TYPE: DNA
<213> ORGANISM: Glycine max
<220> FEATURE:
<221> NAME/KEY: misc_feature
```

<223> OTHER INFORMATION: Ceres CLONE ID no. 674166
<220> FEATURE:
<221> NAME/KEY: misc_feature
<223> OTHER INFORMATION: Ceres SEED LINE ID no. ME03186
<220> FEATURE:
<221> NAME/KEY: misc_feature
<223> OTHER INFORMATION: Encodes the protein at SEQ ID NO: 42

<400> SEQUENCE: 41

| | | |
|---|---|---:|
| atatttttgt gtagatgaag atcaacaaga gaaggtgttg ttgtgagttg tgttgttatg | | 60 |
| gtaccttcct tcaaccacaa aacctctctc cctctaccac ccattctctt ctctctctct | | 120 |
| ctctcccgtc ctccatctct caccttctca atctcttcac caccaccatc atcatcatta | | 180 |
| tcttctccaa tctctataac ctcgaaatcc ctcaaaacct ctccctcaaa ccaaatgaaa | | 240 |
| tgacccttt gtgagaacat ttttccccc ttaagaaaag gtcaaaggct gcaacttttt | | 300 |
| cttaaccaat ctcacatttt tttatttttc aacgtatttt ggccaggttt ggttttctgg | | 360 |
| gttgtcttgg aattcaaaaa agattccaac tttgaagatg ggtaggggtg gaaccgccgc | | 420 |
| ggcggcggcg gaggtcgccg aacccggttt aaggccggtt tatttcaaag aacagcgata | | 480 |
| taggggcgtc agaaaaagac cgtggggccg gttcgctgcc gaaatcagag acccttgaa | | 540 |
| gaaagccagg gtttggctcg gaacctttga caccgccgag gaggcggcgc gtgcctacga | | 600 |
| cacggcggcg agaaccctcc ggggaccaaa ggcgaagacc aatttccctc tttctccgcc | | 660 |
| gttctaccat cccgatccat tttccgatca ccggcacttc gccaacaccg gcgaagattt | | 720 |
| ccacgatcac cggcgaccaa catccagtgg catgagcagc accgtagagt ccttcagcgg | | 780 |
| cccccgtgct gccgtgccgg cgacagcgcc ggtggccacc ggccggagat atccccggac | | 840 |
| gccaccgtt atccccgagg actgccgcag cgactgcgat tcgtcgtcct ccgtcgttga | | 900 |
| cgacggcgaa ggcgacaacg tggcgtcgtc gttcccgcga gaaccgttgc cgtttgatct | | 960 |
| aaacgcgttg ccgttagacg atgctgacgt ggcaaccgat gatctgttct gcaccgttct | | 1020 |
| ttgcctctga tgagaaaaaa tgaaaaaacg gaacgaaatg atgtatttgg ttcgttgacg | | 1080 |
| gaattattat tattttttc tttctt | | 1106 |

<210> SEQ ID NO 42
<211> LENGTH: 210
<212> TYPE: PRT
<213> ORGANISM: Glycine max
<220> FEATURE:
<221> NAME/KEY: misc_feature
<223> OTHER INFORMATION: Ceres CLONE ID no. 674166
<220> FEATURE:
<221> NAME/KEY: misc_feature
<223> OTHER INFORMATION: Ceres SEED LINE ID no. ME03186
<220> FEATURE:
<221> NAME/KEY: misc_feature
<222> LOCATION: (26)..(89)
<223> OTHER INFORMATION: Pfam Name: AP2
    Pfam Description: AP2 domain
<220> FEATURE:
<221> NAME/KEY: misc_feature
<222> LOCATION: (26)..(89)
<223> OTHER INFORMATION: Pfam Name: AP2;
    Pfam Description: AP2 domain

<400> SEQUENCE: 42

Met Gly Arg Gly Gly Thr Ala Ala Ala Ala Glu Val Ala Glu Pro
1               5                   10                  15

Gly Leu Arg Pro Val Tyr Phe Lys Glu Gln Arg Tyr Arg Gly Val Arg
            20                  25                  30

Lys Arg Pro Trp Gly Arg Phe Ala Ala Glu Ile Arg Asp Pro Leu Lys

```
            35                  40                  45
Lys Ala Arg Val Trp Leu Gly Thr Phe Asp Thr Ala Glu Glu Ala Ala
 50                  55                  60

Arg Ala Tyr Asp Thr Ala Ala Arg Thr Leu Arg Gly Pro Lys Ala Lys
 65                  70                  75                  80

Thr Asn Phe Pro Leu Ser Pro Pro Phe Tyr His Pro Asp Pro Phe Ser
                 85                  90                  95

Asp His Arg His Phe Ala Asn Thr Gly Glu Asp Phe Asp His Arg
            100                 105                 110

Arg Pro Thr Ser Ser Gly Met Ser Ser Thr Val Glu Ser Phe Ser Gly
            115                 120                 125

Pro Arg Ala Ala Val Pro Ala Thr Ala Pro Val Ala Thr Gly Arg Arg
            130                 135                 140

Tyr Pro Arg Thr Pro Pro Val Ile Pro Glu Asp Cys Arg Ser Asp Cys
145                 150                 155                 160

Asp Ser Ser Ser Val Val Asp Asp Gly Glu Gly Asp Asn Val Ala
                165                 170                 175

Ser Ser Phe Pro Arg Glu Pro Leu Pro Phe Asp Leu Asn Ala Leu Pro
            180                 185                 190

Leu Asp Asp Ala Asp Val Ala Thr Asp Asp Leu Phe Cys Thr Val Leu
            195                 200                 205

Cys Leu
    210

<210> SEQ ID NO 43
<211> LENGTH: 225
<212> TYPE: PRT
<213> ORGANISM: Glycine max
<220> FEATURE:
<221> NAME/KEY: misc_feature
<223> OTHER INFORMATION: Public GI no. 12322345
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 43

Met Arg Arg Gly Arg Gly Ser Ser Ala Val Ala Gly Pro Thr Val Val
 1               5                  10                  15

Ala Ala Ile Asn Gly Ser Val Lys Glu Ile Arg Phe Arg Gly Val Arg
                 20                  25                  30

Lys Arg Pro Trp Gly Arg Phe Ala Ala Glu Ile Arg Asp Pro Trp Lys
             35                  40                  45

Lys Ala Arg Val Trp Leu Gly Thr Phe Asp Ser Ala Glu Glu Ala Ala
 50                  55                  60

Arg Ala Tyr Asp Ser Ala Ala Arg Asn Leu Arg Gly Pro Lys Ala Lys
 65                  70                  75                  80

Thr Asn Phe Pro Ile Asp Ser Ser Pro Pro Pro Asn Leu Arg
                 85                  90                  95

Phe Asn Gln Ile Arg Asn Gln Asn Gln Asn Val Asp Pro Phe Met
            100                 105                 110

Asp His Arg Leu Phe Thr Asp His Gln Gln Gln Phe Pro Ile Val Asn
            115                 120                 125
```

```
Arg Pro Thr Ser Ser Ser Met Ser Ser Thr Val Glu Ser Phe Ser Gly
    130                 135                 140

Pro Arg Pro Thr Thr Met Lys Pro Ala Thr Thr Lys Arg Tyr Pro Arg
145                 150                 155                 160

Thr Pro Pro Val Val Pro Glu Asp Cys His Ser Asp Cys Asp Ser Ser
                165                 170                 175

Ser Ser Val Ile Asp Asp Asp Asp Ile Ala Ser Ser Ser Arg Arg
            180                 185                 190

Arg Asn Pro Pro Phe Gln Phe Asp Leu Asn Phe Pro Pro Leu Asp Cys
        195                 200                 205

Val Asp Leu Phe Asn Gly Ala Asp Asp Leu His Cys Thr Asp Leu Arg
210                 215                 220

Leu
225

<210> SEQ ID NO 44
<211> LENGTH: 215
<212> TYPE: PRT
<213> ORGANISM: Brassica napus
<220> FEATURE:
<221> NAME/KEY: misc_feature
<223> OTHER INFORMATION: Ceres CLONE ID no. 975672
<220> FEATURE:
<221> NAME/KEY: misc_feature
<222> LOCATION: (21)..(84)
<223> OTHER INFORMATION: Pfam Name: AP2
      Pfam Description: AP2 domain
<220> FEATURE:
<221> NAME/KEY: misc_feature
<222> LOCATION: (174)..(174)
<223> OTHER INFORMATION: Xaa is any aa, unknown, or other
<220> FEATURE:
<221> NAME/KEY: misc_feature
<222> LOCATION: (194)..(194)
<223> OTHER INFORMATION: Xaa is any aa, unknown, or other
<220> FEATURE:
<221> NAME/KEY: misc_feature
<222> LOCATION: (208)..(208)
<223> OTHER INFORMATION: Xaa is any aa, unknown, or other
<220> FEATURE:
<221> NAME/KEY: misc_feature
<222> LOCATION: (209)..(209)
<223> OTHER INFORMATION: Xaa is any aa, unknown, or other
<220> FEATURE:
<221> NAME/KEY: misc_feature
<222> LOCATION: (214)..(214)
<223> OTHER INFORMATION: Xaa is any aa, unknown, or other
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 44

Met Arg Lys Gly Arg Gly Ser Ser Ala Val Pro Pro Ala Leu Pro Gly
1               5                   10                  15

Ser Val Lys Glu Pro Arg Tyr Arg Gly Val Arg Lys Arg Pro Trp Gly
                20                  25                  30

Arg Phe Ala Ala Glu Ile Arg Asp Pro Leu Lys Lys Ser Arg Val Trp
            35                  40                  45

Leu Gly Thr Phe Asp Ser Ala Glu Glu Ala Ala Arg Ala Tyr Asp Ala
50                  55                  60

Ala Ala Arg Asn Leu Arg Gly Pro Lys Ala Lys Thr Asn Phe Gln Ile
65                  70                  75                  80

Asp Cys Ser Pro Ser Ser Pro Leu Gln Pro Leu His His Arg Asn Gln
                85                  90                  95
```

```
Ile Asp Pro Phe Met Asp His Arg Leu Tyr Gly Gly Glu Gln Glu Val
            100                 105                 110

Val Ile Ile Ser Arg Pro Ala Ser Ser Met Ser Ser Thr Val Lys
        115                 120                 125

Ser Cys Ser Gly Val Arg Pro Ala Ser Ser Val Ala Lys Ala Ala
    130                 135                 140

Thr Lys Arg Tyr Pro Arg Thr Pro Pro Val Ala Pro Glu Asp Cys Arg
145                 150                 155                 160

Ser Asp Cys Asp Ser Ser Ser Val Val Glu Asp Gly Xaa Asp Ile
                165                 170                 175

Ala Ser Ser Ser Arg Arg Lys Pro Pro Phe Glu Phe Asp Leu Asn
            180                 185                 190

Phe Xaa Pro Leu Asp Gly Val Asp Leu Phe Val Gly Ala Asp Xaa
        195                 200                 205

Xaa Cys Thr Asp Leu Xaa Leu
    210                 215

<210> SEQ ID NO 45
<211> LENGTH: 211
<212> TYPE: PRT
<213> ORGANISM: Zea mays
<220> FEATURE:
<221> NAME/KEY: misc_feature
<223> OTHER INFORMATION: Ceres CLONE ID no. 273307
<220> FEATURE:
<221> NAME/KEY: misc_feature
<222> LOCATION: (17)..(80)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 45

Met Arg Arg Arg Gly Val Ala Ala Asp Ala Asp Gly Asp Val Glu
1               5                   10                  15

Leu Arg Phe Arg Gly Val Arg Lys Arg Pro Trp Gly Arg Tyr Ala Ala
            20                  25                  30

Glu Ile Arg Asp Pro Ala Lys Lys Ala Arg Val Trp Leu Gly Thr Phe
        35                  40                  45

Asp Ser Ala Glu Asp Ala Ala Arg Ala Tyr Asp Ala Ala Ala Arg Met
    50                  55                  60

Leu Arg Gly Pro Lys Ala Arg Thr Asn Phe Pro Leu Pro Ala Ala Ala
65                  70                  75                  80

Ala Leu His His Pro His Met Pro Ala Ala Ala Ala Ala Ala Pro
            85                  90                  95

Pro Tyr Thr Thr Tyr Pro Thr Ala Thr Gly Val Val Ser Thr Pro Pro
            100                 105                 110

Val Ala Arg Pro Ala Cys Ser Ser Leu Ser Ser Thr Val Glu Ser Phe
        115                 120                 125

Ser Gly Ala Arg Pro Arg Pro Val Leu Pro Pro Arg Phe Pro Pro Pro
    130                 135                 140

Ser Ile Pro Asp Gly Asp Cys Arg Ser Asp Cys Gly Ser Ser Ala Ser
145                 150                 155                 160

Val Val Asp Asp Asp Cys Thr Asp Ala Ala Ala Ser Ala Ser Cys Pro
                165                 170                 175

Phe Pro Leu Pro Phe Asp Leu Asn Leu Pro Pro Gly Gly Gly Gly Ala
            180                 185                 190
```

Gly Val Gly Phe Tyr Ala Asp Glu Glu Asp Glu Leu Arg Leu Thr Ala
        195                 200                 205

Leu Arg Leu
    210

<210> SEQ ID NO 46
<211> LENGTH: 194
<212> TYPE: PRT
<213> ORGANISM: Triticum aestivum
<220> FEATURE:
<221> NAME/KEY: misc_feature
<223> OTHER INFORMATION: Ceres CLONE ID no. 1055099
<220> FEATURE:
<221> NAME/KEY: misc_feature
<222> LOCATION: (20)..(83)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 46

Met Arg Lys Ala Arg Pro Pro Gln Pro Gln Pro Gln Pro Ser Gln Gln
1               5                   10                  15

Ser Pro Glu Ile Arg Tyr Arg Gly Val Arg Lys Arg Pro Ser Gly Arg
            20                  25                  30

Tyr Ala Ala Glu Ile Arg Asp Pro Ala Lys Lys Thr Pro Ile Trp Leu
        35                  40                  45

Gly Thr Phe Asp Cys Ala Glu Asp Ala Ala Arg Ala Tyr Asp Ser Ala
    50                  55                  60

Ala Arg Ser Leu Arg Gly Pro Thr Ala Arg Thr Asn Phe Pro Pro Ser
65                  70                  75                  80

Ser Ala Thr Gln Pro Pro Pro Arg Pro Pro Pro Ala Ala Ala Ala Ala
                85                  90                  95

Ala Ala Ala Thr Ser Ser Gln Ser Ser Thr Val Glu Ser Trp Ser Gly
            100                 105                 110

Gly Gly Pro Arg Ala Pro Ala Arg Ala Arg Ser Ala Ala Arg Ala Gly
        115                 120                 125

Thr Ala Lys Glu Gly Glu Glu Asp Cys Arg Ser Tyr Cys Gly Ser Ser
    130                 135                 140

Ser Ser Val Leu Leu Glu Glu Gly Ala Asp Asp Ala Ala Ala Ser Arg
145                 150                 155                 160

Ser Pro Leu Pro Phe Asp Leu Asn Met Pro Pro Pro Gln Glu Gly Ala
                165                 170                 175

Leu Asp Ala Glu Ala Asp Gln Met Thr Cys Arg Tyr Asp Thr Leu Leu
            180                 185                 190

Arg Leu

<210> SEQ ID NO 47
<211> LENGTH: 660
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1441430
<220> FEATURE:
<221> NAME/KEY: misc_feature
<223> OTHER INFORMATION: Encodes the protein at SEQ ID NO: 48

<400> SEQUENCE: 47

-continued

```
atggggagaa caagaacaac aacaaaacag gctgttgacc caaatggatc tgcaacccaa    60
aatatgttag taattgcaaa agagcccaga tacagaggag tacgaaagag accatgggga   120
agattcgctg cggagattag agatccctgg aaaaagacca gagtttggct gggcaccttc   180
gactctgcag aggatgcagc gcgtgcctac gatgcggctg ctcgcaccct ccgcggagca   240
aaggccaaga caaactttcc tatctccaca acgaaccagt tattcaatca tcaaaatcaa   300
aaccaaagcc caaccgatcc cttcttggat caccacagta taaatcccca agacccaca   360 tctagcagtt tgagcagtac agtggagtct ttcagcggtc ctaggcctcc gcagccaaca   420
acaacaacaa aatcgggaaa tgggccgagg agatctcatc cacggatccc accggttgtt   480
ccagaagatt gtcatagcga ttgcgattca tcttcttcgg tggttgatga cagagatgtc   540
gcatccgctg cttcttcttt gtgccgcaag cctttgcctt tcgatctaaa tttcccaccg   600
ttggaccagg ttgacttggg ctctggtgat gatctccact gcactgcttt atgcctttga   660
```

<210> SEQ ID NO 48
<211> LENGTH: 219
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no. 1441430
<220> FEATURE:
<221> NAME/KEY: misc_feature
<222> LOCATION: (29)..(92)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 48

Met Gly Arg Thr Arg Thr Thr Thr Lys Gln Ala Val Asp Pro Asn Gly
1               5                   10                  15

Ser Ala Thr Gln Asn Met Leu Val Ile Ala Lys Glu Pro Arg Tyr Arg
            20                  25                  30

Gly Val Arg Lys Arg Pro Trp Gly Arg Phe Ala Ala Glu Ile Arg Asp
        35                  40                  45

Pro Trp Lys Lys Thr Arg Val Trp Leu Gly Thr Phe Asp Ser Ala Glu
    50                  55                  60

Asp Ala Ala Arg Ala Tyr Asp Ala Ala Ala Arg Thr Leu Arg Gly Ala
65                  70                  75                  80

Lys Ala Lys Thr Asn Phe Pro Ile Ser Thr Thr Asn Gln Leu Phe Asn
                85                  90                  95

His Gln Asn Gln Asn Gln Ser Pro Thr Asp Pro Phe Leu Asp His His
            100                 105                 110

Ser Ile Asn Pro Gln Arg Pro Thr Ser Ser Ser Leu Ser Ser Thr Val
        115                 120                 125

Glu Ser Phe Ser Gly Pro Arg Pro Pro Gln Pro Thr Thr Thr Thr Lys
    130                 135                 140

Ser Gly Asn Gly Pro Arg Arg Ser His Pro Arg Ile Pro Pro Val Val
145                 150                 155                 160

Pro Glu Asp Cys His Ser Asp Cys Asp Ser Ser Ser Val Val Asp
                165                 170                 175

Asp Arg Asp Val Ala Ser Ala Ala Ser Ser Leu Cys Arg Lys Pro Leu
            180                 185                 190

Pro Phe Asp Leu Asn Phe Pro Pro Leu Asp Gln Val Asp Leu Gly Ser

-continued

```
                195                 200                 205
Gly Asp Asp Leu His Cys Thr Ala Leu Cys Leu
    210                 215

<210> SEQ ID NO 49
<211> LENGTH: 985
<212> TYPE: DNA
<213> ORGANISM: Glycine max
<220> FEATURE:
<221> NAME/KEY: misc_feature
<223> OTHER INFORMATION: Ceres CLONE ID no.1240330
<220> FEATURE:
<221> NAME/KEY: misc_feature
<223> OTHER INFORMATION: Encodes the protein at SEQ ID NO: 50

<400> SEQUENCE: 49
attattcctc ttccatctct attctccata cacccacca caccacttgt gaaaaacctc      60
attaatatca cacactgaca tgtatctctg agctccaatc caatacaaga ccacaccttg    120
tcgtgtcgga cgaaccttgg tgtctgtttt ttttttttt tcattatttt ctccgaagag     180
atgaggaagg gcagaggtgg aggcgcctcg gcggcggcgg tggatgtgaa cggatccatt    240
ttaaaggagc ctcggtaccg gggcgtgagg aagagaccgt gggggagatt cgccgcggag    300
atcagagacc cgttgaagaa agccagggtt tggttgggaa ccttcgattc tgccgaggat    360
gctgctcgtg cctacgacgc cgccgctcgg actctccgag gtcccaaggc caaaacaaat    420 ttccccctc tctcaccttt tgctatcca cacccacca ccgatccttt cttctacact       480
ggtttccacg atcaacacca ccaccacaac aacaacaacc ttaacaaccc tcaaagaccc    540
acttcaagtg gcatgagtag caccgttgag tccttcagtg ggccccgccc tccaccacc    600 accactacca ccacaaccac aactgcgacg ccgttttga ctgctacgcg agatacccg      660 cgcactcccc ctcttgtccc tgaagactgc acagtgact gcgactcttc ctcctccgtc     720
gttgacgacg gcgacgacaa catcgtttcg tcgtcgtttc gacctccctt gccgtttgat    780
ctcaacgcgc tgccgtttga tgatgctgcc gcggatgatg atctacgccg caccgcgctt    840
tgtctctgat gatgattatc gtgcgatgat gattttaat ttctcatttt tttacttgat    900 tttttgtta ttgctatgca gaagaaatat atatttaaaa tgatgatcag atgtaagatt    960
atggtaatat gatcttaatt ctgtg                                          985

<210> SEQ ID NO 50
<211> LENGTH: 222
<212> TYPE: PRT
<213> ORGANISM: Glycine max
<220> FEATURE:
<221> NAME/KEY: misc_feature
<223> OTHER INFORMATION: Ceres CLONE ID no. 1240330
<220> FEATURE:
<221> NAME/KEY: misc_feature
<222> LOCATION: (24)..(87)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 50

Met Arg Lys Gly Arg Gly Gly Ala Ser Ala Ala Ala Val Asp Val
1               5                  10                  15

Asn Gly Ser Ile Leu Lys Glu Pro Arg Tyr Arg Gly Val Arg Lys Arg
            20                  25                  30
```

```
Pro Trp Gly Arg Phe Ala Ala Glu Ile Arg Asp Pro Leu Lys Lys Ala
         35                  40                  45

Arg Val Trp Leu Gly Thr Phe Asp Ser Ala Glu Asp Ala Ala Arg Ala
 50                      55                  60

Tyr Asp Ala Ala Ala Arg Thr Leu Arg Gly Pro Lys Ala Lys Thr Asn
 65                  70                  75                  80

Phe Pro Pro Leu Ser Pro Phe Cys Tyr Pro His Pro Thr Thr Asp Pro
                 85                  90                  95

Phe Phe Tyr Thr Gly Phe His Asp Gln His His His Asn Asn Asn
             100                 105                 110

Asn Leu Asn Asn Pro Gln Arg Pro Thr Ser Ser Gly Met Ser Ser Thr
         115                 120                 125

Val Glu Ser Phe Ser Gly Pro Arg Pro Thr Thr Thr Thr Thr Thr
 130                 135                 140

Thr Thr Thr Thr Ala Thr Pro Phe Leu Thr Ala Thr Arg Arg Tyr Pro
145                 150                 155                 160

Arg Thr Pro Pro Leu Val Pro Glu Asp Cys His Ser Asp Cys Asp Ser
                 165                 170                 175

Ser Ser Ser Val Val Asp Asp Gly Asp Asp Asn Ile Val Ser Ser Ser
             180                 185                 190

Phe Arg Pro Pro Leu Pro Phe Asp Leu Asn Ala Leu Pro Phe Asp Asp
         195                 200                 205

Ala Ala Asp Asp Asp Leu Arg Arg Thr Ala Leu Cys Leu
         210                 215                 220

<210> SEQ ID NO 51
<211> LENGTH: 726
<212> TYPE: DNA
<213> ORGANISM: Zea mays
<220> FEATURE:
<221> NAME/KEY: misc_feature
<223> OTHER INFORMATION: Ceres CLONE ID no.1382611
<220> FEATURE:
<221> NAME/KEY: misc_feature
<223> OTHER INFORMATION: Encodes the protein at SEQ ID NO: 52

<400> SEQUENCE: 51
acttttctct cccattcttt tacaactcac gttgcacagc cttttctct atatattact    60
tgacataaac tactattcac aacacaaaca cacacataac catggcctct tcttcacaag   120
ctttccttt gctcacattg tctatggttt tagttcattt ctctttagct caatctccca   180
tgatggctcc ttctggctcc atgtccatgc cgccaatgcc tagcggcggc tctccaatgc   240
caatgatgac tccaccacct atgccaatga tgactccacc acctatggct atggctccac   300
cacctatgcc tatgactcca ccaccaatgc ccatggctcc gatgccaatg actccatctt   360
caagtccaat gagcccacca actactatgg ccccaagtcc agaaacagtc cctgatatgg   420
cttcgccacc gatgatgcca ggaatggatt cttctccttc tccgggaccc atgccaccgg   480
caatggcctc tccagattcc ggagcattca atgtaagaaa cgacgtcgta gcaatttcgt   540
tccttgttgc agctcatttg ctcctagttt gagattatta ttaaattggc cagcgtcgtg   600
tttgtgtaat ttactttcat ttttttctcg agccattaat tttcatgttt tatcatatat   660
ttgggtttgt gtttgatatg gtacgattca gacatttgtt tgcttaataa gtttatcgtt   720
gactct                                                              726

<210> SEQ ID NO 52
<211> LENGTH: 156
```

```
<212> TYPE: PRT
<213> ORGANISM: Zea mays
<220> FEATURE:
<221> NAME/KEY: misc_feature
<223> OTHER INFORMATION: Ceres CLONE ID no. 1382611
<220> FEATURE:
<221> NAME/KEY: misc_feature
<223> OTHER INFORMATION: Functional Homolog of Ceres CLONE ID no. 30087
      Given in SEQ ID NO: 2

<400> SEQUENCE: 52

Met Ala Ser Ser Ser Gln Ala Phe Leu Leu Leu Thr Leu Ser Met Val
1               5                   10                  15

Leu Val His Phe Ser Leu Ala Gln Ser Pro Met Met Ala Pro Ser Gly
            20                  25                  30

Ser Met Ser Met Pro Pro Met Pro Ser Gly Gly Ser Pro Met Pro Met
        35                  40                  45

Met Thr Pro Pro Pro Met Pro Met Met Thr Pro Pro Pro Met Ala Met
    50                  55                  60

Ala Pro Pro Pro Met Pro Met Thr Pro Pro Met Pro Met Ala Pro
65                  70                  75                  80

Met Pro Met Thr Pro Ser Ser Ser Pro Met Ser Pro Pro Thr Thr Met
                85                  90                  95

Ala Pro Ser Pro Glu Thr Val Pro Asp Met Ala Ser Pro Met Met
                100                 105                 110

Pro Gly Met Asp Ser Ser Pro Ser Gly Pro Met Pro Pro Ala Met
            115                 120                 125

Ala Ser Pro Asp Ser Gly Ala Phe Asn Val Arg Asn Asp Val Val Ala
    130                 135                 140

Ile Ser Phe Leu Val Ala Ala His Leu Leu Leu Val
145                 150                 155

<210> SEQ ID NO 53
<211> LENGTH: 580
<212> TYPE: DNA
<213> ORGANISM: Papaver somniferum
<220> FEATURE:
<221> NAME/KEY: misc_feature
<223> OTHER INFORMATION: Ceres CLONE ID no.1627907
<220> FEATURE:
<221> NAME/KEY: misc_feature
<223> OTHER INFORMATION: Encodes the protein at SEQ ID NO: 54

<400> SEQUENCE: 53
gcagaagcac aaggtaagat tgaaggagga gaccggaact cttcttcgcc aaaaccctag    60
ttcgagctca ccaacaacaa tctttcgcaa tgactaagcg taccaagaag gccggaattg   120
tgggtaaata tggtaccaga tatggagctt cattaaggaa acagattaag aagatggaag   180
tgagtcagca tgcaaagtac ttctgtgagt tctgcggaaa gtacgctgtg aagagacagg   240
ctgttggaat ctggggatgc aaggattgtg gcaaagttaa agctggtggt gcttacactt   300
tgaacaccgc cagtgccgtg acagttagaa gcaccattag aaggttgagg gagcaaactg   360
aatcttagat tgatctcgtt atctatattt tgtattttgg tactgggtga gaggtaccat   420
cagagctaat ttagtgttta tcaccttttc tggtcttcaa gaactagtta gtcattttgt   480
tattcagaga tttttgataa tgtctagtat cttacatttg tgagcagact atttctttgt   540
ttcaaattat ggagttctga tgaatcttat atttattctc                         580

<210> SEQ ID NO 54
<211> LENGTH: 92
```

```
<212> TYPE: PRT
<213> ORGANISM: Papaver somniferum
<220> FEATURE:
<221> NAME/KEY: misc_feature
<223> OTHER INFORMATION: Ceres CLONE ID no. 1627907
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional Homolog of Ceres CLONE ID no. 271922
      Given in SEQ ID NO: 20

<400> SEQUENCE: 54

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ala Lys Tyr Phe Cys Glu Phe Cys Gly Lys Tyr Ala Val Lys
        35                  40                  45

Arg Gln Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 55
<211> LENGTH: 983
<212> TYPE: DNA
<213> ORGANISM: Panicum virgatum
<220> FEATURE:
<221> NAME/KEY: misc_feature
<223> OTHER INFORMATION: Ceres CLONE ID no.1761125
<220> FEATURE:
<221> NAME/KEY: misc_feature
<223> OTHER INFORMATION: Encodes the protein at SEQ ID NO: 56

<400> SEQUENCE: 55
accagaccac accacaccac accgcgtcca catcctcccg cgcttctccg ctcagcccgc      60
gcgtttccgc tgaggaggga tagccgcgcg gcgcgtcgag gggtttgtct ttgatcgggt     120
agctgaggct gagcgggcgg ggcaggatga tgcgcgacac ggcggccgtg gccgtggcgg     180
cgccgcggta caggggcgtg cggaagcggc cgtgggccg gttcgcggcg gagatccgcg      240
acccggcgaa gcgcgcgcgc gtctggctcg gcaccttcga ctccgccgag gccgcggcgc     300
gcgcctacga cgtcgccgcg cggaccctgc gcggcccgct cgccaggacc aacttcccct     360
gcgcctcctc ccgcctcccg ctgccctccc gccaccaagg cggctgtggc ggcggcctcg     420
tcgcgccgcc gcccgccgcg ccgacgtgca gctccagctc caccgtcgag tcctccagcg     480
gaccccgagg ggcgcccagg gctgctgcgc cggcggcgcc tcgaattcgg aggcggtcgg     540
tgaaaaagcc gcggccggca gcgcccgaca tcgactgcca cagcgactgc gcctcgtcgg     600
cctccgtcgt ggacgacggc gacgacgcct ccacggtccg gtcgcgcgcg ccgttcgacc     660
tcaacgtccc ggctccggtg gacggtgacc acgccctcga cctctgcacg gagctgcggc     720
tctgagcaat atgatcctcg aacaacaaca acagcaaaac attgaaggcg atttttcccc     780
ggtcttcttt tcctgactaa attctgatat gatcaatatg ctcgagagtt ctcgttttct     840
ttaacgcctc ttgtatttgg atctgctacc atcttctctg cccattctat ttgtacacca     900
```

-continued

```
gataacatgt aagatgttca cgaattaaca catatctttt cttaaaaaaa tgaattaaca      960
cggaaaaaaa aaaaaaaaaa aaa                                             983
```

<210> SEQ ID NO 56
<211> LENGTH: 192
<212> TYPE: PRT
<213> ORGANISM: Panicum virgatum
<220> FEATURE:
<221> NAME/KEY: misc_feature
<223> OTHER INFORMATION: Ceres CLONE ID no. 1761125
<220> FEATURE:
<221> NAME/KEY: misc_feature
<222> LOCATION: (13)..(76)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 56

```
Met Met Arg Asp Thr Ala Ala Val Ala Val Ala Ala Pro Arg Tyr Arg
1               5                   10                  15

Gly Val Arg Lys Arg Pro Trp Gly Arg Phe Ala Ala Glu Ile Arg Asp
            20                  25                  30

Pro Ala Lys Arg Ala Arg Val Trp Leu Gly Thr Phe Asp Ser Ala Glu
        35                  40                  45

Ala Ala Arg Ala Tyr Asp Val Ala Ala Arg Thr Leu Arg Gly Pro
    50                  55                  60

Leu Ala Arg Thr Asn Phe Pro Cys Ala Ser Ser Arg Leu Pro Leu Pro
65                  70                  75                  80

Ser Arg His Gln Gly Gly Cys Gly Gly Gly Leu Val Ala Pro Pro
                85                  90                  95

Ala Ala Pro Thr Cys Ser Ser Ser Thr Val Glu Ser Ser Ser Gly
            100                 105                 110

Pro Arg Gly Ala Pro Arg Ala Ala Ala Ala Ala Pro Arg Ile Arg
        115                 120                 125

Arg Arg Ser Val Lys Lys Pro Arg Pro Ala Ala Pro Asp Ile Asp Cys
130                 135                 140

His Ser Asp Cys Ala Ser Ser Ala Ser Val Val Asp Asp Gly Asp Asp
145                 150                 155                 160

Ala Ser Thr Val Arg Ser Arg Ala Pro Phe Asp Leu Asn Val Pro Ala
                165                 170                 175

Pro Val Asp Gly Asp His Ala Leu Asp Leu Cys Thr Glu Leu Arg Leu
            180                 185                 190
```

<210> SEQ ID NO 57
<211> LENGTH: 594
<212> TYPE: DNA
<213> ORGANISM: Panicum virgatum
<220> FEATURE:
<221> NAME/KEY: misc_feature
<223> OTHER INFORMATION: Ceres CLONE ID no.1783890
<220> FEATURE:
<221> NAME/KEY: misc_feature
<223> OTHER INFORMATION: Encodes the protein at SEQ ID NO: 58

<400> SEQUENCE: 57

```
gagccctacc cgcacccgcg ccgccgccgc cccgcgcccc gtcgccgcag acgactccgc      60
cccgtcgccg cgatgacgaa gcgcaccaag aaggccggaa tcgtcggcaa atatggaact     120
aggtatggtg ctagcttgcg taagcaaatc aagaagatgg aggtgtctca gcactccaag     180
```

-continued

```
tacttctgcg agttctgtgg aaagtttgct gtgaaaagga aagcagttgg aatctgggga      240
tgcaaggact gcgggaaggt taaggctggt ggtgcttaca ccatgaacac tgctagtgca      300
gtcaccgtca ggagcacaat ccgtcgcttg agggagcaga ctgaagcata atcggagctc      360
ttctctgcag tagtcctgtg cttttttgtac cgtctaagac atatggctgt ttggcctaag     420
aacattcatg aatattctgg ttatgcttaa ggatatcaaa aattatggtg ctaaaatttg      480
tacttcgttg ctgttgcaaa gttgacctgt cttgatccat tcataatgta gaatttcctc      540
atggttctta tctccagttt gctactcttt ggccaaaaaa aaaaaaaaa aaaa             594
```

<210> SEQ ID NO 58
<211> LENGTH: 92
<212> TYPE: PRT
<213> ORGANISM: Panicum virgatum
<220> FEATURE:
<221> NAME/KEY: misc_feature
<223> OTHER INFORMATION: Ceres CLONE ID no. 1783890
<220> FEATURE:
<221> NAME/KEY: misc_feature
<222> LOCATION: (2)..(91)
<223> OTHER INFORMATION: Pfam Name: Ribosomal_L37ae
    Pfam Description: Ribosomal L37ae protein family
<220> FEATURE:
<221> NAME/KEY: misc_feature
<223> OTHER INFORMATION: Functional Homolog of Ceres CLONE ID no. 271922
    Given in SEQ ID NO: 20

<400> SEQUENCE: 58

```
Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90
```

<210> SEQ ID NO 59
<211> LENGTH: 880
<212> TYPE: DNA
<213> ORGANISM: Panicum virgatum
<220> FEATURE:
<221> NAME/KEY: misc_feature
<223> OTHER INFORMATION: Ceres CLONE ID no.1802327
<220> FEATURE:
<221> NAME/KEY: misc_feature
<223> OTHER INFORMATION: Encodes the protein at SEQ ID NO: 60

<400> SEQUENCE: 59

```
acacagatac attcgtcgat ccaccactgt ccagtgcttg gcggttacgc acgcacgcac       60
acagatagga ttatctttta ctacaccaac tcaccaagat actagcaagc cgaatcgaca      120
aacaagcagc aggaagagga ggcatggcgc tcgcggaggg gaacgtcatc ttcggcgagg      180
agcaggaggc gctggtgctc aagtcgtggg ccctcatgaa gaaggactcg gccgacctcg      240
gcctccgctt cttcctcaag atcttcgaga tcgcgccgtc ggcgaagcag atgttctcgt      300
tcctgcgcga ctccgacgtg ccgctcgaga agaaccccaa gctcaagaac cacgccatgt      360
```

```
ccgtcttcgt catgacctgc gaggcggcgg cgcagctacg gaaggccggg aaggtcaccg      420
tcagggagac gacgctcaag cggctgggcg ccacgcactt caagtacggc gtcgccgacg      480
gccacttcga ggtgacgagg ttcgcgctgc tggagacgat aaaggaggcg cttcccgccg      540
acatgtggag cctggagatg aagaacgcct ggagcgaggc ttacaaccag ctggtggcgg      600
ccatcaagca ggagatgaag cctgccgcat gatgctgctg ctgctactga gatgaagcct      660
gcccgcatga tgctgctgct gctactcggc ctccgcgctg agttccccct acgatgcacc      720
accatctcca aattcttcat cgctgttttt tttttttgc tgttttgact tgtattgtgc      780
attttccaaa tctctcgatg gagacaagtg tgatgactaa tttttgagag catgtatata      840
tgttgtgatg agcattgaat aaaaaaaaaa aaaaaaaaa                            880
```

<210> SEQ ID NO 60
<211> LENGTH: 162
<212> TYPE: PRT
<213> ORGANISM: Panicum virgatum
<220> FEATURE:
<221> NAME/KEY: misc_feature
<223> OTHER INFORMATION: Ceres CLONE ID no. 1802327
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 60

```
Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Asn His Ala Met Ser Val Phe Val Met Thr Cys Glu
65                  70                  75                  80

Ala Ala Ala Gln Leu Arg Lys Ala Gly Lys Val Thr Val Arg Glu Thr
                85                  90                  95

Thr Leu Lys Arg Leu Gly Ala Thr His Phe Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Ser Leu Glu Met Lys Asn Ala Trp Ser
    130                 135                 140

Glu Ala Tyr Asn Gln Leu Val Ala Ala Ile Lys Gln Glu Met Lys Pro
145                 150                 155                 160

Ala Ala
```

<210> SEQ ID NO 61
<211> LENGTH: 1017
<212> TYPE: DNA
<213> ORGANISM: Gossypium hirsutum
<220> FEATURE:
<221> NAME/KEY: misc_feature
<223> OTHER INFORMATION: Ceres CLONE ID no.1838364
<220> FEATURE:

<221> NAME/KEY: misc_feature
<223> OTHER INFORMATION: Encodes the protein at SEQ ID NO: 62

<400> SEQUENCE: 61

```
cctgcccatt tccatcttcc ttctttcctt cctctttcct ttgtcttctt gctttatctt     60
cccctttatct tcaatctttt ctgttctgtt tttttcttag attcataggt aagttcgttt    120
tggttggctt gattatttcc tcacttccct tcttttttgg ttcatcgtga tcttttcatc    180
aaccccttt gattgttata tagattgtta ctattctttt aatctttta atatttttt       240
tccatgagga gagggagagg tgccgcagct gcaaacgccg tagctaggag accggcactg    300
caacccagcg gatctattaa agagccgaga tacagaggtg ttagaaaaag gccatggggc    360
agattcgcgg ccgagattcg agacccttgg aagaagacca gggtctggtt agggacgttc    420
gactcggccg aagaagccgc tcgagcctac gatacggcgg cgaggacgct ccgtggaccc    480
aaagctaaaa caaatttccc cataaattct tcaaatatcc cggcttttcc tttcgaaacc    540
aatcatcacc acaacgaagg gttcatcgac caacgccggt tatatccgat gggcgaattt    600
catgaccccg aagtgaatcc acagagaccc acgaggagta gcatgagtag cacggtggag    660
tcgtttagtg gacccagacc ggcccaacca ccgcaaaagt cggcggactt cgcggtggtt    720
tcgactagga agtactatcc gaggccgccg ccagtagagc cagaggattg tcatagtgac    780
tgtgattcat catcgtcggt ggttgatgat ggggatatcg cgttgtcttc ttgtcggaaa    840
actttgcctt tcgatctcaa tttccaccc ttggatgaag atggaagatc tccagtgtac    900
tgctttatgt ctttgatcgc gatgccggtg atgaatgatg atgatcgatt attggatctc    960
tttttcttt ttaaaaaatg ttagcttttt taagcggaaa aaaaaaaaaa aaaaaaa     1017
```

<210> SEQ ID NO 62
<211> LENGTH: 246
<212> TYPE: PRT
<213> ORGANISM: Gossypium hirsutum
<220> FEATURE:
<221> NAME/KEY: misc_feature
<223> OTHER INFORMATION: Ceres CLONE ID no. 1838364
<220> FEATURE:
<221> NAME/KEY: misc_feature
<222> LOCATION: (28)..(91)
<223> OTHER INFORMATION: Pfam Name: AP2
     Pfam Description: AP2 domain
<220> FEATURE:
<221> NAME/KEY: misc_feature
<223> OTHER INFORMATION: Functional Homolog of Ceres CLONE ID no. 674166
     Given in SEQ ID NO: 42

<400> SEQUENCE: 62

```
Met Arg Arg Gly Arg Gly Ala Ala Ala Ala Asn Ala Val Ala Arg Arg
1               5                   10                  15

Pro Ala Leu Gln Pro Ser Gly Ser Ile Lys Glu Pro Arg Tyr Arg Gly
            20                  25                  30

Val Arg Lys Arg Pro Trp Gly Arg Phe Ala Ala Glu Ile Arg Asp Pro
        35                  40                  45

Trp Lys Lys Thr Arg Val Trp Leu Gly Thr Phe Asp Ser Ala Glu Glu
    50                  55                  60

Ala Ala Arg Ala Tyr Asp Thr Ala Ala Arg Thr Leu Arg Gly Pro Lys
65                  70                  75                  80

Ala Lys Thr Asn Phe Pro Ile Asn Ser Ser Asn Ile Pro Ala Phe Pro
                85                  90                  95

Phe Glu Thr Asn His His Asn Glu Gly Phe Ile Asp Gln Arg Arg
            100                 105                 110
```

```
Leu Tyr Pro Met Gly Glu Phe His Asp Pro Glu Val Asn Pro Gln Arg
        115                 120                 125

Pro Thr Arg Ser Ser Met Ser Ser Thr Val Glu Ser Phe Ser Gly Pro
    130                 135                 140

Arg Pro Ala Gln Pro Pro Gln Lys Ser Ala Asp Phe Ala Val Val Ser
145                 150                 155                 160

Thr Arg Lys Tyr Tyr Pro Arg Pro Pro Val Glu Pro Glu Asp Cys
            165                 170                 175

His Ser Asp Cys Asp Ser Ser Ser Val Val Asp Asp Gly Asp Ile
        180                 185                 190

Ala Leu Ser Ser Cys Arg Lys Thr Leu Pro Phe Asp Leu Asn Phe Pro
        195                 200                 205

Pro Leu Asp Glu Asp Gly Arg Ser Pro Val Tyr Cys Phe Met Ser Leu
    210                 215                 220

Ile Ala Met Pro Val Met Asn Asp Asp Asp Arg Leu Leu Asp Leu Phe
225                 230                 235                 240

Phe Phe Phe Lys Lys Cys
            245

<210> SEQ ID NO 63
<211> LENGTH: 708
<212> TYPE: DNA
<213> ORGANISM: Panicum virgatum
<220> FEATURE:
<221> NAME/KEY: misc_feature
<223> OTHER INFORMATION: Ceres CLONE ID no.1876458
<220> FEATURE:
<221> NAME/KEY: misc_feature
<223> OTHER INFORMATION: Encodes the protein at SEQ ID NO: 64

<400> SEQUENCE: 63
acacagatac attcgtcgat ccaccactgt ccagtgcttg gcggttacgc acgcacgcac    60
acagatagga ttatctttta ctacaccaac tcaccaagat actagcaagc cgaatcgaca   120
aacaagcagc aggaagagga ggcatggcgc tcgcggaggg gaacgtcatc ttcggcgagg   180
agcaggaggc gctggtgctc aagtcgtggg ccctcatgaa gaaggactcg gccgacctcg   240
gcctccgctt cttcctcaag atcttcgaga tcgcgccgtc ggcgaagcag atgttctcgt   300
tcctgcgcga ctccgacgtg ccgctcgaga agaaccccaa gctcaagacc acgccatgt   360 ccgtcttcgt catgacctgc gaggcggcgg cgcagctacg gaaggccggg aaggtcaccg   420
tcagggagac gacgctcaag cggctgggcg ccacgcactt caagtacggc gtcgccgacg   480
gccacttcga ggtgacgagg ttcgcgctgc tggagacgat aaaggaggcg cttcccgccg   540
acatgtggag cctggagatg aagtacgcct ggagcgaggc ttacaaccag cttgtggcgg   600
ccatcaagca ggagatgaag cctgccgcat gatgctgctg ctgctactcg gcctccgcgc   660
tgagttcccc ctacgatgca ccaccatctc caaattcttc atcgctgt                708

<210> SEQ ID NO 64
<211> LENGTH: 162
<212> TYPE: PRT
<213> ORGANISM: Panicum virgatum
<220> FEATURE:
<221> NAME/KEY: misc_feature
<223> OTHER INFORMATION: Ceres CLONE ID no. 1876458
<220> FEATURE:
<221> NAME/KEY: misc_feature
<222> LOCATION: (14)..(154)
<223> OTHER INFORMATION: Pfam Name: Globin
        Pfam Description: Globin
```

```
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 64
```

| Met | Ala | Leu | Ala | Glu | Gly | Asn | Val | Ile | Phe | Gly | Glu | Glu | Gln | Glu | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
            35                  40                  45

Gln Met Phe Ser Phe Leu Arg Asp Ser Asp Val Pro Leu Glu Lys Asn
50                  55                  60

Pro Lys Leu Lys Thr His Ala Met Ser Val Phe Val Met Thr Cys Glu
65                  70                  75                  80

Ala Ala Ala Gln Leu Arg Lys Ala Gly Lys Val Thr Val Arg Glu Thr
                85                  90                  95

Thr Leu Lys Arg Leu Gly Ala Thr His Phe Lys Tyr Gly Val Ala Asp
                100                 105                 110

Gly His Phe Glu Val Thr Arg Phe Ala Leu Leu Glu Thr Ile Lys Glu
            115                 120                 125

Ala Leu Pro Ala Asp Met Trp Ser Leu Glu Met Lys Tyr Ala Trp Ser
130                 135                 140

Glu Ala Tyr Asn Gln Leu Val Ala Ala Ile Lys Gln Glu Met Lys Pro
145                 150                 155                 160

Ala Ala

```
<210> SEQ ID NO 65
<211> LENGTH: 712
<212> TYPE: DNA
<213> ORGANISM: Panicum virgatum
<220> FEATURE:
<221> NAME/KEY: misc_feature
<223> OTHER INFORMATION: Ceres CLONE ID no.1879148
<220> FEATURE:
<221> NAME/KEY: misc_feature
<223> OTHER INFORMATION: Encodes the protein at SEQ ID NO: 66

<400> SEQUENCE: 65
acacagatac attcgtcgat ccaccactgt ccagtgctcg gctcggttac gcacgcacgc      60
acacaaattg tagtacctgt gttttacacc accaagatac tagcaagcc gagtcgacaa     120 acaaagcagc aggaagaggc atggcgctcg ctgacgggaa cggcgcggcc atcttcggcg     180
aggagcagga ggcgctggtg ctcaagtcgt gggccctcat gaagaaggac tcggccgacc     240
tcggcctccg cttcttcctc aagatcttcg agatcgcgcc gtcggcgaag cagatgttct     300
cgttcctgcg cgactccgac gtgccgctgg agaagaaccc caagctcaag acccacgcca     360
tgtccgtctt cgtcatgacc tgcgaggcgg cagcgcagct acggaaggcc gggaaggtca     420
ccgtcaggga gacgacgctc aagcggctgg gcgcaacgca cttcaagtac ggcgtcgccg     480
acggccactt cgaggtgaca aggttcgcgc tgctggagac gataaaggag gcgcttcccg     540
ccgacatgtg gagcctggag atgaagaacg cctggagcga ggcttacaac cagctcgtgg     600
cggccatcaa gcaggagatg aagcctgctg catgatgctg catgctgcta catactcggc     660
ctccgagttc ccctacgat gcaccaccat ctccaagttc ttcatcgcta tt              712

<210> SEQ ID NO 66
```

```
<211> LENGTH: 164
<212> TYPE: PRT
<213> ORGANISM: Panicum virgatum
<220> FEATURE:
<221> NAME/KEY: misc_feature
<223> OTHER INFORMATION: Ceres CLONE ID no. 1879148
<220> FEATURE:
<221> NAME/KEY: misc_feature
<222> LOCATION: (16)..(156)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 66
```

| Met | Ala | Leu | Ala | Asp | Gly | Asn | Gly | Ala | Ala | Ile | Phe | Gly | Glu | Glu | Gln |
|---|---|---|---|---|---|---|---|---|---|---|---|---|---|---|---|
| 1 | | | | 5 | | | | | 10 | | | | | 15 | |
| Glu | Ala | Leu | Val | Leu | Lys | Ser | Trp | Ala | Leu | Met | Lys | Lys | Asp | Ser | Ala |
| | | | 20 | | | | | 25 | | | | | 30 | | |
| Asp | Leu | Gly | Leu | Arg | Phe | Phe | Leu | Lys | Ile | Phe | Glu | Ile | Ala | Pro | Ser |
| | | | 35 | | | | | 40 | | | | | 45 | | |
| Ala | Lys | Gln | Met | Phe | Ser | Phe | Leu | Arg | Asp | Ser | Asp | Val | Pro | Leu | Glu |
| | 50 | | | | | 55 | | | | | 60 | | | | |
| Lys | Asn | Pro | Lys | Leu | Lys | Thr | His | Ala | Met | Ser | Val | Phe | Val | Met | Thr |
| 65 | | | | | 70 | | | | | 75 | | | | | 80 |
| Cys | Glu | Ala | Ala | Ala | Gln | Leu | Arg | Lys | Ala | Gly | Lys | Val | Thr | Val | Arg |
| | | | | 85 | | | | | 90 | | | | | 95 | |
| Glu | Thr | Thr | Leu | Lys | Arg | Leu | Gly | Ala | Thr | His | Phe | Lys | Tyr | Gly | Val |
| | | | 100 | | | | | 105 | | | | | 110 | | |
| Ala | Asp | Gly | His | Phe | Glu | Val | Thr | Arg | Phe | Ala | Leu | Leu | Glu | Thr | Ile |
| | | | 115 | | | | | 120 | | | | | 125 | | |
| Lys | Glu | Ala | Leu | Pro | Ala | Asp | Met | Trp | Ser | Leu | Glu | Met | Lys | Asn | Ala |
| | 130 | | | | | 135 | | | | | 140 | | | | |
| Trp | Ser | Glu | Ala | Tyr | Asn | Gln | Leu | Val | Ala | Ala | Ile | Lys | Gln | Glu | Met |
| 145 | | | | | 150 | | | | | 155 | | | | | 160 |
| Lys | Pro | Ala | Ala | | | | | | | | | | | | |

```
<210> SEQ ID NO 67
<211> LENGTH: 1129
<212> TYPE: DNA
<213> ORGANISM: Gossypium hirsutum
<220> FEATURE:
<221> NAME/KEY: misc_feature
<223> OTHER INFORMATION: Ceres CLONE ID no.1884696
<220> FEATURE:
<221> NAME/KEY: misc_feature
<223> OTHER INFORMATION: Encodes the protein at SEQ ID NO: 68

<400> SEQUENCE: 67
atccgccccc atttgttcgc tctgtatatt gaactttct ttctcgattt tctctttgaa      60
caaaaatgat gaagatcttc aaccagactc tcaccggcaa gactatcacg ctcgaggtcg    120
agagctccga caccatcgaa ggcgccaaca ccattctcca agatggaggg agcctccctc    180
cttaccgaac ccgactgatc ttcgccggac aacagcttga ggacggactg accttgtgcg    240
attacaacat cttaaaggag gtcaactctc cacctcttcc tccggttgcg cggtgggatg    300
cttaccttcc ggaggacctt gaccggcaat accatcactc tccaggtcta aagcgccgac    360
tcgatcaagt tcgttcacgc taacatccaa gactaggaag gcgtcccccc ataccaacta    420
cgactctgct tcgaccgaaa acaacttgaa gacggccgta ccttggccga ctacaacatc    480
```

```
cagaaggagt caacgctcca tcttgtcctt cgtttgcgtg gcgggatgca aatcttcgtt    540
aagacgctta cgggaaagac gatcactctc gaggtcgaga gctctgacac gatcgacaac    600
gtgaaagcca aaatccaaga caaggaaggc atcccgccag accagcaacg tctcatcttc    660
gccggaaagc aactcgagga cgggcggact ttagccgatt acaatatcca gaaggaatcg    720
actcttcatc tggtcctgcg tcttggaggt gggatgcaga tcttcgtcaa gactttgacc    780
ggtaagacga ttactttaga agtggagagc tcggatacga ttgataacgt gaaagcgaag    840
attcaggaca agaaggaat tccaccagat cagcaaaggt tgattttgc tgggaaacaa      900 ctggaagacg gaaggacttt ggctgattac aatattcaaa aggattccac tcttcacctt    960
gttcttcgtc ttcgtggtgg gttctaagcc ttaaggtctc ccttaatgtg ggttttctgg   1020
ttttacgtga aggactgtgc cctgtaatgg cctttaaat aatttctagt ctttgtttac    1080
cggttgcatc tatgtatggt ttctcttaga atggaattag catatttac              1129
```

<210> SEQ ID NO 68
<211> LENGTH: 153
<212> TYPE: PRT
<213> ORGANISM: Gossypium hirsutum
<220> FEATURE:
<221> NAME/KEY: misc_feature
<223> OTHER INFORMATION: Ceres CLONE ID no. 1884696
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 68

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Asp Ser Thr Leu His
    130                 135                 140

Leu Val Leu Arg Leu Arg Gly Gly Phe
145                 150
```

<210> SEQ ID NO 69
<211> LENGTH: 679
<212> TYPE: DNA
<213> ORGANISM: Gossypium hirsutum
<220> FEATURE:
<221> NAME/KEY: misc_feature
<223> OTHER INFORMATION: Ceres CLONE ID no.1916866
<220> FEATURE:
<221> NAME/KEY: misc_feature
<223> OTHER INFORMATION: Encodes the protein at SEQ ID NO: 70

<400> SEQUENCE: 69

```
aaatcaaata cctactgcaa ttaaaatccc ggaattactt aaacaacaat ggctacctat      60
gaaggtaaag ttttcactga agaacaagaa gctttggtgg tcaagtcatg gactgtaatg     120
aagaagaacg cagctgaatt gggtcttaaa ttcttcttga agatatttga gattgcacca     180
tcagccaaga aactattctc attcttgaga gactccaatg ttccattgga gcaaaacaca     240
aagctgaagc cccatgccat gtctgtcttt gtcatgacat gtgaatctgc agtgcaactg     300
cgtaaagcag gcaaagttac agtgagggaa tcaaatttga agaaattagg agctacccat     360
tttaagtatg gggtagttga tgaacatttt gaggtaacaa aatttgctct tttggagacc     420
ataaaagaag cagtaccaga tatgtggtca gatgagatga agaatgcatg gggtgaagcc     480
tatgatcgtt tggtcgcagc cattaaaata gaaatgaagg catgctcaca agctgcatga     540
tttcacaagt tccctacatt attgcttgtt aattttgggt ccaataagat tgaaagtttt     600
caatcattta aacatgtaat gtaacatagc tattgctcat cactactgtt ttttccccct     660
agtttgtttg ctcctgttc                                                  679
```

<210> SEQ ID NO 70
<211> LENGTH: 163
<212> TYPE: PRT
<213> ORGANISM: Gossypium hirsutum
<220> FEATURE:
<221> NAME/KEY: misc_feature
<223> OTHER INFORMATION: Ceres CLONE ID no. 1916866
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 70

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala 115                 120                 125
Val Pro Asp Met Trp Ser Asp Glu Met Lys Asn Ala Trp Gly Glu Ala
    130                 135                 140

Tyr Asp Arg Leu Val Ala Ala Ile Lys Ile Glu Met Lys Ala Cys Ser
145                 150                 155                 160

Gln Ala Ala

<210> SEQ ID NO 71
<211> LENGTH: 1003
<212> TYPE: DNA
<213> ORGANISM: Panicum virgatum
<220> FEATURE:
<221> NAME/KEY: misc_feature
<223> OTHER INFORMATION: Ceres CLONE ID no.1950105
<220> FEATURE:
<221> NAME/KEY: misc_feature
<223> OTHER INFORMATION: Encodes the protein at SEQ ID NO: 72

<400> SEQUENCE: 71
atcgccacaa gttcgcgatc tctcgatttc acaaatcgcc gagaagaccc gagcagagaa      60
gttccctccg atcgccttgc caagatgcag atctttgtga agacactcac tggcaagact     120
atcacccttg aggtggagtc ttctgacaca attgacaatg tcaaggcaaa gatccaggac     180
aaggaaggga ttcctccaga ccagcagcgc cttatcttcg ctggcaagca gcttgaggat     240
ggccgtacac ttgcagatta aacattcag aaggagtcca cactgcacct tgtcctcagg     300
ctgcgtggag gcatgcagat tttcgtgaag accctcactg caagacgat caccctggag     360 gtggagtcat ctgacaccat cgacaatgtg aaggcaaaga tccaggacaa ggagggcatc     420 cccctgacc agcagcgcct catctttgca ggcaagcagt tggaggatgg cgaactctg      480 gctgactaya atatccagaa agaatcmacc ctgcacctsg tsctccgcct gcgtggtgga     540
atgcagatct ttgtgaagac gcttaccggc aagaccatca ccttggaggt ggagtcttcg     600
gacaccatcg acaatgtgaa ggcgaagatt caggacaagg agggcattcc tccggaccag     660
crgcgcctca tctttgctgg caagcagcta gaggacgggc gtaccctggc ggattacaac     720
atccagaagg agtccaccct ccaccttgtc ctgcgcctcc gtggtggttt ctgagcctag     780
tgctcctgag ttgccttttg tcgttatggt caacctctgg tttaagtcgt gtgaactctc     840
tgcattgcgt tgctagtgtc tggttgtggt tgtaataaga acatgaagaa catgttgctg     900
tggatcacat gactttttt ttttgaaccg gaagatcaca tgactttcat ggctttaagt     960
tcctgaactc tgaaatctgg accccctttt aagctctgaa ctc                    1003

<210> SEQ ID NO 72
<211> LENGTH: 229
<212> TYPE: PRT
<213> ORGANISM: Panicum virgatum
<220> FEATURE:
<221> NAME/KEY: misc_feature
<223> OTHER INFORMATION: Ceres CLONE ID no. 1950105
<220> FEATURE:
<221> NAME/KEY: misc_feature
<222> LOCATION: (1)..(74)
<223> OTHER INFORMATION: Pfam Name: ubiquitin
    Pfam Description: Ubiquitin family
<220> FEATURE:
<221> NAME/KEY: misc_feature
<222> LOCATION: (77)..(150)
<223> OTHER INFORMATION: Pfam Name: ubiquitin
    Pfam Description: Ubiquitin family
<220> FEATURE:
<221> NAME/KEY: misc_feature
<222> LOCATION: (153)..(226)

```
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40
<220> FEATURE:
<221> NAME/KEY: misc_feature
<222> LOCATION: (135)..(135)
<223> OTHER INFORMATION: Xaa is any aa, unknown, or other
<220> FEATURE:
<221> NAME/KEY: misc_feature
<222> LOCATION: (141)..(141)
<223> OTHER INFORMATION: Xaa is any aa, unknown, or other
<220> FEATURE:
<221> NAME/KEY: misc_feature
<222> LOCATION: (145)..(145)
<223> OTHER INFORMATION: Xaa is any aa, unknown, or other
<220> FEATURE:
<221> NAME/KEY: misc_feature
<222> LOCATION: (146)..(146)
<223> OTHER INFORMATION: Xaa is any aa, unknown, or other
<220> FEATURE:
<221> NAME/KEY: misc_feature
<222> LOCATION: (193)..(193)
<223> OTHER INFORMATION: Xaa is any aa, unknown, or other

<400> SEQUENCE: 72

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Xaa Asn Ile Gln Lys Glu Xaa Thr Leu His
    130                 135                 140

Xaa Xaa Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Xaa Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
    210                 215                 220

Leu Arg Gly Gly Phe
225

<210> SEQ ID NO 73
<211> LENGTH: 724
<212> TYPE: DNA
<213> ORGANISM: Panicum virgatum
```

```
<220> FEATURE:
<221> NAME/KEY: misc_feature
<223> OTHER INFORMATION: Ceres CLONE ID no.1990746
<220> FEATURE:
<221> NAME/KEY: misc_feature
<222> LOCATION: (623)..(623)
<223> OTHER INFORMATION: n is a, c, t, g, unknown, or other
<220> FEATURE:
<221> NAME/KEY: misc_feature
<222> LOCATION: (624)..(624)
<223> OTHER INFORMATION: n is a, c, t, g, unknown, or other
<220> FEATURE:
<221> NAME/KEY: misc_feature
<222> LOCATION: (625)..(625)
<223> OTHER INFORMATION: n is a, c, t, g, unknown, or other
<220> FEATURE:
<221> NAME/KEY: misc_feature
<223> OTHER INFORMATION: Encodes the protein at SEQ ID NO: 74

<400> SEQUENCE: 73
acacagatac actcgtcgat ccaccagacc accactgtcc agtgctcggc tcggttacgc    60
acgcacgcac acaaatagga gtacctgttt tacaccacca agatactagc aagcccaagc   120
cgagtcgaca aacaagcagc aggaagaggc atggcgctcg cggagggaa cggcgcggcc    180 atcttcggcg aggaacagga ggcgctggtg ctcaagtcgt gggccctcat gaagaaggac   240
tcggccgacc tcggcctccg cttcttcctc aagatcttcg agatcgcgcc gtcggcgaag   300
cagatgttct cgttcctgcg cgactccgac gtgccgctgg agaagaaccc caagctcaag   360
acccacgcca tgtccgtctt cgtcatgacc tgcgaggcgg cagtgcagct acggaaggcc   420
gggaaggtca ccgtcaggga gacgacgctc aagcggctgg gcgcaacgca cttcaagtac   480
ggcgtcgccg acggccactt cgaggtgaca aggttcgcgc tgctggagac gataaaggag   540
gcgcttcccg ccgacatgtg gagcctggag atgaagaacg cctggagcga ggcttacaac   600
cagctcgtgg cggccatcaa gcnnnagatg aagcctgccg catgatgctg catgctgcta   660
catactcggc ctccgagtcc cccctacgat gcaccaccat ctcccagttc ttcatcgcta   720
tttt                                                                724

<210> SEQ ID NO 74
<211> LENGTH: 164
<212> TYPE: PRT
<213> ORGANISM: Panicum virgatum
<220> FEATURE:
<221> NAME/KEY: misc_feature
<223> OTHER INFORMATION: Ceres CLONE ID no. 1990746
<220> FEATURE:
<221> NAME/KEY: misc_feature
<222> LOCATION: (16)..(156)
<223> OTHER INFORMATION: Pfam Name: Globin
    Pfam Description: Globin
<220> FEATURE:
<221> NAME/KEY: misc_feature
<223> OTHER INFORMATION: Functional homolog of Ceres Clone ID no. 30469
    given in SEQ ID NO: 7
<220> FEATURE:
<221> NAME/KEY: misc_feature
<222> LOCATION: (158)..(158)
<223> OTHER INFORMATION: Xaa is any aa, unknown, or other
<220> FEATURE:
<221> NAME/KEY: misc_feature
<222> LOCATION: (159)..(159)
<223> OTHER INFORMATION: Xaa is any aa, unknown, or other

<400> SEQUENCE: 74

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
```

```
                     20                   25                  30

Asp Leu Gly Leu Arg Phe Phe Leu Lys Ile Phe Glu Ile Ala Pro Ser
             35                  40                  45

Ala Lys Gln Met Phe Ser Phe Leu Arg Asp Ser Asp Val Pro Leu Glu
 50                  55                  60

Lys Asn Pro Lys Leu Lys Thr His Ala Met Ser Val Phe Val Met Thr
 65                  70                  75                  80

Cys Glu Ala Ala Val Gln Leu Arg Lys Ala Gly Lys Val Thr Val Arg
                 85                  90                  95

Glu Thr Thr Leu Lys Arg Leu Gly Ala Thr His Phe Lys Tyr Gly Val
             100                 105                 110

Ala Asp Gly His Phe Glu Val Thr Arg Phe Ala Leu Leu Glu Thr Ile
         115                 120                 125

Lys Glu Ala Leu Pro Ala Asp Met Trp Ser Leu Glu Met Lys Asn Ala
 130                 135                 140

Trp Ser Glu Ala Tyr Asn Gln Leu Val Ala Ala Ile Lys Xaa Xaa Met
 145                 150                 155                 160

Lys Pro Ala Ala

<210> SEQ ID NO 75
<211> LENGTH: 696
<212> TYPE: DNA
<213> ORGANISM: Panicum virgatum
<220> FEATURE:
<221> NAME/KEY: misc_feature
<223> OTHER INFORMATION: Ceres CLONE ID no.2007485
<220> FEATURE:
<221> NAME/KEY: misc_feature
<223> OTHER INFORMATION: Encodes the protein at SEQ ID NO: 76

<400> SEQUENCE: 75
agagcagggg gatggaagaa aataaactac tggccaaacc ctagccgagc cccgggtccg      60
ctcaccgcct tcccaccccc ccacccaccc acctgcccccc cccccccccc cgccctcgcc     120
gtccgcgatg cgccgggcga agccgccgca gccgcagccg tcgccgtcgc cggagatccg     180
gtaccgcggc gtgcggaggc ggccatcggg gcgctacgcc gccgagatcc gggacccggc     240
caagaagacc ccgatctggc tcggcacctt cgactccgcc gaggccgccg cgcgcgccta     300
cgacgccgcc gcccgatccc tccgcgggcc caccgcccgc accaacttcc ccagcgccgc     360 ggccccccgcg ccgcggcaca gcaggccccc cgcccctcc gccgccgcgc aggcggctgc     420
cgcggcggca gcggccacgt ccagccacag cagcaccata gagtcgtgga gcgacggcgc     480
gacccgcgcc gcgctggcgc gtagcgctgc ctccgtcctg gcgcgcagcg ccgctccgac     540
ggaggaggaa gacgaggact gccgcagcta ctgcggatcc tcgtcgtccg tcctctgcga     600
agacactggg ggcgacgatg cggccgcctc ccgcgcgccc ctgccgttcg atctgaacct     660
gccgccgcct catgacgcgg cctccgagac cgatca                               696

<210> SEQ ID NO 76
<211> LENGTH: 201
<212> TYPE: PRT
<213> ORGANISM: Panicum virgatum
<220> FEATURE:
<221> NAME/KEY: misc_feature
<223> OTHER INFORMATION: Ceres CLONE ID no. 2007485
<220> FEATURE:
<221> NAME/KEY: misc_feature
<222> LOCATION: (17)..(80)
<223> OTHER INFORMATION: Pfam Name: AP2
      Pfam Description: AP2 domain
```

```
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 76

Met Arg Arg Ala Lys Pro Pro Gln Pro Gln Pro Ser Pro Ser Pro Glu
1               5                   10                  15

Ile Arg Tyr Arg Gly Val Arg Arg Pro Ser Gly Arg Tyr Ala Ala
            20                  25                  30

Glu Ile Arg Asp Pro Ala Lys Lys Thr Pro Ile Trp Leu Gly Thr Phe
            35                  40                  45

Asp Ser Ala Glu Ala Ala Ala Arg Ala Tyr Asp Ala Ala Ala Arg Ser
        50                  55                  60

Leu Arg Gly Pro Thr Ala Arg Thr Asn Phe Pro Ser Ala Ala Ala Pro
65              70                  75                  80

Ala Pro Arg His Ser Arg Pro Pro Ala Pro Ser Ala Ala Ala Gln Ala
                85                  90                  95

Ala Ala Ala Ala Ala Ala Ala Thr Ser Ser His Ser Ser Thr Ile Glu
            100                 105                 110

Ser Trp Ser Asp Gly Ala Thr Arg Ala Ala Leu Ala Arg Ser Ala Ala
        115                 120                 125

Ser Val Leu Ala Arg Ser Ala Ala Pro Thr Glu Glu Glu Asp Glu Asp
130                 135                 140

Cys Arg Ser Tyr Cys Gly Ser Ser Ser Ser Val Leu Cys Glu Asp Thr
145                 150                 155                 160

Gly Gly Asp Asp Ala Ala Ala Ser Arg Ala Pro Leu Pro Phe Asp Leu
                165                 170                 175

Asn Leu Pro Pro Pro His Asp Ala Ala Ser Glu Thr Asp Gln Met Gly
            180                 185                 190

Ala Arg Tyr Asp Thr Leu Leu Arg Leu
        195                 200

<210> SEQ ID NO 77
<211> LENGTH: 698
<212> TYPE: DNA
<213> ORGANISM: Panicum virgatum
<220> FEATURE:
<221> NAME/KEY: misc_feature
<223> OTHER INFORMATION: Ceres CLONE ID no.2033803
<220> FEATURE:
<221> NAME/KEY: misc_feature
<223> OTHER INFORMATION: Encodes the protein at SEQ ID NO: 78

<400> SEQUENCE: 77
acacagatac attcgtcgat ccaccagacc accactgtcc agtgctcggc tcggttacgc      60
acgcacgcac acaaatagga gtacctgttt tacaccaaga tactagcaag cccaagccga     120
gtcgacaaac aagcagcagg aagaggcatg gcgctcgcgg agggggaacgg cgcggccatc    180 ttcggcgagg agcaggaggc gctggtgctc aagtcgtggg ccctcatgaa gaaggactcg    240
gccgacctcg gcctccgctt cttcctcaag atcttcgaga tcgcgccgtc ggcgaagcag    300
atgttctcgt tcctgcgcga ctccgacgtg ccgctggaga agaacccaa gctcaagacc    360 cacgccatgt ccgtcttcgt catgacctgc gaggcggcag cgcagctacg gaaggccggg    420
aaggtcaccg tcagggagac gacgctcaag cggctgggcg caacgcactt caagtacggc    480
gtcgccgacg ccacttcga ggtgacaagg ttcgcgcttc ccgccgactt gtggagcctg    540
gagatgaaga acgcctggag cgaggcttac aaccagctcg tggcggccat caagcaggag    600
```

-continued

```
atgaagcctg ccgcatgatg ctgcatgctg ctacatactc ggcctccgag ttccccctac    660
gatgcaccac catctccaag ttctttcatt gtcttgtg                            698
```

<210> SEQ ID NO 78
<211> LENGTH: 156
<212> TYPE: PRT
<213> ORGANISM: Panicum virgatum
<220> FEATURE:
<221> NAME/KEY: misc_feature
<223> OTHER INFORMATION: Ceres CLONE ID no. 2033803
<220> FEATURE:
<221> NAME/KEY: misc_feature
<222> LOCATION: (16)..(148)
<223> OTHER INFORMATION: Pfam Name: Globin
    Pfam Description: Globin
<220> FEATURE:
<221> NAME/KEY: misc_feature
<223> OTHER INFORMATION: Functional homolog of Ceres Clone ID no. 30469
    given in SEQ ID NO: 7

<400> SEQUENCE: 78

```
Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met Thr
65                  70                  75                  80

Cys Glu Ala Ala Ala Gln Leu Arg Lys Ala Gly Lys Val Thr Val Arg
                85                  90                  95

Glu Thr Thr Leu Lys Arg Leu Gly Ala Thr His Phe Lys Tyr Gly Val
            100                 105                 110

Ala Asp Gly His Phe Glu Val Thr Arg Phe Ala Leu Pro Ala Asp Leu
        115                 120                 125

Trp Ser Leu Glu Met Lys Asn Ala Trp Ser Glu Ala Tyr Asn Gln Leu
    130                 135                 140

Val Ala Ala Ile Lys Gln Glu Met Lys Pro Ala Ala
145                 150                 155
```

<210> SEQ ID NO 79
<211> LENGTH: 724
<212> TYPE: DNA
<213> ORGANISM: Panicum virgatum
<220> FEATURE:
<221> NAME/KEY: misc_feature
<223> OTHER INFORMATION: Ceres CLONE ID no.2034916
<220> FEATURE:
<221> NAME/KEY: misc_feature
<223> OTHER INFORMATION: Encodes the protein at SEQ ID NO: 80

<400> SEQUENCE: 79

```
aatccaatct cccccgatcc ccaatcgcga attcccctct ccggcaggcg aagcaatcga    60
ggggcaccct ttcatctcgt caagatgcag atctttgtga agaccctcac tggtaagacc   120
atcaccctcg aggttgagtc ctcggatacc attgacaacg tcaaggctaa aatccaggac   180
aaggagggga tccctccgga ccagcagcgc tcatctttg ccggcaagca gctcgaagat   240
gggaggacgc ttgctgacta caacatccag aaggagtcca ccctccacct cgtgctcagg   300
```

-continued

```
ctcaggggtg gtatgcagat ctttgtcaag actctcaccg gcaagacgat tactcttgag     360
gttgagtcct cggacacgat cgacaatgta aaggtgaaga tccaagacaa ggaggggatc     420
ccaccggacc agcagcgcct catctttgcc ggcaagcagc tcgaggatgg ccgcactctg     480
gctgactaca acattcagaa agagtcgacc cttcaccttg tgctcaggct gaggggaggc     540
atgcaaatat ttgtcaagac tctgactggc aagaccatca cgcttgaggt ggagtcgtct     600
gacaccattg ataatgtgaa ggcgaagatc caagacaagg agggcatccc gccggaccag     660
cagcgcctga tctttgccgg taagcagctg gaggatggtc gtaccctggc agactataat     720
attc                                                                  724
```

```
<210> SEQ ID NO 80
<211> LENGTH: 213
<212> TYPE: PRT
<213> ORGANISM: Panicum virgatum
<220> FEATURE:
<221> NAME/KEY: misc_feature
<223> OTHER INFORMATION: Ceres CLONE ID no. 2034916
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (153)..(213)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 80

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Val Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175
```

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ala Asp Tyr Asn Ile
    210

<210> SEQ ID NO 81
<211> LENGTH: 1194
<212> TYPE: DNA
<213> ORGANISM: Glycine max
<220> FEATURE:
<221> NAME/KEY: misc_feature
<223> OTHER INFORMATION: Ceres CLONE ID no.651581
<220> FEATURE:
<221> NAME/KEY: misc_feature
<222> LOCATION: (678)..(678)
<223> OTHER INFORMATION: n is a, c, t, g, unknown, or other
<220> FEATURE:
<221> NAME/KEY: misc_feature
<222> LOCATION: (679)..(679)
<223> OTHER INFORMATION: n is a, c, t, g, unknown, or other
<220> FEATURE:
<221> NAME/KEY: misc_feature
<223> OTHER INFORMATION: Encodes the protein at SEQ ID NO: 82

<400> SEQUENCE: 81
gtgtagttga aggagcagaa gaagaagaag agaaggtggt accgccttca attctctttt      60
tctctctcca tttctcatcc tcatcatctt attattcctc ttccatctct attctccata     120
acacccacca caccacttgt gaaaaacctc attaatatca cacactgaca tgtatctctg     180
agctccaatc caatacaaga ccacaccttg tcgtgtcgga cgaaccttgg tgtctgtttt     240 ttttttttt  tttcattatt ttctccgaag agatgaggaa gggcaraggt ggaggcgcct     300
cggcggcggc ggtggatgtg aacggatcca ttttaaagga gcctcggtac cggggcgtga     360
ggaagagacc gtgggggaga ttcgccgcgg agatcagaga cccgttgaag aaagccaggg     420
tttggttggg aaccttcaat tctgccgagg atgctgctcg tgcctacrac gccgccgctc     480
ggactctccg aggtcccaag gccaaaaacaa atttccccc  tctctcacct ttttgctatc     540 cacacccac  caccgatcct ttcttstaca ctggtttcca cgatcaacac caccaccaca     600
acaacaacaa ccttaacaac cctcaaagac ccacttcaag tggcatgagt agcmccgttg     660
agtccttcag tgggcccnnc ccttttttccc ccaccaccac cmctaccacc acaaccacaa     720
ctgcgacgcc gttttttgact gctacgcgga gataccccgcg cactcccccct cttgtccctg     780 aagactgcca cagtgactgc gactcttcct cctccgtcgt tgacgacggc gacgacaaca     840
tcgtttcgtc gtcgtttcga cctcccttgc cgtttgatct caacgcgctg ccgtttgatg     900
atgctgccgc ggatgatgat ctacgccgca ccgcgctttg tctctgatga tgattatcgt     960
gcgatgatga tttttaattt ctcatttttt tacttgattt ttttgttatt gctatgcaga    1020
agaaatatat atttaaaatg atgatcagat gtaagattat ggtaatatga tcttaattct    1080
gtgagaggaa gattccgtgt tggttatatt ttcttctttt tattattttt ttaaacattt    1140
ttatttagaa ggaaatattg aatgaaaaga aaaagagaa  agtaattatg atcg           1194

<210> SEQ ID NO 82
<211> LENGTH: 224
<212> TYPE: PRT
<213> ORGANISM: Glycine max
<220> FEATURE:
<221> NAME/KEY: misc_feature
<223> OTHER INFORMATION: Ceres CLONE ID no. 651581

-continued

```
<220> FEATURE:
<221> NAME/KEY: misc_feature
<222> LOCATION: (24)..(87)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42
<220> FEATURE:
<221> NAME/KEY: misc_feature
<222> LOCATION: (137)..(137)
<223> OTHER INFORMATION: Xaa is any aa, unknown, or other

<400> SEQUENCE: 82

Met Arg Lys Gly Arg Gly Gly Ala Ser Ala Ala Val Asp Val
1               5                   10                  15

Asn Gly Ser Ile Leu Lys Glu Pro Arg Tyr Arg Gly Val Arg Lys Arg
            20                  25                  30

Pro Trp Gly Arg Phe Ala Ala Glu Ile Arg Asp Pro Leu Lys Lys Ala
        35                  40                  45

Arg Val Trp Leu Gly Thr Phe Asn Ser Ala Glu Asp Ala Ala Arg Ala
    50                  55                  60

Tyr Asp Ala Ala Ala Arg Thr Leu Arg Gly Pro Lys Ala Lys Thr Asn
65                  70                  75                  80

Phe Pro Pro Leu Ser Pro Phe Cys Tyr Pro His Pro Thr Thr Asp Pro
                85                  90                  95

Phe Phe Tyr Thr Gly Phe His Asp Gln His His His Asn Asn Asn
            100                 105                 110

Asn Leu Asn Asn Pro Gln Arg Pro Thr Ser Ser Gly Met Ser Ser Thr
        115                 120                 125

Val Glu Ser Phe Ser Gly Pro Arg Xaa Phe Ser Pro Thr Thr Thr Thr
    130                 135                 140

Thr Thr Thr Thr Thr Thr Ala Thr Pro Phe Leu Thr Ala Thr Arg Arg
145                 150                 155                 160

Tyr Pro Arg Thr Pro Pro Leu Val Pro Glu Asp Cys His Ser Asp Cys
                165                 170                 175

Asp Ser Ser Ser Val Val Asp Asp Gly Asp Asp Asn Ile Val Ser
            180                 185                 190

Ser Ser Phe Arg Pro Pro Leu Pro Phe Asp Leu Asn Ala Leu Pro Phe
        195                 200                 205

Asp Asp Ala Ala Ala Asp Asp Asp Leu Arg Arg Thr Ala Leu Cys Leu
    210                 215                 220

<210> SEQ ID NO 83
<211> LENGTH: 184
<212> TYPE: PRT
<213> ORGANISM: Oryza sativa subsp. indica
<220> FEATURE:
<221> NAME/KEY: misc_feature
<223> OTHER INFORMATION: Public GI ID no. 125550159
<220> FEATURE:
<221> NAME/KEY: misc_feature
<222> LOCATION: (7)..(70)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 83

Met Cys Glu Ala Ala Ala Pro Arg Tyr Arg Gly Val Arg Lys Arg Pro
```

```
                1               5                   10                  15
Trp Gly Arg Phe Ala Ala Glu Ile Arg Asp Pro Ala Lys Arg Ala Arg
                20                  25                  30

Val Trp Leu Gly Thr Tyr Asp Ser Ala Glu Ala Ala Arg Ala Tyr
        35                  40                  45

Asp Val Ala Ala Arg Asn Leu Arg Gly Pro Leu Ala Arg Thr Asn Phe
50                  55                  60

Pro Leu Val Ser Ser Leu Pro Leu Pro Ser Pro His Tyr His Leu Pro
65                  70                  75                  80

Gly Lys Ala Ala Ala Ala Pro Pro Val Ala Gly Pro Ala Cys Ser
                85                  90                  95

Ala Ser Ser Thr Val Glu Ser Ser Gly Pro Arg Gly Pro Arg Pro
                100                 105                 110

Ala Ala Thr Ala Ala Ala Val Pro Arg Arg Val Pro Arg Pro Ala
                115                 120                 125

Pro Pro Ala Pro Asp Ala Gly Cys His Ser Asp Cys Ala Ser Ser Ala
130                 135                 140

Ser Val Val Asp Asp Ala Asp Asp Ala Ser Thr Val Arg Ser Arg Val
145                 150                 155                 160

Ala Ala Phe Asp Leu Asn Leu Pro Pro Pro Leu Asp Arg Asp His Val
                165                 170                 175

Asp Leu Cys Thr Asp Leu Arg Leu
                180

<210> SEQ ID NO 84
<211> LENGTH: 225
<212> TYPE: PRT
<213> ORGANISM: Arabidopsis thaliana
<220> FEATURE:
<221> NAME/KEY: misc_feature
<223> OTHER INFORMATION: Public GI ID no. 15223609
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 84

Met Arg Arg Gly Arg Gly Ser Ser Ala Val Ala Gly Pro Thr Val Val
1               5                   10                  15

Ala Ala Ile Asn Gly Ser Val Lys Glu Ile Arg Phe Arg Gly Val Arg
                20                  25                  30

Lys Arg Pro Trp Gly Arg Phe Ala Ala Glu Ile Arg Asp Pro Trp Lys
                35                  40                  45

Lys Ala Arg Val Trp Leu Gly Thr Phe Asp Ser Ala Glu Glu Ala Ala
    50                  55                  60

Arg Ala Tyr Asp Ser Ala Ala Arg Asn Leu Arg Gly Pro Lys Ala Lys
65                  70                  75                  80

Thr Asn Phe Pro Ile Asp Ser Ser Ser Pro Pro Pro Asn Leu Arg
                85                  90                  95

Phe Asn Gln Ile Arg Asn Gln Asn Gln Val Asp Pro Phe Met
                100                 105                 110

Asp His Arg Leu Phe Thr Asp His Gln Gln Gln Phe Pro Ile Val Asn
                115                 120                 125
```

```
Arg Pro Thr Ser Ser Met Ser Ser Thr Val Glu Ser Phe Ser Gly
    130                 135             140

Pro Arg Pro Thr Thr Met Lys Pro Ala Thr Thr Lys Arg Tyr Pro Arg
145                 150                 155                 160

Thr Pro Pro Val Val Pro Glu Asp Cys His Ser Asp Cys Asp Ser Ser
                165                 170                 175

Ser Ser Val Ile Asp Asp Asp Asp Ile Ala Ser Ser Ser Arg Arg
            180             185                 190

Arg Asn Pro Pro Phe Gln Phe Asp Leu Asn Phe Pro Pro Leu Asp Cys
            195             200                 205

Val Asp Leu Phe Asn Gly Ala Asp Asp Leu His Cys Thr Asp Leu Arg
    210             215                 220

Leu
225

<210> SEQ ID NO 85
<211> LENGTH: 164
<212> TYPE: PRT
<213> ORGANISM: Arabidopsis thaliana
<220> FEATURE:
<221> NAME/KEY: misc_feature
<223> OTHER INFORMATION: Public GI ID no. 30683885
<220> FEATURE:
<221> NAME/KEY: misc_feature
<223> OTHER INFORMATION: Functional Homolog of Ceres CLONE ID no. 30087
      Given in SEQ ID NO: 2

<400> SEQUENCE: 85

Met Ala Ser Ser Phe Ser Ser Gln Ala Phe Phe Leu Leu Thr Leu Ser
1               5                   10                  15

Met Val Leu Ile Pro Phe Ser Leu Ala Gln Ala Pro Met Met Ala Pro
                20                  25                  30

Ser Gly Ser Met Ser Met Pro Pro Met Ser Ser Gly Gly Ser Ser
            35                  40                  45

Val Pro Pro Val Met Ser Pro Met Pro Met Thr Pro Pro Pro
    50                  55                  60

Met Pro Met Thr Pro Pro Pro Met Pro Met Thr Pro Pro Met Pro
65                  70                  75                  80

Met Ala Pro Pro Met Pro Met Ala Ser Pro Pro Met Met Pro Met
                85                  90                  95

Thr Pro Ser Thr Ser Pro Ser Pro Leu Thr Val Pro Asp Met Pro Ser
                100                 105                 110

Pro Pro Met Pro Ser Gly Met Glu Ser Ser Pro Ser Pro Gly Pro Met
            115                 120                 125

Pro Pro Ala Met Ala Ala Ser Pro Asp Ser Gly Ala Phe Asn Val Arg
    130                 135                 140

Asn Asn Val Val Thr Leu Ser Cys Val Val Gly Val Val Ala Ala His
145                 150                 155                 160

Phe Leu Leu Val

<210> SEQ ID NO 86
<211> LENGTH: 218
<212> TYPE: PRT
<213> ORGANISM: Pisum sativum
<220> FEATURE:
<221> NAME/KEY: misc_feature
<223> OTHER INFORMATION: Public GI ID no. 56384582
<220> FEATURE:
<221> NAME/KEY: misc_feature
<222> LOCATION: (21)..(84)
```

<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 86

Met Gly Arg Gly Gly Ala Thr Thr Ala Ala Ala Val Glu Pro Val
1               5                   10                  15

Phe Phe Lys Glu Pro Arg Tyr Arg Gly Val Arg Lys Arg Pro Trp Gly
            20                  25                  30

Arg Phe Ala Ala Glu Ile Arg Asp Pro Leu Lys Lys Ala Arg Val Trp
        35                  40                  45

Leu Gly Thr Phe Asp Thr Ala Glu Glu Ala Ala Arg Ala Tyr Asp Thr
    50                  55                  60

Ala Ala Arg Asn Leu Arg Gly Pro Lys Ala Lys Thr Asn Phe Pro Leu
65                  70                  75                  80

Ala Gln Pro Phe Tyr Gln Asn Pro Glu Ala Gly Asn Pro Phe Gly Glu
                85                  90                  95

Leu Arg Phe Tyr Ala Gly Gly Ala Gly Glu Gly Phe Gln Asp His Arg
            100                 105                 110

Arg Pro Thr Ser Ser Gly Met Ser Ser Thr Val Glu Ser Phe Gly Gly
        115                 120                 125

Pro Arg Pro Val Arg Pro Met Pro Pro Ser Ala Val Thr Gly Arg
    130                 135                 140

Arg Tyr Pro Arg Thr Pro Pro Val Ala Pro Gly Asp Cys Arg Ser Asp
145                 150                 155                 160

Cys Asp Ser Ser Ser Ser Val Val Asp Asp Ala Asp Asn Asp Asn Ala
                165                 170                 175

Ala Ser Ser Thr Met Leu Ser Phe Lys Arg Gln Pro Leu Pro Phe Asp
            180                 185                 190

Leu Asn Ala Pro Pro Leu Glu Glu Gly Asp Val Ala Asn Gly Leu Gly
        195                 200                 205

Glu Asp Leu His Cys Thr Leu Leu Cys Leu
    210                 215

<210> SEQ ID NO 87
<211> LENGTH: 225
<212> TYPE: PRT
<213> ORGANISM: Nicotiana tabacum
<220> FEATURE:
<221> NAME/KEY: misc_feature
<223> OTHER INFORMATION: Public GI ID no. 57012880
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 87

Met Arg Arg Gly Arg Ala Ala Ala Ala Pro Ala Pro Val Thr Gly Glu
1               5                   10                  15

Pro Asn Gly Ser Gly Gly Ser Lys Glu Ile Arg Phe Arg Gly Val Arg
            20                  25                  30

Lys Arg Pro Trp Gly Arg Phe Ala Ala Glu Ile Arg Asp Pro Trp Lys
        35                  40                  45

-continued

```
Lys Thr Arg Val Trp Leu Gly Thr Phe Asp Ser Ala Glu Asp Ala Ala
 50                  55                  60

Arg Ala Tyr Asp Ala Ala Ala Arg Ala Leu Arg Gly Pro Lys Ala Lys
 65                  70                  75                  80

Thr Asn Phe Pro Leu Pro Tyr Ala His His Gln Phe Asn Gln Gly
                 85                  90                  95

His Asn Pro Asn Asn Asp Pro Phe Val Asp Ser Arg Phe Tyr Pro Gln
                100                 105                 110

Asp Asn Pro Ile Ile Ser Gln Arg Pro Thr Ser Ser Ser Met Ser Ser
                115                 120                 125

Thr Val Glu Ser Phe Ser Gly Pro Arg Pro Pro Ala Pro Arg Gln
130                 135                 140

Gln Thr Thr Ala Ser Ser Arg Lys Tyr Thr Arg Ser Pro Pro Val Val
145                 150                 155                 160

Pro Asp Asp Cys His Ser Asp Cys Asp Ser Ser Ser Val Val Asp
                165                 170                 175

His Gly Asp Cys Glu Lys Glu Asn Asp Asn Asp Asn Asp Asn Ile Ala
                180                 185                 190

Ser Ser Ser Phe Arg Lys Pro Leu Leu Phe Asp Leu Asn Leu Pro Pro
                195                 200                 205

Pro Met Asp Asp Ala Gly Ala Asp Asp Leu His Cys Thr Ala Leu Cys
210                 215                 220

Leu
225

<210> SEQ ID NO 88
<211> LENGTH: 163
<212> TYPE: PRT
<213> ORGANISM: Gossypium hirsutum
<220> FEATURE:
<221> NAME/KEY: misc_feature
<223> OTHER INFORMATION: Public GI ID no. 62548111
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 88

Met Ala Thr Tyr Glu Gly Lys Val Phe Thr Glu Glu Gln Glu Ala Leu
 1                   5                  10                  15

Val Val Lys Ser Trp Thr Val Met Lys Lys Asn Ala Ala Glu Leu Gly
                 20                  25                  30

Leu Lys Phe Phe Leu Lys Ile Phe Glu Ile Ala Pro Ser Ala Lys Lys
             35                  40                  45

Leu Phe Ser Phe Leu Arg Asp Ser Asn Val Pro Leu Glu Gln Asn Thr
 50                  55                  60

Lys Leu Lys Pro His Ala Met Ser Val Phe Val Met Thr Cys Glu Ser
 65                  70                  75                  80

Ala Val Gln Leu Arg Lys Ala Gly Lys Val Thr Val Arg Glu Ser Asn
                 85                  90                  95

Leu Lys Lys Leu Gly Ala Thr His Phe Lys Tyr Gly Val Val Asp Glu
                100                 105                 110

His Phe Glu Val Thr Lys Phe Ala Leu Leu Glu Thr Ile Lys Glu Ala
```

| | 115 | | | 120 | | | 125 | | | | |
|---|---|---|---|---|---|---|---|---|---|---|---|

Val Pro Asp Met Trp Ser Asp Glu Met Lys Asn Ala Trp Gly Glu Ala
130                    135               140

Tyr Asp Arg Leu Val Ala Ala Ile Lys Ile Glu Met Lys Ala Cys Ser
145                    150               155               160

Leu Ala Ala

<210> SEQ ID NO 89
<211> LENGTH: 153
<212> TYPE: PRT
<213> ORGANISM: Gossypium hirsutum
<220> FEATURE:
<221> NAME/KEY: misc_feature
<223> OTHER INFORMATION: Ceres CLONE ID no. 100021733
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 89

Met Gln Ile Phe Val Lys Thr Leu Thr Gly Lys Thr Ile Thr Leu Glu
1                5                   10                15

Val Glu Ser Ser Asp Thr Ile Asp Asn Val Lys Ala Lys Ile Gln Asp
             20                 25                30

Lys Glu Gly Ile Pro Pro Asp Gln Gln Arg Leu Ile Phe Ala Gly Lys
           35                 40                45

Gln Leu Glu Asp Gly Arg Thr Leu Ala Asp Tyr Asn Ile Gln Lys Glu
    50                  55                 60

Ser Thr Leu His Leu Val Leu Arg Leu Arg Gly Gly Met Gln Ile Phe
65                  70                75                80

Val Lys Thr Leu Thr Gly Lys Thr Ile Thr Leu Glu Val Glu Ser Ser
             85                 90                95

Asp Thr Ile Asp Asn Val Lys Ala Lys Ile Gln Asp Lys Glu Gly Ile
              100               105             110

Pro Pro Asp Gln Gln Arg Leu Ile Phe Ala Gly Lys Gln Leu Glu Asp
           115                120              125

Gly Arg Thr Leu Ala Asp Tyr Asn Ile Gln Lys Glu Ser Thr Leu His
    130                135                140

Leu Val Leu Arg Leu Arg Gly Gly Phe
145                  150

<210> SEQ ID NO 90
<211> LENGTH: 775
<212> TYPE: DNA
<213> ORGANISM: Brassica napus
<220> FEATURE:
<221> NAME/KEY: misc_feature
<223> OTHER INFORMATION: Ceres CLONE ID no. 947579
<220> FEATURE:
<221> NAME/KEY: misc_feature
<223> OTHER INFORMATION: Encodes the protein at SEQ ID NO: 3

<400> SEQUENCE: 90

```
ctctctagat cttggatcac tcggacgaca tgtgttggat cccagtgcac tggccctgcc      60
agcctactca aaaaaacswt samttttckc tcccattstt tkacractca tcgttggcac     120
wtcctwcttt ctstatatat tacttgacat wawcyrctmt ycacmwcaca wacacacacw     180
taaccatggc cagcttcaca wgctttcctt ttgctcacat tgyctatggc tttagytcat     240
ytctctttag ctcwatctcc catgatggct ccttctggct ccatgtccat gscgckchat     300
gccatagcgg cggctctcca atgccaatga tgactccacc acctatgcca atgatgactc     360
cmccgcctat ggctatggct ccaccaccta tgcctatgac tccaccacca atgcccatgg     420
ctccgatgcc aatgactcca tcttcaagtc caatgagccc accaactact atggccccaa     480
gtccagaaac agtccctgat atggcttcgc caccgatgat gccgggaatg gagtcttctc     540
cttctccggg acccatgcca ccggcaatgg cctctccaga ttccggagca ttcaatgtaa     600
gaaacgacgt cgtagcaatt tcgttccttg ttgcagctca tttgctccta gtttgagatt     660
attattaaat tggccagcgt cgtgttgtgt aatttacttt catttttttct cgagccatta     720 gttttcatgt tttatcatat atttgggttt gtgtttgata tggtacgatt cagmc          775
```

<210> SEQ ID NO 91
<211> LENGTH: 1032
<212> TYPE: DNA
<213> ORGANISM: Arabidopsis thaliana
<220> FEATURE:
<221> NAME/KEY: misc_feature
<223> OTHER INFORMATION: Ceres CLONE ID no. 36046
<220> FEATURE:
<221> NAME/KEY: misc_feature
<223> OTHER INFORMATION: Encodes the protein at SEQ ID NO: 23

<400> SEQUENCE: 91

```
gctcattagg gtttctcatc tacggcgtgg tgttcctcct tcctgctctg aaaaatggcg      60
aagagaacga agaaggttgg aatcgtcggc aaatacggaa cacgttatgg tgcgagtatc     120
aggaagcaga ttaagaagat ggaggtcagc cagcacagca agtacttctg tgagttctgt     180
ggcaagtacg gagtgaagcg aaaggctgtt ggtatctggg gttgcaagga ttgtggcaag     240
gtcaaggcag gtggtgctta cacaatgaac accgccagtg cggtcactgt tagaagcacg     300
atcagaaggt tgagggagca gatcgagggt taaaagtctg ctgaggaaga tgctgagaca     360
gtatacgctt gtatcgactt ggtatcaacg ataatacaga ggaagctgag gaagatcaag     420
gagaaggact cagaccatgg aaggcacatg aaaggtttca acagattgaa ggtaagggaa     480
ccagtgattg agccggttgt ggaggatgtt gaggacagta ctgactcgag cgtaggagaa     540
gaagaagaag aggatgattt gatcaaggag attgtccgta ccaagacttt cgagatgcca     600
ccattgactg tcgctgaggc agtcgagcag ctggaactag tcagtcacga cttctatggc     660
ttccaaaatg aaaactggtg agataaacat agtgtacaag agaaaagaag gaggttacgg     720
tctgataatc ccaaagaaag acgggaaggc cgagaaggtt gagccgcttc aaccgagca     780 attgaatgaa cactctttcg ccgagtagac tgcctctgca cacaccaaaa ccgataagct     840
catctctcct tacagtttac ctgtgtagga gttagggttc ttgaataaac aatgcaacaa     900
agattgtaga agtcagtgta cataaaaaaa tggccaacca ctctttgtta cttttgtggt     960
gaaaaggaag atcttaattc tctttccatc agatgatagc aatacatttt ttcataaaca    1020
agaatgttac at                                                         1032
```

<210> SEQ ID NO 92
<211> LENGTH: 492

<212> TYPE: DNA
<213> ORGANISM: Parthenium argentatum
<220> FEATURE:
<221> NAME/KEY: misc_feature
<223> OTHER INFORMATION: Ceres CLONE ID no. 1606506
<220> FEATURE:
<221> NAME/KEY: misc_feature
<223> OTHER INFORMATION: Encodes the protein at SEQ ID NO: 5

<400> SEQUENCE: 92

| | | | | | |
|---|---|---|---|---|---|
| atctagcttc | aaccttttt | tcctctcact | actcaattca | atatggctgt | ctcacgttac | 60 |
| attatcctac | tcttatcctt | cacctacttg | gctgccttct | ccaccgctca | agctccatca | 120 |
| atgtcaccaa | tgatgatgcc | catggcacca | ccaccatcga | cgatgcccat | gacaccacca | 180 |
| ccatcgacga | tgcccatgac | accaccacca | acgcccatga | ccatgacacc | accaccaatg | 240 |
| atgatgccca | tgacaccacc | accaatgccc | atggggacac | caccaatgac | aatgcccatg | 300 |
| ggaccgccac | caatgatgat | gcccatgagc | ccaggaccat | ccatgatgcc | agcctccccg | 360 |
| ccatcaccca | tgggaccgtc | catggcacct | gaaccagcta | ccatgtcgcc | tggaccctcc | 420 |
| atgacgcctg | ctgagacacc | agccagtggc | gctatcatgc | agtattctag | catcactatg | 480 |
| ttgggcattg | tg | | | | | 492 |

<210> SEQ ID NO 93
<211> LENGTH: 970
<212> TYPE: DNA
<213> ORGANISM: Glycine max
<220> FEATURE:
<221> NAME/KEY: misc_feature
<223> OTHER INFORMATION: Ceres CLONE ID no. 546001
<220> FEATURE:
<221> NAME/KEY: misc_feature
<223> OTHER INFORMATION: Encodes the protein at SEQ ID NO: 13

<400> SEQUENCE: 93

| | | | | | |
|---|---|---|---|---|---|
| agatataatc | gaaaaaaatt | actgtttgga | tatattccac | tatttagaaa | gcaaaatgga | 60 |
| ctacgaaaac | ttgagtaaca | aggtaagcca | cacaaatggg | aatgactccc | cattacaatg | 120 |
| aagggccaac | ttcattttca | atgaatccca | ctataaaaac | tttagcaatg | caaaagctaa | 180 |
| aacatcaacc | atttcctcat | ccactttcac | tggaatcaca | atcctgaaac | aaaaacatct | 240 |
| tagcatttaa | catactacta | gacaacatga | ccaccacatt | ggaaagaggt | ttctcggaag | 300 |
| agcaagaagc | tctggtggtg | aagtcatgga | atgtcatgaa | gaagaattct | ggagagttgg | 360 |
| gtctcaagtt | tttcttgaaa | atatttgaga | ttgctccatc | agctcagaaa | ttgttctcat | 420 |
| tcttgagaga | ttcaacggtt | cctttggagc | aaaatcccaa | gctcaagccc | catgccgtgt | 480 |
| ctgtctttgt | aatgacctgt | gattcagcag | ttcagctgcg | gaaggccggg | aaagtcactg | 540 |
| tcagagaatc | aaacttgaaa | aaattaggtg | ctacccattt | tagaaccggc | gtagcaaacg | 600 |
| agcatttcga | ggtgacaaag | tttgcactgt | tggagaccat | aaaagaagct | gtaccagaaa | 660 |
| tgtggtcacc | ggctatgaag | aatgcatggg | gagaagctta | tgatcagctg | gtcgatgcca | 720 |
| ttaaatctga | aatgaaacca | ccctcctctt | agactccagt | ttaagcagtt | cctttccttc | 780 |
| cctctcaatt | ctcaaattgt | tatattaata | aaagtgagaa | agtttaggct | tgtgctttta | 840 |
| ttttgtgtga | atgtaatata | ctttgtgtac | gtagacttgg | ctattgggag | ttgctaggtt | 900 |
| gggaagtgtt | tcgcattcaa | caattctgta | gttgaaggtg | attaaatgaa | ttatagctat | 960 |
| ttgtttcttc | | | | | | 970 |

<210> SEQ ID NO 94

<211> LENGTH: 604
<212> TYPE: DNA
<213> ORGANISM: Zea mays
<220> FEATURE:
<221> NAME/KEY: misc_feature
<223> OTHER INFORMATION: Ceres CLONE ID no. 1554560
<220> FEATURE:
<221> NAME/KEY: misc_feature
<223> OTHER INFORMATION: Encodes the protein at SEQ ID NO: 16

<400> SEQUENCE: 94

| | | | | |
|---|---|---|---|---|
| tcgtatccac | ccaacctccc | actgtaaaaa | agagcagcgg | aacgtgcgtg catccatcca | 60 |
| attccaatcc | cagtcccaat | cccaccagtg | tccagtgctc | ggggaaccga cacagctcct | 120 |
| cagcagagaa | gccagcccga | tcagcagaca | gcaggcatgg | cgctcgcgga ggccgacgac | 180 |
| ggcgcggtgg | tcttcggcga | ggagcaggag | gcgctggtgc | tcaagtcgtg ggccgtcatg | 240 |
| aagaaggacg | ccgccaacct | gggcctccgc | ttcttcctca | aggtcttcga gatcgcgccg | 300 |
| tcggcgaagc | agatgttctc | gttcctgcgc | gactccgacg | tgccgctaga gaagaacccc | 360 |
| aagctcaaga | cgcacgccat | gtccgtcttc | gtcatgacct | gcgaggcggc ggcgcagctc | 420 |
| cgcaaggccg | ggaaggtcac | cgtgagggag | accacgctca | agaggctggg cgccacgcac | 480 |
| ttgaggtacg | cgctcgcaga | tggacacttc | gaggtgacgg | ggttcgcgct gcttgagacg | 540 |
| atcaaggagg | cgctccccgc | tgacatgtgg | agcctcgaga | tgaagaaagc ctgggccgag | 600 |
| gcct | | | | | 604 |

<210> SEQ ID NO 95
<211> LENGTH: 846
<212> TYPE: DNA
<213> ORGANISM: Triticum aestivum
<220> FEATURE:
<221> NAME/KEY: misc_feature
<223> OTHER INFORMATION: Ceres CLONE ID no. 839727
<220> FEATURE:
<221> NAME/KEY: misc_feature
<223> OTHER INFORMATION: Encodes the protein at SEQ ID NO: 17

<400> SEQUENCE: 95

| | | | | |
|---|---|---|---|---|
| acgccgtccg | tttctggctc | atcaggaggt | ccaaaggccg | cgcaagtcga cctatataag | 60 |
| cgcctccgct | ccagcttggg | atcaaatcac | gaccaacacg | taccggatct tgaccgaccg | 120 |
| aaccattcag | tgctcgcgct | cactcacgca | tcatagccaa | gttaagcggg aaggaaggaa | 180 |
| ggaaggaagc | catgtctgcc | gcggagggag | ccgtcgtgtt | cagcgaggag aaggaggcgc | 240 |
| tggtgctcaa | gtcatgggcc | atcatgaaga | aggattccgc | caaccttggg ctccgcttct | 300 |
| tcctcaagat | cttcgagatc | gcgccgtcgg | cgaggcagat | gttcccgttc ctgcgcgact | 360 |
| ccgacgtgcc | gctggagacc | aaccccaagc | tcaagaccca | cgccgtgtcc gtcttcgtca | 420 |
| tgacgtgcga | ggctgctgcg | cagctgcgga | aagccgggaa | gatcaccgtc agggagacca | 480 |
| ccctgaagag | gctgggcggc | acgcacttga | aatacggcgt | ggcagatggc cactttgagg | 540 |
| tgacgcggtt | cgctctgctc | gagacgatca | aggaggcgct | tccggcggac atgtgggggc | 600 |
| cggagatgag | gaacgcgtgg | ggcgaggcct | acgaccaact | ggtcgcggcc atcaagcaag | 660 |
| agatgaagcc | ctctgagtag | ctcatccatt | gtactcatat | catatgccac gcaacttccg | 720 |
| tccatatccg | tccaactttc | gttgcttgac | cggttcactc | atgtcaccat attgtgtttg | 780 |
| tattgtgtgt | ttacgtgtac | taacgcatat | tgtaaaatgg | gcattcaata aaggaacaaa | 840 |
| ttgtgc | | | | | 846 |

```
<210> SEQ ID NO 96
<211> LENGTH: 440
<212> TYPE: DNA
<213> ORGANISM: Glycine max
<220> FEATURE:
<221> NAME/KEY: misc_feature
<223> OTHER INFORMATION: Ceres CLONE ID no. 664936
<220> FEATURE:
<221> NAME/KEY: misc_feature
<223> OTHER INFORMATION: Encodes the protein at SEQ ID NO: 25

<400> SEQUENCE: 96
ctcttgtctt agtctaataa acaacacgga cgcagagcct tcgatccaga aaccatgact      60
aagagaacga agaaggcagg cattgtcgga aaatatggta cccgatatgg tgctagtttg     120
cggaagcaga ttaagaagat ggaagttagt cagcatagca aattcttttg tgaattttgt     180
gggaagtatg ctgtgaagag gaaggctgtg ggaatatggg gatgcaagga ttgtggtaaa     240
gtgaaagctg gcggtgccta cactttgaat actgcaagtg ctgtcactgt gcgcagcacc     300
atccggaggt tgagggaaca aaccgagggt tgagcttttt ggttgatgtt agattttgag     360
caaattaact ggagaaatga ttcgtttttg tttaggaagc tgtattgttt caacttacaa     420
tgcagtgtga attgctttcg                                                 440

<210> SEQ ID NO 97
<211> LENGTH: 463
<212> TYPE: DNA
<213> ORGANISM: Glycine max
<220> FEATURE:
<221> NAME/KEY: misc_feature
<223> OTHER INFORMATION: Ceres CLONE ID no. 658438
<220> FEATURE:
<221> NAME/KEY: misc_feature
<223> OTHER INFORMATION: Encodes the protein at SEQ ID NO: 26

<400> SEQUENCE: 97
atatawcttg actctccgca attccctgtc tcckccgccg cagcttccgt ctcccggatt      60
tcgccgcctg ccgcakccgc agcagctcgc cgsccacgcs tcctayccgt cgacgagatg     120
acgaascgca ccaagaaggc tggaattgtc ggcaaatatg gtacccgtta tggtgccagt     180
ttgcgtaagc agatcargaa gatggaggtg tctcagcact ccaagtactt ckgtgagttc     240
tgtgggaagt ttgctgtgaa gaggaaagsa gttggaattt ggggatgcaa tggactgtgg     300
gaaggwsaag gaaaccttcg ccwkaaaccg tgagctcgaa gtgmggtcca ctccaggwgg     360
gccatgctcg gggccttggg swgcagtctt ccccgaagct attgtyccgc aacggggtca     420
agtttggaga agctgtgtgg ttcaaggccg ggtcccagat ctt                       463

<210> SEQ ID NO 98
<211> LENGTH: 458
<212> TYPE: DNA
<213> ORGANISM: Glycine max
<220> FEATURE:
<221> NAME/KEY: misc_feature
<223> OTHER INFORMATION: Ceres CLONE ID no. 1049262
<220> FEATURE:
<221> NAME/KEY: misc_feature
<223> OTHER INFORMATION: Encodes the protein at SEQ ID NO: 27
<220> FEATURE:
<221> NAME/KEY: misc_feature
<222> LOCATION: (224)..(224)
<223> OTHER INFORMATION: n is a, c, t, g, unknown, or other

<400> SEQUENCE: 98
aacaaaccct cgttcacggt tcaacttcag cagccgcgcc tctaacttgt agcagcgata      60
```

```
cctcttctct tatcactaaa aaatgaccaa gagaaccaag aaggccggta ttgttggaaa      120
atacggcacc cgatatggtg ctagtttaag gaagcaaatc aagaagatgg aagttagtca      180
gcacagtaaa ttcttttgtg agttctgtgg aaagtacgct gttnagagga aggccgtggg      240 tatttgggc tgcaaagatt gtggaaaagt gaaggctgga ggtgcttaca cattgaatac       300
tgcgagtgct gtcactgtcc ggagcaccat tcggaggctg agagagcaga ctgagagttg      360
aaagcagttt acacttttca tttgtttcca aagcttattt taaaattatc atacaatttt     420
ggcaggtcta tgttaggaat attagtaatg tgctactt                              458
```

<210> SEQ ID NO 99
<211> LENGTH: 600
<212> TYPE: DNA
<213> ORGANISM: Triticum aestivum
<220> FEATURE:
<221> NAME/KEY: misc_feature
<223> OTHER INFORMATION: Ceres CLONE ID no. 632613
<220> FEATURE:
<221> NAME/KEY: misc_feature
<223> OTHER INFORMATION: Encodes the protein at SEQ ID NO: 28

<400> SEQUENCE: 99

```
ctcaaaaccc taggcttcca tatataactt gactctccac aattccctgt ctccgccgcc      60
gcagctttcg tctcccggat ttcgccgccg cagccgctca ccgcccacgc ctcctacccg      120
tcgacgagat gacgaagcgc accaagaagg ctggtattgt cggcaaatat ggtacccgtt      180
atggtgccag tttgcgtaag cagatcaaga agatggaggt gtctcagcac tccaagtact     240
tctgtgagtt ctgtgggaag tttgctgtga agaggaaagc agttgaatt tggggatgca       300 aggactgtgg gaaggtgaag gctggcggtg cttacactat gaacactgcc agtgcggtca     360
ctgtcaggag cactatccgt cgtttgaggg agcagactga agcataagtt gctactagtg     420
ttttgtccta gtgaatcatc tgggatttcg cagtttagac gatactttgg attcagttcc     480
attggctgtt tagtcaagga ttatctttgt acttggtgcg atgatgttct gttatgttat    540
tctcccaccc ttttgttgcc tgattccact ctgatttact gtggattctg atttgccttc    600
```

<210> SEQ ID NO 100
<211> LENGTH: 546
<212> TYPE: DNA
<213> ORGANISM: Zea mays
<220> FEATURE:
<221> NAME/KEY: misc_feature
<223> OTHER INFORMATION: Ceres CLONE ID no. 1390976
<220> FEATURE:
<221> NAME/KEY: misc_feature
<223> OTHER INFORMATION: Encodes the protein at SEQ ID NO: 29

<400> SEQUENCE: 100

```
aagcatccac aattccacat aacctcgccc gcgccgcctc ccccacgaga cgccttcttg      60
ctctcgcttc cggtgacgcc cgccacttcc tccccgacga gatgacgaaa cgcaccaaga     120
aggcaggaat cgttggcaaa tatggtacca ggtatggtgc cagtttacgt aaacagatca     180
agaagatgga ggtctcgcag cactccaaat acttctgtga gttctgtggc aagtttgccg     240
tgaagaggaa agcagttggt atctggggat gcaaggactg tgggaaggtt aaggccggtg    300
gcgcctacac aatgaacact gctagtgcgg tcactgtgag aagcacaatc cggcgcctgc    360
gggagcagac cgaagcatga ttgcgggcag cttgaaaagg agtacctgga ttttgtagt     420 tcagccaaga gccgtgaacc attttgcctt tttagctaaa tgaacaagaa atgtttatct    480
atctgtagtg accactttgt actcatggtt tgtcatgcta aattgatggt atgcactatg    540
``` caatgc 546

<210> SEQ ID NO 101
<211> LENGTH: 550
<212> TYPE: DNA
<213> ORGANISM: Zea mays
<220> FEATURE:
<221> NAME/KEY: misc_feature
<223> OTHER INFORMATION: Ceres CLONE ID no. 1457185
<220> FEATURE:
<221> NAME/KEY: misc_feature
<223> OTHER INFORMATION: Encodes the protein at SEQ ID NO: 30

<400> SEQUENCE: 101

```
atatataact tgactctccg caattccctg tctccgccgc cgcagcttcc gtctcccgga      60
tttcgccgcc gccgcagccg cagcagctcg ccgcccacgc ctcctacccg tcgacgagat     120
gacgaagcgc accaagaagg ctggaattgt cggcaaatat ggtacccgtt atggtgccag     180
tttgcgtaag cagatcaaga agatggaggt gtctcagcac tccaagtact tctgtgagtt     240
ctgtgggaag tttgctgtga agaggaaagc agttggaatt tggggatgca aggactgtgg     300
gaaggtgaag gctggcggtg cttacaccat gaacactgcc agtgcggtca ctgtcaggag     360
cactatccgt cgcttgaggg agcagactga agcataagtt gctactagtg ttttgtccta     420
gtgaatcatc tgggattttg cagtttagac gatactttgg attcagttct gttggctgtt     480
tagtcaagga ttatctttgt acttggtgcg atgatgttct gttatgttat tctctcaccc     540
ttttttttgcc                                                          550
```

<210> SEQ ID NO 102
<211> LENGTH: 668
<212> TYPE: DNA
<213> ORGANISM: Zea mays
<220> FEATURE:
<221> NAME/KEY: misc_feature
<223> OTHER INFORMATION: Ceres CLONE ID no. 1482731
<220> FEATURE:
<221> NAME/KEY: misc_feature
<223> OTHER INFORMATION: Encodes the protein at SEQ ID NO: 35

<400> SEQUENCE: 102

```
aaaaattcat tgatcgaaaa aagaaaaaa gaaagaaaag aaaagatgca gatcttcgtg       60
aaaaccttga ccggcaaaac cataacccta gaggttgaaa gcagcgacac catcgacaat     120
gtcaaatcca aaatccagga caaagagggg ataccacctg atcaacagag gctcatcttt     180
gctgggaaac aacttgagga tggtcgaacg ctagctgact acaacattca gaaagagtcc     240
actcttcact tggttctgag gcttaggggt gggaccatga tcaaggtcaa gactctcact     300
ggtaaagaaa tcgaaattga tatcgaacct accgatacta ttgaccggat caaggaacgt     360
gttgaggaga agaaggcat ccctcctgtt caacaaaggc tcatctatgc tgggaaacag     420
ctagctgatg acaaaacggc aaaggactac aacatagagg gaggctctgt tcttcatctg     480
gtccttgctc tcaggggtgg ttctgactaa ataactattt gctctagagt tcctttcaat     540
ggctttggtt ggttgaatcc atgagacaaa gtgaatacaa tttggatttc gtgctttggt     600
tactatgatg ctatttcagc tggtttggat caatttacca aaaaaaaaa aaaaaaaaa       660
aaaaaaag                                                             668
```

<210> SEQ ID NO 103
<211> LENGTH: 752
<212> TYPE: DNA

```
<213> ORGANISM: Glycine max
<220> FEATURE:
<221> NAME/KEY: misc_feature
<223> OTHER INFORMATION: Ceres CLONE ID no. 522921
<220> FEATURE:
<221> NAME/KEY: misc_feature
<223> OTHER INFORMATION: Encodes the protein at SEQ ID NO: 36
<220> FEATURE:
<221> NAME/KEY: misc_feature
<222> LOCATION: (639)..(639)
<223> OTHER INFORMATION: n is a, c, t, g, unknown, or other
<220> FEATURE:
<221> NAME/KEY: misc_feature
<222> LOCATION: (674)..(674)
<223> OTHER INFORMATION: n is a, c, t, g, unknown, or other
<220> FEATURE:
<221> NAME/KEY: misc_feature
<222> LOCATION: (690)..(690)
<223> OTHER INFORMATION: n is a, c, t, g, unknown, or other
<220> FEATURE:
<221> NAME/KEY: misc_feature
<222> LOCATION: (697)..(697)
<223> OTHER INFORMATION: n is a, c, t, g, unknown, or other
<220> FEATURE:
<221> NAME/KEY: misc_feature
<222> LOCATION: (700)..(700)
<223> OTHER INFORMATION: n is a, c, t, g, unknown, or other
<220> FEATURE:
<221> NAME/KEY: misc_feature
<222> LOCATION: (714)..(714)
<223> OTHER INFORMATION: n is a, c, t, g, unknown, or other

<400> SEQUENCE: 103
aattacaaat acaaatacga ataccttct ctctcacaca aaacactagt ccctcccttc      60
ttccttgtct ctttctcttc tcaacaacat gcagatcttc gtcaagactt tgactggcaa    120
gaccatcacc ctcgaggtcg agagtagcga caccatcgac aacgtcaagg ccaagatcca    180
ggacaaggaa ggtatccctc ctgaccagca gagtttgatt tttgctggta agcagctgga    240
agatggtcgc actcttgctg attataacat acaaaaggaa tcaacacttc acttggtctt    300
gaggctcagg ggaggaacca tgattaaagt gaagactcta actggaaaag aaattgaaat    360
tgacattgag ccaactgata caatcgaccg gatcaaggaa cgcgttgaag aaaaagaggg    420
aattccacct gtgcagcaga gactcatata tgcaggtaaa cagcttgctg atgacaaaac    480
agctaaagag tacaacattg agggtggttc tgtacttcac ttggtgcttg cattgagggg    540
tggtacttat tagtgtagat gccatatcag aacccaaaga catgaaagga agctctattc    600
ctgccccgtc tctctgaaga catcattgtt ctttatgng cttggttttt gtaattgtgg    660
ctactattgg tggncagtaa ctcagtatcn ttttagntgn atgctattta aaancccntaa   720 ggtgggcctt tatatgaata tctgaaccaa tg                                  752

<210> SEQ ID NO 104
<211> LENGTH: 484
<212> TYPE: DNA
<213> ORGANISM: Brassica napus
<220> FEATURE:
<221> NAME/KEY: misc_feature
<223> OTHER INFORMATION: Ceres CLONE ID no. 1036726
<220> FEATURE:
<221> NAME/KEY: misc_feature
<223> OTHER INFORMATION: Encodes the protein at SEQ ID NO: 37

<400> SEQUENCE: 104
gaaatcaaat aaaaaaatct ttaagcaaga aagaaagaa atgcagatc ttcgtcaaaa       60 ccctgacggg gaaaaccata accctggagg ttgaaagcag cgacaccatc gacaatgtca    120
aagccaaaat ccaggacaaa gaaggaatac cgccggatca gcagaggctg atcttcgctg    180
```

```
ggaagcaact agaagacggt agaacccttg cggactacaa catccagaaa gagtccactc    240
ttcacttggt cttgaggctt aggggtggca ccatgatcaa ggtcaagact ctcactggca    300
aagaaatcga gattgacatc gaacctaccg acaccattga tcgcatcaag gagcgtgttg    360
aggagaaaga aggcatccct cctgttcaac agaggctcat ctacgctgga aaacagctag    420
ctgatgacaa gacggcmaaa gactacaaca tcgagggagg ctctgtttct gcatctggtt    480
cttg                                                                484

<210> SEQ ID NO 105
<211> LENGTH: 580
<212> TYPE: DNA
<213> ORGANISM: Glycine max
<220> FEATURE:
<221> NAME/KEY: misc_feature
<223> OTHER INFORMATION: Ceres CLONE ID no. 513071
<220> FEATURE:
<221> NAME/KEY: misc_feature
<223> OTHER INFORMATION: Encodes the protein at SEQ ID NO: 38
<220> FEATURE:
<221> NAME/KEY: misc_feature
<222> LOCATION: (543)..(543)
<223> OTHER INFORMATION: n is a, c, t, g, unknown, or other

<400> SEQUENCE: 105
aagaaaaagg aaattttctt gggcgttctt cggcttcgtt gtcacaaggt tcgagttcgt     60
caccgtctag tacgactgtg cgagggagga agaggcgagg agaagatgca gatcttcgtg    120
aagaccctga cggggaagac catcaccctc gaggtggaga gcagcgacac cgtcgacaac    180
gtcaaagcca aaatccagga caaggaaggg attcccccag atcaacagcg actgatattc    240
gctggcaagc agctggagga tggacgcacg ctggctgact acaacatcca aaaggagtca    300
actcttcatt tggtcctcag gcttaggggt ggaaccatga tcaaggtcaa aactctcact    360
gggaaagaga tcgagatcga cattgaaccc actgactcga ttgacaggat caaggagcgt    420
gttgaagaga aagaaggcat tcctcccgtg cagcaaaggc tcatctatgc tggtaagcag    480
cttgctgatg acaagaccgc aaaggactac aacatcgagg gtggatctgt cctccatctt    540
gtncttgctc tgaggggtgg ttactagtct aaacctgatg                          580

<210> SEQ ID NO 106
<211> LENGTH: 987
<212> TYPE: DNA
<213> ORGANISM: Brassica napus
<220> FEATURE:
<221> NAME/KEY: misc_feature
<223> OTHER INFORMATION: Ceres CLONE ID no. 975672
<220> FEATURE:
<221> NAME/KEY: misc_feature
<223> OTHER INFORMATION: Encodes the protein at SEQ ID NO: 44

<400> SEQUENCE: 106
attccatcaa cttcagacac acagatctct tctcaatcac attacttctg gttctcccac     60
catgaggaaa gggagaggct cttccgccgt tccacccgcc cttcccggat ctgtgaagga    120
gccgaggtac agaggcgtta ggaagagacc ttggggccgt ttcgccgccg agatccgtga    180
ccccttgaaa aaatcccgag tctggctcgg cacgttcgac tccgcggagg aagccgcacg    240
cgcctacgac gcagccgctc gtaacctccg cggtccaaag gccaagacca acttccaaat    300
cgactgttct ccttcctctc ctctccaacc actccatcat cggaaccaga tcgatccctt    360
tatggaccac cggttatacg gcggagagca ggaggttgtt atcatcagcc ggccggcgag    420
```

-continued

| | |
|---|---|
| tagcagcatg agcagcaccg ttaagtcgtg cagcggagtg agaccagcgt cttcttccgt | 480 |
| ggcgaaggcg gcgacgaaga gatatccacg gactccgccg gtggcgccgg aggattgccg | 540 |
| cagcgactgc gattcgtcgt cgtcggtggt tgaagacgga sacgacatag cttcgtcgtc | 600 |
| ttcgcggcgg aaaccgccgt ttgagtttga tcttaatttt ccsccgttgg atggcgttga | 660 |
| cttattcgta ggcgcggacg atctccactg caccgatctg cgtctttgat cttgagcac | 720 |
| aatgacaaca aagatgatga agaagtgata gggagagaga gtttgtgtta agatctgttg | 780 |
| ttgtaagaac cagatctgtg tttcattcac ttgtctgttt cttataaaga tcaaacctt | 840 |
| gttacatgta acacttatat agctgctgat gattcttaat tattcaaaat ccaaagtctg | 900 |
| tagaatttat acagtatcta tcactgatgt gcttatggat ggtttggagt atgaggctac | 960 |
| attttcataa atacattcaa tgtgtgt | 987 |

<210> SEQ ID NO 107
<211> LENGTH: 1034
<212> TYPE: DNA
<213> ORGANISM: Zea mays
<220> FEATURE:
<221> NAME/KEY: misc_feature
<223> OTHER INFORMATION: Ceres CLONE ID no. 273307
<220> FEATURE:
<221> NAME/KEY: misc_feature
<223> OTHER INFORMATION: Encodes the protein at SEQ ID NO: 45

<400> SEQUENCE: 107

| | |
|---|---|
| ctctccttcc ttcacggatt cccaaatact cgcttccaat accaattctc cgatccacgt | 60 |
| tcgttcccgc accctcgcgc tccgctgatc cggcggcatg cggcgccgcg cgtggcggc | 120 |
| ggctgatgcg gacggtgacg tggagttgcg gttccgcggg gtgcggaaga ggccgtgggg | 180 |
| ccggtacgca gcggagatcc gggacccggc gaagaaggcg cgcgtctggc tcggcacatt | 240 |
| cgactccgcc gaggacgccg cccgcgccta cgacgccgca gcgcggatgc tgcgcgggcc | 300 |
| caaggccagg accaacttcc cgctcccgc cgcagccgcc ctccaccacc ccacatgcc | 360 |
| cgctgctgcc gccgcagcag ctccaccata cacaacatat cccaccgcca cgggcgtcgt | 420 |
| ctcgacgccg ccggtcgcca gaccggcttg cagcagcctc agctccaccg tggagtcctt | 480 |
| cagcggcgcg cggccgcggc ctgtgctccc gccgcggttc cctccgccgt cgattcctga | 540 |
| tggcgactgc cgcagcgact gtggttcctc ggcctcggtc gtggacgacg actgcacgga | 600 |
| cgcggccgcc tctgcgtcgt gccccttccc gctcccgttc gacctcaacc tgccccagg | 660 |
| cggcggcgga gccggcgtcg ggttttacgc cgatgaggag gatgagctca ggctcacggc | 720 |
| gctgcggctg tgacgtcgag ctcaatcgag ccgctgctta gaaagaggaa aaggagaaaa | 780 |
| atatttggtt cttcccttct cttgtagccg acacgaactc tccatccact cgatgttgt | 840 |
| tgtttacttg atctgattat gatatttgcc tgaatcctag tcaacttacc tgcatgcatg | 900 |
| cctgcttgtt ttctggcgat tgaggattat cgccaaacgc caaatcttgc agcagctgtt | 960 |
| gtactgtaat atatcaacat tttacttcct tcctcttatg aggaaagaga cagataaagt | 1020 |
| aacttattc aatc | 1034 |

<210> SEQ ID NO 108
<211> LENGTH: 911
<212> TYPE: DNA
<213> ORGANISM: Triticum aestivum
<220> FEATURE:
<221> NAME/KEY: misc_feature
<223> OTHER INFORMATION: Ceres CLONE ID no. 1055099
<220> FEATURE:

-continued

<221> NAME/KEY: misc_feature
<223> OTHER INFORMATION: Encodes the protein at SEQ ID NO: 46

<400> SEQUENCE: 108

```
aaacaaaaaa ccaccagggg aagaagggaa agacacacgc cactgtgacc aaaccctagg      60
ccggccgcga tgcgcaaggc gaggccgccg cagcccagc cgcagccgtc gcagcagtcg      120
ccggagatcc ggtaccgcgg cgtgcggaag cgcccctcgg gccgctacgc cgccgagatc     180
cgggaccccg ccaagaagac gccgatctgg ctcggcacct tcgactgcgc cgaggacgcc     240
gcccgcgcct acgactccgc cgcccgatcc ctccgcgggc ccaccgcccg caccaacttc     300
ccgcccctcct ccgccacgca gccgccgccg aggcccccctc cccccgcggc cgcggccgcg     360
gccgccacgt ccagccagag cagcaccgtc gagtcctgga gcggcggcgg gccccgcgcc     420
cccgccaggg cccgcagcgc cgcccgagcg ggcacggcca aggaggggga ggaggactgc     480
cgcagctact gcggctcctc gtcctccgtc ctcctcgagg agggcgcgga cgacgcggcc     540
gcctcccgct ccccgctgcc cttcgatctg aacatgccgc cccgcagga ggggcgctt      600
gacgccgagg ccgatcagat gacctgccgg tacgacacgc tgctccgcct ctagctccac     660
gacgacgaga gcaaggattc gtgggagggg aactgggaaa aggaacgaga aaagcgcttg     720
cccccgctcc gctccggtcc gtcttccgat gatctcgtgg tgttctctct tgttagaaa      780
tggataattc ttgccatttt ttttttcttac tttctttcct tcttctttttt ttttcttct     840
taccactttg attcgatatg tgaataattg agtcatgtaa gctgcgagca aggaaatctg     900
agcttttcct t                                                         911
```

<210> SEQ ID NO 109
<211> LENGTH: 160
<212> TYPE: PRT
<213> ORGANISM: Arabidopsis thaliana
<220> FEATURE:
<221> NAME/KEY: misc_feature
<223> OTHER INFORMATION: Ceres GI ID no. GI_15226675
<220> FEATURE:
<221> NAME/KEY: misc_feature
<222> LOCATION: (13)..(152)
<223> OTHER INFORMATION: Pfam Name: Globin
    Pfam Description: Globin
<220> FEATURE:
<221> NAME/KEY: misc_feature
<223> OTHER INFORMATION: Functional homolog of Ceres Clone ID no. 30469
    given in SEQ ID NO: 7

<400> SEQUENCE: 109

```
Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Cys Cys Glu Ser
65                  70                  75                  80

Ala Val Gln Leu Arg Lys Thr Gly Lys Val Thr Val Arg Glu Thr Thr
                85                  90                  95

Leu Lys Arg Leu Gly Ala Ser His Ser Lys Tyr Gly Val Val Asp Glu
            100                 105                 110

His Phe Glu Val Ala Lys Tyr Ala Leu Leu Glu Thr Ile Lys Glu Ala
```

|       | 115                 |       | 120                 |       | 125                 |       |
|-------|---------------------|-------|---------------------|-------|---------------------|-------|

Val Pro Glu Met Trp Ser Pro Glu Met Lys Val Ala Trp Gly Gln Ala
    130                 135                 140

Tyr Asp His Leu Val Ala Ala Ile Lys Ala Glu Met Asn Leu Ser Asn
145                 150                 155                 160

<210> SEQ ID NO 110
<211> LENGTH: 1823
<212> TYPE: DNA
<213> ORGANISM: Arabidopsis thaliana
<220> FEATURE:
<221> NAME/KEY: misc_feature
<223> OTHER INFORMATION: Ceres Promoter 28176

<400> SEQUENCE: 110

| gtctcttaaa | aaggatgaac | aaacacgaaa | ctggtggatt | atacaaatgt | cgccttatac | 60 |
| atatatcggt | tattggccaa | aagagctatt | ttaccttatg | gataatggtg | ctactatggt | 120 |
| tggagttgga | ggtgtagttc | aggcttcacc | ttctggttta | agccctccaa | tgggtaatgg | 180 |
| taaatttccg | gcaaaaggtc | ctttgagatc | agccatgttt | tccaatgttg | aggtcttata | 240 |
| ttccaagtat | gagaaaggta | aaataaatgc | gtttcctata | gtggagttgc | tagatagtag | 300 |
| tagatgttat | gggctacgaa | ttggtaagag | agttcgattt | tggactagtc | cactcggata | 360 |
| cttttttcaat | tatggtggtc | ctggaggaat | ctcttgtgga | gtttgatatt | tgcgagtata | 420 |
| atctttgaac | ttgtgtagat | tgtacccaaa | accgaaaaca | tatcctatat | aaatttcatt | 480 |
| atgagagtaa | aattgtttgt | tttatgtatc | atttctcaac | tgtgattgag | ttgactattg | 540 |
| aaaacatatc | ttagataagt | ttcgttatga | gagttaatga | tgattgatga | catacacact | 600 |
| cctttatgat | ggtgattcaa | cgttttggag | aaaatttatt | tataatctct | cataaattct | 660 |
| ccgttattag | ttgaataaaa | tcttaaatgt | ctcctttaac | catagcaaac | caacttaaaa | 720 |
| atttagattt | taaagttaag | atggatattg | tgattcaacg | attaattatc | gtaatgcata | 780 |
| ttgattatgt | aaaataaaat | ctaactaccg | gaatttattc | aataactcca | ttgtgtgact | 840 |
| gcatttaaat | atatgtttta | tgtcccatta | attaggctgt | aatttcgatt | tatcaatttta | 900 |
| tatactagta | ttaatttaat | tccatagatt | tatcaaagcc | aactcatgac | ggctagggtt | 960 |
| ttccgtcacc | ttttcgatca | tcaagagagt | tttttttataa | aaaaatttat | acaattatac | 1020 |
| aatttcttaa | ccaaacaaca | cataattata | agctatttaa | catttcaaat | tgaaaaaaaa | 1080 |
| aatgtatgag | aattttgtgg | atccattttt | gtaattcttt | gttgggtaaa | ttcacaacca | 1140 |
| aaaaaataga | aaggcccaaa | acgcgtaagg | gcaaattagt | aaaagtagaa | ccacaaagag | 1200 |
| aaagcgaaaa | ccctagacac | ctcgtagcta | taagtaccct | cgagtcgacc | aggattaggg | 1260 |
| tgcgctctca | tatttctcac | atttttcgtag | ccgcaagact | cctttcagat | tcttacttgc | 1320 |
| aggttagata | ttttctctct | ttagtgtctc | cgatcttcat | cttcttatga | ttattgtagc | 1380 |
| tgtttagggt | ttagattctt | agttttagct | ctatattgac | tgtgattatc | gcttattctt | 1440 |
| tgctgttgtt | atactgcttt | tgattctcta | gctttagatc | cgtttactcg | tcgatcaata | 1500 |
| ttgttcctat | tgagtctgat | gtataatcct | ctgattaatt | gatagcgttt | agttttgata | 1560 |
| tcgtcttcgc | atgttttttta | tcatgtcgat | ctgtatctgc | tctggttata | gttgattctg | 1620 |
| atgtatttgg | ttggtgatgt | tccttagatt | tgatatacct | gttgtctcgt | ggtttgatat | 1680 |
| gatagctcaa | ctggtgatat | gtggttttgt | ttcagtggat | ctgtgtttga | ttatattgtt | 1740 |
| gacgttttgg | ttgttgtatg | gttgatggtt | gatgtatttt | tgttgattct | gatgtttcga | 1800 |

```
tttttgtttt tgttttgaca gct                                           1823
```

```
<210> SEQ ID NO 111
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0668

<400> SEQUENCE: 111
atagagtttt actatgcttt tggaatcttt cttctaatgt gccaactaca gagaaataca     60
tgtattacca ctaggaatcg gaccatatca tagatatcag gattagataa ctagttctcg    120
tcgctatcac ttcgcattaa gttctagtaa ttgttaaaga ttctaatttt ttactaaaca    180
aaaactaaat caacatcaaa tatgcaaagt gtgtgttgtc cacacaagtg actcaaagta    240
tacgcaggtg ggattggacc atattattgc aaatcgtttc cgaaccactc atatttcttt    300
ttttctctcc ttttttttatc cggagaatta tggaaccact tcatttcaac ttcaaaacta    360 atttttggt tcagtgatca aatacaaaaa aaaaaaaaaa gttatagata ttaaatagaa    420
aactattcca atcttaaaaa tacaaatgaa accataattt taatttatac aaaactattt    480
aattagctaa gggttgtctt aacgtttaga aaataaaaaa ttatgattgt ctgtttaaaa    540
ttacaatgaa tgaataaaaa aaatatgcaa tgaatgaaag aataaatttt gtacatccga    600
tagaatgaga aaatgaattt tgtacaaacc actcaagaat tcaaaacaat tgtcaaagtt    660
ttcttctcag ccgtgtgtcc tcctctccta gccgccacat ctcacacact aatgctaacc    720
acgcgatgta accgtaagcg ctgagttttt gcatttcaga tttcacttcc accaaacaaa    780
actcgccacg tcatcaatac gaatcattcc gtataaacgt ctagattctt tacagcctac    840
aatgttctct tctttggtcg gccattattt aacgctttga acctaaatct agcccagcca    900
acgaagaaga cgaagcaaat ccaaaccaaa gttctccatt ttcgtagctt ctttaagctt    960
tttcagtatc atagagacac ttttttttttt ttgattagaa                        1000
```

```
<210> SEQ ID NO 112
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0535

<400> SEQUENCE: 112
ttagtgaaat tatgacatta agtaaggttt tcttagttag ctaatgtatg gctattcaat     60
tgttatgtta ggctatttta gttagtatat gaatttaggc agtctatgca aatgatttcg    120
ttttcatttt ttcatatgta aacatcaaga tcaagtaacg ccattcgagt tgatattttt    180
tttttaaatt agtgtgtgta aattttggac cgcttatttg agtttgctaa tgaagttgca    240
tatatattac gttaaaccat aggcaaacta atttgaaaca tccgattcga tttcctgtaa    300
tttttcttgg ttaattgacc aaaatcaaga tcttcagaaa taaaataaaa gacgaaagaa    360
agctgtcgca aagcagattg tgttaaaaaa agtggattgg gctcaaacg caacttgtcc    420 agcccgtgac aattacccta tacgcaagta agagtaacgt atcactggca aaagttggta    480
ttagttacga tatctttgtc atgggggcat gcatgggcat ggcttaagag ttaagcctta    540
agaagagtcc cacactcgtg actctcatga tcacttgttg tttcttacgg gcaaatacat    600
ttaactttat tcttcattta ttcacctata ttcttttgga taataacttt tctctatata    660
```

```
aaataacaaa catcgtacgt ttcatttatt tacaacaagc gatgagaatt aaaaggagac        720
cttaattgat gatactcttc ttttctctcg gttacaacgg gattattaca gataatgata        780
atctatatgg atgctgacgt ggaaaaacaa aatttggtga aacacgtcaa ttaagcacga        840
cttttccatg gctagtggct aagatcgttt catcacatgg ctatatcata taatacttgg        900
atgaattcaa aataaacgac tgagaaaatg tccacgtcac ggcgcaccgc tttggactta        960
agtctcctat aataaataca acaccaaaca ttgcattcca                             1000

<210> SEQ ID NO 113
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0585

<400> SEQUENCE: 113
tgaagtcatt taatatgagt ttgacattag gtaaacctaa tctatgagat tatagaatgt         60
agcaaaacta tcaatgtttc ttttccaaaa tattttgtgg ttttctttt tggttcatta         120 tgttttgtta tttgtgaatt atttaatat gaagtaatta tattgatttt atatgatata         180
catattattt tgatataaaa tttaacactt atccattaaa atagcatggg cataatcaaa         240
atcgggacta ttacgatgaa aaagatagtt aaattgtatg ataaaataaa atgtgtaaga         300
ttaaaatttt gggttttaga aaattactaa acaaaatata gacaaagtat gttgactatt         360
atttaaaatt taaatatcat caataagata tagttaaagt cattaagtgt atagcaaaat         420
gaaaattcta agattaaaat tcgattaaaa tttttttttac taaattaaat atttaaaaat        480
agggattatc atttactatt tacaattcta atatcatggg taaaaattga taactttttt         540
taaacccgcc tatctaggtg ggcctaacct agtttactaa ttactatatg attaacttat         600
taccactttt acttcttctt ttttggtcaa attactttat tgttttttat aaagtcaaat         660
tactctttgc attgtaaata atagtagtaa ctaaaatctt aaaacaaaat attcaacctt         720
tcccattatt ggaatggtaa tgtcttcaac accattgacc aacgttaagg aatgtctttt         780
aatatttttg gaacctaaat gctaatactg tataccacaa tcacttatga gtattgaagt         840
tgagatagag gaggtacaag gagaccttat ctgcagaaga caaaaagcca ttttttagcaa        900 aactaaagaa agaaaaaaga ttgaaacaca aatatgcgcc actcgtagtc caccccctatc       960 tctttggcaa aagccacttc actctttttc cctttttat                               999

<210> SEQ ID NO 114
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0613

<400> SEQUENCE: 114
ttaatactaa cattgtagaa agccacaaaa aagaaattga aatgtgagta gatgctgagt          60
cagaggtttg gtcaatacac aacagctaat tgagataata ttatacacgt cacgatgact        120
tgttttttct cctcccaact tgttaatttc tttattctta aaattaaacc atcgcaaaaa        180
cagaagaaca cagctgtttt tctcgactcc caatttctat tttgctgcta aggacatttc        240
atttcattat ttcccaattc aggactccct agattttcct aaatttgttt tcctaacttg        300
```

```
ctctctctca ttctaacatt ttctcatttt tttagattat cttgtacttt ttagtagatt    360
attttatcag gttttacaaa catacattga cattctaaaa agggcttcta aaaattcagt    420
gtggaatgct gatatactaa aaaaaggtca tgcaaaatta tctacgattt atctaaaatt    480
agataatttg ccatatataa ctattaacta ataatcgatc ctttgatttt ttgtttagat    540
aaaacgaaac agctatatct tttttttttg ttatcggatt ttaatcgaat aaaagctgaa    600
aaataacagt tatatcttct tcttttttaa ctaatgaaac agttatatct taaacaaaca    660
acagaaacag taaaatatta atgcaaatcc gcgtcaagag ataaatttta acaaactaat    720
aacaattgag ataagattag cgcaaaagaa actctaattt tagagcgtgt aaacacaaac    780
acgtcttgaa agtaaacgtg aattacacgc ttctaaaacg agcgtgagtt ttggttataa    840
cgaagatacg gtgaagtgtg acacctttct acgttaatttt cagtttgagg acacaactca    900
agttatgttt gatatctaag gacttgcact gtctccaaat ctgcaggaag gactttttga    960
ttggatcaat ataaatacca tctccattct cgtctccttc                         1000

<210> SEQ ID NO 115
<211> LENGTH: 351
<212> TYPE: DNA
<213> ORGANISM: Arabidopsis thaliana
<220> FEATURE:
<221> NAME/KEY: misc_feature
<223> OTHER INFORMATION: Ceres Promoter PT0625

<400> SEQUENCE: 115
gatcatgatc agtttcaact cgctgtgccc acgtgtcgag agatcggcac gtgcctgagc     60
tctcagccgc tcataaatac acttgtttag tagcaacagt atactatagt agtcctctcc    120
tgtttggctt ttagcttgca tcgatggatg gatggatgga tcgcatgaga gggcttcgcg    180
aaggtacgga accttacaca acgcgtgtcc tttctacgtg gccatcgtgt aggcgtctcg    240
ccatgctacg tgtcccggag gatgtctcga tgccaaccct tataaatact gttccattcc    300
aatcccatcg ccacagccag tgcaaatctg atcgatcaag ataatcgagc a            351

<210> SEQ ID NO 116
<211> LENGTH: 1022
<212> TYPE: DNA
<213> ORGANISM: Arabidopsis thaliana
<220> FEATURE:
<221> NAME/KEY: misc_feature
<223> OTHER INFORMATION: Ceres Promoter PT0633

<400> SEQUENCE: 116
cccgatcggc cttaatctga gtcctaaaaa ctgttatact taacagttaa cgcatgattt     60
gatggaggag ccatagatgc aattcaatca aactgaaatt tctgcaagaa tctcaaacac    120
ggagatctca aagtttgaaa gaaaatttat ttcttcgact caaaacaaac ttacgaaatt    180
taggtagaac ttatatacat tatattgtaa ttttttgtaa caaatgtttt ttattattat    240
tatagaattt tactggttaa attaaaaatg aatagaaaag gtgaattaag aggagagagg    300
aggtaaacat tttcttctat ttttttcatat tttcaggata aattattgta aaagtttaca    360
agatttccat ttgactagtg taaatgagga atattctcta gtaagatcat tatttcatct    420
acttctttta tcttctacca gtagaggaat aaacaatatt tagctccttt gtaaatacaa    480
attaattttc gttcttgaca tcattcaatt ttaattttac gtataaaata aaagatcata    540
cctattagaa cgattaagga gaaatacaat tcgaatgaga aggatgtgcc gtttgttata    600
ataaacagcc acacgacgta aacgtaaaat gaccacatga tgggccaata gacatggacc    660
```

```
gactactaat aatagtaagt tacattttag gatggaataa atatcatacc gacatcagtt    720
tgaaagaaaa gggaaaaaaa gaaaaaataa ataaaagata tactaccgac atgagttcca    780
aaaagcaaaa aaaaagatca agccgacaca gacacgcgta gagagcaaaa tgactttgac    840
gtcacaccac gaaaacagac gcttcatacg tgtccctttta tctctctcag tctctctata    900
aacttagtga gaccctcctc tgttttactc acaaatatgc aaactagaaa acaatcatca    960
ggaataaagg gtttgattac ttctattgga agaaaaaaaa tctttggaaa aggcctgcag   1020
gg                                                                   1022
```

<210> SEQ ID NO 117
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0650

<400> SEQUENCE: 117

```
catacttaat tctaaaaaaa caacacttat agtttataag cagctcttat gataaaaatc     60
tttctgagtt atagctctgt taaacttgta ttcaccccaa aaacggatgt ttcatttctt    120 atttttact tggagtattt tattgtaatt tgtaaaaaaa aatgtaaagt gggggatatc    180
atgaaaaaca acgtcacttt gtttggtcac aatatacatt tgataaaata atggtcgtcg    240
cgtgatttag ttgatttttg ttttatcaac cacgtgtttc acttgatgag tagtttatat    300
agttaacatg attcggccac ttcagatttg ggtttgccca catatgacat accgacatag    360
aaggttaaat ccacgtggga aatgccaata ttcaatgttt ggttttcaaa agagaatcat    420
ttctttatat gatctcaaaa gtatggaatt gaaatgacta atgagcacat gcaattggtg    480
ctatcttaaa aaccgaacgt ctttgaattt aatttgtttt tcaccaaagg tacctaatga    540 aacccttttca ttaaaaaata aaggtaacaa acaaaatttt gtattggaaa aaacattttt    600
tggaatatat aatttggtaa tagaattatg agcaaaaaag aaaaagaaaa gaaagaataa    660
tgagcataat aaagcccttta cagtattact aattgggccg agcagttttg ggctcttgat    720
catgtctagt aatcttaaac agacgataaa gttaactgca atttagttgg ttcaggtgag    780
ctaccaaatc caaaaatacg cagattaggt tcaccgtacc ggaacaaacc ggatttatca    840
aaatccttaa gttatacgaa atcacgcttt tccttcgatt tctccgctct tctccactct    900
tcttctctgt tctatcgcag acatttttgt ttatatgcat acataataat aatacactct    960
tgtcaggatt tttgattctc tctttggttt tctcggaaaa                         1000
```

<210> SEQ ID NO 118
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0660

<400> SEQUENCE: 118

```
caagtcaagt tccaatattc taaggagaaa taatagtata ctaaacatac attagagagg     60
ttaaacttct ttttggattt aagtgtgtat gcataggcta tttattctta agtataacta    120
ttaactgtag ctagatttat acaagaaata cataaaactt tatgcatgtg aggtagccat    180
gaatatacgt acatgttgca atcgattata catgttgtat ttggatttct ctatacatgt    240
```

```
tttaacttgt cattctctaa gtatatacat accattaata ctgtgggcat gagtttatga    300
taagactttt cttttggaga ccagttttgt tttccttttcc acctatattt gtctataggc   360
ttcacggtac actagtttac aagtgttttt atatgttcta aataaaattg agattttccg    420
gaacggtatg atctgtttgc aaataaggac gtatatataa cagtatcaaa tatatttgtt   480
gttataaggc aataatatat tttctgagat attgcgtgtt acaaaaaaga aatatttgtt    540
aagaaaaaaa aagatggtcg aaaaagggga gtaggtgggg gcggtcggct tttgattagt    600
aataaaagaa accacacgag tgacctaccg attcgactca acgagtctac cgagctaaca   660
cagattcaac tcgctcgagc ttcgttttat gacaagttgg tttttttttt ttttttaat    720 tttttcatct tcttgggttt ggttgggtca ctcttcaggt caggtgtgta aaaagaaag    780 aaagaaaaga gagattgttg tgttgtaacc cctttgacta aaatctaatg aacttttta    840 acacaacaaa actccttcag atctgaaagg gttcttcttc tctcttagtc tcttcgtcct   900
tttattctcc gtcgtcgttt catgatctga ctctctggtc ttctcttctt cttcttcttc   960
ttctattttt tcttacttcg tcactgttgt gtctgaac                           998
```

<210> SEQ ID NO 119
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0665

<400> SEQUENCE: 119

```
aaaaaggatg ggtaatggga cctattttcc ccaacatccc acatgcacac ttccctctcc    60
attctctcac atttatttct ttcattctaa tttatccatt ccgtgtgtaa catattcact    120
aataatctca tctcactaac tcattcattg attgtgatat gtttatctag aattagtgtt   180
ttaacactgt gtctacatat gatttccttt tcattgtatg tgaacatgtt aactcactaa   240
tcattttgta ttttcgagtt aacatgagtc tccacttcgg tagactaaag taaagatagg   300
tttgagtata ataaagttta aaatttgctt taaaatcaat atttataaat aagttttat    360 cataagtgat ttttgtatgt tatattggac cttgtataaa cagactacag aagaaaatta   420
tttatgagaa cttgtaatgt tagagtggac ctcgtataaa ctaattatgt gggcttttac    480
cataaactat ttatgaaaat tattatggcc cacaccacta taactaaagc ccacatattt    540
agcagcccag tttcattgta agagacatgt tcgctctgga actagaattt tctggtttt    600 gggtatttgt tttcttatgt gtagagaaat gatggtaacg attaaatgtt gtgtattaca    660
atttacaatg gtaagacgat taatatattt acacacaatt tgttgttgc tgtaacacgt     720 tagtgtgtgt gatgatagaa tttcataaag ctttaactac gaggggcaaa atgttaattc    780
taaatagttg acagcagaaa aagatatgta tacataatat aaggattaaa acgtaaataa    840
taataaataa ggcgagttaa attaaaaccc tgttaaaacc ctagcttgaa acacatgtat    900
aaaaacactt gcgagcgcag cttcatcgcc atcgccattc tctctctcat caaaagcttt   960
tctccttgat tttcgcattc tttagagtct taacgcaaag                         1000
```

<210> SEQ ID NO 120
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0672

<400> SEQUENCE: 120

```
cagccgtaaa tcctccataa atttattttg caagttttgc tcattatata atgagcggaa      60
tttatgatat aatcgtttgt aataatgtta tgttttgatc aaaatttgaa attaaaagta     120
ggtgagaact tgttatacag tgtagataag gtggatcttg aatataaaaa taaaatttat     180
aagatgtatt taaagcagaa aagcataaaa ctttagataa aataatgtaa aaatgtgtta     240
gcatcaatgt tgggatattg gccgacccga acttaatcaa tgtcggaagc cattacttct     300
ctcccaaaag acctttttcc ttcggagaac taggaacttc ctcactacct ttcgcttaac     360
gtgaaagcca taaatttcat atattcataa aaatcagaaa atctaaaact gtttagtatc     420
acctgttttt ggtatagact attggttttg tgttacttcc taaactatat gatttcgtac     480
ttcattggat cttatagaga tgaatattcg taaaaagata agttatctgg tgaaacgtta     540
cttcagtcat gttgggtcta gattacata  ctactatgaa acattttaag ataataatta     600
tcctagccaa ctatatgttc tatattatgg gccaagaaga tatagaacta aaagttcaga     660
atttaacgat ataaattact agtatattct aatacttgaa tgattactgt tttagttgtt     720
tagaataaat agtagcgtgt tggttaagat accatctatc cacatctata tttgtgtggg     780
ttacataaaa tgtacataat attatataca tatatatgta tattttttgat aaagccatat    840
attactcctt gacctctgcc cccatttcct tttactataa ataggaatac tcatgatcct     900
ctaattcagc aatcaacacc aacgaacaca acctttttcca aagccaataa taaaagaaca    960
aaagctttta gtttcatcaa agacgaagct gccttagaa                            999
```

<210> SEQ ID NO 121
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0676

<400> SEQUENCE: 121

```
aagatagtac agtttcagtg ttttgagaaa aaaagctgaa ctaaaactaa aatgtttaag      60
gacacaatat ttagtttcaa ttagataatt caacagtttg aacaattttt ttttttttttt    120
tttgaagtca tttatttata caatgtttta aaacgcatta agcatttagg cagccgacaa     180
acgcctattg tctaactgta aataggcgct tccacttagg ttcatattgc atatttacta     240
tatgtgtata gtgacaaaaa ccaatatttc tcttattttg gatgaaggta tagtagttgt     300
taaatgttca atataattaa gcattaatga caaataaaat aaaattaatt tagttgataa     360
aaagataatc ttataaaaag atcgatgaat agatataatg gtttactgaa ttctatagct     420
cttaccttgc acgactatgt cccaaggaga ggaagtacct taactataat tctgaacata     480
attttgtcta tcttggtgag tattatatga cctaaacccct ttaataagaa aaagtataat    540
actggcgtaa cgtaataaat taacacaatc ataagttgtt gacaagcaaa aaaacataca    600
taatttgttt aatgagatat attagttata gttcttatgt caaagtacaa ttatgcctac    660
caaaattaat taatgatttc aacaggaagt ctgagatgat gggccgacgt gtagttacgt    720
ttcttgaatt gtgagagatg gtatttatta tactgaagaa aacattattt actaaataaa    780
ttttcatttc acatcttctg taatcaatgc gggtagatga agaagttgtt aatacgatgg    840
ccaaccatat ggatctcttt tttggcgttt ctatatatag taacctcgac tccaaaggca    900
ttacgtgact caataaaatc aagtcttttg tttccttttta tccaaaaaaa aaaaaaagtc   960
```

```
ttgtgtttct cttaggttgg ttgagaatca tttcatttca                    1000
```

<210> SEQ ID NO 122
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0678

<400> SEQUENCE: 122

```
aattaaatga aaccgcccct aaattaggag ggatttgggt aagtggtaac acattcactg    60
gaaacatgtg aagaaaggag gatgtcaagt agctgaaaac tcagtatagt aaccaacggc   120
ttctcaccaa cctttcatta ataatttggt catccctata tttttattca acattttgtt   180
tttcaatagc ttagagcacc ttaataccct tcagtgtttt tttataaaaa aacaaaaat   240
tgggattaat catcaatccc caatgtaac gttacttag attatgttca tttttctata    300
cacacaaatc atattctttt gttttaatct tcgaaaacg agaggacatt aaatacccct    360
aaaaaaggag gggacattac taccaacgta cattaacatg tttgatagca aacgatttat    420
tttgttcgtt ttgaaaaggg gaaagtaatg tgtaaattat gtaaagatta ataaactttt    480
atggtatagt aacattttcg aataataaga gagggaaaac actcgccatt gtcggcaatt    540
tagaaccaat attagaaggg tttttttaga gaaaaaggac ttaaaagttt agagaccta    600
acaacaactt atttagaaat agacatgctt aagttgacaa cagcgagttt attttctata    660
tcgaagaaaa atacgaactt tttcttaatt agatttcgaa tgcatgcact atcgagaatc    720
gaccgtcaca agaaaaaact aatatacata ctgtacatat ctatattcaa tattggtggg    780
gatggggttta atgtgtattt ataattcatg gataaattca cacaataagg tccatgaaac    840
tagaaggtac caaaaataag cattaatgac tctttgccac ttatatatat gattctctca    900
tagtaccatt ttattctccc aaacctatct tcttcttcct ctcttgtctc tctcgctctc    960
tctcttctac attgtttctt gaggtcaatc tattaaaa                            998
```

<210> SEQ ID NO 123
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0683

<400> SEQUENCE: 123

```
gattgaatga tgagtgtgca cccttgtatt actaataaaa aatttagcaa cagttataag    60
ctaacgtcat ccatgagtca ttcattagat tcactatttg cgttctcaaa aatcgaattg   120
ttaaatttg agaagctcta atatacgagt caatgagatg tggcaaaagc atgtccttga   180
ccataaaatt tcgagggtc aactcattag ataaggacaa gaatcaacca attgaaggcg    240
tcttctataa caagtttctt tattactaat attaaagtcc aatggggtga gggggagaag    300
aacttaaata aaaggaaata attggtaagt gaataaaatc taaatacgat actagatgat    360
tgatttgtgc tagtgcatgg tattagatca gatatgtgtt actattcgaa ttcaaattgg    420
catattccat gttgttgata agaaaattgt agaagtgtaa aagctgagtt actatattca    480
aactagtggt ttcataaaag tgagacaaca actgtttcac aaaaatgact ataaaatagt    540
aagtagtatt aggtcaattg attttaaaat tttaatcaaa ttcaaatttg tgatataatc    600
```

| | |
|---|---|
| aaatttgttt atagaaaatg ttaagaaatc aattttggca gaactaattc agtgagaaac | 660 |
| aatcatttac aaaaacaatt ttaacattat ttaacagtaa gatttgacat ttaacccgtt | 720 |
| cgtgtgaacc catcatatct aacatggctc tacccatgac gcctccatgc catggacaat | 780 |
| tttgacagat cagaagttct gaacgtggac gaggtaagaa caccatgatg atacgattgg | 840 |
| agttagttat gtcgccaccg acatcactgc caatctcatt aataaaagtg gtactaaatc | 900 |
| tctaatctct attaactata aatataacaa agaaccaaaa gaaagtttct tatctctctt | 960 |
| atctttcata atttccaaga aacacaaacc ttttctacta | 1000 |

<210> SEQ ID NO 124
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0688

<400> SEQUENCE: 124

| | |
|---|---|
| acgttcagag gcatcgcttt tgtacaaatt gaagcgggtt tgttcaatat ttaaaataac | 60 |
| acaggaaaca ttcaaatgta ttattgatgt tgcttaggtt tgtgaaatga tatgaaccat | 120 |
| atcgtatata ttactagatt tttcttatat gtttttaaggg tagtggggct gacctatcat | 180 |
| tctgtttggc attaccaatc agactatcag agtattcacc attcaggatt ccataactag | 240 |
| aaaaagaagg ggtttacatt ttctcatact gtataatttt ctactatcag agattttatc | 300 |
| gattacatta atctccatagt gattattctg atttataaaa aagttgacaa aataattaaa | 360 |
| accagtatttt tataacaaga ttgtctctct cccatggcca ttattttgac ctctgactta | 420 |
| tttaaatctt aattaacagc ataatactgt attaagcgta tttaaatgaa acaaaataaa | 480 |
| agaaaaaaag aacaaaacga aagagtggac cacatgcgtg tcaagaaagg ccggtcgtta | 540 |
| ccgttaaggt gtgtcgaact gtgattgggc cacgttaacg gcgtatccaa aagaaagaaa | 600 |
| gggcacgtgt atagatctag gaaaaaagaa agaatggacg gtttagattg tatctaggta | 660 |
| ccaggaaatg gaacgtcaca ccaaacggta cgtgtcggat cctgcccgtt gatgctgacg | 720 |
| gtcagcaact tccccttatt catgcccccc tgcccgttaa ttacgtgtaa cccttccatg | 780 |
| cgaaaatcaa accctttttt tttttttgcgt tcttcttcaa cttttctttt taaatcaaac | 840 |
| cttttctttt taaaatcaca ttgcatttcc taacgctcaa caaaatctct ctctactaat | 900 |
| atctctctct ctctctctct attgttgaag aagactcata atcggagatt gtttgttttt | 960 |
| ggtttgctct gtaaattgga gaagttttgt tagagatcaa | 1000 |

<210> SEQ ID NO 125
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0695

<400> SEQUENCE: 125

| | |
|---|---|
| aacattttct ttaacttact cttaaatttt aatagtaagt tgatgcatgt tatgttgatc | 60 |
| cgtcttgatc acaaatattg ttttatggac gaattctttg acagtaaatg gctatagtga | 120 |
| ctcagcttgg agcatcccga tatgaaaaca aagtgcagta ttgtgtcgtg gtcatcacta | 180 |
| acgcactttc ctagaactat cgcgcgtgtt tgacctatgc aacacaccag atgtcatgaa | 240 |
| cgtatactta aatagaaaca atgatataga caattggcta tattctgtca tggaacgcaa | 300 |

```
accggataac atgtctatta gattcatcgg acttgatcat ggttatgtct taatagacga    360
attctttgtt aacgattggt taaaacggct cacgttagag catcctacta tgacttcaaa    420
attgataaat attacatgga aatcacttta attttagtta gaaggtagtt aatttagata    480
ttcttattta ataaattaaa aaatagaaga aaaaagatg agaagagttt ttgtttataa     540
aataagaaat atcttttatt gtaatttttaa aattaaacaa atttaattta tattaaaatt   600
atctttgttt tattgttaag gcaataatta tttttttggt gggaattgtt aaaacaataa    660
ttagtatact gttaagtggt cctttaataa taagataacg tgatttaaaa agaacgaga    720 caggctaata tagtagagag gaaaaaatac aatttaggcc caataaagcc caatatagag   780
ttgtgctcaa acacaggtct tcgccagatt cctatgacg ccgtgtgtca atcatgacgc    840
caagtgtcat tcaagaccgt cacgtggcgt tgtttctaca cataggcgat ccatacaaat   900
cagtaacaaa cacgaaaaga gcattcatat gtacgaaagt agaaagaag agactctttg    960 tgataaaact aagtaagaaa tagcataaaa gtaaaaggga                          1000
```

<210> SEQ ID NO 126
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0708

<400> SEQUENCE: 126

```
gtttccaaaa ctagtattct ttatttgctc tattcattat attttttatat ttgtaacgtc   60 ccgaccgtct ttattaggtt tcgacaatca cttctcggaa ggtcgtccat cctgaaatta   120
ctctatccta aacatgttta actataaaat tctctcgaaa cttttgtaac gtatataacc   180
acataaattc tcttaaactt atttgcatac accattatat ttctgaaatc gatatgttac   240
aatattattt aatatttaga ttacttttac tgaatcgaat taaatatcaa atcgaaacaa   300
atctaatcta ccaaaaataa ttttgttata aacatttctt gcctagttct acctcatata   360
cattttagtt aaagaaagaa atcacaacaa ttcccataat tcaataatta aatccacaaa   420
atcttggagt aagtaagaga aataaaaaga tagtatctta acataaacaa ttcaaagatg   480
ctctctcaca caattcacac acacttacaa aacaaaagac agaaacaatg ttttcattca   540
aatcaaaaga agttataaca ctagtacaaa aaaagctcaa attctaatag taactctttt   600
tatttcccaa ttacccaaag attctctctc acttcacaaa actagctttg agagtcgtgt   660
tccacaaaat ccattaaagc tgaaacggtt ttgctcacca ttcaaacaaa tacaaaattg   720
caaaacccca aattataaca aaataatata aaaattaaac cgctaaaaag agtgaaccaa   780
caaaaatcgc cgaatgtgtg tgtaatgaga aaaccgaccc atcatcccaa tcatctcttc   840
ccgtgtcact ctcttcctct cccacgtttc ttctctcttc cctttatggg ttttaacttc   900
tccttcttct tcttcttcaa tcttcagttt tcaaattcaa caacaattca cattttgatt   960
tcttcatcat ctctctctct ctcgcttctc tctcaaatcg                          1000
```

<210> SEQ ID NO 127
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0710

```
<400> SEQUENCE: 127
tagtgcgcgt gggggagaggg aatggtgaaa ccttagtggt taagttatga ggaaaatgat      60
aaaaggataa aacaatcaaa tgcagcttga aacggccata acataaagta ccttatggtg     120
gtgcgaatat ttttgtgttt ctttcactct tttattgctg aaagctacga cacttgtctt     180
aatatattgt ttccgcaagt cacatgatct acttttatt taacgtctag aaacgccgag      240
atatatgatg attagtatat cacgtctatg caaattgtta gttcgtgttt ggccaaaaga     300
tatcgagaca tgtctgaaga accgagtctg gttttgagat atttcttcaa gcattactat     360
acaatagaaa aaggagacac gcgaatatga taatagcaaa aggcataaaa aggcgaaaat     420
taaagaaaaa cgtaaagtga tttggcctca atcaacggga acgtatctta attttagagg     480
ttcttctttt acttttgaga cgagagagtt tgcgtctttg cgagctgctt tggttgacta     540
aacattatca tattgaaaac caaaatacaa cggaggaata tttgtcacag tttcactttc     600
acattgtttc cttaacgttt aatcaacctt gttcaaaatt tctatagttg taatcatcat     660
tgtttacaaa attttcgttc aaagatgatt ttaaataaaa ttgtgaaaga aaccttttc      720
tgaaataagg attggatgat agtgttaaaa gaaaaatatg aactgaggca aaaagaggag     780
tggtccccgg aagattgtga aatgtgtcat ctaaaccagc cagacgtagt cacgtgttct     840
ctctagcttt atgaacttcc ttagccagca ccatcattgt gattgtagta tatatgtaac     900
cctaccttca tctctcccat tttccattct ccatatagac tccttacaa tatacaaaac     960
ctatccaaaa gcgaagaagc caagcaaaca tattataaaa                           1000

<210> SEQ ID NO 128
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter PT0723

<400> SEQUENCE: 128
gtcatatctt atcaacacgt caacgatcaa aacctttagc ctattaaatt caacggctta      60
gatcaaaacg aaactaggtg ggtcccactt ttaatatcgt ggctgcataa catttcctcg     120
ataactgaag ccgttgtggt cttttctcaga atctggtgct taaacactct ggtgagttct     180
agtacttctg ctatgatcga tctcattacc atttcttaaa tttctctccc taaatattcc     240
gagttcttga tttttgataa cttcaggttt tctcttttg ataaatctgg tctttccatt     300
tttttttttt tgtggttaat ttagtttcct atgttcttcg attgtattat gcatgatctg     360
tgtttggatt ctgttagatt atgttattgg tgaatatgta tgtgttttg catgtctggt      420
tttggtctta aaaatgttca aatctgatga tttgattgaa gcttttttag tgttggtttg     480
attcttctca aaactactgt taatttacta tcatgttttc caactttgat tcatgatgac     540
acttttgttc tgctttgtta taaaattttg gttggtttga ttttgtaatt atagtgtaat     600
tttgttagga atgaacatgt tttaatactc tgttttrcga tttgtcacac attcgaatta     660
ttaatcgata atttaactga aaattcatgg ttctagatct tgttgtcatc agattatttg     720
tttcgataat tcatcaaata tgtagtcctt ttgctgattt gcgactgttt catttttct      780
caaaattgtt ttttgttaag tttatctaac agttatcgtt gtcaaaagtc tctttcatt      840
tgcaaaatct tcttttttt tttgtttgta actttgttt ttaagctaca catttagtct      900
gtaaaatagc atcgaggaac agttgtctta gtagacttgc atgttcttgt aacttctatt     960
```

```
tgtttcagtt tgttgatgac tgctttgatt ttgtaggtca aa                  1002
```

<210> SEQ ID NO 129
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter PT0740

<400> SEQUENCE: 129

```
tgtggccact aaagatttac ccttaaccgg gcccatataa gcccacgtca agtggcgctt   60
atacgctctc cgtaagagag ccaacatttg gtatgtaatg ttgcaaatta ttcttcaaga  120
caataaattc aaatataatt caatattgtc caaatatagt gatgtacttc agttgtgcac  180
atagaaactc cactaaacca acttttagat agatgcattc acaaattttc aacaatgtcg  240
cgaaagtcta atccatcacc agattctaac attttaatta ttatatttaa ctatacatac  300
tctaatcagc atgagtcaaa cgtgtacaat agcccaagca taataagaa ccaaagtcaa   360
actcaaataa atgtctccaa actcaaaact tgaaaaagac ctaattatta catggtagat  420
atgactttgt cgacaagtaa accaactaat cctcgaagct accttctctt cccagttatt  480
atgtgtgatc gatttataaa tctcttcttc taataacacc tatatttttc ttatgatgtg  540
aataaatata aaacttttaa ctttaaaaca tatttatccg aaatattgca cttagatttc  600
aaatagataa ataatagtac tatctaactg atattgaaaa gacctaacac ggaaaacagt  660
tttataaaaa atcccaaatg tgggtaatta tcttgatttc ttgggggaaa cagaaaatgg  720
attaagatta atcggagtcg tgtcaagcag ctcgttaata actgtagcaa gttgactgag  780
taagcatcaa cgtgtcatct ccgtaaagcc cattatttct agtctcgccg cgtcttctct  840
tccacgtagc acttcacttt ttctctcctt ttgtttcctt tggaacacaa acgtttctat  900
ttataggaat aattacgtcg tccgtatctg tgtcggaaca tagatccaaa ttaaaagcga  960
cttacttaat tacatatcgt tcgtgttttt ttcttcaaaa a                    1001
```

<210> SEQ ID NO 130
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter PT0743

<400> SEQUENCE: 130

```
tcgattggcc cgatcggccc caaaatcaag ctgagccgct tcaaacttca gcttttgaaa   60
tcacccccaa actcatgtcc tcttatcatt ataactaaag gatctttcat tttatttaac  120
tcatcgtctt gcactaccca acccaaaggt tccaactata cccgaagctt tctaaaggtc  180
caaagacttt ttttttcgag ccagactatt caagccaaga aaagccaaac cccacaagcc  240
agtactttc aattccatat tataaactta tctgtcttgt tttagtccca ctaaaaacaa   300
cagaatttaa tttaggttga gctaaaaccc ttgacaaaag tgtatagtcg tcgattcagt  360
agcacactca tcactcatca gatttgatag ttgacctaaa gtatgactac tccatttcaa  420
ctaacaaatg aaaataaaag agacctaagg gttagaggat tgaaactata ctctcaagtc  480
ttttatcact aggctactac cagctagtta acttgatgga tttaagcaag aaaacgtaga  540
attatattc gagcagattg tttagctaaa aaagcttggg tttgaaattg ccttttctcc   600
catataagca cgtcggttcc taaataactc tttctagcgg agagtgtctt tccaataatt  660
```

```
taataaaaat ggtgtttgta tatcaaaaaa aaaagaaaaa agaaactgat cgagatagaa    720
cgtttgcagt tttataaaca atttaaaaaa caaaaaaaat taaactcaat gtattttta     780 ttaattcaca aacaataata aatcatagga tcgaatattt acacggtatc aaaacctact    840
cgccgctact atataaaaat tgaagtcaaa tatcaaccgc aattattaaa ccagcaagac    900
aataattcat aaacttaata taaacataaa taaattaatg ttacacaacg atatatggtg    960
agggttatta ctatcttctt cctctcaaaa cacatctcct aaccttaagc tttagacggc   1020
ctgc                                                               1024
```

<210> SEQ ID NO 131
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0758

<400> SEQUENCE: 131

```
agctagccac atcagtgacc aaaaaagata attaacaaac caaataaaat aacaaatttt     60
gatcatttgg aataaaattt ataaaaggaa cgaaagcgcc ttctcacggg tcccatccat    120
tgaaatatat tctctctttt tgctctatat aataataacg cgtactaatt tgtagtatat    180
attattacaa agtcgatatt tgattgtttt gtgaacgttg atatattaat tttcttggat    240
gatgacaaaa aaagtcatag aaagtaacgt gtgaacatag cattaacaaa atacaaacat    300
aatatataac caaatatatg aaaataggat aaaatctcat tgaatagatc ttcttctatt    360
caaatatata aatatttgtt tgtctataaa attaacagag cattcacatt atctaaaata    420
atagtaaaat caaaataaaa ctaaataaaa ataactctgg ttttataacg attgatttta    480
aatattagtt tttgttgtaa agagatcatt atatatgtct gtaatatttt tatactgagt    540
tacatgatat ttagttatta tagcgtaatt aactaagata agaaattaac taaagtgata    600
ttctgattat tattattttt gttaggacac gtacgtggaa aaactaaaca ctataggtta    660
caaaacggta taataaactc accattactg gaaaatgttt gcatttgact caataagtaa    720
cttattataa gttactgata taatgcatag ttttgaaatt cttaaataaa ttattttggt    780
ttcgcatgaa aatatgaaag gagagaaatt tattattgtc acttatatat atatacatcg    840
taatcatttt ttcgtgaata attctctctc ccattccatt atttctcagt atctctcttt    900 cttttccctta ctttattgtt gcttttaaac cttcaatttg ctcataaacc aaatatataa    960
tatcaaaaca aacaaacaaa aaatcagaat tcccctaata                        1000
```

<210> SEQ ID NO 132
<211> LENGTH: 921
<212> TYPE: DNA
<213> ORGANISM: Arabidopsis thaliana
<220> FEATURE:
<221> NAME/KEY: misc_feature
<223> OTHER INFORMATION: Ceres Promoter PT0829

<400> SEQUENCE: 132

```
aaagttttga attattggga atcaatttcg aagttttgta attctttggg ggctaatagg     60
atattttatt ttcttggttt cgtctattgt tgttttttcta tttatggttg ggcttttaga    120
actctggaca ggcccatgtc atatgttttc cctctccctt atattttttca ttttcattt    180 tgttaaatta atgcataata tccaaaaaca atttaaattt ttgaaggaac cctttagtta    240
```

-continued

```
cggctccgaa gctttcacaa gtgagaatgt gagatcaaag aaggcaaatg gaggatttta      300
aaagttaaaa tcatctttta tctgcaaaag ttgacaattt ttttgtatca aatctaaatc      360
atcaaactct cttaaactac aagagcataa caacctctat gtaatccatg aaataatctg      420
cttgaaggac ataacataaa tcattatggc tagagtgact aacttcaatc aaatcctctt      480
aactctagct cccttacaat ggtatcgtaa acattatgc attagggatt gttgtcctag       540
gaaaataaaa taaaaatccc cacagaccaa ctaccatttt aacttaaaaa taagcttcgt      600
ccgcgacgaa ttgttttcca tcctaaaaat agaatggtgt aatctgctaa tggtttagtt      660
ccattaactt gcaagttcta ttgaaagcct aaatgtcaat aaagatatta aaattcggag      720
tcaaaagaca aatgaatcaa agcaacaag acaagtcagc tccattcttc actacccatc       780
ttttacaata aatcatctct cttttcacaa atttcaaact actctcattg cccctttagct     840 ttgttataga gccaacacta cagagagact cacacacttg tttcaataat taaatctgaa      900
tttggctctt cttataaact a                                                921
```

<210> SEQ ID NO 133
<211> LENGTH: 763
<212> TYPE: DNA
<213> ORGANISM: Arabidopsis thaliana
<220> FEATURE:
<221> NAME/KEY: misc_feature
<223> OTHER INFORMATION: Ceres Promoter PT0837

<400> SEQUENCE: 133

```
aactacaagg gagacataat atcaccatct ggttcctgtt atcatctgaa gatttcttgt       60
tttaccttcc agtgataaaa tgatccttat aatacatata gatatattaa attgctgtat      120
tttaagatta tagatatata aggtacatga gagtgtttat ttaaaaaat tcacttggaa       180 ttcatgtttt gtgatacgtt agattggaat ccatttggga aaagaagaat catctgttct      240
tatgtctcaa attttgactt cattcacttt tcttcttgtc ttttaagaaa gcttccacaa      300
tctaactgtt cgatgtgaaa actgagattc gagtaagaaa atgtgaactg tgttatactg      360 tttttttaatt agataattta gattgcactc agataaatta ataacattcc tcgaatactt     420
ttatgtgatt ggatatatta ggtatatctg ccaaccaacc aataaactgc tatgtttaaa     480
caaattaaat aaattagtat atgtttactc aagaataaag aagatagaaa agaaaattct     540
atatgagcta aatttgctgg aggaggcatc ggacgtgggt accagacctt tccaagcaca      600
cgagtagtgc ttagccatgt catgctaaca tacaccattt ggttcataca aaatccaaat     660
caaaatctat ttttaaaatc ttttgcacac gtctttgaaa aacacctctc atactatagc     720
tacggaagct tcaatttcaa ggtttgtcta aaagctaacg att                        763
```

<210> SEQ ID NO 134
<211> LENGTH: 751
<212> TYPE: DNA
<213> ORGANISM: Arabidopsis thaliana
<220> FEATURE:
<221> NAME/KEY: misc_feature
<223> OTHER INFORMATION: Ceres Promoter PT0838

<400> SEQUENCE: 134

```
atactggtat gcttaaggtt gaagccaaga tctctgtctt acccaagtaa ccactttcta       60
ttagaaggga tcaacactaa gaatatggag atttaagcct aagggctaag gcggttctca      120
acaatacatg atgtgaatac aatcacagac gatttactga ggtttgttga taagatcttg     180
atcagtctct gcatcatctg ttcaacaatc tcaatctttg actgtttgct ttcggagcca      240
```

```
taaacagagg aatcccttat tccctgttat aggagcaata caccaagtat tatttccatg    300
gctgaaattc tcttatggaa acctaattgt tccattgaag ctgtaaaatc gaatctggtg    360
aatattctcg agcaaagccg catgctaatt atgtcaattc agaagagttt gattaggaga    420
ctcgaagcga gtttgatgat ctttcttgat gttcaactcc gattgtaagg gtataattga    480
cttttcatgt attacggctc caccacctga cactaaggca ctctttgtcc atctcgttgg    540
tatcatcgga ttcggatggt aaaaataaaa agagcagagg aaacttgtta ctcatgcaag    600
cttctcaggt gccacgtcac tccattacgt gtcatcttca cacaccatct cgctcaaaac    660
cgatctcatt tttcaaacct aaaggcaga agcaactgat taagttaaca ctcttgagaa    720
gctctcgatt aagcttgaac ttggaggatc a                                   751
```

```
<210> SEQ ID NO 135
<211> LENGTH: 669
<212> TYPE: DNA
<213> ORGANISM: Arabidopsis thaliana
<220> FEATURE:
<221> NAME/KEY: misc_feature
<223> OTHER INFORMATION: Ceres Promoter PT0848

<400> SEQUENCE: 135
tctctttaaa tcagttaact aaccgtttat atatttacga taaggtttga agagattatt     60
gataaaataa tacatttcat aatcccgcgt tcaaccgttt aaagtaacat ttaagttgac    120
tatatctaat ttttttttcca ttaaatatgg agctggtaaa ctttatcaac ttctaaaaag   180
tgtaacaaca aaaattaggt caatcacaat tctgtttttt ttattatttt ggattgactt    240
ccaattgcaa atagtcttag tgatcaccat tatcatacat atatacatca agtaggtttc    300
atcatgatat accacaaagt atttgacaag ccatatggtt ttggatcaaa aagtcggtcc    360
aaaattaatg ttttatgtgc aagaaccgac ccattgtaca cacgtgttaa catcttcaag    420
actttcatct ctattttct tttggtcatt aagatatccca ttgatccgaa tctgttacat    480
tcccacctac ttttttaatt tttactatcc actccaaatt aaacacaacc gatgattta     540 ataattggaa gcttttaaaa atatttcaaa acaagcctct ttgtgtttgt ctatatatat    600
acacgtaata agaaggtgaa tgaatctcac agcttacttg ttctaaggct tccaataacg    660
aaaacagta                                                            669
```

```
<210> SEQ ID NO 136
<211> LENGTH: 702
<212> TYPE: DNA
<213> ORGANISM: Arabidopsis thaliana
<220> FEATURE:
<221> NAME/KEY: misc_feature
<223> OTHER INFORMATION: Ceres Promoter PT0863

<400> SEQUENCE: 136
cgggaaacga caatctgatc tctagtccag tcgattggcc cgatcggccg attataaact     60
tacatgagac aagtataaat aattattata aacttattaa gtttaagatc aaggcttttg   120
tgcaatgtat caatgaatgt tagatgtgat atgatgaaag caatgtttta aacacataca    180
tagtcattga tcggaatgtg tgttattaga aatgcatgcc taagccgata gggttatcta    240
tgtttggtct tggacattat agccaaattt cgaatctaat tcttccaata tatatttttt    300 ttttttttgct tagggccact actagtattg cttatcaatt ttaagagctc atgaaaatgc    360
aacaatatag tagttgcaaa tccttgtttc aagagaaatc aaagggccac ttgtgaattg   420
```

```
aataataata atatttgcaa ataaccttt c actaaaccat accaacaaaa ccacacagat    480
ttggcaaaga cataaccttt gggagacgtg aaaaggctca aaatttgaca attgtcctta    540
caaattcgct cattagtgca attgtgagat ttgtttgcat ccaaatccaa ttcataactc    600
acactcgtct caaattcgaa aaggcctgca gggccagtgc actgggatcc aacaatgtcc    660
tccgactcgt ccaagatcaa gaggaagcgg aaccgcaccg cg                      702
```

<210> SEQ ID NO 137
<211> LENGTH: 435
<212> TYPE: DNA
<213> ORGANISM: Arabidopsis thaliana
<220> FEATURE:
<221> NAME/KEY: misc_feature
<223> OTHER INFORMATION: Ceres Promoter PT0879

<400> SEQUENCE: 137

```
ttctaggaag actggtcaag ctaagctgtt tctgtttttt gttttgtac tttacttttt    60 gtttgctagt gggaactggg tttattgggc cttgaagttg ataaaagatg aataaaagac   120
atatcgccta aagcccatat gagaagcaga agacaaaaac ctccaacttt gggcataaat   180
tttgattata gttaaaagtc cagacccaat ttggcacctg gcttagttac gattctaagg   240
catgacacct gcctaatatg tttattacag aaaataaaga gaatcagcta ggtgtccctt   300
attgaacaca ttaacaaact ccaacgacac tacgtgtctt cgtgactctt actatatcca   360
aaaacctata gctaaagctg aattttccat gattagtata gtcccaacca aaaaaatact   420
gaagaaggca taagc                                                    435
```

<210> SEQ ID NO 138
<211> LENGTH: 397
<212> TYPE: DNA
<213> ORGANISM: Arabidopsis thaliana
<220> FEATURE:
<221> NAME/KEY: misc_feature
<223> OTHER INFORMATION: Ceres Promoter PT0886

<400> SEQUENCE: 138

```
agtgtatttg aaaacgacat tgaagaatta atatattttt ttttaatttt agttttttat    60
agtacaaata ttaaaacaaa caatcctacc atatcataac atttgtaaat aacattttaa   120
gttttgtttt gagttttaat taattttcta tgacaaaaaa atgaagtcaa tagactaagt   180
gaatcatata gtataaataa acacaattta aatagtttca aataaattta gaaagaataa   240
aacaaataga aatcagaagg tgtctgtttc ctcctcgcaa catacgatca agagaaaca    300 acttgacccct ttacattgct caagagctca tctcttccct ctacaaaaat ggccgcacgt   360
ctccaacctt ctcccaactc cttcttccgc catcatc                            397
```

<210> SEQ ID NO 139
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0007

<400> SEQUENCE: 139

```
agcagaacaa ctatatttat tgtgtcacat aaatctgaga tcatttataa ccaccaaaga    60
acctatacac agtaaatgac aaatgtatct ccctctatct ctattgccca tatgtagatg   120
ctaaagtaag atttctcttt tttttaatgt acttttttt  gtataaagta tattccataa   180
```

```
gaaaaaggaa aagcttgttt atggatcaat tgaccccaaa aaagttttt agatcaaagc        240 ccaatataaa aaaaaaacac agtagtgaca caaaggaact taaataaacc atgaattgat        300
ctataaacag tagagatcga taaggcgaac attttccatg tgaagtgtct tctttcatct        360
ataatatttt tgacatccaa taatttcctc tataatatca ttcacataat tgatagaaac        420
attatgttag aattgtccac atcatttgag ctgtaatata ttctgtttta acaaattata        480
tggtagttgc ttaatcttat gtccatcttc ttctatgcat cgttttcgcg cctagttgtc        540
cagtccattt caactaccta cctctaattc ttatcttaaa acaacatttt ttaatttaag        600
tattatgctc aaagactaac tagatagaaa accgttatta acattaaac gaattaaaag         660 tcttacatgg aaaatgtagg tttataaacc acgagttatg attgacaata aaaaaaatgc        720
aaatcatcaa tcaaaagaga cttgagtgcg actctatatc aaccattgca attaaaatta        780
tctatcacaa aaatttaga cagattaagt taatttagtc taaattcact aatttatttt         840
ctataattag taattaacta tatttattta tttacacatt ttctgataat ttagaaattt        900
gcatgaataa caaatataag atttttggaaa ttagtagcaa atttaattaa taattatttt       960
tgcctaaatg aaccaaacta taaaacctcc acatacacca gtcatcaaat ttacagagac       1020
aaca                                                                    1024

<210> SEQ ID NO 140
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0008

<400> SEQUENCE: 140
ctcgagagat gaagtcttag taatgtttga acaaacaata atcacgtttt ccatcaaatt         60
cgagcattta agtttatat tactacatgc cccaagatga taccgtccat ctcatccgaa          120
aatatttctg aaattgcgct aagacaacaa tgtttgctca aattcgatca tttaaagttt        180
acaaatctct catcaatctt acaaacttct cacactaaac agaggtacat attttcttat         240
aaagacaaaa ggttcgaaca gctggcttct caactcgagt tgtttgtcag ggcctctctt        300
cactaactac aagttggtac ttcaaatatt ggtggctagc ttcacgtgat attgtctaca        360
aattaaaccc atgaaaaagc tgcattaatt gttccaagtg aaccctgagg agtgtcaata        420
gtctttgctt tagtgtgatc attaaaccaa atctctaaat tcctaatttg tactaacatt        480
tggaacgtat ttcctactct tctccctgct ccaactccca aaaataagat tagttagatt        540
tctataacta atatacatgt atactcccaa aaacagtaaa accatattaa taaagctaat        600
tttgcataga tttatttcgg taaaccggcg gttcaagttg gggaaaaaaa agacaaacgg        660
tctaaagtca tccaaagaca aaaaccaaa gacaagttga gagagacgag accaatcaca         720
acattgcttc gtagattgcg tgacatcatc cttgacggct actttcattt gtgtcttatt        780
tggataaaac gcacgtgttt aattcacgaa ccttcatagc aataagaaat ttccattact        840
ttcatatttt caactttttt tattacccat tacatgctta aaatattaat tcacaagtct        900
ttgtcaaaat tcaatatttt ccaggttcat gaaccctttt tatctcaatc tactctataa        960
tatctcccta taaattacaa caaaaacctct ttattttca                             1000

<210> SEQ ID NO 141
<211> LENGTH: 999
<212> TYPE: DNA
```

<213> ORGANISM: Arabidopsis thaliana
<220> FEATURE:
<221> NAME/KEY: misc_feature
<223> OTHER INFORMATION: Ceres Promoter YP0019

<400> SEQUENCE: 141

| | | | | | |
|---|---|---|---|---|---|
| gatataagta | gaatcatttt | ttgccgccgt | ttctcgctaa | cacaccgaaa | actgaatcaa | 60 |
| atctcctagc | tcttctacgc | aaaatcgagt | gcatcgacaa | tggcggaacg | tggtgtcgaa | 120 |
| cgtggtggag | atcgcggcga | tttcggacgt | ggattcggtg | gtcgcggcgg | tggaagaggt | 180 |
| ggtccgagag | gtcgtggtcg | ccgtgcaggt | cgtgctccag | aggaggagaa | atgggtgcca | 240 |
| gtgactaagc | ttggtcgtct | cgtaaaggaa | ggtaagatca | caaagattga | gcagatctac | 300 |
| ctccattctc | tcccagtcaa | ggagtaccag | atcatagatt | tactcgtcgg | tccttcattg | 360 |
| aaagacgaag | tgatgaaaat | catgccggtt | caaaaacaaa | ccagagccgg | tcagagaacg | 420 |
| agattcaagg | ccttcatcgt | cgtcggagat | agtaacggtc | acgtcggatt | aggagtcaaa | 480 |
| tgctccaagg | aagttgcgac | ggcgatcaga | ggcgcgatca | ttctcgcgaa | attgtctgtg | 540 |
| gttccgatac | gaagaggtta | ttggggtaac | aagattggaa | aaccacatac | ggttccgtgt | 600 |
| aaggtaaccg | ggaaatgtgg | atctgttact | gtacgtatgg | ttccagctcc | gagaggttct | 660 |
| ggtattgtgg | cggctagagt | tcctaagaag | gttcttcaat | tcgctggaat | tgatgatgtc | 720 |
| tttacttctt | ctagaggatc | caccaaaact | cttggaaact | tcgtcaaggt | atgtactttc | 780 |
| acaatggctg | ttttggtttg | atgaactctg | aattaggcag | tgaaaaagta | atcattacca | 840 |
| gttaagtgaa | tttatattga | agattaggat | ttagctgatt | gtattggttt | gagcatgtga | 900 |
| gtttgtgttt | aagattgctt | gaattgaaat | gctttaggtt | gtttgattac | gctaaattct | 960 |
| gactaatgta | attcaaattg | ttgttgtttt | tttttggtc | | | 999 |

<210> SEQ ID NO 142
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0028

<400> SEQUENCE: 142

| | | | | | |
|---|---|---|---|---|---|
| gtcagtgaag | tcgattggta | gtacttgaaa | cacttggttg | gtttcatgta | tttggcctat | 60 |
| atataaacaa | acatcgtaat | tatatacgga | ttttttttcgg | aattttacgc | catatctgta | 120 |
| agtatatata | acatgcatgt | cgttttcaaa | ttcatatgat | gaacgatcca | cgtaagtgct | 180 |
| actactccta | caatattgca | tgagagagat | atgtatttat | aaattttatt | ttgaagaaga | 240 |
| aataagaggg | aaggttactt | gggtggatcg | atgtgaaaac | aaaagaagaa | aaagcgaaac | 300 |
| ccactaagcc | attacatgat | atcgaccttc | ttatcttttt | cctctttatt | ttatttttct | 360 |
| catcttcttt | ttgtcaggac | ttttttctac | ttaatgaaac | ctccaaacta | tctaactaat | 420 |
| acactcccat | gtagaataaa | gaaaattata | taagatattg | ttgatatttt | gtaactagaa | 480 |
| aatatatttg | ctctgtaatt | tttcgtaagt | taaatcaaca | ttttaaagta | gaaacaaata | 540 |
| ttactgcaaa | aagtaggatc | attattttttg | tccaaaatct | cagttagcta | tagggttgta | 600 |
| gtaaaaacaa | aacacattct | tgatttgccc | caaaaaataa | agagagagaa | gaatattgtt | 660 |
| caaaagtggt | ctcttctctc | tctaattatg | ttttcactaa | acccaattag | attcaaacag | 720 |
| tctacaaagt | ccaaaagata | aacatgggac | aacaattcga | tgcaaaaaat | cctctttttca | 780 |
| tgctcttttt | ttattctcta | gtcttttaaa | ttactaataa | aaactcacaa | atccaccaaa | 840 |

```
cccattctct acaactcacc ttcatctaga tttacccact cccaccgaga aacacaagaa      900
aaaaaatata catatataaa tatacaagac aacacatgat gctgatgcaa tatacacaac      960
aaagtattaa atcttagata ttgtgggtct ccctttcttc tattcatttt cttattcatt     1020
aaaa                                                                  1024

<210> SEQ ID NO 143
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0039

<400> SEQUENCE: 143
ccgttcgagt atttgaaaat ttcgggtaca cccgcctaaa taggcggacc ttatctagta       60
tatatataca tttgaactat attgtttact ttttagttga tttaggctat gtcatgacat      120
tgacataaat ctacctgtta tttatcacgt gtaattcgtg taaagtgtaa actagaaagt      180
tcaaatacgt atttgttttt gttctgttat ataggattgt catagttgta aatctacaat      240
ttattacaac atgaataagt acacaagcaa tgtaattgga tttaattgct aaactcttta      300
catggtcaat ctaaatttga taagaaatac gtcacatatt actaagactg atagttttttt     360 tgttgtcacc aattattttt gttaaattga cgaaaacaat tccaaaaact caaatgtaca      420
aaatcataca gtctcacaaa catctcatag agaaagatat aaatctccca tatgggaacg      480
ataacacgag gtcgaaatac tattcgtaaa actaaaacgc cttagttata aatcgttagt      540
tgtaaccgcg gtcgagaata catacagatc cacgaaacta ctactacaca tgctgctgaa      600
ttggaatttg gaaaagacca tcttctttag gaagagctca cccaatgagt gacaaaggtg      660
tcggtggctt gttttctacc catatgtata catcaaatgg tagtttcatt aacgtttggt      720
tttgagaaaa gtaagacttt ggctagtagc taggttcgta tataataaac tcttttgaga      780
aagttcatca ctggtggaaa atgttaaacc ggtttttct catttttttcc gccatgttaa      840 ccaccggttt aaaagaccg taacacattg aaagattaat aagggtatat ttgtaattac      900
ggtttgctgg caatttttaa ttattatttt aattagagaa aatagagaag ccctatcaat      960
gtacatggta tatatataaa aggcaaaacc ctagaaaacg atactattcg actcagccgt     1020
cctt                                                                  1024

<210> SEQ ID NO 144
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0050

<400> SEQUENCE: 144
aatctgatct ctagtccagt cgattggtac ttagggaaa catcatattt ttaaaccttg       60
tctcagtaag ctaacacaca cccccttgtga ttacttatcc atgtttatcc acaagaatgc   120
agttggattg agatattttc ttctttgttg aaatcaggcc tcaaggtgtt catgtggtct      180
gcaaaaaaat tcccaaaaat aaagatagtg acatctgaaa tcgataatgg attagacgaa      240
gagtttcgtg ttattccttg gtatgggcgg gtttggggac agatattttg gcacagacga      300
ggactaggcc actgtggtcc tgcagcatta ggtgtcccctt ccatgtcctg cattacattt     360
```

```
tattgatgga ttcatcaccc tatctactac aacggctaca caaactatga agagttttgt      420
ttactaataa atgcccaagt gaggggtcga tcgaacccgg gacacgtttt tcagtttacc      480
atatagaatt atccttggaa cccttgatac tccatagaac atcaccacct ctgttgtcat      540
ctcaggaatc caggttcaaa cctagtctct ctctccctag tgggaggtat atggccactg      600
ggccaatgat gacaaaatgc aaaaaaaata aaatacattt gggttcatta tctaaaatat      660
ctcttgtgtt tgtaagtttt ggttgcacac tcgtgtggtt gaagtgtgtg tgagaggtac      720
tatacaatac actctgcttt tgttttgtac ctatctcttt ctcttctcca catatccaag      780
actttgggga taaagctgag atcattggtt gccatttggt tgtgtagaag caatcaccca      840
tttgctttat ccgaggttga taaatttcct cgggttctcc ttctgacacg tatgacaaat      900
tctaatagta tattcctcgt agatattacc tatatattct caatagttgc aggtacttaa      960
ggctttgtct tggcatcctc gtcctcttca gcaaaactcg tctctcttgc actccaaaaa     1020
gcaa                                                                  1024
```

<210> SEQ ID NO 145
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0086

<400> SEQUENCE: 145

```
cttatccttt aacaatgaac aggttttag aggtagcttg atgattcctg cacatgtgat       60
cttggcttca ggcttaattt tccaggtaaa gcattatgag atactcttat atctcttaca      120
tacttttgag ataatgcaca agaacttcat aactatatgc tttagtttct gcatttgaca      180
ctgccaaatt cattaatctc taatatcttt gttgttgatc tttggtagac atgggtacta      240
gaaaaagcaa actacaccaa ggtaaaatac ttttgtacaa acataaactc gttatcacgg      300
aacatcaatg gagtgtatat ctaacggagt gtagaaacat ttgattattg caggaagcta      360
tctcaggata ttatcggttt atatggaatc tcttctacgc agagtatctg ttattcccct      420
tcctctagct ttcaatttca tggtgaggat atgcagtttt ctttgtatat cattcttctt      480
cttctttgta gcttggagtc aaaatcggtt ccttcatgta catacatcaa ggatatgtcc      540
ttctgaattt ttatatcttg caataaaaat gcttgtacca attgaaacac cagcttttg      600 agttctatga tcactgactt ggttctaacc aaaaaaaaaa aaatgtttaa tttacatatc      660
taaaagtagg tttagggaaa cctaaacagt aaaaatatttg tatattattc gaatttcact      720
catcataaaa acttaaattg caccataaaa ttttgtttta ctattaatga tgtaatttgt      780
gtaacttaag ataaaaataa tattccgtaa gttaaccggc taaaaccacg tataaaccag      840
ggaacctgtt aaaccggttc tttactggat aaagaaatga agcccatgt agacagctcc       900 attagagccc aaaccctaaa tttctcatct atataaaagg agtgacatta gggttttgt       960 tcgtcctctt aaagcttctc gttttctctg ccgtctctc                            999
```

<210> SEQ ID NO 146
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0088

<400> SEQUENCE: 146

```
tcgattggga ttactacttc atctagtaag gttctgaaaa cgtttgttgt tgataaggaa      60
gattcgtctc aggttattac tgttgatctt caaggtttgt gattgtgacg cttatacatg     120
tgctgaaact gtggtgttta tttattgaaa acaaaaaaaa agtctctctt gtagtttcat     180
tgtactaaat agaaacaag aaacgttttt ttctttaatc ttctacattg ataatattgg     240
atcaaaggat tgtttctgca agacacaaca caaacatact tatactagtt tacttctact     300
aagtactaac tacatacccca tacacacact tgcacctaga ctttacttct agacatcatt     360
accctaaggt agaaccaagc ttacaagcaa gttttaccga caactcttac attcaactc      420 tagtctgtag tctttaacgt agacttacta actagtcatt agtggtttaa ttttttaaat     480
tttcatccat atgttttgt tgtagatata aactaaagtc ggtcacattt aataattgtc     540
attatgtccg cgtaaaagtc aattcagcta ttggacattt atgaaatgta agattttctc     600
tctcatttcc ccgtgcgtga agacatgcat tggttttct gtaataatca acaaatccaa     660
accccttttc gatctttatt tggacattgt tagagacaaa attctctat agtcttttc      720 ctaatttgat accatgtttt tgtttctgca caaatttact cactggttta actaactatc     780
cacttattta tgattttacc attaggcgtc agctagccct agtcaaattt gtaaacaagc     840
caagctatct acataaatcg agatgtcatt aacgttaatc gtcgttaatt cgaatttgaa     900
aacatagata gctttagcag tacaatgggc aatggtaaga agaatagcaa aaggcccaat     960
atttggtttg cagaaattaa agccttaaaa aaaagcccac agatatttgt caaagaaccc    1020
taat                                                                  1024

<210> SEQ ID NO 147
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0092

<400> SEQUENCE: 147
aaagattgag ttgagagaga tggtggagac gcagaacaga caaagggagt ttaccatata      60
gtgctctaaa gggcaatgag attgcagtga tgtggctatc cggggaatca tcgcaggtta     120
ttccttccca tgagcaacaa tcaatggatg ggttccaatt cagaggagaa acagaagaag     180 aaacgttttcc agagaaccac agtagggatt ctcgatcttg cgagttgcag agagcctctg     240
aaactgcaat agaaaggaca ctgatgaaaa gaacacactg aaggagtatg ccaatcatgt     300
gaaaactcag agcttgtatt ggtcttgtgg ttgatgaagt tctcacaaaa cctttggctt     360
tgaatctccc ctcattagtc atggtgagaa caagaacaag acgagaaaca gacaaagaag     420
atgaaaaaac ttgttggcca gtgttgacta aggggaata gccccagaca taacaaaatt     480
agacttgtcg tacatcttta atatttttttt atctgtttct ttgtcctgac gctttcatta     540
ttcctgtgat caatttctc ataccattgg tccatcgtta atcctttctt aatttcattt     600
tctacgtaac atgagaggag accaagtcct atgagaacag ttgacgtaac agtggttgtt     660 aagtaagtt aaaagagga agctagtgag agtgaccgtt aggtagagaa gtgagatctt     720
taaccactct tctttctctc tctctctgct ttttttgtcg tctttcacat ctactgttcg     780
caaactctct tatgcttcca ataatggtga taccaattga gacttgcagg agaatctcct     840
cttctccaca ctctatcaac tggtcagcca tggaatggtc gtttcagttt caatattcct     900
ggattctttt taaggattcc tgtttctctt ctgttcctgg tatattctta acgacgaaat     960
```

| | |
|---|---|
| tagtatcgga tcctggtaat acattttgaa gcttttaagt accattgcac tgggatccaa | 1020 |
| caat | 1024 |

<210> SEQ ID NO 148
<211> LENGTH: 1020
<212> TYPE: DNA
<213> ORGANISM: Arabidopsis thaliana
<220> FEATURE:
<221> NAME/KEY: misc_feature
<223> OTHER INFORMATION: Ceres Promoter YP0096

<400> SEQUENCE: 148

| | |
|---|---|
| gaggtcagtg agtcgattgg tgcaaaattg aaaaattgaa gggtgaaaca aatttaaaga | 60 |
| taatatctat taaatcctct aattttaaaa atttagcaaa aattgtattt tcttatggat | 120 |
| ctgttagttc acacgtatct taattagtac caaatcatat ctaatgatta gtgataaaac | 180 |
| tagttagata tctatatgtg tctttaccat ttaacttgaa tccttcttct ttttttacg | 240 |
| taaacaactt gaatccttcg ttaatacata aatttaaagc attttttctt taattctatt | 300 |
| gatcggtata tatttactat aagttttagc tcatatgcaa tttcaaatga tatgctttta | 360 |
| aattttgtct aggtgtgata gttgtatctt taacataaat cttatagcaa aattatactt | 420 |
| gatattctaa atttatctat ttgctcttgt gaacctcata ttagtctaga gaaactttga | 480 |
| aatcctttca attagttgta tgtccaatac attttttacta acatttatta gtcttttaa | 540 |
| ttaagattat tgttagaaaa aaaaagattt tttaaaaata aataatatgt tttagataca | 600 |
| atgtgagtta ggcttcttat atttaaaaa ataaatttat ttcatactta aaaatagttt | 660 |
| ggaatttcaa tttatttggc tgaataccat aaaatatgtc aatttgaacc ttatacccat | 720 |
| tgactatttg gtgttagaaa cccttttaaca aaaaaaaact atttggtgtt agatatcaaa | 780 |
| ataaaaaaag tttaaccatt ggtttcttat attgaattgg atattgttac atgtattaaa | 840 |
| gttttttttgg tttaattttg aaacgttgat agaaactatt aagttaagt ttggtagtat | 900 |
| atttatttgt ggaaaattta attgccatta aatataacgt caactttttt tggttttttt | 960 |
| tgagaagtta cgttgtgatt ttgatttcct atataaagt tagattacgt cattttttaa | 1020 |

<210> SEQ ID NO 149
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0097

<400> SEQUENCE: 149

| | |
|---|---|
| ttcatctta tatttaagag tttaaaaact gcaacttttg ttttctttc actaagtctt | 60 |
| atggccacag ttaattaaaa gcagatgaaa ggtggtccaa tggaaaagga gaatgtgatt | 120 |
| gggctagttg ggagagttct gatgtctagt gttgggtaca cgtgtccgtc agttacacat | 180 |
| agcattaaat cagacggcat gtcattattc aaatctagtt cacatagtac gactaatagc | 240 |
| tgataaaatta atgattatac agcatatgaa ttatgaattc aaaaaaaaaa aaaaattgaa | 300 |
| aatgttaagg agatgctata ttttacaaaa ttcatcgcaa tgcttctac taatttgcta | 360 |
| agtggtcttc tccagttagt cttgtcgatt ccaagcgata ttattaaatc ttgaagcatc | 420 |
| gctcaaagca ttagctta agataaccaa attgttatta aaaacaccta gtgaaatttt | 480 |
| taaattaaaa caatttgat atctttgtaa tatctaatac tactcttct gtgtctaaaa | 540 |

```
ggattaattt tcaaaaattt cacacatatt aaaaaaaaaa aaaaattact agctaaacaa      600
ttttcaataa tcataaaaca atagtaactt aataattttt ttttattttc aaaatagtcc      660
ttcaagttta caattcattt tagtattata atcaacaaaa tttgtattaa aaagttggaa      720
aattaatctt tgtggaacaa aaaaatctag aaatcattt ttagaattag agagaggttt       780
gataaaaaaa aataaaaaaa aatagagaga ggtagtacat actaaacgat gtgatactac      840
tattgacaaa atcttaattc tcagtttagt agaataaact agaaggaatg aatgaagtaa      900
atgcgaatcc aactactaac aaacccctact tagtcatcat attttcccat atgaaatccc    960
tatataaacc catcatcatc tcccactttt ttcatatcca                           1000

<210> SEQ ID NO 150
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0101

<400> SEQUENCE: 150
ttctcgttct ctagaatatt gctggaccgg attaggtcaa tattattggg ccagattaga      60
tattgaattg tcgacgttgc ttacgttacg ttatatcttg tttaagaatt aaacctatcg      120
acttagtctt aattaagaaa acattgcctt aaattctctg gtctgcgacc gttttttga      180 ccgttaaccc ctaattaaag aaacaaaata attatagaaa gagcactgaa atgtgattat      240
tttaacagta ctcttatgag aaaattcgta cttttttagtt ttttttttgt acaaatctct    300
aagaaaaaca ctactactaa ttaagaaacg tttcaaacaa ttttattttc gttggctcat     360
aatctttctt tctcggtccg ggactaaccg ttggcaaaaa aaaaaaaaaa gttgacaata     420
attattaaag cgtaaatcat acctctcaaa taaaaacttg aatttggaaa caaagacaac    480
taaaaaactc gaatttaaga gaattcctaa aatcaagtga agtatcatca cttggtaaaa     540
tttcataacc gttggcttct atttctatgt gtgccttggt ttgcaggaga taatatttca    600
tttccaacca atgatattcg tacacatagt caaacaaatg tttgtctttg ttattatatt    660
gagaaagaaa caagaaagag agagagagat agataagacg aaggaagtga agcttccaag    720
cgcccaccgt taaaaatctc gtgtgcaagt ttcaaataca agtggccggt ggtctccata    780
atttgatcgt catccaatta aaaggaaga aaaagcgtgt tttatacaag aaaactcatt      840
aaaatagcaa gtctagaaat atctcaacac taatctacca cgtctattac acacacacac    900
acacacactt gatcttaatt tattttcaag attcaagaaa atacccattc cattaccaca    960
acttgaccac acgcctatat ataaaacata aaagcccttt cccc                      1004

<210> SEQ ID NO 151
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0102

<400> SEQUENCE: 151
atttggttga taacgttttc actcgactaa ttatatactt cagaaggata gtaatagaat      60
accaaaataa ttaaatgatt ggttagtgcc ttagtggaga cttttaacc gattctaata      120 gactaatgat gtagctaagc atttatttgg gatcatcact gtttgaaaac gtgaaatgtg     180
ataaaagtta tgaaacgatt aaaatataaa ataaccgtac aaaacattat gtaccgtttt    240
```

```
tttctctgtt cttttggcga tttggtttag ttcgttacac tctaaatgtt attgcagata      300
tatatataat gatgcatttg catctgagga acatataatt ccggttaaca cttccaaatc      360
ttatatccgt ctaggtaggg attttataaa tcatttgtgt catcatgcgt tatgcttgtc      420
ggctttgacc ataacgcaga gatatagaac tagcttttac ttaactttta gatttattat      480
ttgatctaga gttaagtgga gatatatagt gtttttgtta gattattggt ggatgtgaga      540
gtttgtcttt agtttcaagt tgagaatata aggcaagagg agactctgag gcaatcagag      600
gttttgattg gcaaaatatc caaaaggccc aaaccaagtc gaagcccatc tcgtacaaaa      660
aaagaaagag atctgtaaga aaaaatattc tttgatattc ttacaaaaat aagtgtaaaa      720
cttttattag tcaaaatctt caatctttaa aaactctcat cactcctacg aaagcgcgtg      780
agagttatga gacattcctt aatagcatta ctcacaagtc acaagttcaa aacgtctgac      840
tgaaacagaa acaagccttt gttgaagtct tgaagaagag acattagtac tcgtcgtata      900
gccataaaag gtaatatacg aaatttcttc gctaatctct tcaccttcct ctacgcgttt      960
cactttcact ttataaatcc aaatctccct tcgaaaacat                           1000

<210> SEQ ID NO 152
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0103

<400> SEQUENCE: 152
gttttgaaga acaatctgga tcgaaatcta acataaggtc atcgtattca agttacgcag       60
tcaaggactt gacatcatcc tactctggtc tgaggttacc acttccaaag atgggatttt      120
tcgactcggt atgcttccta agaaattcgt tttattgaac ctagcaaata tcttgtaatg      180
taagattcct gagatgatga agaaaaaaca aacttttgtt acagcaggag aacggagaga      240
aagaaaacag agaaccaaat gctcttgaag caaacagaag aagaagacac aaatccaaac      300
ttgagacttc ttctcacacca gaaaaccgca gcattctggg acaacgcaaa acacgaaagt      360
gaaacgggca atgatatata tgtcttgggt gcgttacaag gcatcgtttg caactgttga      420
gttggataag tcaactgtct tcttttcctt tggttagtagt agctgccttt tttttccttt      480
gttgctttaa gaaatagccc gaaaaaaga atgttctaca tttcggagca gaaaactaac      540
cgaatgagtt tttggtcgga tcatcggatc gatcagatat attttgagtt acgaactgtt      600
ataaaaaaag ccataatttt gtgttgagtt tgcaaaatac cttataactt gttatttgag      660
attgcacctc catatatatt aattcgtaag agtatttatt aagtaagctt tagtataaat      720
ccttttttcc tttaaagtaa gttaatgttc tactaaataa tagtaaagtt gaagaaccgc      780
tccgttttta caccatgcac gtgttatcta acaaagaaaa tatggtacac ctaatggcta      840
atgcaaagga caacacaatg aaactaactt gactctgtgt tatagaaacc catagacatc      900
tgcatacatc ctagtatttg tataaattgg actcaaattc ctgaggacaa tcatagcaaa      960
caatcacatc atcgcaatat acataaacaa aagaggaaga aaaa                     1004

<210> SEQ ID NO 153
<211> LENGTH: 1003
<212> TYPE: DNA
<213> ORGANISM: Arabidopsis thaliana
<220> FEATURE:
<221> NAME/KEY: misc_feature
```

<223> OTHER INFORMATION: Ceres Promoter YP0107

<400> SEQUENCE: 153

```
taacaatcct tgggaacatt gcatccatag atatccggtt aagatcgatc tttgaactca      60
taaaaactag tagattggtt ggttggtttc catgtaccag aaggcttacc ctattagttg     120
aaagttgaaa ctttgttccc tactcaattc ctagttgtgt aaatgtatgt atatgtaatg     180
tgtataaaac gtagtactta aatgactagg agtggttctt gagaccgatg agagatggga     240
gcagaactaa agatgatgac ataattaaga acgaatttga aaggctctta ggtttgaatc     300
ctattcgaga atgtttttgt caaagatagt ggcgattttg aaccaaagaa aacatttaaa     360
aaatcagtat ccggttacgt tcatgcaaat agaaagtggt ctaggatctg attgtaattt     420
tagacttaaa gagtctctta agattcaatc ctggctgtgt acaaaactac aaataatcta     480
ttttagacta tttgggcctt aactaaactt ccactccatt atttactgag gttagagaat     540
agacttgcga ataaacacat tccccgagaa atactcatga tcccataatt agtcggaggg     600
tatgccaatc agatctaaga acacacattc cctcaaattt aatgcacat gtaatcatag      660
tttagcacaa ttcaaaaata atgtagtatt aaagacagaa atttgtagac ttttttttgg     720
cgttaaaaga agactaagtt tatacgtaca ttttatttta agtggaaaac cgaaattttc     780
catcgaaata tatgaattta gtatatatat ttctgcaatg tactattttg ctattttggc     840
aactttcagt ggactactac tttattacaa tgtgtatgga tgcatgagtt tgagtataca     900
catgtctaaa tgcatgcttt gtaaaacgta acggaccaca aaagaggatc catacaaata     960
catctcatag cttcctccat tattttccga cacaaacaga gca                      1003
```

<210> SEQ ID NO 154
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0110

<400> SEQUENCE: 154

```
gggatgcggt tccgcttcct cttgatcttg gacgagtcgg aggacattgt tggatcccag      60
tgcaatggta atataaaaca agaaaacaag agattttata ggacaatcac taaatgacat     120
ttaattgatt aaacatttat tcattaataa ttgtatgtta ctaacttcaa catttaataa     180
ttttgtttaa gatacgttta catcagagac tattaatatt tttacaggtt gtaactttaa     240
actttgtctt gaatcgaaca tgactataga tttttgggcaa acttaaagat aacaacattt     300
ccgtttttt tcaaattatt acaaatcaaa ctgatatatt agacacaaca cgattacacg     360
taatgaaaaa agaaaaagat aaaaagataa agaagggat cgattctgtt tggtctggtt      420
tagtgagatt caaagttaag ctcttccttt caagacatgc cttcttaaac cgggaatgtg     480
aacgtttgta atgtagtccg tccagttaat gcttccaaca tcaaatccaa attctctctt     540
ctcgtcctct gacatattct ccattaatct ctggggtatt gctgttatca aatctgtaaa     600
agaaaccaaa aaaaaagat gaaactttg cgggtaccgg ttttgtctgc tctaagaatt     660
agaatgttaa tgagttctgt cttaccttcc accatagaaa gtgtatggct cataaatagt     720
agcaaggtgt ttggcttgtt caacagattt cttgcatata aactttagct tctgcatcat     780
cttactatcc actgaactca taccactcat caacccactc cgttcttgag catctctcca     840
caaatgatcc gagaaatcat caacggaatt gaaaagtttc atcaaacgca ccataatagg     900
```

```
atcaccttta gagtccatgc atggagatgt tttgtagtgg ttataaagaa gctccgctaa    960
gtcttcgaaa accagcgggt ttatcgccga agaagcgatc tgatacacgt ttatttcagg   1020
ttcc                                                                1024
```

```
<210> SEQ ID NO 155
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0111

<400> SEQUENCE: 155
```

```
cgattggatt tagtctatac attatagggc gcaagtttgt ggatttaaga attatataaa     60
aacttgaaat atagttttt tatgcattct cctcttgtgt aatacataaa ccaaatatga    120
gataggttaa tctgtatttc agataatatt aaattccaaa caatattttt acttgttata    180
agaaggcaat taatatctct ctgttaatgg caagtggtac caagtagtat taaactatta    240
atgcaatgga agagtactgt tggaaattat aatcctctat cacacattca aacagatctc    300
ctgaaatctt ctcttccaaa cttgtacttc tctgatccaa atgtaggctc caaaatatag    360
acatttacca tttactaagt ccacaactcc tttcttgtct ccttcaaaaa tgactcttgt    420
gtaaccacca tatgactccg acagttcggc attgccatga tgagagctta aaaattcacc    480
ttcctgagca tttcaagtct tcactccctt agcttgacct gaaccaagat aaaatgcctt    540
tgtcgtcccg taatatccat cctgctttgg acggcatcat agttacattc gatccatcct    600
atttacaatg ttattttagt attaaaaaca tgacaataaa tttgttgtta aacatattca    660
aatacaatat gattggattt ataagtaatt gtaatatgaa atgtccttag taatatgtta    720
aaaaatacat agatacacac acgtactaaa agaggcaacg cgggagatgt cattagagga    780
agaactagga agcagagcgt tcatgcaaaa tgctaccaaa aacgttaatg caatatctca    840
actaatcagc acagtccatt tcatactgag aatgtaaaaa ccaatcagca tcgtccattt    900
tttcatctaa ttatttgtta actcttaatt ggccacaact tccaaccaca tgacgctctt    960
tctattccct ttatatattc ccatctcaaa tgttcttgga gacacaaaat atcataaaca   1020
tata                                                               1024
```

```
<210> SEQ ID NO 156
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0115

<400> SEQUENCE: 156
```

```
gtcgattgga tgatgaacat tctacatata taattattat gtttaagcac ttagacagca     60
taaattcttt ctaattatat aaatctaacc ttgttacatt gtacatctat aaattacttg    120
aagaaataac gagttctatt tcttttttaaa aattaaaaat actataccat atctcagtga    180
ttaagttgaa ccaaaaggta cggaggagaa acaagcattt gattcttcct tattttattt    240
tattcatctc tcactaatga tggtggagaa aaaagaaaa tacctaacaa acaaatatat    300
attgtcatac aaaaatattt ctatatttt agttaattag tttatattcc tcacttttca    360
gggcttatat aagaaagtga gcaaacacaa atcaaaatgc agcagcaaat actatcatca    420
cccatctcct tagttctatt ttataattcc tcttcttttt gttcatagct ttgtaattat    480
```

| agtcttattt ctctttaagg ctcaataaga ggaggtacta ttactacact tctctctact | 540 |
| tttacttgta ttttagcatt aaaatcctaa atccgtttt aaattcaaaa ataaacttag | 600 |
| agatgtttaa tctcgattcg gtttttcggc tttaggagaa taattatatg aaattagtat | 660 |
| ggatatcttt actagtttcc attcaaatga ttctgatttc aatctaatac tctcactctt | 720 |
| taattaaact atatgtagtg taatttcaca ctgttaaatt tctaccatgt catgtatatt | 780 |
| agagttgcat agaaaattgt aaaacatcca tttgaattcg aatgaaacaa aatgttttaa | 840 |
| aataaaattt tggtttttaa aagaaaaatc taaaactgaa ttatatcgtt taaccaagtt | 900 |
| gtaaaagtca taaaacgtag tatcttgtaa atcgctcttc cacggtccaa atagacttct | 960 |
| agtaataaac aagtaaaact aattttggtt tcttac | 996 |

<210> SEQ ID NO 157
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0117

<400> SEQUENCE: 157

| gtcagtgagt cgattggatc acagtccttt atgataaaac aaactcataa ttattccacc | 60 |
| gacaacatgc gttttaaatt attttttctt aaattatatt atattatatt gatatcaacc | 120 |
| tagctaaaat aattcggatg gcgaaatcgg acaattttta atagaaaaaa tgggtatgaa | 180 |
| gatagtctat gattccgttc ttagcgacta gagggacctg ctcaaatctc ccgggtgata | 240 |
| cgcgatgtca agctcaatag aaccccacaa ccgacgagac cgagaaatcc ttgatttggg | 300 |
| ctagaagatt ttgaaataaa tttaatatat tctaagtaac ttgcttaaat ttttttttcaa | 360 |
| actctaaaga cataactaac ataagtaaa aaaaaaaag ttaatacatg ggaagaaaaa | 420 |
| aattaaacta atgattagct ctctaacgtg tttaatctcg tatcaagttt ttttttaaaa | 480 |
| attatattgc tattaaaaca ttgtactatt gtttctattt tgtttagcta ttattcttgt | 540 |
| gaaatgaaaa gttgtgttta ttcaattact aaatggcaat atttatcttg gaaaactata | 600 |
| cctctaattg gattaggccc tagacatcct ctttagctta ttgacgttaa aattattccc | 660 |
| aaaactatta agtttagta gtttgaaaga tgcatcaaga cctactcaga taggtaaaag | 720 |
| tagaaaacta cagttagtgt gattatattt taaaatatat aaaacaatct tattaaacta | 780 |
| aatattcaag atatatactc aaatggaaga taaaaacatt tagtctgtta ccactaccag | 840 |
| cctagctagt cactaatagt cactttggaa ctgagtagat atttgcatct tgagttacca | 900 |
| tggactcaaa agtccaaaaa gagaccccga gtgaaaatgc taccaactta ataacaaaga | 960 |
| agcatttaca gcggtcaaaa agtatctata aatgtttaca caacagtagt cataagcacc | 1020 |
| attg | 1024 |

<210> SEQ ID NO 158
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0119

<400> SEQUENCE: 158

| taccaaaaat aaggagtttc caaagatgg ttctgatgag aaacagagcc catccctctc | 60 |

| | |
|---|---|
| cttttcccct tcccatgaaa gaaatcggat ggtcctcctt caatgtcctc cacctactct | 120 |
| tctcttcttt cttttttttct ttcttattat taaccattta attaatttcc ccttcaattt | 180 |
| cagtttctag ttctgtaaaa agaaaataca catctcactt atagatatcc atatctattt | 240 |
| atatgcatgt atagagaata aaaaagtgtg agtttctagg tatgttgagt atgtgctgtt | 300 |
| tggacaattg ttagatgatc tgtccatttt tttctttttt cttctgtgta taaatatatt | 360 |
| tgagcacaaa gaaaaactaa taaccttctg ttttcagcaa gtagggtctt ataaccttca | 420 |
| aagaaatatt ccttcaattg aaaacccata aaccaaaata gatattacaa aaggaaagag | 480 |
| agatattttc aagaacaaca taattagaaa agcagaagca gcagttaagt ggtactgaga | 540 |
| taaatgatat agtttctctt caagaacagt ttctcattac ccaccttctc cttttgctg | 600 |
| atctatcgta atcttgagaa ctcaggtaag gttgtgaata ttatgcacca ttcattaacc | 660 |
| ctaaaaataa gagatttaaa ataaatgttt cttctttctc tgattcttgt gtaaccaatt | 720 |
| catgggtttg atatgtttct tggttattgc ttatcaacaa agagatttga tcattataaa | 780 |
| gtagattaat aactcttaaa cacacaaagt ttctttatt tttagttaca tccctaattc | 840 |
| tagaccagaa catggatttg atctatttct tggttatgta ttcttgatca ggaaaaggga | 900 |
| tttgatcatc aagattagcc ttctctctct ctctctagat atctttcttg aatttagaaa | 960 |
| tctttattta attatttggt gatgtcatat ataggatcaa | 1000 |

<210> SEQ ID NO 159
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0120

<400> SEQUENCE: 159

| | |
|---|---|
| tagttttttga tttaatctac gttttttctta atcataaatg ggtaattatt agttttttgca | 60 |
| aaatcaaaat ccaaaaattg ttctaaacac tgcaaccatt taaggcctat atcactcaga | 120 |
| aaatttctgg tgggagaact aatcgtttgt cctttctaaa tctcacatat tagaatttag | 180 |
| aattagtgtg ctacataaga atattagttc agctcggaac aactattttt tggtaaaaca | 240 |
| gagaacttaa acaaatgcat tatttttatca acatgcattt tgaattgaat ataaaatttc | 300 |
| ataattgtaa agacataaat tacataaaat tttacatgaa aaaatagata tagaaagaaa | 360 |
| atgaaactaa ctgatgatat gctctctaaa ttttttaatc tcataacaag aattcaaatt | 420 |
| aattagttca tattttttggt taatataaca tttacctgtc taagttggaa cttttcatttt | 480 |
| tttctgttt gtttagtcag tattcttaat gtgaaacgga agttgaatt tattcaaact | 540 |
| taaattcaat agcattaatt aaaggcgaaa gctattatct ctacatgtgg ttcaaactag | 600 |
| acatccaatt taattagctt attgacgttg aaatgttttc caaaactact atagtttggc | 660 |
| aatttgaaag atgcatcaga actactcaga caggtaaaag tagaacctct agctgtgtga | 720 |
| attgtatgtt agtccataaa gaacatcttg taaacttcat acttaagata tatattacaa | 780 |
| tatatacttg aatggtagat aaaaacgatt agtctgattg ctagcatact cacaactatt | 840 |
| tggaaatgag taagatattg gcattctaga gttactacta tggagacaaa agtcgaataa | 900 |
| aagagacctc acgtgaaaat gttacgagct agtaaaaaaa gcatttacac taacggtaaa | 960 |
| aaaagtatct ataatgtttt acacaaggta gtagtcatt | 999 |

<210> SEQ ID NO 160

```
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0121

<400> SEQUENCE: 160
ttggattttt tttttgttga gtcagcagac catctaatct ctcttttttcc accacagcct      60 gctttctatg aagcatttgg gcttacggtt gtggaatcaa tgacttgtgc actcccaacg     120
tttgctacct gtcatggtgg acccgcagag attatcgaaa acggagtttc tgggttccac     180
attgacccat atcatccaga ccaggttgca gctaccttgg tcagcttctt tgagacctgt     240
aacaccaatc caaatcattg ggttaaaatc tctgaaggag ggctcaagcg aatctatgaa     300
aggttggccc attctccttg acaggcttaa caatacaact tgtatcgctt caacaagatg     360
atggcttaat aaggattttt gcatgtatag gtacacatgg aagaagtact cagagagact     420
gcttaccctg gctggagtct atgcattctg gaaacatgtg tctaagctcg aaaggagaga     480
aacacgacgt tacctagaga tgttttactc attgaaattt cgtgatttgg ttagtgtaac     540
ccactgttat tcttttgatg tctacatcta ctttacttac attattcttt tcttcggttt     600
gcaggccaat tcaatcccgc tggcaacaga tgagaactga tcatgacagg gtaggatttt     660
atttcctgca ctttctttag atcttttgtt tgtgttatct tgaataaaaa ttgttgggtt     720
ttgtttcctt cagtggtttg attttggact tatttgtgtt aatgttgttt tggctgttct     780
cttaatatca ataacaaata aatttactgg ttggtatcta agatctaaca atagttacta     840
tttttagagg taaagacacc aaccttgtta tattggtcag agagctaaaa ccttgacttg     900
ttgggaaaac aaaactctaa tgacagaaaa tctgacatga tgccttataa ttcacagcct     960
catgttctac ataaatccta acaatagcac tttgtttct                            999

<210> SEQ ID NO 161
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0128

<400> SEQUENCE: 161
gataaactga taatggaaaa gaacaaagaa accagttttt aactatttgc atatgtaatt      60
tatttgttgc aaattatatt tagttaaaat gtttcctcta tttatatata tatatatcag     120
tcaagcacta tgtataagaa atgtcaattt ataaattttt acatgtcctt taacagaaag     180
aaaatgaatt tttacatgtc attcatagag agtcactcgt ttatttctta tatagagaat     240
aacacactca catgcatatg catgcaatat gatacatttt atgacaaaga taatcaacgg     300
aaacggtcaa gacataattt gataaacaac ttgcacgatg cacagatctg atcaaatata     360 taactctttta acatatccaa aatattcaaa aagaaaaact cgatccaaac tagcaacatc     420
acgctcacgc ggtaggctaa aaatttatta atctccaaaa gtctttctta tgaacactgc     480
aaacacaaca acttgaaaag tcatataggt ttagatgatg acgcgtattg gctatcgctt     540
accggagtgg ctcataaata caataaacaa tacgtaaaag tcaaagtcaa atatatttag     600
tcaactataa ccattaatcg ggcaaaacct ttagctgtca aaacaacgtg aaaacgatat     660
ttgtatatat catcaagaat cagtagataa gagaatgatt taatcccctg actattacaa     720
ttttggtgta ataaacagtc tctattggtt tttattcttt gttttaattt ctcatgacct     780
```

```
atagagagaa ttaggtagtt tcgaaaattg gctaatcaac ttttgaaaac tactgtctac    840
tttgcttaaa ttctctacac ttagtttcgg ataagataat tgtcggacta atagttaatc    900
ccttgacaat ctttgatatt ataaaaggtt tagttaatct cttctctata taaatattca    960
tacaccagct ttcaaaaata tataatccaa acaccaaaaa caaa                    1004

<210> SEQ ID NO 162
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0137

<400> SEQUENCE: 162
gtggcacatg ctgaaacccc gagcatctct ccggaagaca cgcgtcgttc gctccaaaga     60
aaacagtcac agctgccgga gaatctccgc cgtcttcttc tgccaccgga aaaactctct    120
ccaccacttt cagtgcccac ctcgtgttat atccactgta tcctcgtagc accatatcag    180
cctaataaaa ttttatgtat caaattttaa gacatagccg aaactacact atactagaca    240
ataataatat gatttgtttc ctgaaaaatt atggtttcat gagaaacatt aatcatctat    300
aaaacaaatt agctatggca tcgaagagtt atcaatcaaa actgatgaat ctttacttaa    360
tatatacaac atatctttac cttgcgcgg agaagatcgg cgagagaagc accccagcca    420
ccgtcactaa aggattcttc agtgatggaa tcaccaaaga gaaaaacctt ccgtctcatc    480
atcttccaca caatcttctt gagaaaatct gagagataag aaaggtgtag tggttttgct    540
gaagtgatcg tgtttgattt agtaaagaaa tgctttattt attgttgggg gaaacataaa    600
taaataaagt aaaagtggat gcactaaatg ctttcaccca ctaatcaccg acctttcatg    660
gtttattgtg aaatacactc atagatagac atacaatacc ttatgtacgt aaataacatt    720
ttatttgtcg acacttatgt aagtaacgca tagattattt tctatgtgat tgccactctc    780
agactctcag tttcaaccaa taataacaat aactacaaca acattaatca taaacatatg    840
ctctggttta caattaaagc ttagattaag aaactgtaac aacgttacag aaaaaaaatg    900
ttatttacgt tttgtaagat tagtctctag aatcatcacc gttttttata tattaatgat    960
tctttcttat atataaaacc tttctcgaaa tacccatgaa a                       1001

<210> SEQ ID NO 163
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0143

<400> SEQUENCE: 163
atacaacaga tggcagatat cgagttaaat acgtgaatca gccgttacga tattttaaaa     60
ctagaaaatt atttaaaaat attgcaaaat accatttaat ttcattgttc ataaaaaaaa    120
gaaattcaaa aacttaaaaa ctgattcaaa aatttggatt aattctcatt aacagtcttc    180
aacactacaa caacatgttt ctaatttatt ttatatttta ataattaaac aatatatacg    240
tctgcacatt gttgctccga cataatctag tataaaaata gttgcagcat atgtgaaaag    300
caagcagcat ttatcactca atactttaa ttttatctgt tgtatgtatt aaggttttgt     360
agctttaaga aaacgcttat aatataaaat aacttctaaa agatatttca tgcgtataca    420
```

```
ataaatattt gtgaaaaaac atttcgaaaa cgtgtacaat atataaacta ttgtgttatc    480
ttttgacatt caaacaaatg ttgacaatgt aattttatcc atgatatgat tggccaatta    540
gctgcgaggt aaaaatccgt atacgagtaa aagtaagata aaatttcgca agaagatttt    600
tagcaggaaa tctaagacaa gtgtcatgaa cgtgtcaatc aacaaacgaa aaggagaatt    660
atagaatcca gattcgacgt accacattaa taaatatcaa acatttttat gttattttat    720
ttttgctctg gcagttacac tcttttttcat tgctccaata aaaaaatcac tcgcatgcat    780
gcatatatat acaccatagt aaactccgcc tcttcttcat tttaaaagta tcagtttaca    840
ctgacacaat ccttaactat tttcctttgt tcttcttcat ctttattaca cattttttc     900 aaggtaacaa ataatctttt taagtcactt ttatactctt taaatcttag attgatatat    960
gaatgcatgt taatatttca agatttatag gtctaccaaa c                      1001

<210> SEQ ID NO 164
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0144

<400> SEQUENCE: 164
aaacgttgca agattattga ttgtgagaaa gagtgctcaa ggtagtactg atttctgtaa     60
agctcacggt ggtgggaaac gatgttcttg gggagatggg aaatgtgaga aaatttgcta   120
gaggaaagaa gcggtttatg cgctgcgcat aacactatta tgtctcggga gaacaaagat   180
ggaagcaaga gcggtttgat tggaccggga ctctttagtg gccttgtttt tggctctact   240
tctgatcatt ctcagtctgg agctagcgct gtctctgatt gtactgattc tgttgaacga   300
atacagtttg agaataggca gaagaacaag aagatgatga taccgatgca ggttctagta   360
ccttcatcaa tgaaatctcc aagtaattca catgaaggag aaacaaacat ctatgacttc   420
atggttccgg aggagagagt tcacggcggt gggctagtaa tgtctttact tggtggctcc   480
attgatcgaa actgaaagcc atttatggta aaagtgtcac attctcagca aaaacctgtg   540
taaagctgta aaatgtgtgg aatctccga atctgtttgt agccggttac gttatgctgg    600
atcaaaaact caagatttgt tggatattgt tatgctggat cggtggtgaa accacttccc   660
ggttgctaaa taaataaacg ttttttgtttt ataatctttt tcactaaacg gcagtatggg   720
cctttagtgg gcttccttta agcgaccaat acaatcgtcg caccggaatc tactaccatt   780
tataggttta ttcatgtaaa acctcggaaa atttgagagc cacaacgtc aagagacaaa    840 aacaacttga agataaaggg ataaggaagg cttcctacat gatggacaac atttctttcc   900
acacaaattc tcataataaa aatcttataa tacaaatact tacgtcataa tcattcaatc   960
tagtccccat gttttaaggt cctgtttctt gtctgataca aat                    1003

<210> SEQ ID NO 165
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0156

<400> SEQUENCE: 165
ttggtttgca ttgtgaagat ttgtattaac tatagaacat tgaattgatg gtgttaagtt     60
cttacacaag cgtgcttctc ggtttgaact gtttcttttg tatgttgaat cagagcttag    120
```

```
tttataggaa ccagagtatc tacttagtca ttctctgatg ctaagtgcta aggttctacc    180
tagttgccct ctaggccctt atgttattga taacttatga agctatttga acacttgatt    240
cttaggagac ctaagttggt acagccagat agagtgtatg ttcttgttct ctatgtgaca    300
ggatcaagct gccacacata gttcaagggt atgctctgtg tgggtttgct cagattgagg    360
acaaatctat acaaggaagt agagtctttg acattttgat gttgtatgat aagaagaaga    420
aaggagagta ataagaaag agaaaaggga aacagaaaca cgtgggagaa catcccaaag    480
aggaagcaca cgcggatctt catgcaaagc tccccgattc tcccatgtgg tccctttctc    540
cctttgtccc cctcctcttt cttcttttct cattttactc ctttttttac cattatacaa    600
cgaatctttt ttatcataat ttttggttt tggtttattt tccaataaca ctttcttggt    660
tacttcccat tctcactttt tcatataaga aactcactt gggaaactta tgtttgagaa    720
tgacaagtct ttttagagaa agtgatgtaa caaatctaaa gtgattatat aataaccttg    780
cacaatgttt tgattttttt gtaagattcg aatattaggt ttattattcg tagggaataa    840
acttactttc aaaagcgttc ataagttaat actttcatat atgatcataa gtacggacac    900
tattgttttt tgtttgtttg tgtttattct aaaagaaagt agcttttaat tgaaatgtcc    960
tcggaggcac agtttaaagt tcgagtgtaa cagtttctaa ggca                   1004
```

<210> SEQ ID NO 166
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0158

<400> SEQUENCE: 166

```
ttattagatt aatagattgc attgcattgc ttgtgctttc aatttacaaa ttgtctccca     60
actccatcga cacatctctt tttgtgtata taagattcag acttgttata tttttttat    120 aaatatgtta ttagcatctt aagttaaatt gatttttat atctgcatta aggattacac    180
gactatattt gcgattgtgt gttggttaaa atataattta ggattgtctt taactacatt    240
taggattata tgactatatt tggttaaata taaaatctag ctgtgattat tagtattcaa    300
aaataagtag cctaaccaat taaaacaacg gctattgggg caaattagaa cattttagtg    360
tgtccaaaat ataatggtca ttaggtcata ttcctcctag cttcatcgca gcataattga    420
atgattgcct tatttagaag agcttttcca ctttcccaaa atctaggtgg gatctttttg    480
ttttgacctt cattttcctt gtttaccatt tttagctaaa ttatttacga ttacaaaaga    540
tatcaaaagt tggatcataa tacaatttat agcttactg tagaaaattc gtatgtacaa    600
gtacaacaaa ttcttcataa taaattttga aaattctatt acaaatgttg taagaaatag    660
aatttgaaat atatataaac taaggagaaa aaaaaagaga acatgcattg ctctagtcag    720
agtggaccaa catcaacgag ataagataac ataaaaacca actcaccata actaaaaaca    780
tcccaagaga tccaacgatt catatcaaac acaaaaacat cgaacgatca gatttaaacc    840
atctctggta tctccaaaac acaaacactt tttttttct tttgtctgaa tggaacaaaa    900
gcatgcgaca tctctgtgtc tttatcttct ctctcctctt cttgaaaaac tgaacccttta    960 attctttctt cacatctcct ttagctttct gaagctgcta                        1000
```

<210> SEQ ID NO 167
<211> LENGTH: 1005

```
<212> TYPE: DNA
<213> ORGANISM: Arabidopsis thaliana
<220> FEATURE:
<221> NAME/KEY: misc_feature
<223> OTHER INFORMATION: Ceres Promoter YP0188

<400> SEQUENCE: 167
gattggtatg aaatttcgga gaccaacaaa aaaaacttta ttgagcttgg agtgaagcta      60
tatatatggg gcaagatcat aatatgttta tatcggcctt ttcgttaact gaaaataata    120
gttttgagaa atatatcaaa tggtaaacag acatcatctt tgaaaaatac catcaatgaa    180
gttaatattg ttattggcat atggtttacc catcttaatt ttaatgcaac caaacaaaca    240
agaaacaaaa actgtataag atacaaggtg ttttacgatt ttccgtctta aaaccgaaat    300
attttgttc ctacgacttt aaacggactt tgcttaagtt gtgtgcatgt aagctcgtcg     360
tccctcgatt gtcatcaaca ttcaccaata tcagcctcta tcacacgagt gaaggtggtg    420
attcggctta atgaaaacag agaaatattt caatatgatt cctattaaat tttaaatctt    480
ttttctcaat ctctagattt tcattaaaag catcatgatt ttttccact atgttcatat     540
atctctatca cagttttagg tacattgtag aaattggata agatacgtca tacgtctaac    600
atgaatttgg tctagcaagg aaggtttgag ataataagtg aaaagaaaac acaagataat    660
aaattataat ttataaatgc tttatagtat tgaaaaataa gatgattttt tttttttta    720
ataccggatt ggctgatcca cttatgatga ctcaaatgtt attaagtttc aagacaattt    780
atgatgacac aaatcacaat gagtcaatag tagccacgaa gccagaaaaa aaaaatgtac    840
tacaaaaaga taatgatagt acaaaatgat acgtcgtact gccacatgta cgacacaact    900
cgattaccaa aaagcagagc catccaacca taaaactcaa aacacacaga ttccactggc    960
gtgtgctctc ctcacttcac tcgtccttga aacttgaggt actga                  1005

<210> SEQ ID NO 168
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter YP0190

<400> SEQUENCE: 168
taaatagtga cattggtaag aagaaaaaaa acactattaa atagtgaaaa aatggtttat     60
aactctctta attaacatta cttattattg ctagcaccta aaatctccca caaatatttt   120
gttgtaaaac acaaatttac aaaatgattt tgtttttaaa ttagtaacac atgttcatat    180
atacgttaat aagaacatac cctatatgat tttatataaa aaaatttctt tgagacgtct    240
tattcttttt tctttaataa tatgcaattg tgagagtttg gatttgaatg gtagcattag    300
aagcaaactt gaaccaaaca tatttcatga agtcaaactt gaaccaatgt gatcactaat    360
cacagtgttc gcagtgtaag gcatcagaaa atagaagaag ggacatagct atgaatcata    420
taatcttgac acatgtttta taggttttag gtgtgtatgc taacaaaaaa tgagacagct    480
ttcttctaat agacttaata tttgggctaa atgtaccaca gttgtgaatt tcttacaaaa    540
atgggccgag ctacaaaaaa ctacaggccc actctcaact cttatcaaac gacagcgttt    600
tacttttta aaagcacaca cttttttgttt ggtgtcggtg acggtgagtt tcgtccgctc    660
ttccttaaa ttgaagcaac ggttttgatc cgatcaaatc caacggtgct gattacacaa     720
agcccgagac gaaaacgttg actattaagt taggttttaa tctcagccgt taatctacaa    780
```

-continued

| | |
|---|---|
| atcaacggtt ccctgtaaaa cgaatcttcc ttccttcttc acttccgcgt cttctctctc | 840 |
| aatcacctca aaaaaatcga tttcatcaaa atattcaccc gcccgaattt gactctccga | 900 |
| tcatcgtctc cgaatctaga tcgacgagat caaaaccta gaaatctaaa tcggaatgag | 960 |
| aaattgattt tgatacgaat tagggatctg tgtgttgagg ac | 1002 |

<210> SEQ ID NO 169
<211> LENGTH: 995
<212> TYPE: DNA
<213> ORGANISM: Arabidopsis thaliana
<220> FEATURE:
<221> NAME/KEY: misc_feature
<223> OTHER INFORMATION: Ceres Promoter YP0212

<400> SEQUENCE: 169

| | |
|---|---|
| agtcgattgg tacactctta atttaattag agtaagagat caacaaaaat atagaatttt | 60 |
| ctttatatcg aagtgctacg accttatata tatagaaaaa aaagcatagg tgaatctcta | 120 |
| aattgagatt gtgctgtagt aaacatatta agttttttagt tttttttaaga aatgaatctt | 180 |
| tttgttgatt aattcaaact agtagtcatt aagattccgg agattccaat ttagaaaagt | 240 |
| caaagattca agaacaagt ccaggtccac atgttgaatc cgattcatca tccactcatc | 300 |
| cttcatatct tcctccaccg tctccgccca aaaaatcaat aacaataaaa aatcctaaaa | 360 |
| aaacatattt gattttgaaa aactttatc atatattata ttaattaaat agttatccga | 420 |
| tgactcatcc tatggtcagg gccttgctgt ctctgacgtc cttaattatc attattttta | 480 |
| aatttgtctc tctcagaaaa ttcgccaca atcttcctct ttccctttc cgaaaacagc | 540 |
| taatatttgt ggacctaaac taaataacgt agcctctaga ttttatataa ttactaatac | 600 |
| tatatgctac tacttgttat tatttactcc aatcatatat gataccaatc aagaatcact | 660 |
| acataagtag aaaactttgc aatgagtcca ttaattaaaa ttaagaataa acttaaaatt | 720 |
| ttatggtatt ttaagattcc ctttggattg taatgacaag aaatcagcaa attagtcgta | 780 |
| actcgtaaga ataaacaaga tcaattttta ctttctttac aaagattccg ttgtaatttt | 840 |
| agaaattttt ttttgtcact gttttttttat agattaattt atctgcatca atccgattaa | 900 |
| gaagtgtaca catgggcatc tatatatatc taacaggtaa aacgtgtatg tacatgcata | 960 |
| aggttttacg tgcttctata aatatatgtg gcagt | 995 |

<210> SEQ ID NO 170
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0214

<400> SEQUENCE: 170

| | |
|---|---|
| ccagtcgatt ggcgcctcgc atgcctatca tatttaaccg tcaataatgg atttggcggt | 60 |
| tttggtaggc cgggtcaacc ggattaaaag aaaacggttt ggagtccttc cttgcaattg | 120 |
| aattttcaca cattcgggtt ttgtgatttc tctgtcataa tgggcccggc acatatggtt | 180 |
| cataacccat gtgggcctat ggtataattt ttccaattaa aactattgtt aggtcgataa | 240 |
| aacaaaaaac aataaaaacg agtggaatac acataccaaa aagaatgtga tgaacattag | 300 |
| taattttatt ttgatggtta atgaaaaaca aaataaatgc atcttggcat cttccgttgg | 360 |
| aaagcgcaaa tagggcagat tttcagacag atatcactat gatgggggt gagagaaaga | 420 |
| aaacgaggcg tacctaatgt aacactactt aattagtcgt tagttatagg acttttttt | 480 |

```
tgtttgggcc tagttatagg atcataaggt aaaaatgaag aatgaatatt agattagtag    540
gagctaatga tggagttaag tatgcacgtg taagaactgg gaagtgaaac ctcctgtatg    600
gtgaagaaac tatacaacaa agccctttgt tggtgtatac gtattaattt ttattctttt    660
atcacaagcg atacgtatct taagacataa taaatatata tcttactcat aataaatatc    720
ttaagatata tatacagtat acacctgtat atatataata aataggcata tagtagaaat    780
taatatgagt tgttgttgtt gcaaatatat aaatcaatca aaagatttaa aacccaccat    840
tcaatcttgg taagtaacga aaaaaaaggg aagcaagaag aaccacagaa aaggggggcta    900 acaactagac acgtagatct tcatctgccc gtccatctaa cctaccacac tctcatcttc    960
tttttcccgt gtcagtttgt tatataagct ctcactctcc ggtatatttc cccattgcac   1020
tgga                                                                1024

<210> SEQ ID NO 171
<211> LENGTH: 911
<212> TYPE: DNA
<213> ORGANISM: Arabidopsis thaliana
<220> FEATURE:
<221> NAME/KEY: misc_feature
<223> OTHER INFORMATION: Ceres Promoter YP0263

<400> SEQUENCE: 171
atctagctgt ggattccacc aaaattctgg cagggccatg atctaaaaac tgagactgcg     60
cgtgttgttt tgcagtgatt tgtatttcat atttgcacca tcctacacag tccacttggt    120
atcgtaacca aacataagga gaacctaatt acattattgt tttaatttcg tcaaactggt    180
ttttaccttt tagttacata gttgattctt catttgtttt agtagttatg gagcacaata    240
atgtgcaaca aagaaagatc atagtggatt aatatgttga gaggtcagaa attcttggtt    300
aacaaaaaaa agttacaagg actgagattt tgggtgggag aaagccatag cttttaaaac    360
atgattgaac ttaaaagtga tgttatggtt tgaggggaaa aaggttgatg tcaactaaga    420
tagttgaagt aatgtcttaa actaaagtaa accaccggtc caaccgtggt ccggaagcat    480
ctctggtatg atttatccta aaaatcaaaa tagtagaaac atactttaaa tatatacatt    540
gatcggacga aaattgtaaa ctagtatagt ttcaaaaact agttgaacag gttatgtacc    600
ttaaacattt atttcaaact taaacactaa agaacatata tgaatagaag tttatataaa    660
ttactatata tctaccataa atctcttata attatgatgt cacgatgagg aagtgttgaa    720
acgttaaaat gccaaaatat aagcatgcga cggaattttg gcagaagatt gtagagttgt    780
aatctgtcgc aatcattact cgtgctagca ttttttcattt tcccttcatt tgtggataac    840
gcacgatata acattctaca caccaacaag attctataaa aacgcaaagg ttgtctccat    900
agaatatcgt c                                                         911

<210> SEQ ID NO 172
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0275

<400> SEQUENCE: 172
aaacattaat atgtagtaac tatgggcgta tgctttactt tttaaaatgg gcctatgcta     60
taattgaatg acaaggatta acaactaat aaaattgtag atgggttaag atgacttatt    120
```

```
tttttactta ccaatttata aatgggcttc gatgtactga aatatatcgc gcctattaac    180
gaggccattc aacgaatgtt ttaagggccc tatttcgaca ttttaaagaa cacctaggtc    240
atcattccag aaatggatat tataggattt agataatttc ccacgtttgg tttatttatc    300
tattttttga cgttgaccaa cataatcgtg cccaaccgtt tcacgcaacg aatttatata    360
cgaaatatat atatttttca aattaagata ccacaatcaa aacagctgtt gattaacaaa    420
gagatttttt ttttttggtt ttgagttaca ataacgttag aggataaggt ttcttgcaac    480
gattaggaaa tcgtataaaa taaaatatgt tataattaag tgttttattt tataatgagt    540
attaatataa ataaaacctg caaaggata gggatattga ataataaaga gaaacgaaag     600
agcaatttta cttctttata attgaaatta tgtgaatgtt atgtttacaa tgaatgattc    660
atcgttctat atattgaagt aaagaatgag tttattgtgc ttgcataatg acgttaactt    720
cacatataca cttattacat aacatttatc acatgtgcgt cttttttttt ttttactttg    780
taaaatttcc tcacttttaa gactttata acaattacta gtaaaataaa gttgcttggg     840
gctacaccct ttctccctcc aacaactcta tttatagata acattatatc aaaatcaaaa    900
catagtccct ttcttctata aaggttttt cacaaccaaa tttccattat aaatcaaaaa     960
ataaaaactt aattagtttt tacagaagaa aagaaaaca                          999

<210> SEQ ID NO 173
<211> LENGTH: 981
<212> TYPE: DNA
<213> ORGANISM: Arabidopsis thaliana
<220> FEATURE:
<221> NAME/KEY: misc_feature
<223> OTHER INFORMATION: Ceres Promoter YP0285

<400> SEQUENCE: 173
gggattatat atgatagacg attgtatttg cgggacattg agatgtttcc gaaaatagtc     60
atcaaatatc aaaccagaat ttgatgtgaa aacactaatt aaaacatata attgacaact    120
agactatatc atttgttaag ttgagcgttg aaagaaaatg aaagagtgta gactgtagta    180
cgtatgagtt tcccaaaaga tggtgctga atattattgg gaagagactt tggttggttc     240
ggttgaatga agatttttac ctgccatgtt gatagagaaa ggcaaataaa tgtaggggtc    300
gatgtctaac gtaaagactg gatcaaccaa gagtcctcct cctcgtcttc accaaaaaaa    360
aagagtcctc ctcgtggaaa cttatttctt ctccagccaa gatctcatct catctcttca    420
ctctatgaaa tataaaggaa tcttatggtt tttctaaaaa ctatagtacg tctatatacc    480
aaaggaaaca atataaaatc agttaatctg ataaattttg agtaaataat aaagttaact    540
ttgtacttac ctatatcaaa ctaattcaca aaataaagta ataataacaa agaattttta    600
gtagatccac aatatacaca cacactatga gaaatcataa tagagaattt taatgatttt    660
gtctaactca tagcaacaag tcgctttggc cgagtggtta aggcgtgtgc ctgctaagta    720
catgggctct gcccgcgaga gttcgaatct ctcaggcgac gtttcttttg ttttcggcca    780
taaaggaaaa agcccaatta acacgtctcg cttataagcc cataaagcaa acaatgggct    840
gtctctgtct cactcacaca cgcgttttcc tactttttga ctatttttat aaccggcggg    900
tctgacttaa ttagggtttt ctttaataat cagacactct ctcactcgtt tcgtcaacat    960
tgaacacaga caaaaccgcg t                                              981

<210> SEQ ID NO 174
<211> LENGTH: 996
<212> TYPE: DNA
```

```
<213> ORGANISM: Arabidopsis thaliana
<220> FEATURE:
<221> NAME/KEY: misc_feature
<223> OTHER INFORMATION: Ceres Promoter YP0286

<400> SEQUENCE: 174
gaaaacaatc ataggttacg ctattatcat cgaaaggtat gtgatgcata ttcccattga      60
accagatttc catatatttt atttgtaaag tgataatgaa tcacaagatg attcaatatt     120
aaaaatgggt aactcacttt gacgtgtagt acgtggaaga atagttagct atcacgcata     180
catatatcta tgaataagtg tgtatgacat aagaaactaa aatatttacc taaagtccag     240
ttactcatac tgatttcatg catatatgta ttatttattt attttttaata aagaagcgat     300 tggtgttttc atagaaatca tgatagattg ataggtattt cagttccaca aatctagatc     360
tgtgtgctat acatgcatgt attaattttt tccccttaaa tcatttcagt tgataatatt     420
gctctttgtt ccaactttag aaaaggtatg aaccaacctg acgattaaca agtaaacatt     480
aattaatctt tatatgagat aaaaccgagg atatatatga ttgtgttgct gtctattgat     540
gatgtgtcga tattatgctt gttgtaccaa tgctcgagcc gagcgtgatc gatgccttga     600
caaactatat atgtttcccg aattaattaa gttttgtatc ttaattagaa taacattttt     660
atacaatgta atttctcaag cagacaagat atgtatccta tattaattac tatatatgaa     720
ttgccgggca cctaccagga tgtttcaaat acgagagccc attagtttcc acgtaaatca     780
caatgacgcg acaaaatcta gaatcgtgtc aaaactctat caatacaata atatatattt     840
caagggcaat ttcgacttct cctcaactca atgattcaac gccatgaatc tctatataaa     900
ggctacaaca ccacaaagga tcatcagtca tcacaaccac attaactctt caccactatc     960
tctcaatctc tcgtttcatt tcttgacgcg tgaaaa                                 996

<210> SEQ ID NO 175
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0337

<400> SEQUENCE: 175
taattttttt attttttggaa ctaacactta ttagtttagg tttccatcac ctatttaatt      60
cgtaattctt atacatgcat ataatagaga tacatatata caaatttatg atcattttg     120 cacaacatgt gatctcattc attagtatgc attatgcgaa aacctcgacg cgcaaaagac     180
acgtaatagc taataatgtt actcatttat aatgattgaa gcaagacgaa aacaacaaca     240
tatatatcaa attgtaaact agatatttct taaaagtgaa aaaaaacaaa gaaatataaa     300
ggacaatttt gagtcagtct cttaatatta aaacatatat acataaataa gcacaaacgt     360
ggttacctgt cttcatgcaa tgtggacttt agtttatcta atcaaaatca aaataaaagg     420
tgtaatagtt ctcgtcattt ttcaaatttt aaaaatcaga accaagtgat ttttgtttga     480
gtattgatcc attgtttaaa caatttaaca cagtatatac gtctcttgag atgttgacat     540
gatgataaaa tacgagatcg tctcttggtt ttcgaatttt gaactttaat agttttcttt     600
tttagggaaa ctttaatagt tgtttatcat aagattagtc acctaatggt tacgttgcag     660
taccgaacca atttttttacc cttttttcta aatgtggtcg tggcataatt tccaaaagag     720
atccaaaacc cggtttgctc aactgataag ccggtcggtt ctggtttgaa aaacaagaaa     780
taatctgaaa gtgtgaaaca gcaacgtgtc tcggtgtttc atgagccacc tgccacctca     840
```

| | | |
|---|---|---|
| ttcacgtcgg tcattttgtc gtttcacggt tcacgctcta gacacgtgct ctgtccccac | | 900 |
| catgactttc gctgccgact cgcttcgctt tgcaaactca acatgtgtg tatatgtaag | | 960 |
| tttcatccta ataagcatct cttaccacat taattaaaaa | | 1000 |

<210> SEQ ID NO 176
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0356

<400> SEQUENCE: 176

| | | |
|---|---|---|
| ttagttcatt gaaacgtcaa cttttactt gcaaccactt tgtaggacca ttaactgcaa | | 60 |
| aataagaatt ctctaagctt cacaaggggt tcgtttggtg ctataaaaac attgttttaa | | 120 |
| gaactggttt actggttcta taaatctata aatccaaata tgaagtatgg caataataat | | 180 |
| aacatgttag cacaaaaaat actcattaaa ttcctaccca aaaaaaatct ttatatgaaa | | 240 |
| ctaaaactta tatacacaat aatagtgata caaagtaggt cttgatattc aactattcgg | | 300 |
| gatttctgg tttcgagtaa ttcgtataaa aggtttaaga tctattatgt tcactgaaat | | 360 |
| cttaactttg ttttgtttcc agttttaact agtagaaatt gaaatttta aaaattgtta | | 420 |
| cttacaataa aatttgaatc aatatcctta atcaaaggat cttaagacta gcacaattaa | | 480 |
| aacatataac gtagaatatc tgaaataact cgaaaatatc tgaactaagt tagtagtttt | | 540 |
| aaaatataat cccggtttgg accgggcagt atgtacttca atacttgtgg gttttgacga | | 600 |
| ttttggatcg gattgggcgg gccagccaga ttgatctatt acaaatttca cctgtcaacg | | 660 |
| ctaactccga acttaatcaa agattttgag ctaaggaaaa ctaatcagtg atcacccaaa | | 720 |
| gaaaacattc gtgaataatt gtttgctttc catggcagca aaacaaatag gacccaaata | | 780 |
| ggaatgtcaa aaaaagaaa gacacgaaac gaagtagtat aacgtaacac acaaaaataa | | 840 |
| actagagata ttaaaaacac atgtccacac atggatacaa gagcatttaa ggagcagaag | | 900 |
| gcacgtagtg gttagaaggt atgtgatata attaatcggc ccaaatagat tggtaagtag | | 960 |
| tagccgtcta tatcatccat actcatcata acttcaacct | | 1000 |

<210> SEQ ID NO 177
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0374

<400> SEQUENCE: 177

| | | |
|---|---|---|
| aagacacccg taaatgttgt catgtagaag aaactagaaa cgttaaacgc atcaaatcaa | | 60 |
| gaaattaaat tgaaggtaat ttttaacgcc gcctttcaaa tattcttcct aggagaggct | | 120 |
| acaagacgcg tatttctttc gaattctcca aaccattacc attttgatat ataataccga | | 180 |
| catgccgttg ataaagtttg tatgcaaatc gttcattggg tatgagcaaa tgccatccat | | 240 |
| tggttcttgt aattaaatgg tccaaaaata gtttgttccc actactagtt actaatttgt | | 300 |
| atcactctgc aaaataatca tgatataaac gtatgtgcta tttctaatta aaactcaaaa | | 360 |
| gtaatcaatg tacaatgcag agatgaccat aaaagaacat taaacacta cttccactaa | | 420 |
| atctatgggg tgccttggca aggcaattga ataaggagaa tgcatcaaga tgatatagaa | | 480 |

| | | |
|---|---|---|
| aatgctattc agtttataac attaatgttt tggcggaaaa ttttctatat attagacctt | 540 | |
| tctgtaaaaa aaaaaaaatg atgtagaaaa tgctattatg tttcaaaaat ttcgcactag | 600 | |
| tataatacgg aacattgtag tttacactgc tcattaccat gaaaaccaag gcagtatata | 660 | |
| ccaacattaa taaactaaat cgcgatttct agcaccccca ttaattaatt ttactattat | 720 | |
| acattctctt tgcttctcga ataataaac ttctctatat cattctacat aataaataag | 780 | |
| aaagaaatcg acaagatcta aatttagatc tattcagctt tttcgcctga gaagccaaaa | 840 | |
| ttgtgaatag aagaaagcag tcgtcatctt cccacgtttg gacgaaataa aacataacaa | 900 | |
| taataaaata ataaatcaaa tatataaatc cctaatttgt ctttattact ccacaatttt | 960 | |
| ctatgtgtat atatataccc acctctctct tgtgtatttg | 1000 | |

<210> SEQ ID NO 178
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0377

<400> SEQUENCE: 178

| | | |
|---|---|---|
| tataaaccat tcctataaca ccatatttaa acataacaat gaattgcttg gatttcaaac | 60 | |
| tttattaaat ttggatttta aattttaatt tgattgaatt ataccccctt aattggataa | 120 | |
| attcaaatat gtcaactttt tttttgtaag attttttttat ggaaaaaaaa attgattatt | 180 | |
| cactaaaaag atgacaggtt acttataatt taatatatgt aaaccctaaa aagaagaaaa | 240 | |
| tagtttctgt tttcactttta ggtcttatta tctaaacttc tttaagaaaa tcgcaataaa | 300 | |
| ttggtttgag ttctaactttt aaacacatta atatttgtgt gctatttaaa aaataattta | 360 | |
| caaaaaaaaa aacaaattga cagaaaatat caggttttgt aataagatat ttcctgataa | 420 | |
| atatttaggg aatataacat atcaaaagat tcaaattctg aaaatcaaga atggtagaca | 480 | |
| tgtgaaagtt gtcatcaata tggtccactt ttctttgctc tataacccaa aattgacccct | 540 | |
| gacagtcaac ttgtacacgc ggccaaacct ttttataatc atgctattta ttccttcat | 600 | |
| ttttattcta tttgctatct aactgatttt tcattaacat gataccagaa atgaatttag | 660 | |
| atggattaat tcttttccat ccacgacatc tggaaacact tatctcctaa ttaaccttac | 720 | |
| ttttttttta gtttgtgtgc tccttcataa aatctatatt gtttaaaaca aaggtcaata | 780 | |
| aatataaata tggataagta taataaatct ttattggata tttctttttt taaaaaagaa | 840 | |
| ataaatcttt tttggatatt ttcgtggcag catcataatg agagactacg tcgaaaccgc | 900 | |
| tggcaaccac ttttgccgcg tttaatttct ttctgaggct tatataaata gatcaaaggg | 960 | |
| gaaagtgaga tataatacag acaaaacaag agaaaaga | 998 | |

<210> SEQ ID NO 179
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0380

<400> SEQUENCE: 179

| | | |
|---|---|---|
| acaagtacca ttcacttttt tacttttcaa tgtatacaat catcatgtga taaaaaaaaa | 60 | |
| aatgtaacca atcaacacac tgagatacgg ccaaaaaatg gtaatacata aatgtttgta | 120 | |
| ggttttgtaa tttaaatact ttagttaagt tatgatttta ttattttttgc ttatcactta | 180 | |

```
tacgaaatca tcaatctatt ggtatctctt aatcccgctt tttaatttcc accgcacacg    240
caaatcagca aatggttcca gccacgtgca tgtgaccaca tattgtggtc acagtactcg    300 tcctttttt ttcttttgta atcaataaat ttcaatccta aaacttcaca cattgagcac    360
gtcggcaacg ttagctccta aatcataacg agcaaaaaag ttcaaattag ggtatatgat    420
caattgatca tcactacatg tctacataat taatatgtat tcaaccggtc ggtttgttga    480
tactcatagt taagtatata tgtgctaatt agaattagga tgaatcagtt cttgcaaaca    540
actacggttt catataatat gggagtgtta tgtacaaaat gaaagaggat ggatcattct    600
gagatgttat gggctcccag tcaatcatgt tttgctcgca tatgctatct tttgagtctc    660
ttcctaaact catagaataa gcacgttggt tttttccacc gtcctcctcg tgaacaaaag    720
tacaattaca ttttagcaaa ttgaaaataa ccacgtggat ggaccatatt atatgtgatc    780
atattgcttg tcgtcttcgt tttcttttaa atgtttacac cactacttcc tgacacgtgt    840
ccctattcac atcatccttg ttatatcgtt ttacttataa aggatcacga acaccaaaac    900
atcaatgtgt acgtcttttg cataagaaga aacagagagc attatcaatt attaacaatt    960
acacaagaca gcgagattgt aaaagagtaa gagagagag                          999
```

<210> SEQ ID NO 180
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0381

<400> SEQUENCE: 180

```
cacggtcaaa gtattgctaa catggtcatt acattgaaaa agaaaattaa ttgtctttac     60
tcatgtttat tctatacaaa taaaaatatt aaccaaccat cgcactaaca aaatagaaat    120
cttattctaa tcacttaatt gttgacaatt aaatcattga aaaatacact taaatgtcaa    180
atattcgttt tgcatacttt tcaatttaaa tacatttaaa gttcgacaag ttgcgtttac    240
tatcatagaa aactaaatct cctaccaaag cgaaatgaaa ctactaaagc gacaggcagg    300
ttacataacc taacaaatct ccacgtgtca attaccaaga gaaaaaaga gaagataagc    360 ggaacacgtg gtagcacaaa aaagataatg tgatttaaat taaaaaacaa aaacaaagac    420
acgtgacgac ctgacgctgc aacatcccac cttacaacgt aataaccact gaacataaga    480
cacgtgtacg atcttgtctt tgttttctcg atgaaaacca cgtgggtgct caaagtcctt    540
gggtcagagt cttccatgat tccacgtgtc gttaatgcac caaacaaggg tactttcggt    600
attttggctt ccgcaaatta gacaaaacag ctttttgttt gattgatttt tctcttctct    660
ttttccatct aaattctctt tgggctctta atttctttt gagtgttcgt tcgagatttg    720
tcggagattt tttcggtaaa tgttgaaatt ttgtgggatt ttttttatt tcttattaa    780 acttttttt attgaattta taaaaggga aggtcgtcat taatcgaaga aatggaatct    840
tccaaaattt gatattttgc tgttttcttg ggatttgaat tgctctttat catcaagaat    900
ctgttaaaat ttctaatcta aaatctaagt tgagaaaaag agagatctct aatttaaccg    960
gaattaatat tctccgaccg aagttattat gttgcaggct                         1000
```

<210> SEQ ID NO 181
<211> LENGTH: 999
<212> TYPE: DNA
<213> ORGANISM: Arabidopsis thaliana

```
<220> FEATURE:
<221> NAME/KEY: misc_feature
<223> OTHER INFORMATION: Ceres Promoter YP0384

<400> SEQUENCE: 181
tttaaaaaat tggataaaac accgataaaa attcacattt gcaaatttta ttcagtcgga      60
atatatattt gaaacaagtt ttgaaatcca ttggacgatt aaaattcatt gttgagagga     120
taaatatgga tttgttcatc tgaaccatgt cgttgattag tgattgacta ccatgaaaaa     180
tatgttatga aaagtataac aacttttgat aaatcacatt tattaacaat aaatcaagac     240
aaaatatgtc aacaataata gtagtagaag atattaattc aaattcatcc gtaacaacaa     300
aaaatcatac cacaattaag tgtacagaaa aacctttttgg atatatttat tgtcgctttt    360
caatgatttt cgtgaaaagg atatatttgt gtaaaataag aaggatcttg acgggtgtaa     420
aaacatgcac aattcttaat ttagaccaat cagaagacaa cacgaacact tctttattat     480
aagctattaa acaaaatctt gcctatttttg cttagaataa tatgaagagt gactcatcag    540
ggagtggaaa atatctcagg atttgctttt agctctaaca tgtcaaacta tctagatgcc     600
aacaacacaa agtgcaaatt ctttttaatat gaaaacaaca ataatatttc taatagaaaa    660 ttaaaaggg aaataaaata ttttttttaaa atatacaaaa gaagaaggaa tccatcatca     720
aagttttata aaattgtaat ataatacaaa cttgtttgct tccttgtctc tccctctgtc    780
tctctcatct ctcctatctt ctccatatat acttcatctt cacacccaaa actccacaca    840
aaatatctct ccctctatct gcaaattttc caagttgca tcctttcaat ttccactcct    900
ctctaatata attcacattt tcccactatt gctgattcat ttttttttgt gaattatttc    960
aaacccacat aaaaaaatct ttgtttaaat ttaaaacca                            999

<210> SEQ ID NO 182
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0385

<400> SEQUENCE: 182
actcaacaat aggacaagcc aaaaaaattc caattattgt gttactctat tcttctaaat      60
ttgaacacta atagactatg acatatgagt atataatgtg aagtcttaag atattttcat     120
gtgggagatg aataggccaa gttggagtct gcaaacaaga agctcttgag ccacgacata     180
agccaagttg atgaccgtaa ttaatgaaac taaatgtgtg tggttatata ttagggaccc     240
atggccatat acacaatttt tgtttctgtc gatagcatgc gtttatatat atttctaaaa     300
aaactaacat atttactgga tttgagttcg aatattgaca ctaatataaa ctacgtacca     360
aactacatat gtttatctat atttgattga tcgaagaatt ctgaactgtt ttagaaaatt     420
tcaatacact taacttcatc ttacaacggt aaaagaaatc accactagac aaacaatgcc     480
tcataatgtc tcgaaccctc aaactcaaga gtatacattt tactagatta gagaatttga     540
tatcctcaag ttgccaaaga attggaagct tttgttacca aacttagaaa cagaagaagc     600
cacaaaaaaa gacaaaggga gttaaagatt gaagtgatgc atttgtctaa gtgtgaaagg     660
tctcaagtct caactttgaa ccataataac attactcaca ctcccttttt ttttctttttt    720 ttttcccaaa gtaccctttt taattccctc tataacccac tcactccatt ccctctttct    780
gtcactgatt caacacgtgg ccacactgat gggatccacc tttcctctta cccacctccc    840
```

```
ggtttatata aacccttcac aacacttcat cgctctcaaa ccaactctct cttctctctt    900
ctctcctctc ttctacaaga agaaaaaaaa cagagccttt acacatctca aaatcgaact    960
tactttaacc accaaatact gattgaacac acttgaaa                           998
```

```
<210> SEQ ID NO 183
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0396

<400> SEQUENCE: 183
```

```
catagtaaaa gtgaatttaa tcatactaag taaaataaga taaaacatgt tatttgaatt     60
tgaatatcgt gggatgcgta tttcggtatt tgattaaagg tctggaaacc ggagctccta    120
taacccgaat aaaaatgcat aacatgttct tccccaacga ggcgagcggg tcagggcact    180
agggtcattg caggcagctc ataaagtcat gatcatctag gagatcaaat tgtatgtcgg    240
ccttctcaaa attacctcta agaatctcaa acccaatcat agaacctcta aaaagacaaa    300
gtcgtcgctt tagaatgggt tcggttttg gaaccatatt tcacgtcaat ttaatgttta    360
gtataatttc tgaacaacag aattttggat ttatttgcac gtatacaaat atctaattaa    420
taaggacgac tcgtgactat ccttacatta agtttcactg tcgaaataac atagtacaat    480
acttgtcgtt aatttccacg tctcaagtct ataccgtcat ttacggagaa agaacatctc    540 tgttttcat ccaaactact attctcactt tgtctatata tttaaaatta agtaaaaaag     600
actcaatagt ccaataaaat gatgaccaaa tgagaagatg gttttgtgcc agattttagg    660
aaaagtgagt caaggtttca catctcaaat ttgactgcat aatcttcgcc attaacaacg    720
gcattatata tgtcaagcca atttttccatg ttgcgtactt ttctattgag gtgaaaatat    780
gggtttgttg attaatcaaa gagttttgcct aactaatata actacgactt tttcagtgac    840
cattccatgt aaactctgct tagtgtttca tttgtcaaca atattgtcgt tactcattaa    900
atcaaggaaa aatatacaat tgtataattt tcttatattt taaaattaat tttgatgtat    960 tacccccttta taaataggct atcgctacaa caccaataac                         1000
```

```
<210> SEQ ID NO 184
<211> LENGTH: 1514
<212> TYPE: DNA
<213> ORGANISM: Arabidopsis thaliana
<220> FEATURE:
<221> NAME/KEY: misc_feature
<223> OTHER INFORMATION: Ceres Promoter p13879

<400> SEQUENCE: 184
```

```
tttcgatcct cttctttttt aggtttcttg atttgatgat cgccgccagt agagccgtcg     60
tcggaagttt cagagattaa aaccatcacc gtgtgagttg gtagcgaatt aacgaaaagt    120
ctaagtcaag attttttaaa aagaaattta tgtgtgaaaa gaagccgttg tgtatattta    180
tataatttag aaaatgtttc atcattttaa ttaaaaaatt aataatttgt agaagaaaga    240 agcattttt atacataaat catttacctt ctttactgtg ttttcttca cttacttcat     300 ttttactttt ttacaaaaaa gtgaaaagta aattacgtaa ttggtaacat aaattcactt    360
taaatttgca tatgttttgt tttcttcgga aactatatcg aaaagcaaac ggaaagaact    420
tcacaaaaaa ccctagctaa ctaaagacgc atgtgttctt cttattcttc atatatcctc    480
tgtttcttgt gttctgtttt gagtcttaca ttttcaatat ctgactctga ttactatatc    540
```

```
taaaagggaa catgaagaac ttgagaccat gttaaactgt acaatgcctt caaacatggc    600
taactaaaga tacattagat ggctttacag tgtgtaatgc ttattatctt taggtttttt    660
aaatcccttg tattaagtta tttaccaaat tatgttcttg tactgcttat tggcttggtt    720
gttgtgtgct ttgtaaacaa cacctttggc tttatttcat cctttgtaaa cctactggtc    780
tttgttcagc tcctcttgga agtgagtttg tatgcctgga acgggtttta atggagtgtt    840
tatcgacaaa aaaaaaatgt agcttttgaa atcacagaga gtagttttat attcaaatta    900
catgcatgca actaagtagc aacaaagttg atatggccga gttggtctaa ggcgccagat    960
taaggttctg gtccgaaagg gcgtgggttc aaatcccact gtcaacattc tcttttctc    1020 aaattaatat ttttctgcct caatggttca ggcccaatta tactagacta ctatcgcgac   1080
taaaataggg actagccgaa ttgatccggc ccagtatcag ttgtgtatca ccacgttatt   1140
tcaaatttca aactaaggga taaagatgtc atttgacata tgagatattt ttttgctcca   1200
ctgagatatt tttctttgtc ccaagataaa atatcttttc tcgcatcgtc gtctttccat   1260
ttgcgcatta aaccaaaaag tgtcacgtga tatgtcccca accactacga attttaacta   1320
cagatttaac catggttaaa ccagaattca cgtaaaccga ctctaaacct agaaaatatc   1380
taaaccttgg ttaatatctc agcccccctta taaataacga gacttcgtct acatcgttct   1440
acacatctca ctgctcacta ctctcactgt aatcccttag atcttctttt caaatttcac   1500
cattgcactg gatg                                                     1514
```

<210> SEQ ID NO 185
<211> LENGTH: 1954
<212> TYPE: DNA
<213> ORGANISM: Arabidopsis thaliana
<220> FEATURE:
<221> NAME/KEY: misc_feature
<223> OTHER INFORMATION: Ceres Promoter p326

<400> SEQUENCE: 185

```
gtgggtaaaa gtatccttct ttgtgcattt ggtattttta agcatgtaat aagaaaaacc     60
aaaatagacg gctggtattt aataaaagga gactaatgta tgtatagtat atgatttgtg    120
tggaatataa taaagttgta aaatatagat gtgaagcgag tatctatctt ttgactttca    180
aaggtgatcg atcgtgttct ttgtgatagt tttggtcgtc ggtctacaag tcaacaacca    240
ccttgaagtt ttcgcgtctc ggtttcctct tcgcatctgg tatccaatag catacatata    300
ccagtgcgga aaatggcgaa gactagtggg cttgaaccat aaggtttggc cccaatacgg    360
attccaaaca acaagcctag cgcagtcttt tgggatgcat aagactaaac tgtcgcagtg    420
atagacgtaa gatatatcga cttgattgga atcgtctaag ctaataagtt taccttgacc    480
gtttatagtt gcgtcaacgt ccttatggag attgatgccc atcaaataaa cctgaaaatc    540
catcaccatg accaccataa actcccttgc tgccgctgct ttggcttgag caaggtgttt    600
ccttgtaaag ctccgatctt tggataaagt gttccacttt ttgcaagtag ctctgacccc    660
tctcagagat gtcaccggaa tcttagacag aacctcctct gccaaatcac ttggaagatc    720
ggacaatgtc atcattttg caggtaattt ctccttcgtt gctgctttgg cttgagcacg    780
gtgcttcttt gtaaagctcc gatctttgga taagagcgga tcggaatcct ctaggaggtg    840
ccagtccctt gacctattaa tttatagaag gttttagtgt attttgttcc aatttcttct    900
ctaacttaac aaataacaac tgcctcatag tcatgggctt caaattttat cgcttggtgt    960
atttcgttat ttgcaaggcc ttggcccatt ttgagcccaa taactaaatc tagccttttc   1020
```

-continued

```
agaccggaca tgaacttcgc atattggcgt aactgtgcag ttttacctttt ttcggatcag    1080 acaagatcag atttagacca cccaacaata gtcagtcata tttgacaacc taagctagcc    1140
gacactacta aaaagcaaac aaaagaagaa ttctatgttg tcattttacc ggtggcaagt    1200
ggacccttct ataaaagagt aaagagacag cctgtgtgtg tataatctct aattatgttc    1260
accgacacaa tcacacaaac ccttctctaa tcacacaact tcttcatgat ttacgacatt    1320
aattatcatt aactctttaa attcacttta catgctcaaa aatatctaat ttgcagcatt    1380
aatttgagta ccgataacta ttattataat cgtcgtgatt cgcaatcttc ttcattagat    1440
gctgtcaagt tgtactcgca cgcggtggtc cagtgaagca aatccaacgg tttaaaacct    1500 tcttacatttt ctagatctaa tctgaaccgt cagatatcta gatctcattg tctgaacaca    1560
gttagatgaa actgggaatg aatctggacg aaattacgat cttacaccaa ccccctcgac    1620
gagctcgtat atataaagct tatacgctcc tccttcacct tcgtactact actaccacca    1680
catttcttta gctcaaccttt cattactaat ctcccttttaa ggtatgttca cttttcttcg    1740
attcatactt tctcaagatt cctgcatttc tgtagaattt gaaccaagtg tcgattttg    1800 tttgagagaa gtgttgattt atagatctgg ttattgaatc tagattccaa ttttaattg    1860 attcgagttt gttatgtgtg tttatactac ttctcattga tcttgtttga tttctctgct    1920
ctgtattagg tttctttcgt gaatcagatc ggaa                                 1954
```

<210> SEQ ID NO 186
<211> LENGTH: 2016
<212> TYPE: DNA
<213> ORGANISM: Arabidopsis thaliana
<220> FEATURE:
<221> NAME/KEY: misc_feature
<223> OTHER INFORMATION: Ceres Promoter p32449

<400> SEQUENCE: 186

```
gatcggcctt cttcaggtct tctctgtagc tctgttactt ctatcacagt tatcgggtat      60
ttgagaaaaa agagttagct aaaatgaatt tctccatata atcatggttt actacaggtt     120
tacttgattc gcgttagctt tatctgcatc caaagttttt tccatgatgt tatgtcatat     180
gtgataccgt tactatgttt ataactttat acagtctggt tcactggagt ttctgtgatt     240
atgttgagta catactcatt catcctttgg taactctcaa gtttaggttg tttgaattgc     300
ctctgttgtg atacttattg tctattgcat caatcttcta atgcaccacc ctagactatt     360
tgaacaaaga gctgtttcat tcttaaacct ctgtgtctcc ttgctaaatg gtcatgcttt     420
aatgtcttca cctgtctttc tcttctatag atatgtagtc ttgctagata gttagttcta     480
cagctctctt ttgtagtctt gttagagagt tagttgagat attacctctt aaaagtatcc     540
ttgaacgctt tccggttatg accaatttgt tgtagctcct tgtaagtaga acttactggg     600
accagcgaga cagtttatgt gaatgttcat gcttaagtgt cgaacgtatc tatctctact     660
atagctctgt agtcttgtta gacagttagt tttatatctc catttttttg tagtcttgct     720
agttgagata ttacctcttc tcttcaaagt atccttgaac gctcaccggt tatgaaatct     780
ctacactata gctctgtagt cttgctagat agttagttct ttagctctct ttttgtagcc     840 tagttctttta gctctccttt tgtagccttg ctacagagta agatgggata ttacctcctt     900
gaacgctctc cggttatgac caatttgttt tagctccttg taagtagaac ttaggataga     960
gtgagtcaac tttaagaaag aacctagtat gtggcataac cagattgcag gctctgtctc    1020
ggctacagta acgtaactct atagctcttt gttttgttca gaaagaacca gtgattggat    1080
```

```
gattcgtcct tagaaactgg acctaacaac agtcattggc tttgaaatca agccacaaca      1140
atgcctatat gaaccgtcca tttcatttat ccgtttcaaa ccagcccatt acatttcgtc      1200
ccattgataa ccaaaagcgg ttcaatcaga ttatgtttta attttaccaa attctttatg      1260
aagtttaaat tatactcaca ttaaaaggat tattggataa tgtaaaaatt ctgaacaatt      1320
actgattttg gaaaattaac aaatattctt tgaaatagaa gaaaaagcct ttttcctttt      1380
gacaacaaca tataaaatca tactcccatt aaaaagattt taatgtaaaa ttctgaatat      1440
aagatatttt ttacaacaac aaccaaaaat atttattttt ttccttttt acagcaacaa      1500 gaaggaaaaa cttttttttt tgtcaagaaa aggggagatt atgtaaacag ataaaacagg      1560
gaaaataact aaccgaactc tcttaattaa catcttcaaa taaggaaaat tatgatccgc      1620
atatttagga agatcaatgc attaaaacaa cttgcacgtg gaaagagaga ctatacgctc      1680
cacacaagtt gcactaatgg tacctctcac aaaccaatca aaatactgaa taatgccaac      1740
gtgtacaaat tagggtttta cctcacaacc atcgaacatt ctcgaaacat tttaaacagc      1800
ctggcgccat agatctaaac tctcatcgac caattttga ccgtccgatg gaaactctag      1860
cctcaaccca aaactctata taagaaatc ttttccttcg ttattgctta ccaaatacaa      1920
accctagccg ccttattcgt cttcttcgtt ctctagtttt ttcctcagtc tctgttctta      1980
gatcccttgt agtttccaaa tcttccgata aggcct                               2016

<210> SEQ ID NO 187
<211> LENGTH: 667
<212> TYPE: DNA
<213> ORGANISM: Arabidopsis thaliana
<220> FEATURE:
<221> NAME/KEY: misc_feature
<223> OTHER INFORMATION: Ceres Promoter PD1367

<400> SEQUENCE: 187
acagttttct tttctcatct tacaacaagt ttccaggagg atagagacat aaacgaagct        60
cggattgtat cgttcttttt agcttttatt cacatccgaa agtcctgtag tttagattct       120
gttatcttgc ggttttgagt taatcagaaa cagagtaatc aatgtaatgt tgcaggctag       180
atctttcatc tttggaaatt tgttttttc tcatgcaatt tctttagctt gaccatgagt       240
gactaaaaga tcaatcagta gcaatgattt gatttggcta agagacattt gtccacttgg       300
catcttgatt tggatggtta caacttgcaa gacccaattg gatacttgct atgacaactc       360
caactcaaga gtgtcgtgta actaagaacc ttgactaatt tgtaatttca atcccaagtc       420
atgttactat atgttttttt gtttgtatta ttttctctcc tacaattaag ctctttgacg       480
tacgtaatct ccggaaccaa ctcctatatc caccatttac tccacgttgt ctccaattat       540
tggacgttga aacttgacac aacgtaaacg tatctacgtg gttgattgta tgtacatatg       600
tacaaacgta caccttctc ctctttcact tcatcacttg gcttgtgaat tcattaattc       660
ctgcgaa                                                                 667

<210> SEQ ID NO 188
<211> LENGTH: 1836
<212> TYPE: DNA
<213> ORGANISM: Oryza sativa
<220> FEATURE:
<221> NAME/KEY: misc_feature
<223> OTHER INFORMATION: Ceres Promoter p530c10

<400> SEQUENCE: 188
```

```
gcctctcgac cacgagttta gcacttgtgc aacatatatg cgtgcgatga acatctactg      60
atgcgccatg cgaattttag cgttcgttca tgacgcttcc aacggcacag aggctgagca     120
gcagcatgca tgcatggctc ttgtgaaaac aaaaaaggtt actggtaaat gacatgctgc     180
tgtagctagc tagcagaatg caaggcccat gcatatgcaa tgctatgcga caagtacagt     240
accagcatgt atggtagcca gctaactaat ctatcagcag aggcagcaag ctcgtgcatg     300
gtgtgatgca cttctctcca gtaatctagt ggtaattttc acccaaagcg ttgctcatat     360
ggacagtaat tagtaatatt accaaggttc acaatcccgt tacctgacca aatactactc     420
acgaatggta tctctggttt tcgttaaaac cgttggtaaa ccagcaaaaa tagacaaaat     480
ttgtcaaaat tttaaatttt agtttttttt ttttaactta gccgggaaac cttgaagttt     540
gtgctgtcga gctgtcctgg gaaggacggt tttggttggg attgtgaacc ctggttactg     600
cacttcattt ttgaacagat attagtgcaa cagacaaatg ccaacgcatt tttttctgtt     660
taccggcaag ctgaagcttt tacgatcccc atacagccgt tgctgcaaac ctgccaagaa     720
agagcagcag aaacaggtgt catttttgtgg tggaaagcca agtaaagtaa acagaagatg     780
```

```
cctatctcgt cacggacagc tcacaagtta atgtgattta tctcactata gatacgaaga    240
acatggagta tcctacatcc aaaggaagtg cccatgaagt tgtggagcat cgctacgatt    300
tgtgaccaaa tttgggtgca tgtgggcaat cgtattacag ccaccctgtt gttgatctat    360
atcgactatt atccgacgat atttatcatt atattatgac tagttagttt gtagattttg    420
agagggcaac ataagaagca atccagctta acctgttatg ttcttgatgg tagattctag    480
ttcatgtgtt gaatctgttc tccctgctgt agaatgtatc gagttgctgc tctctactct    540
gtacttttag aataccttttt caatcatttg gagtcagctg attgttgtac tacttatacg    600
ccacctgatt agtcatgtca acaattaaac ttgagcactg gttaagttaa gagtggcctg    660
attgtagttg ataatcacat tttattcgta gacattgtat gctggatctt tatcagccac    720
cgtcagatca tcctctgtaa taaatcttca tcagacgtgt gtgccaatcg caaggaacac    780
gaaatgcatc cgaaatgtta ctctgagtta atcaatacta taattcttgg tcaaattaat    840
tatttatatc tataaagttt aaattaaatt taggaaaatg aattcatgca aatcttgtgg    900
taagttgtca atttcataaa aaatccagct tactactccc ttttaggag tgtgttgtgg    960 ctgcacactt ctgccttttg atatatacgg ttctattctc ggtgtactcc tttattatta   1020
ttaaaacaat cccagttact tggtaagtgc taatcacgaa tcaaagtcaa cataacaaat   1080
catgtgcgta cagctataac tcgattacac aaacaacaaa attcatattt gaacataaat   1140
ccagttgtag catatctggt agtataaagt tttttttttg tatagaagag ttttaatttc   1200
tgtaagtttt ggaaagcatt taatcctaga aattgtagtg tagctcaact aaaaaataaa   1260
tgaacttgaa tcgaaattgg gttgtatcat aaatctttac cactcaaacg aatatttatc   1320
ctaaaccaca aatgactctt ttcatcaagg aatgttttgt tttcagcatt ttaaaaaaaa   1380
acttttctaa tatggttttc atgtttcgtt cttttgaaat ttaacatcta tttaatttgc   1440
acggctccat aaattcaacg gatacatatt ctgaataatt actaaggagg catatatcgg   1500
ctctcttaat acaaccgctt gtttctcaaa atttattttg agttttgtct acacattctc   1560
aaggacggta caaacacact atagatgttc acaattttttt ttttctaaag ttgattgatg   1620
gacaaatgtt tgaacatata aacatataag cactgaatat ttgcttatgc aggaggtatt   1680
tatatcaagt tcgatacttt actaccatag tccctaggac actaaaatgc cttcaatgat   1740
ctgatgaagc ctaagagaga atattgatca gtggagcgac ttgcaactac acatggcaca   1800
agtagactag acacggtata tattcatatt aacttgttaa aattttacta cttaacagtt   1860
cacttgtggt gcatccatat caattcttac ttacacaata tttgtaaaaa caacctaaca   1920
ctataggatg acctagacaa cctttatgtc aatcacactt agaagatgat cgtcttttta   1980
ataaataatg tgtactacac accatgctct ccatatagat caagatctac aaacccttcc   2040
acttataaac cttaccacca aaaactcatt aagttgcttc atttatctat gctattaaga   2100
aaaaaactta tttcgtttat gccatttcta gaaatggcta gtcacactat tcacaatatt   2160
atataataaa taaagttttc aaatattcat ccaccaaaaa tcatcaagtc gtgggactta   2220
tatgttaatt agagaagtcc ctttgggtgc aatcgatttt ggaaacccta aattttttct   2280
atacatagaa gagagagatg tctagttgca attgcttttg cgatgtgcca accacccttc   2340
tagctttcat ccacgtctac ttaattgcca ttcttcttct tctttttctt cactattact   2400
acctcctatc ttagcgaatc ttcttcttct tcactattac tacctcccac cttagtgaat   2460
tcatcctcat tgttcacaat gacattgcta agttaactag gtatgctaag tacacaatta   2520
gaatataacc tagagccttt gtttccatca tacttaaaag atgacatttt tatatagata   2580
```

```
aagtgtgcta ctcacaaggc ttactatata tatgtatgat acacacaaac tccacaaccc    2640
aaaactcttt caagttgtgt ggcccatcta tgctattaaa aagcccattt agcccatcca    2700
acatgagaaa ccctagggtt ttttccctat aaaagatacc taggttattg ttgcttttcc    2760
accccgcccg ccgccgctcc ctattcctat ttaatcccat ctctcttcct catcaccgct    2820
ctcctctctc caggcaagag gtacgcactt tttgtttcgg atttgaaatc tttgcttcgt    2880
tttactatca ttggtcataa gttcttttt gaagatgttt gagaataagt ttatcattga     2940
gattatcgtc acttgtgata ggaagtacgc aacctcaagc cggacaagac gtgagcaaag    3000
```

<210> SEQ ID NO 190
<211> LENGTH: 2023
<212> TYPE: DNA
<213> ORGANISM: Oryza sativa
<220> FEATURE:
<221> NAME/KEY: misc_feature
<223> OTHER INFORMATION: Ceres Promoter pOsMEA

<400> SEQUENCE: 190

```
gagagcagaa catagtagcc gctgttttct gggggtgcaa tttgtgcaag atcgctatcc      60
ttatggacca tgcaagcacc aagcaatatt aagccaggtc caacagcggt cttggggaat    120
tcagaaatga gcttaaaaac ctccttgagc tggccagctc agccaaggag gtccatcatg    180
catgtgcatg ctcaatactt ggaattattg caaaatgatc ggtcattgac tggaagactt    240
tgcgcccttc ctcagccaac cttatgtggc tgcatgcata gagtaccaac aggaaggtag    300
cgtttgttgg aataaggttt gcatccagca tgtccttgta gagcttcaaa gcctcagcac    360
cttggcccat gaaggccata tccagctaat tgcattccat gagaccacat tcttgctatc    420
catactgttg aagtgaagat gctccgagct tcggaaatgc ttccacacta tgcatacatg    480
tcaatgagca ctgtcatgac ataaacattg gccccaagt cctcctcagc gataatccta      540
tgcagccact ttcccaggga caaagctcca agctgtgcac acgctgaaag agagctagaa    600
atgatgattg gatttggtca cacgctaagt accagcattt gctcaaagag ggcaattgcc    660
atctccgtcc agccattcta ggcataccct ggtattattg cttcatga ttccgattcc        720 gtggtcttct atggcatcgc attgaaggcc ttccttgcag actccatatc atttaaccta    780
cagtacaata tggtaattgc tgtcgacact ggagaattcg cagtaaatcc agacttgaga    840
ggaccatgta agcattgatc aagcagttca ttcccaaaca gactatacgg gatcagtgcc    900
agtgctcgag tttggcttca attccaaggc catcaaccca ataaacagat taactgatga    960
accaaccatg caattcgccg agcaaacata gattaagcat tgtaggcaac caaatctgga   1020
ttctccatca agtcaaagag acgccatgca gaattcccaca tccccgctgt atacaccgag   1080
atcaaccggt cagaacatgc tcatactccg ccaaccctct cttcagaaca tgctcatact   1140
ccgccaaccc tctcttctct gcaagaggca tcctccccaa ttcccattg ttatatctgt      1200 tgctggtaag accgttgcca gcgtggttgt gtcagaccga acagactctg cactcgccat   1260
cctcacgaac gactccaggg cctccgaacc aggaagcccg gccggccatc agcgtgttcc   1320
acataacggt atccggcgac tgcacagtgt cgaacacctt gcgtgcgtgg tcacctctgg   1380
acagcatgaa gcgtacaggc tacagcttgg ccaatgcgga cgccacgaac gtgtcggcgg   1440
cgtaacccgc gcgtgcagcg cgccgcgcgc gggctgcgga gtcggttgga gacgacacgc   1500
cgccgccatg agagcaatga gcgaggtggc ggcgaaggcg aaggagaagt agtcgaggca   1560
agcggaagag aaggcggcag cggagaaagc gatcggggcg gcggaggagg tgggtgggag   1620
```

```
ggagggacgc gtagcggagg tcggaggagg agggagctga ggtttccggg gcggggtcg      1680 agagggtagt gtacggaggc gagggacacg gcgaggatct ggtcgaggta gcgcagtgtg    1740
aaggaaagcg cgatgaggcg gagggcgccg gcgaagagcg gcgcggcgga tagcgggagg    1800
aggcggcgcc ggcggggtct catccgattg gaaacagatt gggaagggggg aggggtagg     1860 aatacgtggc gtcggcagta ttaggtagag agagaaaccc tttccatcct ttgtctctta   1920
gccccgaagg agagagaaaa atcagaaaaa aaaaaccctc cgcgtgtggg ggaagcagag    1980
ctccggacgc tggcgccgct cgcgccaccg cacccgcacc gcc                     2023
```

<210> SEQ ID NO 191
<211> LENGTH: 2034
<212> TYPE: DNA
<213> ORGANISM: Oryza sativa
<220> FEATURE:
<221> NAME/KEY: misc_feature
<223> OTHER INFORMATION: Ceres Promoter pOsYp102

<400> SEQUENCE: 191

```
gaacgaccca aacgcgtaaa tggtggtact ggtttccctg ctttgccgag taccagcagc     60
cacgaagaac gttacacaat cgagtacaaa atctataaga gcaagtttaa tagcatagcc    120
aaatactacc tctaaatcat ctatagccaa tttaatagtt catttattca ataattactt    180
ataaacatat actacaatca ttaatatatg gtcttacttc ttatacacat aatattttgg    240
agtccgtgtt acagctggct ataaatataa gggattttgg ttggatgtgg tacatcctat    300
tataatgaat ctagacatga aacctgtcca aattcatcgt gctaggatac gccacatcta    360
accaaaatct cttatcttta gggatggaga gagtaataat taaatgaagc taggtagagt    420
ttcccggtca atacgcttgc gtgtgcttat aagagcatgg ccaacagttt cccgatactc    480
ttcccaatat cagttttgag gagttttgtt ggaaaaaatc gctccaacag tagacctaaa    540
tcacccctaa aagcttggcg tttccaaacc cgcatatttc gttctccact tgtagggaag    600
agactcggcg cccaatcctt caaccgcatg cacttcgcgc gcgctgtgtg aaaattttcc    660
taccaggttc ttctttgtgc gttcgtctac ctgtgagtca atccatcacg ccagcagcct    720
catcttcccc gcagctgtct gggaaagcag ccatggctcc cccaagcttc cccagcgtcg    780 acatttttttt ctcagcggca gcgccagacc catctccaac ccaattgggc ggaccttcgt    840
cggcgctccc ccagcaccac caccgactcg aatcggccgt cgcccctatt catctccaat    900
cgtccctcga ccctaccgca tcctgcagca cagcctgtct ctcgcgtcag actggcgctg    960
cgctcccccc ggtaatgtgc aggcgacaaa ggccccatgc gatgcgacca gcagccggcg   1020
acaaccggag gtgcccagtc gctggccttc atcgaatcat cgtgcacctc ggtcggagtc   1080
gatttctgat tgttgctgct gctcaaatct ggagcttgct attgctgaga actgcttggt   1140
ggtggtactg gaaatttgtt gtttgctggc tgatgaaaac tgttgttctt tgctgctaaa    1200
aactgctgct tgctagtact gaaaagtact attgcagctg ctgaaatatc ttgctgcttg    1260
ctgctgaaaa cttcaagttg ttaacaccgt tcacactaaa aaagctgaaa tttttttttct   1320 gggctgaaaa ccccattgtt gatgattgca gaaccaatat ttttccatgt aaaatacagg    1380
agatcgtggt aataatcaag tgaaatatca ttttggggca aatactcaga tcgtacctga    1440
agccaatgga aacattgttc aatgcttaaa ctgtcagtta tgatgtcaaa gagattgatc    1500
actgaatgtc ctgaaaggag ccgtgaggag gatgcagcat tgcagcgtgc gcgagcgtga    1560
gtggaggaga ggaatgacga ttctgttggt agttgtcgat gtggcctact ttttttgttt    1620
```

```
tgaggattaa attttgggaa tctcttggag ataaaaggta ttctcatacc ttaaatcctt    1680
tttagagatc taaaaaaaat gatttagggg attgaatttt gggtggctgt tggtgatgct    1740
ctaagttgca catcctgggg aaaaacctcc ctaatccatc agcaaaccga tcaaccaccc    1800
acgacaagtc gacgccaccg tttttttttt ctccctccta agtcctaacc ccacaaaaat    1860
cccgcgaact ttcgtctcac cacgcgccgc gtgccccta caaataccaa acaacaccca    1920
ccacgtccac tcacaaacca cgcaggaaac ctcagaaaat caccgtacgc gacgcgggcc    1980
caagaaaacc ccgacagaaa ccgcgcagca gcaacaccac caccggcgtc ggag          2034
```

<210> SEQ ID NO 192
<211> LENGTH: 1877
<212> TYPE: DNA
<213> ORGANISM: Oryza sativa
<220> FEATURE:
<221> NAME/KEY: misc_feature
<223> OTHER INFORMATION: Ceres Promoter pOsYp285

<400> SEQUENCE: 192

```
ggcccgagtt aaacgatctt ccacgtgtca gcgaatccta gtcgttcgat gaatctgaat      60
ctgacttgtg gtggttggac ggccacgtgt taaaaaggg aaacgtccgc atcacccgat     120
gctgggacat ttgcaatttc gatccagctg tagattgacc agttgttact ctctttttt     180 taacaccata caaacgtaat actccctctg tcccaaaata taagtatttt ttttaacctc    240
ggttcagtct tcgaggtgct actttgacca ataatattta taaaaataag atgttttaaa    300
taaagagagt tgcatattat gatagctcgt ttaatgataa acaaagtacc atcaaattta    360
catgattaat cttttaatt tatttgctat taatagttaa aattaaaaa gtttgacttc      420 acactgttct aaaatactt atattttggg acggagggag tacacattag agcaggtaca     480
atagcagact agtagccagc tataaacata ttttaatgag ataaagatg agagagaaca     540 gcgggctaca gatctgtagc cagctgcagc acggactcca agacattgtg tgtgtatgac    600
aggtgggacc atatattaat agtacagtaa gtaactattg tatgaattgg ctattagatt    660
agctataggt gaattgtagc tagtagtggg ctatactatt gaacttactc ttatatctct    720
caatatctcc agaaaactag gacgatatat attgatatta acaaagtcat catagatatc    780
tcgctatcga catatatatt acctatcact gaaaaataa ttaatcataa atgcaagcac     840
atatactacg ttcaacactg aatgtaggta gattggtaga cgggttccac cgcaagaaaa    900
gcattgcacc agtgaagaaa gaaacatcgg aatttgtatg tagtttgttg tttgatgaat    960
tcttttgatt aaaaaaaact aaaatcagag ttgattcagt taatggtgtt gcctacgata   1020
tacttccata tcatgatatc actgtagact atgaatcata tctttaatta aaactaaatc   1080
aagaaattaa gtatgagacc tcaactcaat gaagaatttc tagttgaaaa acattcctag   1140
tgtgcgttcg gatggaggta gggatcttct ctccgttcat ataaaaccgg atggttcatt   1200
agaacatgat taattaagca acagttaatc taaaaataaa ttaatatttt ttaagaaatt   1260
tttgtataga gatctttga aaaaaataca ttggttagaa agcatactaa taaaagaga    1320 aaaataagaa catagtacta tagtagaaaa tgagaacttg gagtatttga gaggatggga   1380
aataagaaga ttaagaagat gcgtaaagtg aacggttaac gcatgattga ttaattaaat   1440
attaattatt ttaaatttgg aaaataaatt agtatgattt ttaagcaaca tatatatata   1500
tatatatata tatatagaaa aacatagttt tagaaaatat aagcgtgtaa aacgatatgc   1560
aggaacgaaa cgttgagcat tcaaaatttc aaattgaaca tatgaatcaa gagagaataa   1620
```

```
aaaaagaggc cttctaggct ggcatggaca attggacatg ttttcaacta gggtttcaag      1680
cttcgagcat ccacttttgt ccttgcaaac tttatacggc aaggcccgtg aatctagccc      1740
cccacaccac cccacccgcc cgcgccgcgc ggccgcctcg cctcccctcc cttctcctcc      1800
tctccgcccc cgccgccagg ccgtccacct ccgccgtctc ctccccatt cgcacccaag      1860 gcgctggcgc ggaaggc                                                    1877

<210> SEQ ID NO 193
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0565

<400> SEQUENCE: 193
caccaaatat agtgttattt caatactaaa atggtgttat ggttggagat gccctaaaga       60
taaacatgac gagacacgag atttattaat ttcttgatca accataactt ataacttaa      120 tattaatttc acttaataat ttccaattaa gtgaatcttt acttcaccaa aagttcctaa      180
cgaactctta ttttctagca tcaatattac catgaactag catcaatact atcatgaaaa      240
attcctactt cctatccaac tcttaataac aatgctagtc ttaacaatat tcatcaaaaa      300
cttgatatag accttctaac ttagccacga ctagtatcgg tgaataccaa aattaatgta      360
ttcatgagaa cttgagattt ctctaatgta ttcttgttac taaacaagta acaacactca      420
agaaatatca tgatcaaata ttttactcat aaactccata tttcacattt tgaaaatttt      480
aaacagcaaa tcacattgaa ttttcgtggt aaaagtattt aaaattgaaa atagcagct      540 cctgatttca atgtataaat ttatctttat atggtttatg tctccaactt attttaaaaa      600
agagagaaag agcacccaaa aggtgaccgt ttgaaattcg aatttatttc cgtttgaaat      660
tcgaattcaa aaaagtaaa ccgaaccgag tctcgttact gactgtcaca cattgtttcc      720
ctaaaagcta attaacccat acgtggcgta atataacagg tcagtgatca atactaaata      780
acagacatac acctttaaaa ttcgtgcacg ctccaaaaca aaatctacac ttcaaaatca      840
acggtcacga tcattcctca aatttcaaaa aattatttaa cctcacttcc ttcgctttgt      900
ttttaaaacc tctctctctt tctctttctc tttcgccatt aaaactctgt ttcctttttc      960
agagattctc agagaagatt cattttaccc taagaaaaaa                          1000

<210> SEQ ID NO 194
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0015

<400> SEQUENCE: 194
ttgagcctta ttgttgttat tgacttttag ccaatagaaa gagatggaaa ttcaataatt       60
atccacaaaa ttccaaatca ttggtgtaca aaaagatcta aggctgttat attttcaaaa      120
aagaaagaaa agaaatgcaa caaatatgga ttaaactgtg gtttgtaaat tgagctttgc      180
atgaaaactt tatcactatg atttcactac tccatattta ttgactaaag tggcactaat      240
gaatttctta atcatgaaat cttgtatcaa aaagtactaa aataaacatg acattggcaa      300
ttaggaaaat tctaaattag aaattagtaa aaatgaaagg tgaaagggaa agatgatgat      360
```

| | |
|---|---|
| atgaattggt tggtgaccag gagaaatgta tcccgatttt tgcagacact ttcagtgtcc | 420 |
| ccattcatat aattatggcc cacctcgtta agattttca ttcaccacca taacaagatc | 480 |
| taagcttaga tttcatgtaa ttaaacatat aatatacttg ccaatactat ctaataaagt | 540 |
| atacttaagc aaaaattatt actctagtgt aaggcgatga aatataagtt tagttgaaaa | 600 |
| tttatgtcga tataacaaag tataatgaat taagaccttg gttttcgatt aacaaactaa | 660 |
| ttaaacacta gttttgccta ataaaaccgg gaatcgtatt caaaaccgaa cgacaaaaca | 720 |
| agggacaagt tgagagacaa aaccaaatca gcatctttct tccagaaatg tcatgaccac | 780 |
| atgacgtcat cttgacccct cttcattgtg atatctgtgg ataaagcgca cgtgtttaat | 840 |
| tcacgaacct tcgtagtaac gaaaaatcca caactttcat attttttaat tacccactaa | 900 |
| actaaaacaa atttggaaaa acatgaaaaa cttttctctt ttttccaggt tcgtgaacct | 960 |
| cgtaccctct atataaacct cttaaccacc ttccacata | 999 |

<210> SEQ ID NO 195
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0087

<400> SEQUENCE: 195

| | |
|---|---|
| tgaattgagt aaaatgtgtt ttcaaacagt taggtggtag aaggtaaagg taataacatc | 60 |
| atgatcttac taaagaatt gttgcatact aactatcaat attctcaaca acataatata | 120 |
| atgttttttt aggtaatttt ccattttaat tttttgtgat taaacaatta aacaactcga | 180 |
| atgatgatga taaaaaaaaa aaattaacaa ctcgaataag ttaaagtagc aatacacatg | 240 |
| tcgttcaatt caaccaataa agtaagactt atattttaa gaagttgact aatagcttaa | 300 |
| taagttggaa aacttgtgta gtttcttaat tcccacgtgc agtaagaaat aaaaatgaaa | 360 |
| aaaattatta tatccttccc actctgcgac ttttctttta ttatcaaa tattaaaaag | 420 |
| attcatatca cagtttacac attgaaatca taaacgataa ttatgtattt tgtaataaaa | 480 |
| agttagttct gaagctcata ctttggatag tcgctagtcg ctaatatgct ccttgtaata | 540 |
| attaaagtca ctacgacgca cgtcaaagcc gatatttagg gcttaattga tgcgtgtttt | 600 |
| tcttttcata taatagtaat ataaattagt actaataaag tatgatggat ggttgagaca | 660 |
| gaaaagaaaa aagatgactg tatggtcatc attacaaaga gaatgtatt cttcatgttc | 720 |
| ttaagaataa taaaatgtca cttgtaaatc aagttggtaa gcattttgag aactttgttc | 780 |
| gatgcaacgt atgatgattt atgtagacaa aagataaaac cgtatcttca actattgcca | 840 |
| agaaaagata aaacctaatc tagtcagtct ctcaacataa atacaaccca atagccaaac | 900 |
| tgtgtccaat tcggagagaa actaaactaa aacaaaacac aaaagcccaa cataagccca | 960 |
| ataaacccca tttataaaac agaacattac taacactca | 999 |

<210> SEQ ID NO 196
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0093

<400> SEQUENCE: 196

| | |
|---|---|
| atgatgaaca ttctacatat ataattatta tgtttaagca cttagacagc ataaattctt | 60 |

```
tctaattata taaatctaac cttgttacat tgtacatcta taaattactt gaagaaataa      120
cgagttctat ttcttttaa aaattaaaaa tactatacca tatctcagtg attaagttga      180
accaaaaggt acggaggaga acaagcatt tgattcttcc ttatttatt ttattcatct       240 ctcactaatg atggtggaga aaaaagaaa atacctaaca acaaatata tattgtcata      300 caaaaatatt tctatatttt tagttaatta gtttatattc ctcactttc agggcttata    360 taagaaagtg agcaaacaca aatcaaaatg cagcagcaaa tactatcatc acccatctcc    420
ttagttctat tttataattc ctcttctttt tgttcatagc tttgtaatta tagtcttatt    480
tctctttaag gctcaataag aggaggtact attactacac ttctctctac ttttacttgt    540
attttagcat taaaatccta aaatccgttt taaattcaaa ataaactta gagatgttta    600 atctcgattc ggtttttcgg ctttaggaga taattatat gaaattagta tggatatctt    660
tactagtttc cattcaaatg attctgattt caatctaata ctctcactct ttaattaaac    720
tatatgtagt gtaatttcac actgttaaat ttctaccatg tcatgtatat tagagttgca    780
tagaaaattg taaacatcc atttgaattc gaatgaaaca aaatgtttta aaataaaatt    840
ttggttttta aagaaaaat ctaaaactga attatatcgt ttaaccaagt tgtaaaagtc    900
ataaaacgta gtatcttgta aatcgctctt ccacggtcca aatagacttc tagtaataaa    960
caagtaaaac taattttggt ttcttactaa ttttcacaga                          1000

<210> SEQ ID NO 197
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0108

<400> SEQUENCE: 197
ttagctgaac caggaaattg atctcttata ccagtttccg ggtttagatt ggtttgatgg     60
cgatttgatt aaaccccga aattttatgt cgtagttgtg catagtatta ttattctttg    120
cggacaatag acgtatcggg accaagttct gtagcaaaat tgtataagct taagtttgat    180
gaaatttaaa ggtaatcact aaaacccaaa tgggacaata aaccggtgaa gatttagagt    240
ttttaatttt gactcatgaa tctggagaaa gagccctcgt taaaaggagt gaatcaatcc    300
atagggaaaa aagttttgtc ttttaaaaa ctaaagaacc aaaccttaat agaagcagct    360
caatgtgtga caactttcca ctggcactaa gataaagtga ctagcgatga gtgcaattat    420
tgaaatagta gatggtaaat attacataca agagtaaaaa tatctttatg tcaatgctta    480
attcagtgtt tctggttaac aagagaaact tctctaactt tcgtaattgg gtcttataaa    540 atttttatgca attatgattt tacccttta ctactttca ttagctttca cgaatctatt    600
ttgacaagag aaatcattag aggtaaacat gcttttggt caagggcctt aacagttcca    660
ccaatcaagc tcaaaagttg tacttaaccg acatcttctg tgaaaacata taattacatg    720
tacaaatcaa aactacctta tgaaataaat agaaatattg cagttcatttt ctaatttaac    780 ctcttcaact tttaaaacta tttacatttc tttatgtcat ttctagtcat tttgatgcaa    840
attgtaccat ttatggatta tcttcacaaa ttttttaagtt ggtgaaaact ttttggtggg    900
tagttaaaac ttgaaataga aatttacttt accaaaataa actaatgaaa agtaatcact    960
ccactcccta taataagatt tccaacgttc ccactaagc                            999
```

```
<210> SEQ ID NO 198
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0022

<400> SEQUENCE: 198
tagttccatt acaatttcca aatgatttgt tacaaagcta caagattatt cgaaatagga      60
tttcatccat aagagagaat ggtgtggtcg acgctacaat gttgatttat tggttgtggt     120
ttgcatcttg gggatgtcaa atcctaagtt tcaagttctt gtaaaaacgt tttcaggttt     180
ctttaatata ttttaatatt aatgtaaaaa gaaaagatat agcttttgta caaaaaaatt     240
tgtttaatca ctatgtagga ggatgcgatc aaattcatgg aatgatgtat tattagcttt     300
tctatcctca ctctaaaaac aatactatag tgagttaaat aatttgatca tttcaatgta     360
gattaaaatt ttattaaaag aagaaaaatt taaaagccta taacaaaata aaaaaggagg     420
ctcgaggtat gatgggtgta gcagaagagc tggcaacagc tatcgactga gtgattacga     480
actcagtact cagtgttctc agctcacaca ctcttttttt gttctctttc ttttggacag     540 cttttcatttt ctcttttctt ttttctattt tgtttcaaaa ttccatccat attaaaatag     600
gcctgatcat gagaataaag gaaatactaa tgatgagttt ctcaataatg caataagatg     660
caattattat gagctatttta ctattgaaaa tgagcaaata aatgtcaaaa cacaatctgg     720
ttaagttaga gcaactccat tgtataggat tcatgtagtt tctaagaaaa caaaatgtat     780
taatatttta cttttacatc caaaaaacca acttatatga gtaatagaaa cgatcctaat     840
attaggaatt ttagagattt tctctcatct gtttcttaac ttttcaatat ttttattttt     900
taaaattgta tgagtttcta ctaagaaact actgctggag ttggtcttag cttcccaatg     960
cttctccacc tatatatatg catatctcct tcttaaaac                            999

<210> SEQ ID NO 199
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0080

<400> SEQUENCE: 199
aagcggcaat ttagtaagaa gtactcaaag tatcatttac caaaagtata tggttttggg      60
aagagttgtt agggatgtat tcttctaaa cagatgatat gacgatgttc ttgaaaacta     120
atgttaaaga cggaatctct ggcatcttca ctcgggagat atattaaacc gttgattgta     180
gttagccatg tacttagctt agtgcacaaa taatctgctg caagaaatct ttttctatta     240
taatatctct catttaaaca ttagaacata ttgtttaact tgttcttcta gaaataaaac     300
tgctaatttc ttatggtaaa ctatttttcct ttagattgca caatcgaact cgaaaatcta     360
gtggagacta tgtgactatg tttatatata tgaaacctaa atcaaattat cccaataatt     420
gggagacaca aaagaaaaat tacgaaagaa aacaggaaat caaatcaaaa gataaagaga     480
aggtaaaaaa aggcaagaag cactaatgtt taatatttat agttttctcc attaaagaaa     540
aagcgatgat gtgtgttctc atctttgtg aaagtatata tattgctttt gcttttctca     600
aaagcaaaag actcatccaa caagaacaaa aaaaaaaact aaagctcaat ccaaaagacg     660
aagaatgcat tggatactac aacttctttt tcactttttct ttcaaattta caattatgat     720
```

| | | |
|---|---|---|
| tttcacaata cagtttattc aaaaataaat aaaaaaacga ggcatgaaaa taatgattat | 780 | |
| cctcttcact tattaagcca ctcactataa gcagagcaac tccagaacat agtgagcccc | 840 | |
| caaaacatta aagcatgatg atgtctaatg atgatgatct tcttcgttcc atttctctaa | 900 | |
| attttttggga tttctgcgaa gacccttctt ctctttctct tctctgaact tcaagattcg | 960 | |
| tgtcggacaa attttttgttt ttattttttct gatgttaca | 999 | |

<210> SEQ ID NO 200
<211> LENGTH: 3000
<212> TYPE: DNA
<213> ORGANISM: Arabidopsis thaliana
<220> FEATURE:
<221> NAME/KEY: misc_feature
<223> OTHER INFORMATION: Ceres Promoter PR0924

<400> SEQUENCE: 200

| | | |
|---|---|---|
| atctataacg agttaacatg ttgccagttt gaatcaagaa gcttggatga tgaatgaatg | 60 | |
| gatcggtttg tggtacaatt cttaaaattg tagtagagga gacagagaaa aaacatgata | 120 | |
| agactttggt atttacaact tgacggagac aagacagtaa gccaaatctg tcacaaaaac | 180 | |
| actcaaactc ttttctcagt gttttgagtt taaagagaga cttattcact tcccctttcg | 240 | |
| taacacttat ttgtctccca accaaacagt ttctgtcctt tcccttgtcc tcccacgtgc | 300 | |
| atctttatat ctcatgactt ttcgtttcta gatcttgaat aatgtcttag tggattaggt | 360 | |
| ttgttgtcgg taaattaggt gaccgttttt ttcttatatt tggaagatcg cgggatgaag | 420 | |
| cagatactga gtttcagggc atacacacct aatttgaaaa tcattgttag tccaatttca | 480 | |
| ctttaatctt gtttacaaaa aaattgatct gaaaatgttg atgggataag taaaaatgta | 540 | |
| agttttgcta gtagtcatga tataataata gcaaaaccag atcaattttg agcaaaagga | 600 | |
| agaaacaaaa aacagatcga tcccacgagc aagactaagt gtaaagtggt tcccacaaga | 660 | |
| gccatatgga tatggtcctt caacttttaa agcccattac ttcagtggtc gacccgacat | 720 | |
| tacgccacga gtagtcacgc acgcacgact ccgttcacgt gacattcacg ttgatatttc | 780 | |
| cccctctact ctcttctgct tggttgatct aaaaaaacatg aagagaccaa cctaatttca | 840 | |
| tattaatata tgatatagac ttcatactca acagtcactt tcgtaatcca aatccatatc | 900 | |
| ttacgaaatt agttcttaat aaaggttgtg gattaagtta taatattgtg ttaagagtta | 960 | |
| agacacagca tataaccttg taccaacagt gctttattct taaatggaaa caaaacatat | 1020 | |
| gtcaatgtca agcatacagc taaaatatca ttatctaata ttaagagtaa aacaagataa | 1080 | |
| ttaaaaattg aaacaacacc atattttat agctttactt atcgtatttt tctagtcttc | 1140 | |
| atggtaattg tgttgcttta ttttgtttat aaatgaattt ggttcgacca gatagtctaa | 1200 | |
| tatcagtttt taaacactgg ttttaataaa atcatatgtc ggcaattcaa cctgttacgt | 1260 | |
| tgtatgattg tatcctagtc aaatagggga ggaggtacta gtcgtttcaa ttagtttacg | 1320 | |
| taatcaatcc aaagaaacta taagctataa agatcctcaa tttgttggtt acaataaaaa | 1380 | |
| caacagttgt caaaatttat gtttataaaa agtaataact atgttccttc ccatatagag | 1440 | |
| caaagtacct caggataggc aaaccgtact taatagccct tattcataat ttgatccaac | 1500 | |
| tcttccccac aaaattgcaa ctgatgaagt caatacttgt atagtgagtc aagctataaa | 1560 | |
| tgtctagtga tagttttgtc tcttaaaagg ttaacaaaag ttatgacaag ctgaaaaatc | 1620 | |
| agagtttgct aggagtatta cttacagtta tcagtttaag tatcacattt atagtattgt | 1680 | |
| atacaatgat tcttaaattc cacctttttcc gtgcgaaacc aaatttttcta ttggaaacat | 1740 | |

| | |
|---|---|
| agaatgtaaa caaaaatatg ggacgttgtc cgttccaaca ttaaccaaac ttgtctatta | 1800 |
| ctaatattcg tgttggtttg atgttggatg tctaaattcg ttgaatcatg tgtctcttga | 1860 |
| cgaaatatgc atcttcttat ttcttagtat agatgcactt tatcattctt ttagtacatg | 1920 |
| cttaattttt ttttttaaaa tatgttgatt gtcatattgc caaaagtatg aattaaagac | 1980 |
| gcacatctaa cacaagttag cagccgtaaa tccttccata aatttatttt gcaagttttg | 2040 |
| ctcattatat aatgagcgga atttatgata taatcgtttg taataatgtt atgttttgat | 2100 |
| caaaatttga aattaaaagt aggtgagaac ttgttataca gtgtagataa ggtggatctt | 2160 |
| gaatataaaa ataaaattta taagatgtat ttaaagcaga aaagcataaa actttagata | 2220 |
| aaataatgta aaaatgtgtt agcatcaatg ttgggatatt ggccgacccg aacttaatca | 2280 |
| atgtcggaag ccattacttc tctcccaaaa gaccttttc cttcggagaa ctaggaactt | 2340 |
| cctcactacc tttcgcttaa cgtgaaagcc ataaatttca tatattcata aaaatcagaa | 2400 |
| aatctaaaac tgtttagtat cacctgtttt tggtatagac tattggtttt gtgttacttc | 2460 |
| ctaaactata tgatttcgta cttcattgga tcttatagag atgaatattc gtaaaaagat | 2520 |
| aagttatctg gtgaaacgtt acttcagtca tgttgggtct agatttacat actactatga | 2580 |
| aacattttaa gataataatt atcctagcca actatatgtt ctatattatg ggccaagaag | 2640 |
| atatagaact aaaagttcag aatttaacga tataaattac tagtatattc taatacttga | 2700 |
| atgattactg ttttagttgt ttagaataaa tagtagcgtg ttggttaaga taccatctat | 2760 |
| ccacatctat atttgtgtgg gttacataaa atgtacataa tattatatac atatatatgt | 2820 |
| atattttga taaagccata tattactcct tgacctctgc ccccatttcc ttttactata | 2880 |
| aataggaata ctcatgatcc tctaattcag caatcaacac caacgaacac aaccttttcc | 2940 |
| aaagccaata ataaaagaac aaaagctttt agtttcatca aagacgaagc tgccttagaa | 3000 |

<210> SEQ ID NO 201
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0388

<400> SEQUENCE: 201

| | |
|---|---|
| agaagtattc acgcaccaag gttatatttg tagtgacata ttctacaatt atcacatttt | 60 |
| tctcttatgt ttcgtagtcg cagatggtca atttttttcta taataatttg tccttgaaca | 120 |
| caccaaactt tagaaacgat gatatatacc gtattgtcac gctcacaatg aaacaaacgc | 180 |
| gatgaatcgt catcaccagc taaaagccta aaacaccatc ttagtttttca ctcagataaa | 240 |
| aagattattt gttccaacc tttctattga attgattagc agtgatgacg taattagtga | 300 |
| tagtttatag taaacaaat ggaagtggta ataaatttac acaacaaaat atggtaagaa | 360 |
| tctataaaat aagaggttaa gagatctcat gttatattaa atgattgaaa gaaaaacaaa | 420 |
| ctattggttg atttccatat gtaatagtaa gttgtgatga aagtgatgac gtaattagtt | 480 |
| gtatttatag taaacaaat taaaatggta aggtaaattt ccacaacaaa acttggtaaa | 540 |
| aatcttaaaa aaaaaaaaag aggtttagag atcgcatgcg tgtcatcaaa ggttcttttt | 600 |
| cactttaggt ctgagtagtg ttagactttg attggtgcac gtaagtgttt cgtatcgcga | 660 |
| tttaggagaa gtacgtttta cacgtggaca caatcaacgg tcaagatttc gtcgtccaga | 720 |
| tagaggagcg atacgtcacg ccattcaaca atctcctctt cttcattcct tcattttgat | 780 |

| | |
|---|---|
| tttgagtttt gatctgcccg ttcaaaagtc tcggtcatct gcccgtaaat ataaagatga | 840 |
| ttatatttat ttatatcttc tggtgaaaga agctaatata aagcttccat ggctaatctt | 900 |
| gtttaagctt ctcttcttct tctctctcct gtgtctcgtt cactagtttt ttttcggggg | 960 |
| agagtgatgg agtgtgtttg ttgaatagtt ttgacgatca | 1000 |

<210> SEQ ID NO 202
<211> LENGTH: 283
<212> TYPE: DNA
<213> ORGANISM: Arabidopsis thaliana
<220> FEATURE:
<221> NAME/KEY: misc_feature
<223> OTHER INFORMATION: Ceres Promoter PD0901

<400> SEQUENCE: 202

| | |
|---|---|
| caaagtattt gacaagccat atggttttgg atcaaaaagt cggtccaaaa ttaatgtttt | 60 |
| atgtgcaaga accgacccat tgtacacacg tgttaacatc ttcaagactt tcatctctat | 120 |
| ttttcttttg gtcattaaga tacccattga tccgaatctg ttacattccc acctactttt | 180 |
| ttaattttta ctatccactc caaattaaac acaaccgatg attttaataa ttggaagctt | 240 |
| tttaaaatat ttctccacgt gcctctttgt gtttgtctat ata | 283 |

<210> SEQ ID NO 203
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0623

<400> SEQUENCE: 203

| | |
|---|---|
| aaagttattg acattttgaa aggaccgtaa atattaccaa aaaactgacg gagttaggat | 60 |
| cggccacgta gaaagggaca agagagaaac agtcacggac tcggccagac taagtatggg | 120 |
| cctgtctgaa tccaaactca gctaagttcc aaaagcataa agagagatgt gtaatgaaat | 180 |
| gaacgtattc tagaaacgaa agcaatgtta tgctttgttt ttgagccaca tgttttrggg | 240 |
| agatggagag aatctttttt acgtttttaa cctaacccac ttggcacttg gccaaaaaag | 300 |
| tgagaagaaa ctgtggcgaa tgagtaggcc acgccatgga ctttgttcct tgtccttcaa | 360 |
| aagttaaatt tatgttatgc gtggggacaa tctaagcaac gtggttcctt taaatatcgc | 420 |
| agcttcctct tttacacttt tggagcctac gtgttttgtt ttggaccggc caaatacacg | 480 |
| agtcagtcag tttagaaata atttggatgt ccaaaaatct tggagatcca ataaaataa | 540 |
| ttagcatgtt ttagttcata agaatatgaa atgtagataa actgtctata ttaattttc | 600 |
| catagaattg gcttttttatc gaggtgatgt acttaatgac tttgttgatt actactcgta | 660 |
| taacaataaa gaatatgata ctatgtgaga cttataatga atttggtgtg tgttaattaa | 720 |
| tccagttgaa acagtttaat aacaaatcag aataaaaatt gtagtaagaa atttgaacg | 780 |
| ctgatccttc aacctagata gtgaaccttt caaatactat atgattcacg tgtaatgttt | 840 |
| ttgaccgttg gttatttttg tgtgaactat attaacttat caatatcgaa aggctaaata | 900 |
| agtaaataac taaagaaaag ttcaggaaac aactcgacct aatgacctat catttctgat | 960 |
| cacccgtcct ataaatacat acgtaagatc attcgttact | 1000 |

<210> SEQ ID NO 204
<211> LENGTH: 33
<212> TYPE: PRT
<213> ORGANISM: Artificial Sequence

```
<220> FEATURE:
<223> OTHER INFORMATION: Truncated version of Ceres CLONE ID no.
      100021733
<220> FEATURE:
<221> NAME/KEY: misc_feature
<223> OTHER INFORMATION: Ceres CLONE ID no. 100021733_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 204

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 205
<211> LENGTH: 33
<212> TYPE: PRT
<213> ORGANISM: Artificial Sequence
<220> FEATURE:
<223> OTHER INFORMATION: Truncated version of Ceres CLONE ID no. 1036726
<220> FEATURE:
<221> NAME/KEY: misc_feature
<223> OTHER INFORMATION: Ceres CLONE ID no. 1036726_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 205

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 206
<211> LENGTH: 33
<212> TYPE: PRT
<213> ORGANISM: Artificial Sequence
<220> FEATURE:
<223> OTHER INFORMATION: Truncated version of Ceres CLONE ID no. 1482731
<220> FEATURE:
<221> NAME/KEY: misc_feature
<223> OTHER INFORMATION: Ceres CLONE ID no. 1482731_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 206

Met Gln Ile Phe Val Lys Thr Leu Thr Gly Lys Thr Ile Thr Leu Glu
```

```
1               5                   10                  15
Val Glu Ser Ser Asp Thr Ile Asp Asn Val Lys Ser Lys Ile Gln Asp
            20                  25                  30

Lys

<210> SEQ ID NO 207
<211> LENGTH: 80
<212> TYPE: PRT
<213> ORGANISM: Artificial Sequence
<220> FEATURE:
<223> OTHER INFORMATION: Truncated version of Ceres CLONE ID no. 1554560
<220> FEATURE:
<221> NAME/KEY: misc_feature
<223> OTHER INFORMATION: Ceres CLONE ID no. 1554560_T
<220> FEATURE:
<221> NAME/KEY: misc_feature
<222> LOCATION: (17)..(78)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 207

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45

Ser Ala Lys Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

<210> SEQ ID NO 208
<211> LENGTH: 77
<212> TYPE: PRT
<213> ORGANISM: Artificial Sequence
<220> FEATURE:
<223> OTHER INFORMATION: Truncated version of Ceres CLONE ID no. 1802327
<220> FEATURE:
<221> NAME/KEY: misc_feature
<223> OTHER INFORMATION: Ceres CLONE ID no. 1802327_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 208

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Asn His Ala Met Ser Val Phe Val Met
```

```
            65                  70                  75

<210> SEQ ID NO 209
<211> LENGTH: 77
<212> TYPE: PRT
<213> ORGANISM: Artificial Sequence
<220> FEATURE:
<223> OTHER INFORMATION: Truncated version of Ceres CLONE ID no. 1876458
<220> FEATURE:
<221> NAME/KEY: misc_feature
<223> OTHER INFORMATION: Ceres CLONE ID no. 1876458_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 209

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Thr His Ala Met Ser Val Phe Val Met
65                  70                  75

<210> SEQ ID NO 210
<211> LENGTH: 79
<212> TYPE: PRT
<213> ORGANISM: Artificial Sequence
<220> FEATURE:
<223> OTHER INFORMATION: Truncated version of Ceres CLONE ID no. 1879148
<220> FEATURE:
<221> NAME/KEY: misc_feature
<223> OTHER INFORMATION: Ceres CLONE ID no. 1879148_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 210

Met Ala Leu Ala Asp Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75

<210> SEQ ID NO 211
<211> LENGTH: 33
```

```
<212> TYPE: PRT
<213> ORGANISM: Artificial Sequence
<220> FEATURE:
<223> OTHER INFORMATION: Truncated version of Ceres CLONE ID no. 1884696
<220> FEATURE:
<221> NAME/KEY: misc_feature
<223> OTHER INFORMATION: Ceres CLONE ID no. 1884696_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 211

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 212
<211> LENGTH: 76
<212> TYPE: PRT
<213> ORGANISM: Artificial Sequence
<220> FEATURE:
<223> OTHER INFORMATION: Truncated version of Ceres CLONE ID no. 1916866
<220> FEATURE:
<221> NAME/KEY: misc_feature
<223> OTHER INFORMATION: Ceres CLONE ID no. 1916866_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 212

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75

<210> SEQ ID NO 213
<211> LENGTH: 33
<212> TYPE: PRT
<213> ORGANISM: Artificial Sequence
<220> FEATURE:
<223> OTHER INFORMATION: Truncated version of Ceres CLONE ID no. 1950105
<220> FEATURE:
<221> NAME/KEY: misc_feature
<223> OTHER INFORMATION: Ceres CLONE ID no. 1950105_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
```

-continued

```
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 213

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 214
<211> LENGTH: 79
<212> TYPE: PRT
<213> ORGANISM: Artificial Sequence
<220> FEATURE:
<223> OTHER INFORMATION: Truncated version of Ceres CLONE ID no. 1990746
<220> FEATURE:
<221> NAME/KEY: misc_feature
<223> OTHER INFORMATION: Ceres CLONE ID no. 1990746_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 214

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75

<210> SEQ ID NO 215
<211> LENGTH: 79
<212> TYPE: PRT
<213> ORGANISM: Artificial Sequence
<220> FEATURE:
<223> OTHER INFORMATION: Truncated version of Ceres CLONE ID no. 2033803
<220> FEATURE:
<221> NAME/KEY: misc_feature
<223> OTHER INFORMATION: Ceres CLONE ID no. 2033803_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 215

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30
```

```
Asp Leu Gly Leu Arg Phe Phe Leu Lys Ile Phe Glu Ile Ala Pro Ser
         35                  40                  45

Ala Lys Gln Met Phe Ser Phe Leu Arg Asp Ser Asp Val Pro Leu Glu
     50                  55                  60

Lys Asn Pro Lys Leu Lys Thr His Ala Met Ser Val Phe Val Met
 65                 70                  75
```

<210> SEQ ID NO 216
<211> LENGTH: 33
<212> TYPE: PRT
<213> ORGANISM: Artificial Sequence
<220> FEATURE:
<223> OTHER INFORMATION: Truncated version of Ceres CLONE ID no. 2034916
<220> FEATURE:
<221> NAME/KEY: misc_feature
<223> OTHER INFORMATION: Ceres CLONE ID no. 2034916_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 216

```
Met Gln Ile Phe Val Lys Thr Leu Thr Gly Lys Thr Ile Thr Leu Glu
 1               5                  10                  15

Val Glu Ser Ser Asp Thr Ile Asp Asn Val Lys Ala Lys Ile Gln Asp
             20                  25                  30

Lys
```

<210> SEQ ID NO 217
<211> LENGTH: 33
<212> TYPE: PRT
<213> ORGANISM: Artificial Sequence
<220> FEATURE:
<223> OTHER INFORMATION: Truncated version of Ceres CLONE ID no. 513071
<220> FEATURE:
<221> NAME/KEY: misc_feature
<223> OTHER INFORMATION: Ceres CLONE ID no. 513071_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 217

```
Met Gln Ile Phe Val Lys Thr Leu Thr Gly Lys Thr Ile Thr Leu Glu
 1               5                  10                  15

Val Glu Ser Ser Asp Thr Val Asp Asn Val Lys Ala Lys Ile Gln Asp
             20                  25                  30

Lys
```

<210> SEQ ID NO 218
<211> LENGTH: 33
<212> TYPE: PRT
<213> ORGANISM: Artificial Sequence
<220> FEATURE:
<223> OTHER INFORMATION: Truncated version of Ceres CLONE ID no. 522921
<220> FEATURE:
<223> OTHER INFORMATION: Ceres CLONE ID no. 522921_T

```
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 218

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 219
<211> LENGTH: 76
<212> TYPE: PRT
<213> ORGANISM: Artificial Sequence
<220> FEATURE:
<223> OTHER INFORMATION: Truncated version of Ceres CLONE ID no. 546001
<220> FEATURE:
<221> NAME/KEY: misc_feature
<223> OTHER INFORMATION: Ceres CLONE ID no. 546001_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 219

Met Thr Thr Thr Leu Glu Arg Gly Phe Ser Glu Gln Glu Ala Leu
1               5                   10                  15

Val Val Lys Ser Trp Asn Val Met Lys Lys Asn Ser Gly Glu Leu Gly
            20                  25                  30

Leu Lys Phe Phe Leu Lys Ile Phe Glu Ile Ala Pro Ser Ala Gln Lys
        35                  40                  45

Leu Phe Ser Phe Leu Arg Asp Ser Thr Val Pro Leu Glu Gln Asn Pro
    50                  55                  60

Lys Leu Lys Pro His Ala Val Ser Val Phe Val Met
65                  70                  75

<210> SEQ ID NO 220
<211> LENGTH: 76
<212> TYPE: PRT
<213> ORGANISM: Artificial Sequence
<220> FEATURE:
<223> OTHER INFORMATION: Truncated version of Ceres CLONE ID no. 651581
<220> FEATURE:
<221> NAME/KEY: misc_feature
<223> OTHER INFORMATION: Ceres CLONE ID no. 651581_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 220
```

```
Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Asp Leu Gly
                20                  25                  30

Leu Lys Leu Phe Ile Lys Ile Phe Glu Ile Ala Pro Thr Ala Lys Lys
            35                  40                  45

Leu Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75
```

<210> SEQ ID NO 221
<211> LENGTH: 77
<212> TYPE: PRT
<213> ORGANISM: Artificial Sequence
<220> FEATURE:
<223> OTHER INFORMATION: Truncated version of Ceres CLONE ID no. 839727
<220> FEATURE:
<221> NAME/KEY: misc_feature
<223> OTHER INFORMATION: Ceres CLONE ID no. 839727_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 221

```
Met Ser Ala Ala Glu Gly Ala Val Val Phe Ser Glu Glu Lys Glu Ala
1               5                   10                  15

Leu Val Leu Lys Ser Trp Ala Ile Met Lys Lys Asp Ser Ala Asn Leu
                20                  25                  30

Gly Leu Arg Phe Phe Leu Lys Ile Phe Glu Ile Ala Pro Ser Ala Arg
            35                  40                  45

Gln Met Phe Pro Phe Leu Arg Asp Ser Asp Val Pro Leu Glu Thr Asn
    50                  55                  60

Pro Lys Leu Lys Thr His Ala Val Ser Val Phe Val Met
65                  70                  75
```

<210> SEQ ID NO 222
<211> LENGTH: 76
<212> TYPE: PRT
<213> ORGANISM: Artificial Sequence
<220> FEATURE:
<223> OTHER INFORMATION: Truncated version of Public GI ID no. 11095158
<220> FEATURE:
<221> NAME/KEY: misc_feature
<223> OTHER INFORMATION: Public GI ID no. 11095158_T
<220> FEATURE:
<221> NAME/KEY: misc_feature
<222> LOCATION: (13)..(76)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 222

```
Met Gly Thr Leu Asp Thr Lys Gly Phe Thr Glu Glu Gln Glu Ala Leu
1               5                   10                  15

Val Val Lys Ser Trp Asn Ala Met Lys Lys Asn Ser Ala Glu Leu Gly
                20                  25                  30
```

-continued

Leu Lys Leu Phe Leu Lys Ile Phe Glu Ile Ala Pro Ser Ala Gln Lys
             35                  40                  45

Leu Phe Ser Phe Leu Lys Asp Ser Lys Val Pro Leu Glu Gln Asn Thr
 50                  55                  60

Lys Leu Lys Pro His Ala Met Ser Val Phe Leu Met
 65                  70                  75

<210> SEQ ID NO 223
<211> LENGTH: 71
<212> TYPE: PRT
<213> ORGANISM: Artificial Sequence
<220> FEATURE:
<223> OTHER INFORMATION: Truncated version of Public GI ID no. 12963875
<220> FEATURE:
<221> NAME/KEY: misc_feature
<223> OTHER INFORMATION: Public GI ID no. 12963875_T
<220> FEATURE:
<221> NAME/KEY: misc_feature
<222> LOCATION: (8)..(69)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 223

Met Ser Ser Phe Ser Glu Glu Gln Ala Leu Val Val Lys Ser Trp
 1               5                  10                  15

Gly Ser Met Lys Lys Asp Ala Gly Trp Gly Leu Lys Phe Phe Leu
                 20                  25                  30

Lys Ile Phe Glu Ile Ala Pro Ser Ala Lys Lys Met Phe Ser Phe Leu
             35                  40                  45

Lys Asp Ser Asn Val Pro Leu Asp Gln Asn Pro Lys Leu Lys Ile His
 50                  55                  60

Ala Lys Ser Val Leu Val Met
 65                  70

<210> SEQ ID NO 224
<211> LENGTH: 84
<212> TYPE: PRT
<213> ORGANISM: Artificial Sequence
<220> FEATURE:
<223> OTHER INFORMATION: Truncated version of Public GI ID no. 14701800
<220> FEATURE:
<221> NAME/KEY: misc_feature
<223> OTHER INFORMATION: Public GI ID no. 14701800_T
<220> FEATURE:
<221> NAME/KEY: misc_feature
<222> LOCATION: (21)..(82)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 224

Met Ala Leu Val Glu Gly Asn Asn Gly Val Ser Gly Gly Ala Val Ser
 1               5                  10                  15

Phe Ser Glu Glu Gln Glu Ala Leu Val Leu Lys Ser Trp Ala Ile Met
                 20                  25                  30

Lys Lys Asp Ser Ala Asn Ile Gly Leu Arg Phe Phe Leu Lys Ile Phe
             35                  40                  45

Glu Val Ala Pro Ser Ala Ser Gln Met Phe Ser Phe Leu Arg Asn Ser
 50                  55                  60

```
Asp Val Pro Leu Glu Lys Asn Pro Lys Leu Lys Thr His Ala Met Ser
65                  70                  75                  80

Val Phe Val Met

<210> SEQ ID NO 225
<211> LENGTH: 76
<212> TYPE: PRT
<213> ORGANISM: Artificial Sequence
<220> FEATURE:
<223> OTHER INFORMATION: Truncated version of Public GI ID no. 15226675
<220> FEATURE:
<221> NAME/KEY: misc_feature
<223> OTHER INFORMATION: Public GI ID no. 15226675_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 225

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
                20                  25                  30

Leu Lys Leu Phe Ile Lys Ile Phe Glu Ile Ala Pro Thr Thr Lys Lys
            35                  40                  45

Met Phe Ser Phe Leu Arg Asp Ser Pro Ile Pro Ala Glu Gln Asn Pro
        50                  55                  60

Lys Leu Lys Pro His Ala Met Ser Val Phe Val Met
65                  70                  75

<210> SEQ ID NO 226
<211> LENGTH: 76
<212> TYPE: PRT
<213> ORGANISM: Artificial Sequence
<220> FEATURE:
<223> OTHER INFORMATION: Truncated version of Public GI ID no. 15824736
<220> FEATURE:
<221> NAME/KEY: misc_feature
<223> OTHER INFORMATION: Public GI ID no. 15824736_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 226

Met Ala Thr Tyr Glu Gly Lys Val Phe Thr Glu Glu Gln Glu Ala Leu
1               5                   10                  15

Val Val Lys Ser Trp Thr Val Met Lys Lys Thr Ala Glu Leu Gly
                20                  25                  30

Leu Lys Phe Phe Leu Lys Ile Phe Glu Ile Ala Pro Ser Ala Lys Lys
            35                  40                  45

Leu Phe Ser Phe Leu Arg Asp Ser Asn Val Pro Leu Glu Gln Asn Thr
        50                  55                  60

Lys Leu Lys Pro His Ala Met Ser Val Phe Val Met
65                  70                  75
```

<210> SEQ ID NO 227
<211> LENGTH: 76
<212> TYPE: PRT
<213> ORGANISM: Artificial Sequence
<220> FEATURE:
<223> OTHER INFORMATION: Truncated version of Public GI ID no. 30909306
<220> FEATURE:
<221> NAME/KEY: misc_feature
<223> OTHER INFORMATION: Public GI ID no. 30909306_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 227

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Asp Leu Gly
                20                  25                  30

Leu Lys Leu Phe Ile Lys Ile Phe Glu Ile Ala Pro Thr Ala Lys Lys
            35                  40                  45

Leu Phe Ser Phe Leu Arg Asp Ser Pro Ile Pro Ala Glu Gln Asn Pro
        50                  55                  60

Lys Leu Lys Pro His Ala Met Ser Val Phe Val Met
65                  70                  75

<210> SEQ ID NO 228
<211> LENGTH: 73
<212> TYPE: PRT
<213> ORGANISM: Artificial Sequence
<220> FEATURE:
<223> OTHER INFORMATION: Truncated version of Public GI ID no. 37903656
<220> FEATURE:
<221> NAME/KEY: misc_feature
<223> OTHER INFORMATION: Public GI ID no. 37903656_T
<220> FEATURE:
<221> NAME/KEY: misc_feature
<222> LOCATION: (10)..(71)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 228

Met Glu Gly Lys Val Phe Thr Glu Glu Gln Glu Thr Leu Val Val Lys
1               5                   10                  15

Ser Trp Gly Val Met Lys Lys Asn Ala Ala Glu Leu Gly Leu Lys Phe
                20                  25                  30

Phe Leu Lys Ile Phe Glu Ile Ala Pro Ser Ala Gln Lys Leu Phe Ser
            35                  40                  45

Phe Leu Arg Asp Ser Asp Ile Pro Leu Glu Lys Asn Pro Lys Leu Lys
        50                  55                  60

Pro His Ala Met Ser Val Phe Val Met
65                  70

<210> SEQ ID NO 229
<211> LENGTH: 76
<212> TYPE: PRT
<213> ORGANISM: Artificial Sequence

```
<220> FEATURE:
<223> OTHER INFORMATION: Truncated version of Public GI ID no. 62548111
<220> FEATURE:
<221> NAME/KEY: misc_feature
<223> OTHER INFORMATION: Public GI ID no. 62548111_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 229

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75
```